US012624026B2

(12) United States Patent
Hughes et al.

(10) Patent No.: US 12,624,026 B2
(45) Date of Patent: May 12, 2026

(54) INHIBITORS OF SARM1

(71) Applicant: Disarm Therapeutics, Inc., Cambridge, MA (US)

(72) Inventors: Robert Owen Hughes, Newtown, CT (US); Rajesh Devraj, Chesterfield, MO (US); Todd Bosanac, New Milford, CT (US); Richard Andrew Jarjes-Pike, Newbury (GB); Andrew Simon Brearley, Chilton (GB); Jonathan Bentley, Abingdon (GB)

(73) Assignee: DISARM THERAPEUTICS, INC., Cambridge, MA (US)

( * ) Notice: Subject to any disclaimer, the term of this patent is extended or adjusted under 35 U.S.C. 154(b) by 0 days.

(21) Appl. No.: 16/972,670

(22) PCT Filed: Jun. 6, 2019

(86) PCT No.: PCT/US2019/035846

§ 371 (c)(1),
(2) Date: Dec. 7, 2020

(87) PCT Pub. No.: WO2019/236890

PCT Pub. Date: Dec. 12, 2019

(65) Prior Publication Data

US 2021/0261537 A1 Aug. 26, 2021

Related U.S. Application Data

(60) Provisional application No. 62/682,054, filed on Jun. 7, 2018.

(51) Int. Cl.

| | |
|---|---|
| *C07D 417/12* | (2006.01) |
| *A61K 31/425* | (2006.01) |
| *A61K 31/427* | (2006.01) |
| *A61P 25/28* | (2006.01) |
| *C07D 275/03* | (2006.01) |
| *C07D 417/04* | (2006.01) |
| *C07D 417/06* | (2006.01) |
| *C07D 417/08* | (2006.01) |
| *C07D 417/14* | (2006.01) |
| *C07D 471/04* | (2006.01) |
| *C07D 471/08* | (2006.01) |
| *C07D 495/04* | (2006.01) |
| *C07F 5/02* | (2006.01) |

(52) U.S. Cl.

CPC ............ *C07D 417/12* (2013.01); *A61P 25/28* (2018.01); *C07D 275/03* (2013.01); *C07D 417/06* (2013.01); *C07D 417/14* (2013.01); *C07D 471/04* (2013.01); *C07D 471/08* (2013.01); *C07D 495/04* (2013.01); *C07F 5/022* (2013.01)

(58) Field of Classification Search

CPC ................ C07D 417/12; C07D 275/03; C07D 417/14; C07D 417/06; C07D 471/04; C07D 471/08; C07D 495/04; C07F 5/022; A61K 31/425; A61K 31/427

See application file for complete search history.

(56) References Cited

U.S. PATENT DOCUMENTS

| | | | |
|---|---|---|---|
| 4,894,371 | A | 1/1990 | Jung et al. |
| 8,067,452 | B2 | 11/2011 | Wu et al. |
| 8,242,271 | B2 | 8/2012 | Singh et al. |
| 8,586,600 | B2 | 11/2013 | Singh et al. |
| 9,067,929 | B2 | 6/2015 | Singh et al. |
| 9,486,521 | B2 | 11/2016 | Freeman et al. |
| 2004/0039037 | A1 | 2/2004 | Zhang et al. |
| 2004/0106646 | A1 | 6/2004 | Takayama et al. |
| 2004/0147574 | A1 | 7/2004 | Munchhof |
| 2006/0194802 | A1 | 8/2006 | Abdellaoui et al. |
| 2006/0217390 | A1* | 9/2006 | Gunic .................. C07D 275/03 544/405 |
| 2008/0153828 | A1 | 6/2008 | Collins et al. |
| 2008/0300268 | A1 | 12/2008 | Singh et al. |
| 2010/0324049 | A1 | 12/2010 | Ando et al. |
| 2011/0144084 | A1 | 6/2011 | Braganza et al. |
| 2012/0328629 | A1 | 12/2012 | Freeman |
| 2016/0130269 | A1 | 5/2016 | Dorsch et al. |

FOREIGN PATENT DOCUMENTS

| | | | |
|---|---|---|---|
| IN | 1999DE00823 | A | 1/2009 |
| JP | 1985105685 | | 6/1985 |
| WO | 99/62890 | A1 | 12/1999 |

(Continued)

OTHER PUBLICATIONS

Varaprasad, et al., Bioorganic & Medicinal Chemistry Letters (2006), 16(15), 3975-3980. (Year: 2006).*

Chen, et. al., Journal of Life Sciences, (2011), 5(6),434-442. (Year: 2011).*

Ke, Shaoyong, Journal of Heterocyclic Chemistry (2017), 54(3), 1957-1962 (Year: 2017).*

Shaoyong Ke, Journal of Heterocyclic Chemistry, 54, 1957 (2017). (Year: 2017).*

(Continued)

*Primary Examiner* — Bruck Kifle

(74) *Attorney, Agent, or Firm* — Quarles & Brady, LLP

(57) ABSTRACT

Compounds having a structure set forth in Formula I below are provided herein. Such compounds and methods disclosed herein, may be useful, for example, for inhibiting SARM1 and/or treating and/or preventing axonal degeneration.

Formula I

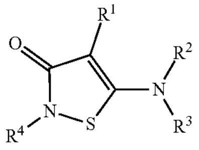

1 Claim, 2 Drawing Sheets

Specification includes a Sequence Listing.

(56) References Cited

FOREIGN PATENT DOCUMENTS

| | | | | |
|---|---|---|---|---|
| WO | 2003/105857 | A1 | 12/2003 | |
| WO | 2005/081997 | A2 | 9/2005 | |
| WO | 2005/082001 | A2 | 9/2005 | |
| WO | WO 2006133417 | * | 12/2006 | ........... C07D 275/03 |
| WO | 2008/118626 | A2 | 10/2008 | |
| WO | 2009041567 | A1 | 4/2009 | |
| WO | 2011/019678 | A1 | 2/2011 | |
| WO | 2011100502 | A1 | 8/2011 | |
| WO | 2012106343 | A2 | 8/2012 | |
| WO | 2012/178022 | A2 | 12/2012 | |
| WO | 2014198848 | A2 | 12/2014 | |
| WO | 2018011628 | A1 | 1/2018 | |
| WO | 2018035204 | A1 | 2/2018 | |
| WO | 2018057989 | A1 | 3/2018 | |
| WO | 2018071794 | A1 | 4/2018 | |
| WO | 2018/198123 | A1 | 11/2018 | |
| WO | 2019/236879 | A1 | 12/2019 | |
| WO | 2019/236884 | A1 | 12/2019 | |
| WO | 2020/247701 | A2 | 12/2020 | |

OTHER PUBLICATIONS

Pubchem, Substance Record for SID 348596632, Available Date: Dec. 18, 2017 [retrieved on Aug. 14, 2019]. Retrieved from the Internet: <URL: https://pubchem.ncbi.nim.nih.gov/substance/348596632>.
International Search Report mailed Sep. 17, 2019, for PCT/US2019/035846, filed on Jun. 6, 2019.
Ke Shaoyong: "Convenient Structural Diversity-Guided Synthesis of Functionalized Sulfur-Containing Heterocycles via [alpha]-Substituted Cyanoacetamides", Journal of Heterocyclic Chemistry, vol. 54, No. 3, May 1, 2017 (May 1, 2017), pp. 1957-1962.
Basheer Ahmad et al: "A Rich Array of Reactions of Cyanomonothiocarbonylmalonamides RNHCSCH(CN)CONHR' and Their Thioenols RNCH(SH)C(CN)CONHR' 1", The Journal of Organic Chemistry, vol. 73, No. 4. Feb. 1, 2008 (Feb. 1, 2008), pp. 1386-1396.
Yan et al: Isothiazoles as active-site inhibitors of HCV NS5B polymerase, Bioorganic & Medicinal Chemistry Letters, Elsevier, Amsterdam, NL, vol. 17, No. 1, Dec. 22, 2006 (Dec. 22, 2006), pp. 28-33.
Walker Lauren J et al: "MAPK signaling promotes axonal degeneration by speeding the turnover of the axonal maintenance factor NMNAT2", Elife, vol. 6, Jan. 17, 2017.
Okajima and Okada, Journal of Heterocyclic Chemistry, Mar./Apr. 1990 (27) 567-574, Synthesis of Thiocarbonyl and Heterocyclic Compounds from 2-Methylene-1,3-dithietanes.
CAS Registry No. 2733031-14-4, published Nov. 16, 2021 (accessed Jul. 27, 2023).
CAS Registry No. 2733774-78-0, published Nov. 17, 2021 (accessed Jul. 27, 2023).
Pubchem, Substance Record for SID 275452201, Available Date: Dec. 25, 2015 (retrieved on Aug. 28, 2020 & Oct. 15, 2021]. Retrieved from the Internet: <URL: https://pubchem.ncbi.nlm.nih.gov/substance/275452201>.
Basheer. Journal of Organic Chemistry (2008), 73(4), 1386-1396.
Bhattacharyya et al. International Journal of Life Science and Pharma Research (2016), 6(1), L23-L33.
Caldwell et al. Journal of Medicinal Chemistry (2011), 54(2), 580-590.
Carlessi et al. Molecular Cancer Therapeutics (2007), 6(3), 935-944.
Chen et al. Journal of Life Sciences (2011), 5(6), 434-442.
El Abdellaoui et al. Bioorganic & Medicinal Chemistry Letters (2006), 16(21), 5561-5566.
Goerdeler et al. Chemische Berichte (1964), 97(11), 3106-17.
Gorakh et al. World Journal of Pharmaceutical Research (2014), 3(3), 3945-3974.
Hilton et al. Bioorganic & Medicinal Chemistry (2010), 18(12), 4591.
Hilton et al. Bioorganic & Medicinal Chemistry (2010), 18(2), 707-718.
Ke. Journal of Heterocyclic Chemistry (2017), 54(3), 1957-1962.
Larson et al. Bioorganic & Medicinal Chemistry Letters (2007), 17(1), 172-175.
Melagraki et al. Chemical Biology & Drug Design (2010), 76(5), 397-406.
Nguyen et al. ACS Chemical Biology (2012), 7(1), 172-184.
Pasha et al. Chemical Biology & Drug Design (2009), 73(3), 292-300.
Reddy et al. Chemical Biology & Drug Design (2012), 79(1), 84-91.
Shishoo et al. Journal of Heterocyclic Chemistry (1988), 25(3), 759-65.
Silva-Santisteban et al. PLoS One (2013), 8(6), e65689.
Therese et al. Journal of Chemical Information and Modeling (2014), 54(2), 539-552.
Varaprasad et al. Bioorganic & Medicinal Chemistry Letters (2006), 16(15), 3975-3980.
Varshney et al. Medicinal Chemistry (2012), 8(3), 491-504.
Wang et al. Bioorganic & Medicinal Chemistry Letters (2013), 23(23), 6286-6291.
Yan et al. Bioorganic & Medicinal Chemistry Letters (2007), 17(1), 28-33.
CAS Registry Entries, "Chemical Catalog," Mar. 9, 2016.
CAS Registry Entries, "GVK BIO Catalog," Mar. 3, 2016.
CAS Registry Entry 1222845-17-1, European Bioinformatics Institute, May 13, 2010.
CAS Registry Entry 771583-07-4, Rare Chemicals GmbH, Oct. 29, 2004.
CAS Registry Entry 959658-93-6, National Institute of Allergy and Infectious Diseases, Dec. 28, 2007.
Geisler et al., Brain, 2016, 139, 3092-3108.
Bosanac et al., Brain, 2021, 144; 3226-3238.
Pubchem, Substance Record CID 5798 Sep. 16, 2004.
Gallou, Fet al., Practical regioselective bromination of azaindoles and diazaindoles, Synlett, 2007, No. 2, pp. 211-214.
Fisher, M. H. et al., Azaindole anthelmintic agents, Journal of Medicinal Chemistry, 1972, vol. 15, No. 11, pp. 1168-1171.
Registry[online], Oct. 27, 2009-Jul. 23, 2012, [Retrieved on May 19, 2023], Retrieved from: STN, CAS No. 1190318-02-5, 1384079-12-2.
Babetto et al, Cell Rep. 2010, 3, 1422-1429.
Baskin et al. Proc natl Acad Sci USA 2007, 104, 16793-16797.
Belenky et al, Trends Biochemical Sciences, Jan. 2007, vol. 32, issue 1, pp. 12-19.
Chiarugi et al, Nature Reviews Cancer, Sep. 28, 2012, 12, 741-752.
Geisler "Prevention of vincristine-induced pheripheral" Brain, 139(Pt 12):3092-3108 (2016).
Gerdts "Axon Self-Destruction: New Links among SARM1, MARKs, and NAD+ Metabolism" Neruon, Cell Press, US, vol. 89, No. 3; Feb. 3, 2016 pp. 449-460, XP029406975, ISSN: 0896-6273. DOI: 10.1016/J.Neuron.2015.12.023 figure 2, p. 455, col. 2, last paragraph.
Gerdts "SARM1 activation triggers axon degeneration locally via NAD+ destruction", Science vol. 348, No. 6233, Apr. 24, 2015, pp. 453-457, XP055431673, XP055431673, ISSN: 0036-8075, DOI: 10.1126/science. 1258366 p. 455, col. 2, p. 456, last paragraph.
Gerdts Sarm 1-mediated axon degeneration requires both SAM and TIR interactions, J Neurosci., 33(33): 13569-80 (2013).
Gerdts, J., et al., "SARM1 activation triggers axon degeneration locally via NAD+ destruction" Science, 2015, 348, 453-457.
Henninger Attenuated traumatic axonal injury and improved functional outcome after traumatic brain injury in mice lacking Sarm1:, Brain, vol. 139, No. 4, Apr. 24, 2016, pp. 1094-1105, SP055432558, GB ISSN: 0006-8950, DOI: 10.1093/brain/aww001 p. 1103, col. 2.
O'Neill et al., "The family of five: TIR-domain-contraining adaptors in Toll-like receptor signalling" Nature Reviews Immunology, 7: 353-364 (2007).
Osterloh, J.M., et al., "dSarm/Sarm1 Is Required for Activation of any Injury-Induced Axon Death Pathway" Science, 2012, 337, 481-484.

(56) References Cited

OTHER PUBLICATIONS

Qiao, F. & Bowie, J.U., "The Many Faces of SAM" Sci. STKE 2005, re7, 2005.
Sasaki et al., "Characterization of Leber Congenital Amaurosis-associated NMNAT1 Mutants" J. Biol. Chem 2015, 290, 17228-17238.
Sasaki, et al., "Nicotinamide Mononucleotide Adenylyl Transferase-Mediated Axonal Protection Requires Enzymatic Activity But No Increased Levels of Neuronal Nicotinamide Adenine Dinucleotide" The Journal of Neuroscience, 29(17) 5525-5535; 2009.
Sun et al. "Carbohydrate and Protein Immobilization onto Solid Surfaces by Sequential Diels-Alder and Azide-Alkyne Cycloadditions" Bioconjugate Chem., 2006, 17, 52-57.
Tewari, R., et al., "Armadillo-repeat protein functions: questions for little creatures" Trends Cell Biol., 2010, 20, 470-481.
Whitmore et al "The proapoptotic proteins Bax and Bak are not involved in Wallerian degeneration" Cell Death & Differentiation 10, 260-261 (2003).
International Search Report and Written Opinion of PCT/US2019/035846 (filed on Jun. 6, 2019 by Eli Lilly and Company), International Search Completed on Aug. 16, 2019, Mailed on Sep. 17, 2019 by the European Patent Office, 7 pages.

* cited by examiner

SEQUENCE LISTING

```
<160> NUMBER OF SEQ ID NOS: 1

<210> SEQ ID NO 1
<211> LENGTH: 10329
<212> TYPE: DNA
<213> ORGANISM: Artificial Sequence
<220> FEATURE:
<223> OTHER INFORMATION: Chemically synthesized oligonucleotide

<400> SEQUENCE: 1

gtcgacggat cgggagatct cccgatcccc tatggtgcac tctcagtaca atctgctctg     60

atgccgcata gttaagccag tatctgctcc ctgcttgtgt gttggaggtc gctgagtagt    120

gcgcgagcaa aatttaagct acaacaaggc aaggcttgac cgacaattgc atgaagaatc    180

tgcttagggt taggcgtttt gcgctgcttc gcgatgtacg ggccagatat acgcgttgac    240

attgattatt gactagttat taatagtaat caattacggg gtcattagtt catagcccat    300

atatggagtt ccgcgttaca taacttacgg taaatggccc gcctggctga ccgcccaacg    360

acccccgccc attgacgtca ataatgacgt atgttcccat agtaacgcca atagggactt    420

tccattgacg tcaatgggtg gagtatttac ggtaaactgc ccacttggca gtacatcaag    480

tgtatcatat gccaagtacg ccccctattg acgtcaatga cggtaaatgg cccgcctggc    540

attatgccca gtacatgacc ttatgggact ttcctacttg gcagtacatc tacgtattag    600

tcatcgctat taccatggtg atgcggtttt ggcagtacat caatgggcgt ggatagcggt    660

ttgactcacg gggatttcca agtctccacc ccattgacgt caatgggagt ttgttttggc    720

accaaaatca acgggacttt ccaaaatgtc gtaacaactc cgccccattg acgcaaatgg    780

gcggtaggcg tgtacggtgg gaggtctata taagcagcgc gttttgcctg tactgggtct    840

ctctggttag accagatctg agcctgggag ctctctggct aactagggaa cccactgctt    900
```

```
aagcctcaat aaagcttgcc ttgagtgctt caagtagtgt gtgcccgtct gttgtgtgac    960
tctggtaact agagatccct cagacccttt tagtcagtgt ggaaaatctc tagcagtggc   1020
gcccgaacag ggacttgaaa gcgaaaggga aaccagagga gctctctcga cgcaggactc   1080
ggcttgctga agcgcgcacg gcaagaggcg aggggcggcg actggtgagt acgccaaaaa   1140
ttttgactag cggaggctag aaggagagag atgggtgcga gagcgtcagt attaagcggg   1200
ggagaattag atcgcgatgg gaaaaaattc ggttaaggcc agggggaaag aaaaaatata   1260
aattaaaaca tatagtatgg gcaagcaggg agctagaacg attcgcagtt aatcctggcc   1320
tgttagaaac atcagaaggc tgtagacaaa tactgggaca gctacaacca tcccttcaga   1380
caggatcaga agaacttaga tcattatata atacagtagc aaccctctat tgtgtgcatc   1440
aaaggataga gataaaagac accaaggaag ctttagacaa gatagaggaa gagcaaaaca   1500
aaagtaagac caccgcacag caagcggccg ctgatcttca gacctggagg aggagatatg   1560
agggacaatt ggagaagtga attatataaa tataaagtag taaaaattga accattagga   1620
gtagcaccca ccaaggcaaa gagaagagtg gtgcagagag aaaaaagagc agtgggaata   1680
ggagctttgt tccttgggtt cttgggagca gcaggaagca ctatgggcgc agcgtcaatg   1740
acgctgacgg tacaggccag acaattattg tctggtatag tgcagcagca gaacaatttg   1800
ctgagggcta ttgaggcgca acagcatctg ttgcaactca cagtctgggg catcaagcag   1860
ctccaggcaa gaatcctggc tgtggaaaga tacctaaagg atcaacagct cctggggatt   1920
tggggttgct ctggaaaact catttgcacc actgctgtgc cttggaatgc tagttggagt   1980
aataaatctc tggaacagat ttggaatcac acgacctgga tggagtggga cagagaaatt   2040
aacaattaca caagcttaat acactcctta attgaagaat cgcaaaacca gcaagaaaag   2100
aatgaacaag aattattgga attagataaa tgggcaagtt tgtggaattg gtttaacata   2160
acaaattggc tgtggtatat aaaattattc ataatgatag taggaggctt ggtaggttta   2220
agaatagttt ttgctgtact ttctatagtg aatagagtta ggcagggata ttcaccatta   2280
tcgtttcaga cccacctccc aaccccgagg ggacccgaca ggcccgaagg aatagaagaa   2340
gaaggtggag agagagacag agacagatcc attcgattag tgaacggatc ggcactgcgt   2400
gcgccaattc tgcagacaaa tggcagtatt catccacaat tttaaaagaa aaggggggat   2460
tggggggtac agtgcagggg aaagaatagt agacataata gcaacagaca tacaaactaa   2520
agaattacaa aaacaaatta caaaaattca aaattttcgg gtttattaca gggacagcag   2580
agatccagtt tggttaatta agggtgcagc ggcctccgcg ccgggttttg gcgcctcccg   2640
cgggcgcccc cctcctcacg gcgagcgctg ccacgtcaga cgaagggcgc aggagcgttc   2700
ctgatccttc cgcccggacg ctcaggacag cggcccgctg ctcataagac tcggccttag   2760
aaccccagta tcagcagaag gacattttag gacgggactt gggtgactct agggcactgg   2820
ttttctttcc agagagcgga acaggcgagg aaaagtagtc ccttctcggc gattctgcgg   2880
agggatctcc gtggggcggt gaacgccgat gattatataa ggacgcgccg ggtgtggcac   2940
agctagttcc gtcgcagccg ggatttgggt cgcggttctt gtttgtggat cgctgtgatc   3000
gtcacttggt gagttgcggg ctgctgggct ggccggggct ttcgtggccg ccgggccgct   3060
cggtgggacg gaagcgtgtg gagagaccgc caagggctgt agtctgggtc cgcgagcaag   3120
gttgccctga actgggggtt ggggggagcg cacaaaatgg cggctgttcc cgagtcttga   3180
atggaagacg cttgtaaggc gggctgtgag gtcgttgaaa caaggtgggg ggcatggtgg   3240
```

-continued

```
gcggcaagaa cccaaggtct tgaggccttc gctaatgcgg gaaagctctt attcgggtga   3300
gatgggctgg ggcaccatct ggggaccctg acgtgaagtt tgtcactgac tggagaactc   3360
gggtttgtcg tctggttgcg gggcggcag ttatgcggtg ccgttgggca gtgcacccgt   3420
acctttggga gcgcgcgcct cgtcgtgtcg tgacgtcacc cgttctgttg gcttataatg   3480
cagggtgggg ccacctgccg gtaggtgtgc ggtaggcttt tctccgtcgc aggacgcagg   3540
gttcgggcct agggtaggct ctcctgaatc gacaggcgcc ggacctctgg tgaggggagg   3600
gataagtgag gcgtcagttt ctttggtcgg ttttatgtac ctatcttctt aagtagctga   3660
agctccggtt ttgaactatg cgctcggggt tggcgagtgt gttttgtgaa gtttttttagg   3720
cacctttttga aatgtaatca tttgggtcaa tatgtaattt tcagtgttag actagtaaag   3780
cttctgcagg tcgactctag aaaattgtcc gctaaattct ggccgttttt ggcttttttg   3840
ttagacgaag cttgggctgc aggtcgactc tagaggatcc ggatccgcca ccatgtcagc   3900
ttggagccac ccacaattcg aaaaaggcgg tggctcaggc ggtggctcag gtggctcagc   3960
ttggagccac ccacaattcg aaaaaggcgg tggctcatct ggcggaggtg gcggtggctc   4020
atctggcgga ggtgctagcg tgcccagctg gaaggaggcc gaggttcaga cgtggctgca   4080
gcagatcggt ttctccaagt actgcgagag cttccgggag cagcaggtgg atggcgacct   4140
gcttctgcgg ctcacggagg aggaactcca gaccgacctg ggcatgaaat cgggcatcac   4200
ccgcaagagg ttctttaggg agctcacgga gctcaagacc ttcgccaact attctacgtg   4260
cgaccgcagc aacctggcgg actggctggg cagcctggac ccgcgcttcc gccagtacac   4320
ctacggcctg gtcagctgcg gcctggaccg ctccctgctg caccgcgtgt ctgagcagca   4380
gctgctggaa gactgcggca tccacctggg cgtgcaccgc gcccgcatcc tcacggcggc   4440
cagagaaatg ctacactccc cgctgccctg tactggtggc aaacccagtg ggacactcc   4500
agatgtcttc atcagctacc gccggaactc aggttcccag ctggccagtc tcctgaaggt   4560
gcacctgcag ctgcatggct tcagtgtctt cattgatgtg gagaagctgg aagcaggcaa   4620
gttcgaggac aaactcatcc agagtgtcat gggtgcccgc aactttgtgt tggtgctatc   4680
acctggagca ctggacaagt gcatgcaaga ccatgactgc aaggattggg tgcataagga   4740
gattgtgact gctttaagct gcggcaagaa cattgtgccc atcattgatg gcttcgagtg   4800
gcctgagccc caggtcctgc ctgaggacat gcaggctgtg cttactttca acggtatcaa   4860
gtggtcccac gaataccagg aggccaccat tgagaagatc atccgcttcc tgcagggccg   4920
ctcctcccgg gactcatctg caggctctga caccagtttg gagggtgctg cacccatggg   4980
tccaacctaa actctagaat tcgatatcaa gcttatcgat aatcaacctc tggattacaa   5040
aatttgtgaa agattgactg gtattcttaa ctatgttgct ccttttacgc tatgtggata   5100
cgctgcttta atgcctttgt atcatgctat tgcttcccgt atggctttca ttttctcctc   5160
cttgtataaa tcctggttgc tgtctcttta tgaggagttg tggcccgttg tcaggcaacg   5220
tggcgtggtg tgcactgtgt ttgctgacgc aacccccact ggttggggca ttgccaccac   5280
ctgtcagctc ctttccggga ctttcgcttt ccccctccct attgccacgg cggaactcat   5340
cgccgcctgc cttgcccgct gctggacagg ggctcggctg ttgggcactg acaattccgt   5400
ggtgttgtcg gggaaatcat cgtcctttcc ttggctgctc gcctgtgttg ccacctggat   5460
tctgcgcggg acgtccttct gctacgtccc ttcggccctc aatccagcgg accttccttc   5520
ccgcggcctg ctgccggctc tgcggcctct tccgcgtctt cgccttcgcc ctcagacgag   5580
tcggatctcc ctttgggccg cctccccgca tcgataccgt cgacctcgag acctagaaaa   5640
```

```
acatggagca atcacaagta gcaatacagc agctaccaat gctgattgtg cctggctaga   5700
agcacaagag gaggaggagg tgggttttcc agtcacacct caggtacctt taagaccaat   5760
gacttacaag gcagctgtag atcttagcca ctttttaaaa gaaaaggggg gactggaagg   5820
gctaattcac tcccaacgaa gacaagatat ccttgatctg tggatctacc acacacaagg   5880
ctacttccct gattggcaga actacacacc agggccaggg atcagatatc cactgacctt   5940
tggatggtgc tacaagctag taccagttga gcaagagaag gtagaagaag ccaatgaagg   6000
agagaacacc cgcttgttac accctgtgag cctgcatggg atggatgacc cggagagaga   6060
agtattagag tggaggtttg acagccgcct agcatttcat cacatggccc gagagctgca   6120
tccggactgt actgggtctc tctggttaga ccagatctga gcctgggagc tctctggcta   6180
actagggaac ccactgctta agcctcaata aagcttgcct tgagtgcttc aagtagtgtg   6240
tgcccgtctg ttgtgtgact ctggtaacta gagatccctc agaccctttt agtcagtgtg   6300
gaaaatctct agcagggccc gtttaaaccc gctgatcagc ctcgactgtg ccttctagtt   6360
gccagccatc tgttgtttgc ccctcccccg tgccttcctt gaccctggaa ggtgccactc   6420
ccactgtcct ttcctaataa aatgaggaaa ttgcatcgca ttgtctgagt aggtgtcatt   6480
ctattctggg gggtggggtg gggcaggaca gcaaggggga ggattgggaa gacaatagca   6540
ggcatgctgg ggatgcggtg ggctctatgg cttctgaggc ggaaagaacc agctggggct   6600
ctagggggta tccccacgcg ccctgtagcg gcgcattaag cgcggcgggt gtggtggtta   6660
cgcgcagcgt gaccgctaca cttgccagcg ccctagcgcc cgctcctttc gctttcttcc   6720
cttcctttct cgccacgttc gccggctttc cccgtcaagc tctaaatcgg gggctccctt   6780
tagggttccg atttagtgct ttacggcacc tcgaccccaa aaaacttgat tagggtgatg   6840
gttcacgtag tgggccatcg ccctgataga cggtttttcg ccctttgacg ttggagtcca   6900
cgttctttaa tagtggactc ttgttccaaa ctggaacaac actcaaccct atctcggtct   6960
attcttttga tttataaggg attttgccga tttcggccta ttggttaaaa aatgagctga   7020
tttaacaaaa atttaacgcg aattaattct gtggaatgtg tgtcagttag ggtgtggaaa   7080
gtccccaggc tccccagcag gcagaagtat gcaaagcatg catctcaatt agtcagcaac   7140
caggtgtgga aagtccccag gctccccagc aggcagaagt atgcaaagca tgcatctcaa   7200
ttagtcagca accatagtcc cgcccctaac tccgcccatc ccgcccctaa ctccgcccag   7260
ttccgcccat tctccgcccc atggctgact aattttttt atttatgcag aggccgaggc    7320
cgcctctgcc tctgagctat tccagaagta gtgaggaggc ttttttggag gcctaggctt   7380
ttgcaaaaag ctcccgggag cttgtatatc cattttcgga tctgatcagc acgtgttgac   7440
aattaatcat cggcatagta tatcggcata gtataatacg acaaggtgag gaactaaacc   7500
atggccaagt tgaccagtgc cgttccggtg ctcaccgcgc gcgacgtcgc cggagcggtc   7560
gagttctgga ccgaccggct cgggttctcc cgggacttcg tggaggacga cttcgccggt   7620
gtggtccggg acgacgtgac cctgttcatc agcgcggtcc aggaccaggt ggtgccggac   7680
aacaccctgg cctgggtgtg ggtgcgcggc ctggacgagc tgtacgccga gtggtcggag   7740
gtcgtgtcca cgaacttccg ggacgcctcc gggccggcca tgaccgagat cggcgagcag   7800
ccgtgggggc gggagttcgc cctgcgcgac ccggccggca actgcgtgca cttcgtggcc   7860
gaggagcagg actgacacgt gctacgagat ttcgattcca ccgccgcctt ctatgaaagg   7920
ttgggcttcg gaatcgtttt ccgggacgcc ggctggatga tcctccagcg cggggatctc   7980
```

-continued

```
atgctggagt tcttcgccca ccccaacttg tttattgcag cttataatgg ttacaaataa   8040
agcaatagca tcacaaattt cacaaataaa gcattttttt cactgcattc tagttgtggt   8100
ttgtccaaac tcatcaatgt atcttatcat gtctgtatac cgtcgacctc tagctagagc   8160
ttggcgtaat catggtcata gctgtttcct gtgtgaaatt gttatccgct cacaattcca   8220
cacaacatac gagccggaag cataaagtgt aaagcctggg gtgcctaatg agtgagctaa   8280
ctcacattaa ttgcgttgcg ctcactgccc gctttccagt cgggaaacct gtcgtgccag   8340
ctgcattaat gaatcggcca acgcgcgggg agaggcggtt tgcgtattgg gcgctcttcc   8400
gcttcctcgc tcactgactc gctgcgctcg gtcgttcggc tgcggcgagc ggtatcagct   8460
cactcaaagg cggtaatacg gttatccaca gaatcagggg ataacgcagg aaagaacatg   8520
tgagcaaaag gccagcaaaa ggccaggaac cgtaaaaagg ccgcgttgct ggcgtttttc   8580
cataggctcc gcccccctga cgagcatcac aaaaatcgac gctcaagtca gaggtggcga   8640
aacccgacag gactataaag ataccaggcg tttccccctg gaagctccct cgtgcgctct   8700
cctgttccga ccctgccgct taccggatac ctgtccgcct ttctcccttc gggaagcgtg   8760
gcgctttctc atagctcacg ctgtaggtat ctcagttcgg tgtaggtcgt tcgctccaag   8820
ctgggctgtg tgcacgaacc ccccgttcag cccgaccgct gcgccttatc cggtaactat   8880
cgtcttgagt ccaacccggt aagacacgac ttatcgccac tggcagcagc cactggtaac   8940
aggattagca gagcgaggta tgtaggcggt gctacagagt tcttgaagtg gtggcctaac   9000
tacggctaca ctagaagaac agtatttggt atctgcgctc tgctgaagcc agttaccttc   9060
ggaaaaagag ttggtagctc ttgatccggc aaacaaacca ccgctggtag cggtggtttt   9120
tttgtttgca agcagcagat tacgcgcaga aaaaaaggat ctcaagaaga tcctttgatc   9180
ttttctacgg ggtctgacgc tcagtggaac gaaaactcac gttaagggat tttggtcatg   9240
agattatcaa aaaggatctt cacctagatc cttttaaatt aaaaatgaag ttttaaatca   9300
atctaaagta tatatgagta aacttggtct gacagttacc aatgcttaat cagtgaggca   9360
cctatctcag cgatctgtct atttcgttca tccatagttg cctgactccc cgtcgtgtag   9420
ataactacga tacgggaggg cttaccatct ggccccagtg ctgcaatgat accgcgagac   9480
ccacgctcac cggctccaga tttatcagca ataaaccagc cagccggaag ggccgagcgc   9540
agaagtggtc ctgcaacttt atccgcctcc atccagtcta ttaattgttg ccgggaagct   9600
agagtaagta gttcgccagt taatagtttg cgcaacgttg ttgccattgc tacaggcatc   9660
gtggtgtcac gctcgtcgtt tggtatggct tcattcagct ccggttccca acgatcaagg   9720
cgagttacat gatcccccat gttgtgcaaa aaagcggtta gctccttcgg tcctccgatc   9780
gttgtcagaa gtaagttggc cgcagtgtta tcactcatgg ttatggcagc actgcataat   9840
tctcttactg tcatgccatc cgtaagatgc ttttctgtga ctggtgagta ctcaaccaag   9900
tcattctgag aatagtgtat gcggcgaccg agttgctctt gcccggcgtc aatacgggat   9960
aataccgcgc cacatagcag aactttaaaa gtgctcatca ttggaaaacg ttcttcgggg  10020
cgaaaactct caaggatctt accgctgttg agatccagtt cgatgtaacc cactcgtgca  10080
cccaactgat cttcagcatc ttttactttc accagcgttt ctgggtgagc aaaaacagga  10140
aggcaaaatg ccgcaaaaaa gggaataagg gcgacacgga aatgttgaat actcatactc  10200
```

-continued
| | |
|---|---|
| ttccttttc aatattattg aagcatttat cagggttatt gtctcatgag cggatacata | 10260 |
| tttgaatgta tttagaaaaa taaacaaata ggggttccgc gcacatttcc ccgaaaagtg | 10320 |
| ccacctgac | 10329 |

INHIBITORS OF SARM1

CROSS REFERENCE TO RELATED APPLICATIONS

This application claims the benefit of U.S. Provisional Application No. 62/682,054, filed Jun. 7, 2018, which is herein incorporated by reference in its entirety.

SEQUENCE LISTING

The instant application contains a Sequence Listing, which has been submitted electronically in ASCII format and is hereby incorporated by reference in its entirety. The ASCII copy, created Jun. 6, 2019, is named 2012800-0024_SL.txt, and is 13,851 bytes in size.

BACKGROUND

Axonal degeneration is a hallmark of several neurological disorders including peripheral neuropathy, traumatic brain injury, and neurodegenerative diseases (Gerdts et al., SARM1 activation triggers axon degeneration locally via NAD(+) destruction. Science 348 2016, pp. 453-457, hereby incorporated by reference in its entirety). Neurodegenerative diseases and injuries are devastating to both patients and caregivers. Costs associated with these diseases currently exceed several hundred billion dollars annually in the Unites States alone. Since the incidence of many of these diseases and disorders increases with age, their incidence is rapidly increasing as demographics change.

SUMMARY

The present disclosure provides technologies useful, among other things, for treating and/or preventing neurodegeneration (e.g., for reducing axonal degeneration). In some embodiments, provided technologies inhibit SARM1.

In some embodiments, the present disclosure provides certain compounds and/or compositions that are useful in medicine, and particularly for treating neurodegeneration (e.g., for reducing axonal degeneration).

In some embodiments, the present disclosure provides compounds having a structure as set forth in Formula I.

I

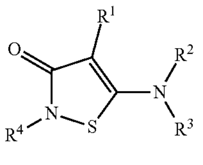

or a pharmaceutically acceptable salt thereof, wherein

- $R^1$ is selected from —CN, —$NO_2$, —C(O)R, —$S(O)_2R$, —$CON(R)_2$, —$S(O)_2N(R)_2$, and —$CO_2R$;
- $R^2$ is —R;
- $R^3$ is —$(CH_2)_{0-2}$Cy, or:
  - $R^2$ and $R^3$, together with the nitrogen atom to which they are attached, form a 4- to 7-membered saturated or partially unsaturated ring fused to Cy or a 4- to 7-membered saturated or partially unsaturated ring substituted with -Cy;
- Cy is selected from phenyl, a 5- to 6-membered heteroaryl ring having 1-3 heteroatoms independently selected from nitrogen, oxygen, and sulfur, an 8- to 10-membered bicyclic heteroaryl ring having 1-3 heteroatoms independently selected from nitrogen, oxygen, and sulfur, and an 8- to 10-membered bicyclic aryl ring, wherein each phenyl, heteroaryl and aryl ring is substituted with 0-4 $R^x$;
- each $R^x$ is independently selected from halogen, —CN, —$NO_2$, —OR, —SR, —$N(R)_2$, —$SO_2R$, —$SO_2N(R)_2$, —$CO_2R$, —$CON(R)_2$, —$N(R)SO_2R$, —N(R)C(O)R, and optionally substituted $C_{1-6}$ aliphatic;
- $R^4$ is —R; and
- each R is independently hydrogen or optionally substituted $C_{1-6}$ aliphatic, or:
  - two instances of R, together with the atom to which they are attached, form a 3- to 6-membered saturated or partially unsaturated heterocyclic ring.

In some embodiments, provided compounds have structures of Formulae I-a, I-a-i, I-a-ii, I-a-iii, I-a-iv, I-a-v, I-a-vi, I-b, I-b-i, I-b-ii, I-b-iii, I-b-iv, I-b-v, I-b-vi, I-c, I-c-i, I-c-ii, I-c-iii, I-c-iv, I-c-v, and I-c-vi, as set forth below.

In some embodiments, the present disclosure provides compounds having a structure as set forth in Formula II:

II

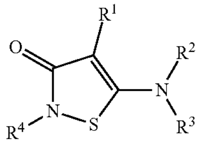

or a pharmaceutically acceptable salt thereof, wherein

- $R^1$ is selected from —CN, —$NO_2$, —C(O)R, —$S(O)_2R$, —$CON(R)_2$, —$S(O)_2N(R)_2$, —$CO_2R$, —C(=NR)N(R)$_2$, and a 5-membered heteroaryl ring having 2-3 heteroatoms independently selected from nitrogen, oxygen, and sulfur;
- $R^2$ is —R;
- $R^3$ is —$(CH_2)_{0-2}$Cy, or:
  - $R^2$ and $R^3$, together with the nitrogen atom to which they are attached, form a 4- to 7-membered saturated or partially unsaturated ring fused to Cy or a 4- to 7-membered saturated or partially unsaturated ring substituted with -Cy;
- Cy is selected from phenyl, a 3- to 7-membered saturated or partially unsaturated carbocyclic ring, a 5- to 6-membered heteroaryl ring having 1-3 heteroatoms independently selected from nitrogen, oxygen, and sulfur, an 8- to 10-membered bicyclic heteroaryl ring having 1-3 heteroatoms independently selected from nitrogen, oxygen, and sulfur, and an 8- to 10-membered bicyclic aryl ring, wherein each phenyl, carbocyclic, heteroaryl and aryl ring is substituted with 0-4 $R^x$;
- each $R^x$ is independently selected from halogen, —CN, —$NO_2$, —OR, —SR, —$N(R)_2$, —$SO_2R$, —$SO_2N(R)_2$, —$CO_2R$, —$CON(R)_2$, —$N(R)SO_2R$, —N(R)C(O)R, an optionally substituted $C_{1-6}$ aliphatic group, an optionally substituted 5- to 6-membered saturated or partially unsaturated heterocyclic ring having 1-2 heteroatoms independently selected from nitrogen, oxygen, and sulfur, and an optionally substituted 8- to 10-membered heteroaryl ring having 1-2 heteroatoms independently selected from nitrogen, oxygen, and sulfur;
- $R^4$ is —R; and
- each R is independently hydrogen, an optionally substituted $C_{1-6}$ aliphatic, an optionally substituted phenyl, and an optionally substituted 3- to 7-membered saturated or partially unsaturated carbocyclic ring, or:

two instances of R, together with the atom to which they are attached, form a 3- to 6-membered saturated or partially unsaturated heterocyclic ring.

In some embodiments, one or more compounds of Formula I or Formula II are provided and/or utilized in a solid form (e.g., a crystal form or an amorphous form).

In some embodiments, the present disclosure provides compositions that comprise and/or deliver a compound of Formula I or Formula II (e.g., in a form as described herein), a prodrug or active metabolite thereof.

In some embodiments, the present disclosure provides compositions that comprise and/or deliver a compound of Formula I or Formula II. In some embodiments, such compositions are pharmaceutical compositions that include at least one pharmaceutically acceptable carrier, diluent or excipient.

In some embodiments, provided SARM1 inhibitors reduce or inhibit binding of NAD+ by SARM1. In some embodiments, provided SARM1 inhibitors bind to SARM1 within a pocket comprising one or more catalytic residues (e.g., a catalytic cleft of SARM1).

In some embodiments, provided compounds and/or compositions inhibit activity of SARM1. Alternatively or additionally, in some embodiments, provided compounds alleviate one or more attributes of neurodegeneration. In some embodiments, the present disclosure provides methods of treating a neurodegenerative disease or disorder associated with axonal degeneration.

In some embodiments, one or more compounds and/or compositions as described herein are useful, for example, in the practice of medicine. In some embodiments, one or more compounds and/or compositions as described herein are useful, for example, to treat, prevent, or ameliorate axonal degeneration (e.g., one or more features or characteristics thereof). In some embodiments, one or more compounds and/or compositions as described herein are useful, for example, to inhibit axonal degeneration, including axonal degeneration that results from reduction or depletion of NAD+. In some embodiments, one or more compounds and/or compositions as described herein are useful, for example, to prevent the axon distal to an axonal injury from degenerating.

In some embodiments, one or more compounds and/or compositions as described herein are useful, for example, to treat one or more neurodegenerative diseases, disorders or conditions selected from the group consisting of neuropathies or axonopathies. In some embodiments, one or more compounds and/or compositions as described herein are useful, for example, to treat a neuropathy or axonopathy associated with axonal degeneration. In some embodiments, a neuropathy associated with axonal degeneration is a hereditary or congenital neuropathy or axonopathy. In some embodiments, a neuropathy associated with axonal degeneration results from a de novo or somatic mutation. In some embodiments, a neuropathy associated with axonal degeneration is selected from a list contained herein. In some embodiments, a neuropathy or axonopathy is associated with axonal degeneration, including, but not limited to, Parkinson's disease, non-Parkinson's disease, Alzheimer's disease, Herpes infection, diabetes, amyotrophic lateral sclerosis (ALS), a demyelinating disease, ischemia or stroke, chemical injury, thermal injury, and AIDS.

In some embodiments, subjects to which a compound or composition as described herein is administered may be or comprise subjects suffering from or susceptible to a neurodegenerative disease, disorder or condition. In some embodiments, a neurodegenerative disease, disorder or condition may be or comprise a traumatic neuronal injury. In some embodiments, a traumatic neuronal injury is blunt force trauma, a closed-head injury, an open head injury, exposure to a concussive and/or explosive force, a penetrating injury in or to the brain cavity or innervated region of the body. In some embodiments, a traumatic neuronal injury is a force which causes axons to deform, stretch, crush or sheer.

In some embodiments, provided methods comprise administering a compound described herein (e.g., a compound of Formula I or Formula II) to a patient in need thereof. In some such embodiments, the patient is at risk of developing a condition characterized by axonal degeneration. In some embodiments, the patient has a condition characterized by axonal degeneration. In some embodiments, the patient has been diagnosed with a condition characterized by axonal degeneration.

In some embodiments, provided methods comprise administering a composition as described herein to a patient population in need thereof. In some embodiments, the population is drawn from individuals who engage in activities where the potential for traumatic neuronal injury is high. In some embodiments, the population is drawn from athletes who engage in contact sports or other high-risk activities In some embodiments, the patient is at risk of developing a neurodegenerative disorder. In some embodiments the patient is elderly. In some embodiments, the patient is known to have a genetic risk factor for neurodegeneration.

In certain embodiments, the present disclosure provides compounds that are useful, for example, as analytical tools, as probes in biological assays, or as therapeutic agents in accordance with the present disclosure. Compounds provided by this disclosure are also useful for the study of SARM1 function in biological and pathological phenomena and the comparative evaluation of new SARM1 activity inhibitors in vitro or in vivo.

In some embodiments, one or more compounds and/or compositions as described herein are useful, for example, as a method for inhibiting the degradation of neurons derived from a subject. In some embodiments, one or more compounds and/or compositions as described herein are useful for inhibiting the degeneration of a neuron, or a portion thereof, cultured in vitro. In some embodiments, one or more compounds and/or compositions as described herein are useful as stabilizing agents to promote in vitro neuronal survival.

DEFINITIONS

Figure 1:
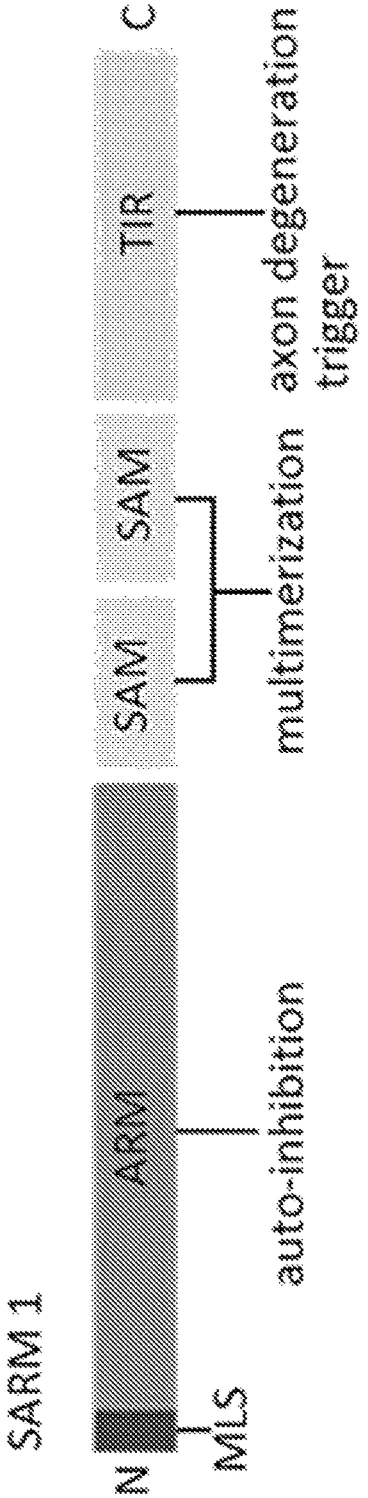
FIG. 1 illustrates the structure of the SARM1 protein.

Aliphatic: The term "aliphatic" refers to a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle" or "cycloaliphatic"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle") refers to a monocyclic $C_3$-$C_8$ hydrocarbon or a bicyclic $C_7$-$C_{10}$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof.

Alkyl: The term "alkyl", used alone or as part of a larger moiety, refers to a saturated, optionally substituted straight or branched chain or cyclic hydrocarbon group having 1-12, 1-10, 1-8, 1-6, 1-4, 1-3, or 1-2 carbon atoms. The term "cycloalkyl" refers to an optionally substituted saturated ring system of about 3 to about 10 ring carbon atoms. Exemplary monocyclic cycloalkyl rings include cyclopropyl, cyclobutyl, cyclopentyl, cyclohexyl, and cycloheptyl.

Alkylene: The term "alkylene" refers to a bivalent alkyl group. In some embodiments, "alkylene" is a bivalent straight or branched alkyl group. In some embodiments, an "alkylene chain" is a polymethylene group, i.e., $-(CH_2)_n-$, wherein n is a positive integer, e.g., from 1 to 6, from 1 to 4, from 1 to 3, from 1 to 2, or from 2 to 3. An optionally substituted alkylene chain is a polymethylene group in which one or more methylene hydrogen atoms is optionally replaced with a substituent. Suitable substituents include those described below for a substituted aliphatic group and also include those described in the specification herein. It will be appreciated that two substituents of the alkylene group may be taken together to form a ring system. In certain embodiments, two substituents can be taken together to form a 3- to 7-membered ring. The substituents can be on the same or different atoms.

Alkenyl: The term "alkenyl", used alone or as part of a larger moiety, refers to an optionally substituted straight or branched chain or cyclic hydrocarbon group having at least one double bond and having 2-12, 2-10, 2-8, 2-6, 2-4, or 2-3 carbon atoms. The term "cycloalkenyl" refers to an optionally substituted non-aromatic monocyclic or multicyclic ring system containing at least one carbon-carbon double bond and having about 3 to about 10 carbon atoms. Exemplary monocyclic cycloalkenyl rings include cyclopentyl, cyclohexenyl, and cycloheptenyl.

Alkynyl: The term "alkynyl", used alone or as part of a larger moiety, refers to an optionally substituted straight or branched chain hydrocarbon group having at least one triple bond and having 2-12, 2-10, 2-8, 2-6, 2-4, or 2-3 carbon atoms.

Aryl: The term "aryl" refers to monocyclic and bicyclic ring systems having a total of five to fourteen ring members, wherein at least one ring in the system is aromatic and wherein each ring in the system contains three to seven ring members. The term "aryl" may be used interchangeably with the term "aryl ring". In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl", as it is used herein, is a group in which an aromatic ring is fused to one or more non-aromatic rings, such as indanyl, phthalimidyl, naphthimidyl, phenanthridinyl, or tetrahydronaphthyl, and the like.

Binding: It will be understood that the term "binding", as used herein, typically refers to a non-covalent association between or among two or more entities. "Direct" binding involves physical contact between entities or moieties; indirect binding involves physical interaction by way of physical contact with one or more intermediate entities. Binding between two or more entities can typically be assessed in any of a variety of contexts—including where interacting entities or moieties are studied in isolation or in the context of more complex systems (e.g., while covalently or otherwise associated with a carrier entity and/or in a biological system or cell).

Biological Sample: As used herein, the term "biological sample" typically refers to a sample obtained or derived from a biological source (e.g., a tissue or organism or cell culture) of interest, as described herein. In some embodiments, a source of interest comprises an organism, such as an animal or human. In some embodiments, a biological sample is or comprises biological tissue or fluid. In some embodiments, a biological sample may be or comprise bone marrow; blood; blood cells; ascites; tissue or fine needle biopsy samples; cell-containing body fluids; free floating nucleic acids; sputum; saliva; urine; cerebrospinal fluid, peritoneal fluid; pleural fluid; feces; lymph; gynecological fluids; skin swabs; vaginal swabs; oral swabs; nasal swabs; washings or lavages such as a ductal lavages or broncheoalveolar lavages; aspirates; scrapings; bone marrow specimens; tissue biopsy specimens; surgical specimens; feces, other body fluids, secretions, and/or excretions; and/or cells therefrom, etc. In some embodiments, a biological sample is or comprises cells obtained from an individual. In some embodiments, obtained cells are or include cells from an individual from whom the sample is obtained. In some embodiments, a sample is a "primary sample" obtained directly from a source of interest by any appropriate means. For example, in some embodiments, a primary biological sample is obtained by methods selected from the group consisting of biopsy (e.g., fine needle aspiration or tissue biopsy), surgery, collection of body fluid (e.g., blood, lymph, feces etc.), etc. In some embodiments, as will be clear from context, the term "sample" refers to a preparation that is obtained by processing (e.g., by removing one or more components of and/or by adding one or more agents to) a primary sample. For example, filtering using a semi-permeable membrane. Such a "processed sample" may comprise, for example, nucleic acids or proteins extracted from a sample or obtained by subjecting a primary sample to techniques such as amplification or reverse transcription of mRNA, isolation and/or purification of certain components, etc.

Biomarker: The term "biomarker" is used herein to refer to a to an entity, event, or characteristic whose presence, level, degree, type, and/or form, correlates with a particular biological event or state of interest, so that it is considered to be a "marker" of that event or state. To give but a few examples, in some embodiments, a biomarker may be or comprise a marker for a particular disease state, or for likelihood that a particular disease, disorder or condition may develop, occur, or reoccur. In some embodiments, a biomarker may be or comprise a marker for a particular disease or therapeutic outcome, or likelihood thereof. Thus, in some embodiments, a biomarker is predictive, in some embodiments, a biomarker is prognostic, in some embodiments, a biomarker is diagnostic, of the relevant biological event or state of interest. A biomarker may be or comprise an entity of any chemical class, and may be or comprise a combination of entities. For example, in some embodiments, a biomarker may be or comprise a nucleic acid, a polypeptide, a lipid, a carbohydrate, a small molecule, an inorganic agent (e.g., a metal or ion), or a combination thereof. In some embodiments, a biomarker is a cell surface marker. In some embodiments, a biomarker is intracellular. In some embodiments, a biomarker is detected outside of cells (e.g., is secreted or is otherwise generated or present outside of cells, e.g., in a body fluid such as blood, urine, tears, saliva, cerebrospinal fluid, etc. In some embodiments, a biomarker may be or comprise a genetic or epigenetic signature. In some embodiments, a biomarker may be or comprise a gene expression signature.

In some embodiments, a biomarker may be or comprise a marker for neurodegeneration, or for likelihood that a neurodegenerative disease, disorder or condition may develop, occur, or reoccur. In some embodiments, a biomarker may be or comprise a marker of neurodegeneration a therapeutic outcome, or likelihood thereof. Thus, in some embodiments, a biomarker is predictive, in some embodiments, a biomarker is prognostic, in some embodiments, a biomarker is diagnostic, of a neurodegenerative disease, disorder or condition. In some embodiments changes in biomarker levels can be detected via cerebral spinal fluid (CSF), plasma and/or serum.

In some embodiments, neurodegeneration may be assessed, for example, by detecting an increase and/or decrease in the concentration of neurofilament protein light (NF-L) and/or neurofilament protein heavy (NF-H) contained the cerebral spinal fluid of a subject. In some embodiments, the incidence and/or progression of neurodegeneration can be assessed via positron emission tomography (PET) with a synaptic vesicle glycoprotein 2a (SV2A) ligand. In some embodiments, a detectable change in constitutive NAD and/or cADPR levels in neurons can be used to assess neurodegeneration.

In some embodiments, a detectable change in one or more neurodegeneration associated proteins in a subject, relative to a healthy reference population can be used as a biomarker of neurodegeneration. Such proteins include, but are not limited to, albumin, amyloid-β (Aβ)38, Aβ40, Aβ42, glial fibrillary acid protein (GFAP), heart-type fatty acid binding protein (hFABP), monocyte chemoattractin protein (MCP)-1, neurogranin, neuron specific enolayse (NSE), soluble amyloid precursor protein (sAPP)α, sAPPβ, soluble triggering receptor expressed on myeloid cells (sTREM) 2, phospho-tau, and/or total-tau. In some embodiments, an increase in cytokines and/or chemokines, including, but not limited to, Ccl2, Ccl7, Ccl12, Csf1, and/or Il6, can be used as a biomarker of neurodegeneration.

Carrier: As used herein, the term "carrier" refers to a diluent, adjuvant, excipient, or vehicle with which a composition is administered. In some exemplary embodiments, carriers can include sterile liquids, such as, for example, water and oils, including oils of petroleum, animal, vegetable or synthetic origin, such as, for example, peanut oil, soybean oil, mineral oil, sesame oil and the like. In some embodiments, carriers are or include one or more solid components.

Combination therapy: As used herein, the term "combination therapy" refers to those situations in which a subject is simultaneously exposed to two or more therapeutic regimens (e.g., two or more therapeutic agents). In some embodiments, the two or more regimens may be administered simultaneously; in some embodiments, such regimens may be administered sequentially (e.g., all "doses" of a first regimen are administered prior to administration of any doses of a second regimen); in some embodiments, such agents are administered in overlapping dosing regimens. In some embodiments, "administration" of combination therapy may involve administration of one or more agent(s) or modality(ies) to a subject receiving the other agent(s) or modality(ies) in the combination. For clarity, combination therapy does not require that individual agents be administered together in a single composition (or even necessarily at the same time), although in some embodiments, two or more agents, or active moieties thereof, may be administered together in a combination composition, or even in a combination compound (e.g., as part of a single chemical complex or covalent entity).

Composition: Those skilled in the art will appreciate that the term "composition" may be used to refer to a discrete physical entity that comprises one or more specified components. In general, unless otherwise specified, a composition may be of any form—e.g., gas, gel, liquid, solid, etc.

Domain: The term "domain" as used herein refers to a section or portion of an entity. In some embodiments, a "domain" is associated with a particular structural and/or functional feature of the entity so that, when the domain is physically separated from the rest of its parent entity, it substantially or entirely retains the particular structural and/or functional feature. Alternatively or additionally, a domain may be or include a portion of an entity that, when separated from that (parent) entity and linked with a different (recipient) entity, substantially retains and/or imparts on the recipient entity one or more structural and/or functional features that characterized it in the parent entity. In some embodiments, a domain is a section or portion of a molecule (e.g., a small molecule, carbohydrate, lipid, nucleic acid, or polypeptide). In some embodiments, a domain is a section of a polypeptide; in some such embodiments, a domain is characterized by a particular structural element (e.g., a particular amino acid sequence or sequence motif, α-helix character, β-sheet character, coiled-coil character, random coil character, etc.), and/or by a particular functional feature (e.g., binding activity, enzymatic activity, folding activity, signaling activity, etc.).

Dosage form or unit dosage form: Those skilled in the art will appreciate that the term "dosage form" may be used to refer to a physically discrete unit of an active agent (e.g., a therapeutic or diagnostic agent) for administration to a subject. Typically, each such unit contains a predetermined quantity of active agent. In some embodiments, such quantity is a unit dosage amount (or a whole fraction thereof) appropriate for administration in accordance with a dosing regimen that has been determined to correlate with a desired or beneficial outcome when administered to a relevant population (i.e., with a therapeutic dosing regimen). Those of ordinary skill in the art appreciate that the total amount of a therapeutic composition or agent administered to a particular subject is determined by one or more attending physicians and may involve administration of multiple dosage forms.

Dosing regimen or therapeutic regimen: Those skilled in the art will appreciate that the terms "dosing regimen" and "therapeutic regimen" may be used to refer to a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which is separated in time from other doses. In some embodiments, individual doses are separated from one another by a time period of the same length; in some embodiments, a dosing regimen comprises a plurality of doses and at least two different time periods separating individual doses. In some embodiments, all doses within a dosing regimen are of the same unit dose amount. In some embodiments, different doses within a dosing regimen are of different amounts. In some embodiments, a dosing regimen comprises a first dose in a first dose amount, followed by one or more additional doses in a second dose amount different from the first dose amount. In some embodiments, a dosing regimen comprises a first dose in a first dose amount, followed by one or more additional doses in a second dose amount same as the first dose amount. In some embodiments, a dosing regimen is correlated with a desired or beneficial outcome when administered across a relevant population (i.e., is a therapeutic dosing regimen).

Excipient: as used herein, refers to a non-therapeutic agent that may be included in a pharmaceutical composition, for example, to provide or contribute to a desired consistency or stabilizing effect. Suitable pharmaceutical excipients include, for example, starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like.

Heteroaryl: The terms "heteroaryl" and "heteroar-", used alone or as part of a larger moiety, e.g., "heteroaralkyl", or "heteroaralkoxy", refer to groups having 5 to 10 ring atoms, preferably 5, 6, 9, or 10 ring atoms; having 6, 10, or 14 π□electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted.

Heterocycle: As used herein, the terms "heterocycle", "heterocyclyl", "heterocyclic radical", and "heterocyclic ring" are used interchangeably and refer to a stable 3- to 8-membered monocyclic or 7-10-membered bicyclic heterocyclic moiety that is either saturated or partially unsaturated, and having, in addition to carbon atoms, one or more, such as one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur and nitrogen, the nitrogen may be N (as in 3,4-dihydro-2H-pyrrolyl), NH (as in pyrrolidinyl), or $NR^+$ (as in N-substituted pyrrolidinyl). A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, piperidinyl, decahydroquinolinyl, oxazolidinyl, piperazinyl, dioxanyl, dioxolanyl, diazepinyl, oxazepinyl, thiazepinyl, morpholinyl, and thiamorpholinyl. A heterocyclyl group may be mono-, bi-, tri-, or polycyclic, preferably mono-, bi-, or tricyclic, more preferably mono- or bicyclic. The term "heterocyclylalkyl" refers to an alkyl group substituted by a heterocyclyl, wherein the alkyl and heterocyclyl portions independently are optionally substituted. Additionally, a heterocyclic ring also includes groups in which the heterocyclic ring is fused to one or more aryl rings.

Inhibitory agent: As used herein, the term "inhibitory agent" refers to an entity, condition, or event whose presence, level, or degree correlates with decreased level or activity of a target. In some embodiments, an inhibitory agent may act directly (in which case it exerts its influence directly upon its target, for example, by binding to the target); in some embodiments, an inhibitory agent may act indirectly (in which case it exerts its influence by interacting with and/or otherwise altering a regulator of the target, so that level and/or activity of the target is reduced). In some embodiments, an inhibitory agent is one whose presence or level correlates with a target level or activity that is reduced relative to a particular reference level or activity (e.g., that observed under appropriate reference conditions, such as presence of a known inhibitory agent, or absence of the inhibitory agent in question, etc.).

Neurodegeneration: As used herein, the term "neurodegeneration" refers to a reduction in one or more features, structures, or characteristics of a neuron or neuronal tissue. In some embodiments, neurodegeneration is observed as a pathological reduction in an organism. Those skilled in the art will appreciate that neurodegeneration is associated with certain diseases, disorders and conditions, including those that affect humans. In some embodiments, neurodegeneration may be transient (e.g., as sometimes occurs in association with certain infections and/or chemical or mechanical disruptions); in some embodiments, neurodegeneration may be chronic and/or progressive (e.g., as is often associated with certain diseases, disorders or conditions such as, but not limited to, Parkinson's disease, amyotrophic lateral sclerosis, multiple sclerosis, Huntington disease, or Alzheimer's disease). In some embodiments, neurodegeneration may be assessed, for example, by detecting in a subject an increase in a biomarker associated with neurodegeneration. In some embodiments, neurodegeneration may be assessed, for example, by detecting in a subject a decrease in a biomarker associated with neurodegeneration. Alternatively or additionally, in some embodiments, neurodegeneration may be assessed by magnetic resonance imaging (MRI), biomarkers containing cerebral spinal fluid, or other biomarkers observed in patients. In some embodiments, neurodegeneration is defined as a score of below 24 on the mini-mental state examination. In some embodiments, neurodegeneration refers to loss of synapses. In some embodiments, neurodegeneration refers to a reduction in neural tissue relating to a traumatic injury (e.g. exposure to an external force which disrupts the integrity of the neural tissue). In some embodiments, neurodegeneration refers to a reduction in peripheral neural tissue. In some embodiments, neurodegeneration refers to a reduction in central nervous tissue.

Oral: The phrases "oral administration" and "administered orally" as used herein have their art-understood meaning referring to administration by mouth of a compound or composition.

Parenteral: The phrases "parenteral administration" and "administered parenterally" as used herein have their art-understood meaning referring to modes of administration other than enteral and topical administration, usually by injection, and include, without limitation, intravenous, intramuscular, intra-arterial, intrathecal, intracapsular, intraorbital, intracardiac, intradermal, intraperitoneal, transtracheal, subcutaneous, subcuticular, intraarticulare, subcapsular, subarachnoid, intraspinal, and intrasternal injection and infusion.

Partially Unsaturated: As used herein, the term "partially unsaturated" refers to a ring moiety that includes at least one double or triple bond between ring atoms. The term "partially unsaturated" is intended to encompass rings having multiple sites of unsaturation, but is not intended to include aromatic (e.g., aryl or heteroaryl) moieties, as herein defined.

Patient: As used herein, the term "patient" refers to any organism to which a provided composition is or may be administered, e.g., for experimental, diagnostic, prophylactic, cosmetic, and/or therapeutic purposes. Typical patients include animals (e.g., mammals such as mice, rats, rabbits, non-human primates, and/or humans). In some embodiments, a patient is a human. In some embodiments, a patient is suffering from or susceptible to one or more disorders or conditions. In some embodiments, a patient displays one or more symptoms of a disorder or condition. In some embodiments, a patient has been diagnosed with one or more disorders or conditions. In some embodiments, the patient is receiving or has received certain therapy to diagnose and/or to treat a disease, disorder, or condition.

Pharmaceutical composition: As used herein, the term "pharmaceutical composition" refers to an active agent, formulated together with one or more pharmaceutically acceptable carriers. In some embodiments, the active agent is present in unit dose amount appropriate for administration in a therapeutic or dosing regimen that shows a statistically significant probability of achieving a predetermined therapeutic effect when administered to a relevant population. In some embodiments, pharmaceutical compositions may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream, or foam; sublingually; ocularly; transdermally; or nasally, pulmonary, and to other mucosal surfaces.

Pharmaceutically acceptable: As used herein, the phrase "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Pharmaceutically acceptable carrier: As used herein, the term "pharmaceutically acceptable carrier" means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

Pharmaceutically acceptable salt: The term "pharmaceutically acceptable salt", as used herein, refers to salts of such compounds that are appropriate for use in pharmaceutical contexts, i.e., salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in *J. Pharmaceutical Sciences,* 66: 1-19 (1977). In some embodiments, pharmaceutically acceptable salts include, but are not limited to, nontoxic acid addition salts, which are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. In some embodiments, pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. In some embodiments, pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

Prevent or prevention: As used herein, the terms "prevent" or "prevention", when used in connection with the occurrence of a disease, disorder, and/or condition, refer to reducing the risk of developing the disease, disorder and/or condition and/or to delaying onset of one or more characteristics or symptoms of the disease, disorder or condition. Prevention may be considered complete when onset of a disease, disorder or condition has been delayed for a predefined period of time.

Specific: The term "specific", when used herein with reference to an agent having an activity, is understood by those skilled in the art to mean that the agent discriminates between potential target entities or states. For example, in some embodiments, an agent is said to bind "specifically" to its target if it binds preferentially with that target in the presence of one or more competing alternative targets. In many embodiments, specific interaction is dependent upon the presence of a particular structural feature of the target entity (e.g., an epitope, a cleft, a binding site). It is to be understood that specificity need not be absolute. In some embodiments, specificity may be evaluated relative to that of the binding agent for one or more other potential target entities (e.g., competitors). In some embodiments, specificity is evaluated relative to that of a reference specific binding agent. In some embodiments, specificity is evaluated relative to that of a reference non-specific binding agent. In some embodiments, the agent or entity does not detectably bind to the competing alternative target under conditions of binding to its target entity. In some embodiments, a binding agent binds with higher on-rate, lower off-rate, increased affinity, decreased dissociation, and/or increased stability to its target entity as compared with the competing alternative target(s).

Subject: As used herein, the term "subject" refers to an organism, typically a mammal (e.g., a human, in some embodiments including prenatal human forms). In some embodiments, a subject is suffering from a relevant disease, disorder or condition. In some embodiments, a subject is susceptible to a disease, disorder, or condition. In some embodiments, a subject displays one or more symptoms or characteristics of a disease, disorder or condition. In some embodiments, a subject does not display any symptom or characteristic of a disease, disorder, or condition. In some embodiments, a subject is someone with one or more features characteristic of susceptibility to or risk of a disease, disorder, or condition. In some embodiments, a subject is a patient. In some embodiments, a subject is an individual to whom diagnosis and/or therapy is and/or has been administered.

Substituted or optionally substituted: As described herein, compounds of the invention may contain "optionally substituted" moieties. In general, the term "substituted," whether preceded by the term "optionally" or not, means that one or more hydrogens of the designated moiety are replaced with a suitable substituent. "Substituted" applies to one or more hydrogens that are either explicit or implicit from the structure (e.g.,

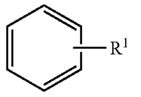

refers to at least

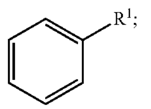

and

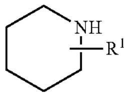

refers to at least

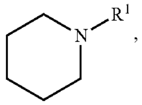

,

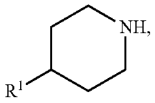

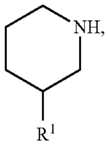

or

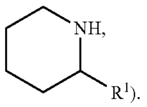

Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —$(CH_2)_{0-4}R^{\circ}$; —$(CH_2)_{0-4}OR^{\circ}$; —$O(CH_2)_{0-4}R^{\circ}$, —O—$(CH_2)_{0-4}C(O)OR^{\circ}$; —$(CH_2)_{0-4}CH(OR^{\circ})_2$; —$(CH_2)_{0-4}SR^{\circ}$; —$(CH_2)_{0-4}Ph$, which may be substituted with $R^{\circ}$; —$(CH_2)_{0-4}O(CH_2)_{0-1}Ph$ which may be substituted with $R^{\circ}$; —CH═CHPh, which may be substituted with $R^{\circ}$; —$(CH_2)_{0-4}O(CH_2)_{0-1}$-pyridyl which may be substituted with $R^{\circ}$; —$NO_2$; —CN; —$N_3$; —$(CH_2)_{0-4}N(R^{\circ})_2$; —$(CH_2)_{0-4}N(R^{\circ})C(O)R^{\circ}$; —$N(R^{\circ})C(S)R^{\circ}$; —$(CH_2)_{0-4}N(R^{\circ})C(O)NR^{\circ}_2$; —$N(R^{\circ})C(S)NR^{\circ}_2$; —$(CH_2)_{0-4}N(R^{\circ})C(O)OR^{\circ}$; —$N(R^{\circ})N(R^{\circ})C(O)R^{\circ}$; —$N(R^{\circ})N(R^{\circ})C(O)NR^{\circ}_2$; —$N(R^{\circ})N(R^{\circ})C(O)OR^{\circ}$; —$(CH_2)_{0-4}C(O)R^{\circ}$; —$C(S)R^{\circ}$; —$(CH_2)_{0-4}C(O)OR^{\circ}$; —$(CH_2)_{0-4}C(O)SR^{\circ}$; —$(CH_2)_{0-4}C(O)OSiR^{\circ}_3$; —$(CH_2)_{0-4}OC(O)R^{\circ}$; —$OC(O)(CH_2)_{0-4}SR^{\circ}$; —$(CH_2)_{0-4}SC(O)R^{\circ}$; —$(CH_2)_{0-4}C(O)NR^{\circ}_2$; —$C(S)NR^{\circ}_2$; —$C(S)SR^{\circ}$; —$SC(S)SR^{\circ}$, —$(CH_2)_{0-4}OC(O)NR^{\circ}_2$; —$C(O)N(OR^{\circ})R^{\circ}$; —$C(O)C(O)R^{\circ}$; —$C(O)CH_2C(O)R^{\circ}$; —$C(NOR^{\circ})R^{\circ}$; —$(CH_2)_{0-4}SSR^{\circ}$; —$(CH_2)_{0-4}S(O)_2R^{\circ}$; —$(CH_2)_{0-4}S(O)_2OR^{\circ}$; —$(CH_2)_{0-4}OS(O)_2R^{\circ}$; —$S(O)_2NR^{\circ}_2$; —$(CH_2)_{0-4}S(O)R^{\circ}$; —$N(R^{\circ})S(O)_2NR^{\circ}_2$; —$N(R^{\circ})S(O)_2R^{\circ}$; —$N(OR^{\circ})R^{\circ}$; —$C(NH)NR^{\circ}_2$; —$P(O)_2R^{\circ}$; —$P(O)R^{\circ}_2$; —$OP(O)R^{\circ}_2$; —$OP(O)(OR^{\circ})_2$; $SiR^{\circ}_3$; —($C_{1-4}$ straight or branched alkylene)O—$N(R^{\circ})_2$; or —($C_{1-4}$ straight or branched alkylene)C(O)O—$N(R^{\circ})_2$, wherein each $R^{\circ}$ may be substituted as defined below and is independently hydrogen, $C_{1-6}$ aliphatic, —$CH_2Ph$, —$O(CH_2)_{0-1}Ph$, —$CH_2$-(5- to 6-membered heteroaryl ring), a 5- to 6-membered saturated, partially unsaturated, or aryl ring having 0-4 heteroatoms independently selected from nitrogen, oxygen, or sulfur, or an 8- to 10-membered bicyclic aryl ring having 0-4 heteroatoms independently selected from nitrogen, oxygen, or sulfur, or, notwithstanding the definition above, two independent occurrences of $R^{\circ}$, taken together with their intervening atom(s), form a 3- to 12-membered saturated, partially unsaturated, or aryl mono- or bicyclic or bridged ring having 0-4 heteroatoms independently selected from nitrogen, oxygen, or sulfur, which may be substituted as defined below.

Suitable monovalent substituents on $R^{\circ}$ (or the ring formed by taking two independent occurrences of $R^{\circ}$ together with their intervening atoms), are independently halogen, $-(CH_2)_{0-2}R^{\bullet}$, -(halo$R^{\bullet}$), $-(CH_2)_{0-2}OH$, $-(CH_2)_{0-2}0R^{\bullet}$, $-(CH_2)_{0-2}CH(OR^{\bullet})_2$; —O(halo$R^{\bullet}$), —CN, $-N_3$, $-(CH_2)_{0-2}C(O)R^{\bullet}$, $-(CH_2)_{0-2}C(O)OH$, $-(CH_2)_{0-2}C(O)OR^{\bullet}$, $-(CH_2)_{0-2}SR^{\bullet}$, $-(CH_2)_{0-2}SH$, $-(CH_2)_{0-2}NH_2$, $-(CH_2)_{0-2}NHR^{\bullet}$, $-(CH_2)_{0-2}NR^{\bullet}_2$, $-NO_2$, $-SiR^{\bullet}_3$, $-OSiR^{\bullet}_3$, $-C(O)SR^{\bullet}$, —($C_{1-4}$ straight or branched alkylene)$C(O)OR^{\bullet}$, or $-SSR^{\bullet}$ wherein each $R^{\bullet}$ is unsubstituted or where preceded by "halo" is substituted only with one or more halogens, and is independently selected from $C_{1-4}$ aliphatic, $-CH_2Ph$, $-O(CH_2)_{0-1}Ph$, or a 3- to 6-membered saturated, partially unsaturated, or aryl ring having 0-4 heteroatoms independently selected from nitrogen, oxygen, or sulfur. Suitable divalent substituents on a saturated carbon atom of $R^{\circ}$ include =O and =S.

Suitable divalent substituents on a saturated carbon atom of an "optionally substituted" group include the following: =O ("oxo"), =S, $=NNR^*_2$, =NNHC(O)R*, =NNHC(O)OR*, $=NNHS(O)_2R^*$, =NR*, =NOR*, $-O(C(R^*_2))_{2-3}O-$, or $-S(C(R^*_2))_{2-3}S-$, wherein each independent occurrence of R* is selected from hydrogen, $C_{1-6}$ aliphatic which may be substituted as defined below, or an unsubstituted 5- to 6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: $-O(CR^*_2)_{2-3}O-$, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, $-R^{\bullet}$, -(halo$R^{\bullet}$), —OH, $-OR^{\bullet}$, —O(halo$R^{\bullet}$), —CN, —C(O)OH, $-C(O)OR^{\bullet}$, $-NH_2$, $-NHR^{\bullet}$, $-NR^{\bullet}_2$, or $-NO_2$, wherein each $R^{\bullet}$ is unsubstituted or where preceded by "halo" is substituted only with one or more halogens, and is independently $C_{1-4}$ aliphatic, $-CH_2Ph$, $-O(CH_2)_{0-1}Ph$, or a 5- to 6-membered saturated, partially unsaturated, or aryl ring having 0-4 heteroatoms independently selected from nitrogen, oxygen, or sulfur.

Suitable substituents on a substitutable nitrogen of an "optionally substituted" group include $-R^{\dagger}$, $-NR^{\dagger}_2$, $-C(O)R^{\dagger}$, $-C(O)OR^{\dagger}$, $-C(O)C(O)R^{\dagger}$, $-C(O)CH_2C(O)R^{\dagger}$, $-S(O)_2R^{\dagger}$, $-S(O)_2NR^{\dagger}_2$, $-C(S)NR^{\dagger}_2$, $-C(NH)NR^{\dagger}_2$, or $-N(R^{\dagger})S(O)_2R^{\dagger}$; wherein each $R^{\dagger}$ is independently hydrogen, $C_{1-4}$ aliphatic which may be substituted as defined below, unsubstituted —OPh, or an unsubstituted 5- to 6-membered saturated, partially unsaturated, or aryl ring having 0-4 heteroatoms independently selected from nitrogen, oxygen, or sulfur, or, notwithstanding the definition above, two independent occurrences of R, taken together with their intervening atom(s) form an unsubstituted 3- to 12-membered saturated, partially unsaturated, or aryl mono- or bicyclic ring having 0-4 heteroatoms independently selected from nitrogen, oxygen, or sulfur.

Suitable substituents on the aliphatic group of $R^{\dagger}$ are independently halogen, $-R^{\bullet}$, -(halo$R^{\bullet}$), —OH, $-OR^{\bullet}$, —O(halo$R^{\bullet}$), —CN, —C(O)OH, $-C(O)OR^{\bullet}$, $-NH_2$, $-NHR^{\bullet}$, $-NR^{\bullet}_2$, or $-NO_2$, wherein each $R^{\bullet}$ is unsubstituted or where preceded by "halo" is substituted only with one or more halogens, and is independently $C_{1-4}$ aliphatic, $-CH_2Ph$, $-O(CH_2)_{0-1}Ph$, or a 5- to 6-membered saturated, partially unsaturated, or aryl ring having 0-4 heteroatoms independently selected from nitrogen, oxygen, or sulfur.

Therapeutic agent: As used herein, the phrase "therapeutic agent" in general refers to any agent that elicits a desired pharmacological effect when administered to an organism. In some embodiments, an agent is considered to be a therapeutic agent if it demonstrates a statistically significant effect across an appropriate population. In some embodiments, the appropriate population may be a population of model organisms. In some embodiments, an appropriate population may be defined by various criteria, such as a certain age group, gender, genetic background, preexisting clinical conditions, etc. In some embodiments, a therapeutic agent is a substance that can be used to alleviate, ameliorate, relieve, inhibit, prevent, delay onset of, reduce severity of, and/or reduce incidence of one or more symptoms or features of a disease, disorder, and/or condition. In some embodiments, a "therapeutic agent" is an agent that has been or is required to be approved by a government agency before it can be marketed for administration to humans. In some embodiments, a "therapeutic agent" is an agent for which a medical prescription is required for administration to humans.

Treat: As used herein, the terms "treat," "treatment," or "treating" refer to any method used to partially or completely alleviate, ameliorate, relieve, inhibit, prevent, delay onset of, reduce severity of, and/or reduce incidence of one or more symptoms or features of a disease, disorder, and/or condition. Treatment may be administered to a subject who does not exhibit signs of a disease, disorder, and/or condition. In some embodiments, treatment may be administered to a subject who exhibits only early signs of the disease, disorder, and/or condition, for example, for the purpose of decreasing the risk of developing pathology associated with the disease, disorder, and/or condition.

DETAILED DESCRIPTION OF CERTAIN EMBODIMENTS

Programmed Axonal Degeneration and SARM1

Axonal degeneration is a major pathological feature of neurological diseases such as, but not limited to, Alzheimer's disease, Parkinson's disease, ALS, multiple sclerosis, diabetic peripheral neuropathy, chemotherapy-induced peripheral neuropathy, inherited neuropathy, traumatic brain injury, and/or glaucoma. Damaged or unhealthy axons are eliminated via an intrinsic self-destruction program that is distinct from traditional cellular death pathways like apoptosis known as Wallerian degeneration. (Gerdts, J., et al., *Neuron,* 2016, 89, 449-460; Whitmore, A. V. et al., *Cell Death Differ.,* 2003, 10, 260-261). In Wallerian degeneration, a peripheral nerve undergoes selective breakdown of the axon segment distal to an injury, whereas the proximal axon segment and cell body remain intact. This degeneration is characterized, first, by a depletion of nicotinamide mononucleotide adenyltransferase (NMNAT), followed by nicotinamide adenine dinucleotide (NAD+) loss, adenosine triphosphate (ATP) loss, neurofilament proteolysis, and finally axonal degradation approximately 8 to 24 hours following injury. (Gerdts, J., et al., *Neuron,* 2016, 89, 449-460).

NAD+ is a ubiquitous metabolite with critical roles in energy metabolism and cell signaling (Belenkey et al., *Trends Biochem.*, 2007, 32, 12-19; Chiarugi et al., *Nat. Rev. Cancer,* 2012, 12, 741-752). The homeostatic regulation of NAD+ levels is also responsible for maintaining axonal stability and integrity. Accordingly, manipulations that increase axonal localization of NMNAT1 confer axonal protection (Babetto et al., *Cell Rep.,* 2010, 3, 1422-1429; Sasaki et al., *J. Neurosci.,* 2009).

In a genome-wide RNAi screen in primary mouse neurons, Sterile Alpha and TIR motif-containing 1 (SARM1) was identified, in which knockdown of SARM1 led to long-lasting protection of sensory neurons against injury-induced axon degeneration (Gerdts et al., *J Neurosci,* 2013, 33, 13569-13580). SARM1 belongs to the family of cytosolic adaptor proteins, but is unique among its members because it is the most evolutionary ancient adaptor, paradoxically inhibits TLR signaling, and has been identified as the central executioner of the injury-induced axon death pathway (O'Neill, L. A. & Bowie, A. G., *Nat. Rev. Immunol.,* 2007, 7, 353-364; Osterloh, J. M., et al., *Science,* 2012, 337, 481-484; Gerdts, J., et al., *J. Neurosci.* 33, 2013, 13569-13580). Activation of SARM1 via axonal injury or forced dimerization of SARM1-TIR domains promotes rapid and catastrophic depletion of Nicotinamide Adenine Dinucleotide (NAD+), followed soon after by axonal degradation, thus highlighting the central role of NAD+ homeostasis in axonal integrity. (Gerdts, J., et al., *Science,* 2015, 348, 453-457). SARM1 is required for this injury-induced NAD+ depletion both in vitro and in vivo and SARM1 activation triggers axon degeneration locally via NAD(+) destruction (Gerdts et al., et al., *Science,* 2015 348, 452-457; Sasaki et al., *J. Biol. Chem.* 2015, 290, 17228-17238; both of which are hereby incorporated by reference in their entireties).

From genetic loss-of-function studies it is clear that SARM1 serves as the central executioner of the axonal degeneration pathway following an injury. Genetic knockout of SARM1 allows for preservation of axons for up to 14 days after nerve transection (Osterloh, J. M., et al., *Science,* 2012, 337, 481-484; Gerdts, J., et al., *J. Neurosci.,* 2013, 33, 13569-13580) and also improves functional outcomes in mice after traumatic brain injury (Henninger, N. et al., *Brain* 139, 2016, 1094-1105). In addition to the role of SARM1 in direct axonal injury, SARM1 is also required for axonal degeneration observed in chemotherapy-induced peripheral neuropathy. Loss of SARM1 blocks chemotherapy-induced peripheral neuropathy, both inhibiting axonal degeneration and heightened pain sensitivity that develops after chemotherapeutic vincristine treatment (Geisler et al, *Brain,* 2016, 139, 3092-3108).

SARM1 contains multiple conserved motifs including SAM domains, ARM/HEAT motifs and a TIR domain (FIG. 1) that mediate oligomerization and protein-protein interactions (O'Neill, L. A. & Bowie, A. G., *Nat. Rev. Immunol.,* 2007, 7, 353-364; Tewari, R., et al., *Trends Cell Biol.,* 2010, 20, 470-481; Qiao, F. & Bowie, J. U., *Sci. STKE* 2005, re7, 2005). TIR domains are commonly found in signaling proteins functioning in innate immunity pathways where they serve as scaffolds for protein complexes (O'Neill, L. A. & Bowie, A. G., *Nat. Rev. Immunol.,* 2007, 7, 353-364). Interestingly, dimerization of SARM1-TIR domains is sufficient to induce axonal degeneration and to rapidly trigger degradation of NAD+ by acting as the NAD+ cleaving enzyme (Milbrandt et al., WO 2018/057989; Gerdts, J., et al., *Science,* 2015, 348, 453-457). Given the central role of SARM1 in the axonal-degeneration pathway and its identified NADase activity, efforts have been undertaken to identify agents that can regulate SARM1, and potentially act as useful therapeutic agents, for example, to protect against neurodegenerative diseases including peripheral neuropathy, traumatic brain injury, and/or neurodegenerative diseases.

Among other things, the present disclosure provides certain compounds and/or compositions that act as SARM1 inhibitory agents (e.g., as SARM1 inhibitory agents), and technologies relating thereto.

Compounds

In some embodiments, the present disclosure provides a compound of Formula I:

II

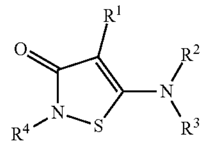

or a pharmaceutically acceptable salt thereof, wherein:

$R^1$ is selected from —CN, —$NO_2$, —C(O)R, —$S(O)_2R$, —$CON(R)_2$, —$S(O)_2N(R)_2$, and —$CO_2R$;

$R^2$ is —R;

$R^3$ is —$(CH_2)_{0-2}Cy$, or:

$R^2$ and $R^3$, together with the nitrogen atom to which they are attached, form a 4- to 7-membered saturated or partially unsaturated ring fused to Cy or a 4- to 7-membered saturated or partially unsaturated ring substituted with -Cy;

Cy is selected from phenyl, a 5- to 6-membered heteroaryl ring having 1-3 heteroatoms independently selected from nitrogen, oxygen, and sulfur, an 8- to 10-membered bicyclic heteroaryl ring having 1-3 heteroatoms independently selected from nitrogen, oxygen, and sulfur, and an 8- to 10-membered bicyclic aryl ring, wherein each phenyl, heteroaryl and aryl ring is substituted with 0-4 $R^x$;

each $R^x$ is independently selected from halogen, —CN, —$NO_2$, —OR, —SR, —$N(R)_2$, —$SO_2R$, —$SO_2N(R)_2$, —$CO_2R$, —$CON(R)_2$, —$N(R)SO_2R$, —N(R)C(O)R, and optionally substituted $C_{1-6}$ aliphatic;

$R^4$ is —R; and each R is independently hydrogen or optionally substituted $C_{1-6}$ aliphatic; or:

two instances of R, together with the atom to which they are attached, form a 3- to 6-membered saturated or partially unsaturated heterocyclic ring.

In some embodiments, the present disclosure provides compounds having a structure as set forth in Formula II:

II

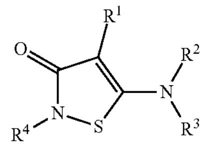

or a pharmaceutically acceptable salt thereof, wherein $R^1$ is selected from —CN, —$NO_2$, —C(O)R, —$S(O)_2R$, —$CON(R)_2$, —$S(O)_2N(R)_2$, —$CO_2R$, —C(=NR)N$(R)_2$, and a 5-membered heteroaryl ring having 2-3 heteroatoms independently selected from nitrogen, oxygen, and sulfur;

$R^2$ is —R;

$R^3$ is —$(CH_2)_{0-2}$Cy, or:

$R^2$ and $R^3$, together with the nitrogen atom to which they are attached, form a 4- to 7-membered saturated or partially unsaturated ring fused to Cy or a 4- to 7-membered saturated or partially unsaturated ring substituted with -Cy;

Cy is selected from phenyl, a 3- to 7-membered saturated or partially unsaturated carbocyclic ring, a 5- to 6-membered heteroaryl ring having 1-3 heteroatoms independently selected from nitrogen, oxygen, and sulfur, an 8- to 10-membered bicyclic heteroaryl ring having 1-3 heteroatoms independently selected from nitrogen, oxygen, and sulfur, and an 8- to 10-membered bicyclic aryl ring, wherein each phenyl, carbocyclic, heteroaryl and aryl ring is substituted with 0-4 $R^x$;

each $R^x$ is independently selected from halogen, —CN, —$NO_2$, —OR, —SR, —$N(R)_2$, —$SO_2R$, —$SO_2N(R)_2$, —$CO_2R$, —$CON(R)_2$, —$N(R)SO_2R$, —N(R)C(O)R, an optionally substituted $C_{1-6}$ aliphatic group, an optionally substituted 5- to 6-membered saturated or partially unsaturated heterocyclic ring having 1-2 heteroatoms independently selected from nitrogen, oxygen, and sulfur, and an optionally substituted 8- to 10-membered heteroaryl ring having 1-2 heteroatoms independently selected from nitrogen, oxygen, and sulfur;

$R^4$ is —R; and each R is independently hydrogen, an optionally substituted $C_{1-6}$ aliphatic, an optionally substituted phenyl, or an optionally substituted 3- to 7-membered saturated or partially unsaturated carbocyclic ring, or:

two instances of R, together with the atom to which they are attached, form a 3- to 6-membered saturated or partially unsaturated heterocyclic ring.

As defined generally above, $R^1$ is selected from —CN, —$NO_2$, —C(O)R, —$S(O)_2R$, —$CON(R)_2$, —$S(O)_2N(R)_2$, and —$CO_2R$. In some embodiments, $R^1$ is selected from —CN, —$C(O)N(R)_2$ and —$CO_2R$. In some embodiments, $R^1$ is —CN. In some embodiments, $R^1$ is —$CON(R)_2$. In some such embodiments, each R is independently selected from hydrogen and $C_{1-6}$ aliphatic. In some embodiments, $R^1$ is —$CON(R)_2$, wherein each R is independently selected from hydrogen and optionally substituted $C_{1-6}$ aliphatic. In some embodiments, $R^1$ is

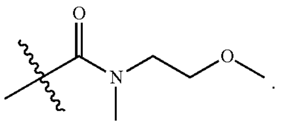 [SMILES: *C(=O)N(C)CCOC]

In some embodiments, $R^1$ is —$CON(R)_2$, wherein each R is independently selected from hydrogen and $C_{1-6}$ alkyl. In some embodiments, $R^1$ is —$CON(R)_2$, wherein each R is independently selected from hydrogen and —$CH_3$. In some embodiments, $R^1$ is —$CONH_2$. In some embodiments, $R^1$ is —$CON(CH_3)_2$. In some embodiments, $R^1$ is

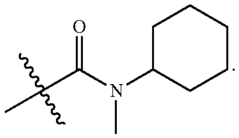 [SMILES: *C(=O)N(C)C1CCCCC1]

In some embodiments, $R^1$ is —$CON(R)_2$, wherein each R is independently selected from $C_{1-6}$ alkyl and optionally substituted phenyl. In some embodiments, $R^1$ is

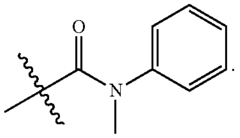 [SMILES: *C(=O)N(C)c1ccccc1]

In some embodiments, $R^1$ is —$CON(R)_2$, wherein R is optionally substituted $C_{1-6}$ aliphatic and two instances of R, together with the atom to which they are attached, form a 3- to 6-membered saturated or partially unsaturated heterocyclic ring having 1-2 heteroatoms independently selected from nitrogen, oxygen, or sulfur. In some embodiments, $R^1$ is

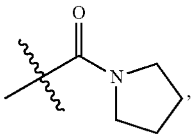,
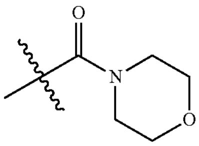
or
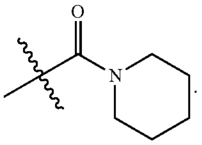

In some embodiments, $R^1$ is —$CON(R)_2$, wherein R is optionally substituted $C_{1-6}$ aliphatic and two instances of R, together with the atom to which they are attached, form an 8- to 10-membered bridged bicyclic saturated or partially unsaturated heterocyclic ring having 1-2 heteroatoms independently selected from nitrogen, oxygen, or sulfur. In some embodiments, $R^1$ is

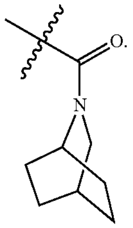 [SMILES: *C(=O)N1CC2CCC1CC2]

In some embodiments, $R^1$ is —$CO_2R$. In some such embodiments, R is selected from hydrogen and $C_{1-6}$ aliphatic. In some embodiments, $R^1$ is —$CO_2R$, wherein R is selected from hydrogen and $C_{1-6}$ alkyl. In some embodiments, $R^1$ is —$CO_2R$, wherein R is selected from hydrogen and —$CH_3$. In some embodiments, $R^1$ is —$CO_2H$. In some embodiments, $R^1$ is —$CO_2CH_3$. In some embodiments, $R^1$ is —$NO_2$. In some embodiments, $R^1$ is —C(O)R. In some embodiments, $R^1$ is —$S(O)_2R$. In some embodiments, $R^1$ is —$S(O)_2N(R)_2$.

In some embodiments of Formula II, $R^1$ is —C(=NR)N$(R)_2$. In some embodiments of Formula II, $R^1$ is —C(=NR)N$(R)_2$, wherein R is selected from hydrogen and optionally substituted $C_{1-6}$ aliphatic. In some embodiments of Formula II, $R^1$ is —C(=NR)N$(R)_2$, wherein R is selected from hydrogen and —$CH_3$. In some embodiments of Formula II, $R^1$ is —C(=NH)$NHCH_3$. In some embodiments, $R^1$ is —C(=NH)$N(CH_3)_2$. In some embodiments of Formula II, $R^1$ is —C(=NR)$N(R)_2$, wherein R is selected from hydrogen and $C_{1-6}$ aliphatic substituted with —$(CH_2)_{0-4}OR^{\circ}$. In some embodiments of Formula II, $R^1$ is —C(=NR)$N(R)_2$, wherein R is selected from hydrogen and $C_{1-6}$ aliphatic substituted with —OH. In some embodiments of Formula II, $R^1$ is

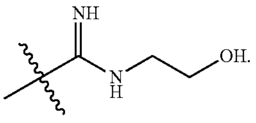 [SMILES: *C(=N)NCCO]

In some embodiments of Formula II, $R^1$ is —C(=NR)N$(R)_2$, wherein R is selected from H, —$CH_3$ and $C_{1-6}$ aliphatic substituted with —$OR^{\circ}$. In some embodiments of Formula II, $R^1$ is

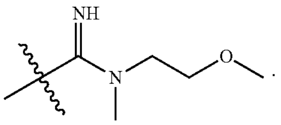 [SMILES: *C(=N)N(C)CCOC]

In some embodiments of Formula II, $R^1$ is —C(=NH)N$(R)_2$, wherein R is optionally substituted $C_{1-6}$ aliphatic and two instances of R, together with the atom to which they are attached, form a 3- to 6-membered saturated or partially unsaturated heterocyclic ring having 1-2 heteroatoms independently selected from nitrogen, oxygen, or sulfur. In some embodiments of Formula II, $R^1$ is or

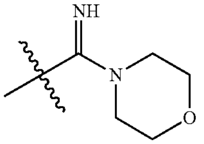 or 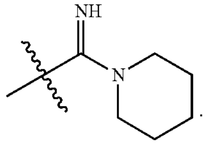

In some embodiments of Formula II, $R^1$ is a 5-membered heteroaryl ring having 2-3 heteroatoms independently selected from nitrogen, oxygen, and sulfur. In some embodiments of Formula II, $R^1$ is a 5-membered heteroaryl ring having 3 heteroatoms independently selected from nitrogen, oxygen, and sulfur. In some embodiments, $R^1$ is

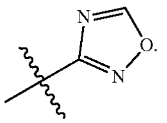 [SMILES: *c1ncon1]

In some embodiments, $R^1$ is selected from —CN,

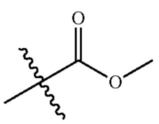 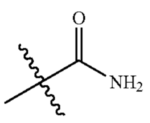 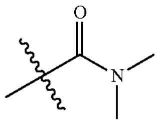

-continued

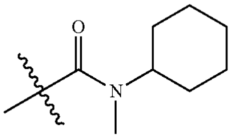 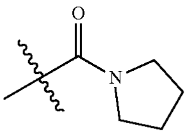

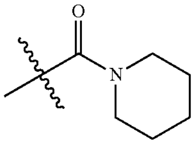 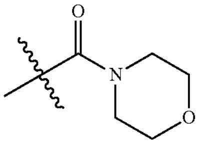

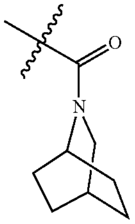 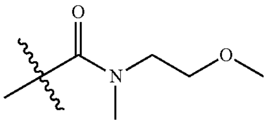

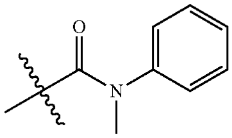 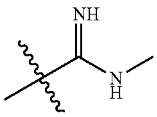 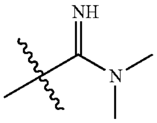

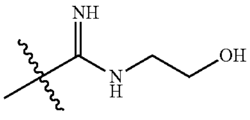 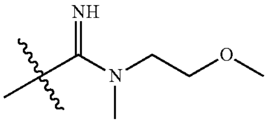

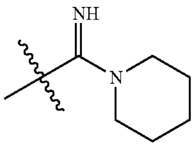 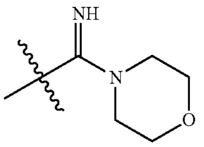

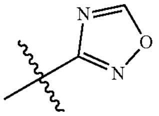

As defined generally above, $R^2$ is —R. In some such embodiments, —R is hydrogen. Accordingly, in some embodiments, $R^2$ is —H. In some embodiments, $R^2$ is —R, wherein —R is optionally substituted $C_{1-6}$ aliphatic. In some embodiments, $R^2$ is —R, wherein —R is $C_{1-6}$ aliphatic. In some embodiments, $R^2$ is —$C_{1-6}$ alkyl. In some such embodiments, $R^2$ is —$CH_3$.

As defined generally above, $R^3$ is —$(CH_2)_{0-2}$Cy. In some embodiments, $R^3$ is -Cy. In some embodiments, $R^3$ is —$CH_2$—Cy. In some embodiments, $R^3$ is —$(CH_2)_2$-Cy.

As defined generally above, Cy is selected from phenyl, a 5- to 6-membered heteroaryl ring having 1-3 heteroatoms independently selected from nitrogen, oxygen, and sulfur, an 8- to 10-membered bicyclic heteroaryl ring having 1-3 heteroatoms independently selected from nitrogen, oxygen, and sulfur, and an 8- to 10-membered bicyclic aryl ring, wherein each phenyl, heteroaryl and aryl ring is substituted with 0-4 $R^x$.

In some embodiments, Cy is phenyl. In some embodiments, Cy is phenyl substituted with 1 $R^x$. In some embodiments, Cy is phenyl substituted with 2 $R^x$. In some embodiments, Cy is selected from

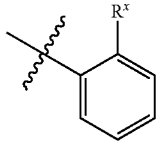
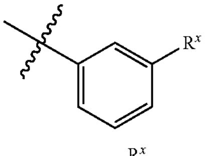
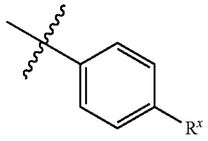
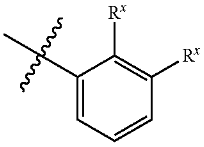
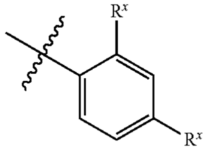
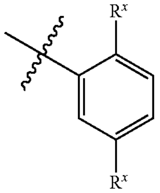
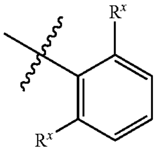
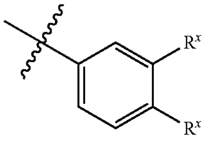
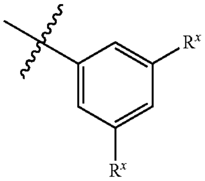

In some embodiments, Cy is a 5- to 6-membered heteroaryl ring having 1-3 heteroatoms independently selected from nitrogen, oxygen, and sulfur. In some embodiments, Cy is a 5-membered heteroaryl ring having 1-3 heteroatoms independently selected from nitrogen, oxygen, and sulfur. In some embodiments, Cy is a 6-membered heteroaryl ring having 1-3 nitrogen atoms. In some embodiments, Cy is a 6-membered heteroaryl ring having 1-2 nitrogen atoms. In some such embodiments, Cy is substituted with 1 $R^x$. In some embodiments, Cy is pyridinyl. In some such embodiments, Cy is pyrimidin-2-yl, pyrimidin-3-yl, or pyrimidin-4-yl. In some embodiments, Cy is pyridazinyl. In some embodiments, Cy is pyrazinyl. In some embodiments, Cy is pyrimidinyl. In some embodiments, Cy is selected from:

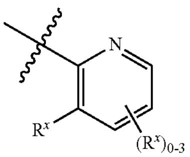
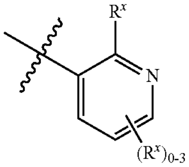
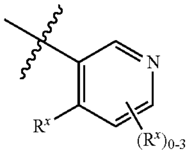
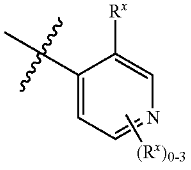

-continued

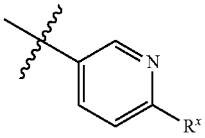
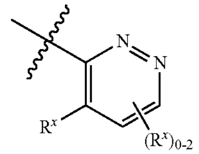
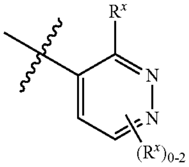
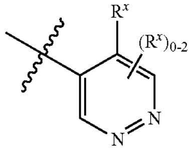
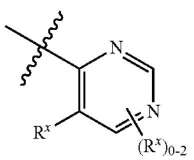
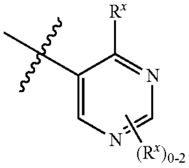
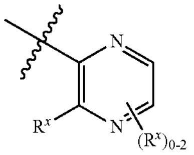

In some embodiments, Cy is an 8- to 10-membered bicyclic heteroaryl ring having 1-3 heteroatoms independently selected from nitrogen, oxygen, and sulfur. In some embodiments, Cy is an 8- to 10-membered bicyclic heteroaryl ring having 1-3 nitrogen atoms. In some embodiments, Cy is an 10-membered bicyclic heteroaryl ring having 1-3 nitrogen atoms. In some embodiments, Cy is an 10-membered bicyclic heteroaryl ring having 1 nitrogen atom. In some such embodiments, Cy is substituted with 1 $R^x$. In some embodiments, Cy is quinolin-2-yl, quinolin-3-yl, quinolin-4-yl, quinolin-5-yl, quinolin-6-yl, quinolin-7-yl, or quinolin-8-yl.

In some embodiments, Cy is selected from

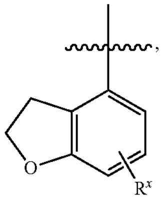,
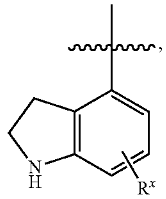,
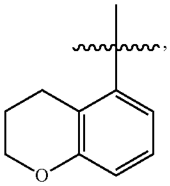,
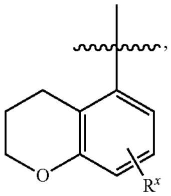,
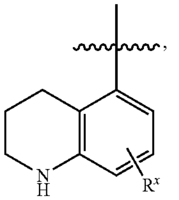,
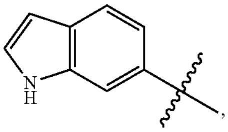,

-continued

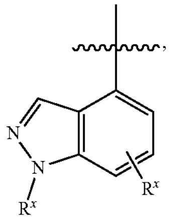

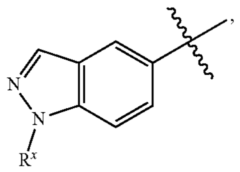

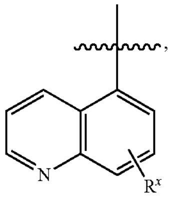

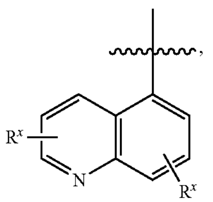

and

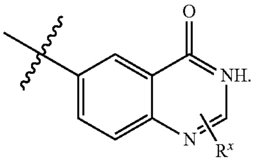

In some embodiments, Cy is an 8- to 10-membered bicyclic aryl ring. In some embodiments, Cy is a 10-membered bicyclic aryl ring. In some such embodiments, Cy is substituted with 1 $R^x$. In some embodiments, Cy is naphth-1-yl. In some embodiments, Cy is naphth-2-yl.

In some embodiments of Formula II, Cy is a 3- to 7-membered saturated or partially unsaturated carbocyclic ring, wherein Cy is substituted with 0-4 $R^x$. In some embodiments, Cy is a 3- to 7-membered saturated carbocyclic ring. In some embodiments, Cy is cyclohexyl.

In some embodiments, $R^2$ and $R^3$, together with the nitrogen atom to which they are attached, form a 4- to 7-membered saturated or partially unsaturated ring fused to Cy or a 4- to 7-membered saturated or partially unsaturated ring substituted with -Cy. In some embodiments, $R^2$ and $R^3$, together with the nitrogen atom to which they are attached, form a ring selected from:

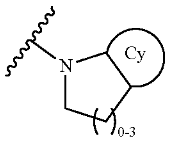

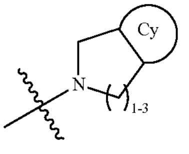

and

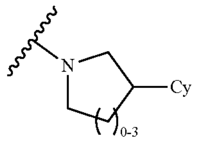

wherein Cy is substituted with 0-4 $R^x$.

In some embodiments, $R^2$ and $R^3$, together with the nitrogen atom to which they are attached, form a 5-membered saturated ring fused to Cy. In some such embodiments, -Cy is phenyl. In some embodiments, $R^2$ and $R^3$, together with the nitrogen atom to which they are attached, form

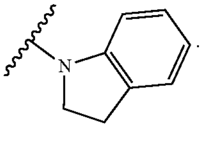 [SMILES: *N1CCc2ccccc21]

As defined generally above, each $R^x$ is independently selected from halogen, —CN, —$NO_2$, —OR, —SR, —$N(R)_2$, —$SO_2R$, —$SO_2N(R)_2$, —$CO_2R$, —$CON(R)_2$, —$N(R)SO_2R$, and —N(R)C(O)R, and optionally substituted $C_{1-6}$ aliphatic.

In some embodiments, $R^x$ is halogen. In some such embodiments, $R^x$ is fluoro. In some embodiments, $R^x$ is chloro. In some embodiments, $R^x$ is bromo.

In some embodiments, $R^x$ is —CN.

In some embodiments, $R^x$ is optionally substituted $C_{1-6}$ aliphatic. In some embodiments, $R^x$ is optionally substituted —$C_{1-6}$ alkyl. In some embodiments, $R^x$ is —$C_{1-6}$ alkyl optionally substituted with halogen. In some embodiments, $R^x$ is optionally substituted —$CH_3$. In some such embodiments, $R^x$ is —$CF_3$.

In some embodiments, $R^x$ is $C_{1-6}$ aliphatic. In some embodiments, $R^x$ is —$C_{1-6}$ alkyl. In some embodiments, $R^x$ is —$CH_3$. In some embodiments, $R^x$ is —$CH(CH_3)_2$. In some embodiments, $R^x$ is —$C(CH_3)_3$. In some embodiments, $R^x$ is cyclopropyl.

In some embodiments, $R^x$ is —OR. In some such embodiments, R is $C_{1-6}$ aliphatic. In some embodiments, $R^x$ is —OR, wherein R is $C_{1-6}$ alkyl. In some embodiments, $R^x$ is —$OCH_3$.

In some embodiments, $R^x$ is —OR. In some such embodiments, R is optionally substituted $C_{1-6}$ aliphatic. In some embodiments, $R^x$ is —OR, wherein R is optionally substituted $C_{1-6}$ alkyl. In some embodiments, $R^x$ is —OR, wherein R is optionally substituted —$CH_3$. In some embodiments, $R^x$ is —OR, wherein R is —$CF_3$. Accordingly, in some embodiments, $R^x$ is —$OCF_3$.

In some embodiments, $R^x$ is —$SO_2R$. In some such embodiments, R is optionally substituted $C_{1-6}$ aliphatic. In some embodiments, $R^x$ is —$SO_2R$, wherein R is $C_{1-6}$ alkyl. In some embodiments, $R^x$ is —$SO_2R$, wherein R is —$CH_3$. Accordingly, in some embodiments, $R^x$ is —$SO_2CH_3$.

In some embodiments, $R^x$ is —$SO_2N(R)_2$. In some such embodiments, R is selected from hydrogen or optionally substituted $C_{1-6}$ aliphatic. In some embodiments, $R^x$ is —$SO_2N(R)_2$, wherein R is selected from hydrogen and $C_{1-6}$ alkyl. In some embodiments, $R^x$ is —$SO_2N(R)_2$, wherein R is selected from hydrogen and —$CH_3$. Accordingly, in some embodiments, $R^x$ is —$SO_2NHCH_3$ or —$SO_2N(CH_3)_2$.

In some embodiments, $R^x$ is —SR. In some such embodiments, R is optionally substituted $C_{1-6}$ aliphatic. In some embodiments, $R^x$ is —SR, wherein R is $C_{1-6}$ alkyl. In some embodiments, $R^x$ is —SR, wherein R is —$CH_3$. Accordingly, in some embodiments, $R^x$ is —$SCH_3$.

In some embodiments, $R^x$ is —$N(R)_2$. In some such embodiments, R is selected from hydrogen and optionally substituted $C_{1-6}$ aliphatic. In some embodiments, $R^x$ is —$NH_2$, In some embodiments, $R^x$ is —NHR, wherein R is $C_{1-6}$ alkyl. In some embodiments, $R^x$ is —NHR, wherein R is —$CH_3$. Accordingly, in some embodiments, $R^x$ is —$NHCH_3$.

In some embodiments, $R^x$ is —$CON(R)_2$. In some embodiments, $R^x$ is —$CONH_2$.

In some embodiments, $R^x$ is —$CO_2R$. In some embodiments, $R^x$ is —$CO_2H$.

In some embodiments, $R^x$ is —N(R)$SO_2$R. In some such embodiments, R is selected from hydrogen or optionally substituted $C_{1-6}$ aliphatic. In some embodiments, $R^x$ is —N(R)$SO_2$R, wherein R is selected from hydrogen and $C_{1-6}$ alkyl. In some embodiments, $R^x$ is —N(R)$SO_2$R, wherein R is selected from hydrogen and —$CH_3$. Accordingly, in some embodiments, $R^x$ is —$NHSO_2CH_3$ or —N($CH_3$)$SO_2CH_3$.

As defined generally above for Formula II, each $R^x$ is independently selected from halogen, —CN, —$NO_2$, —OR, —SR, —N$(R)_2$, —$SO_2$R, —$SO_2$N$(R)_2$, —$CO_2$R, —CON$(R)_2$, —N(R)$SO_2$R, —N(R)C(O)R, an optionally substituted $C_{1-6}$ aliphatic group, an optionally substituted 5- to 6-membered saturated or partially unsaturated heterocyclic ring having 1-2 heteroatoms independently selected from nitrogen, oxygen, and sulfur, and an optionally substituted 8- to 10-membered heteroaryl ring having 1-2 heteroatoms independently selected from nitrogen, oxygen, and sulfur. In some embodiments of Formula II, $R^x$ is an optionally substituted 5- to 6-membered saturated or partially unsaturated heterocyclic ring having 1-2 heteroatoms independently selected from nitrogen, oxygen, and sulfur. In some embodiments of Formula II, $R^x$ is a 5-membered saturated heterocyclic ring having 1-2 heteroatoms independently selected from nitrogen, oxygen, and sulfur. In some such embodiments of Formula II, R is selected from

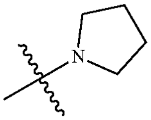,
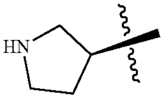,
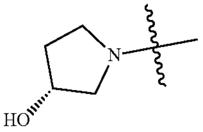, and
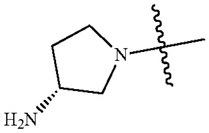.

In some embodiments of Formula II, $R^x$ is a 6-membered saturated heterocyclic ring having 1-2 heteroatoms independently selected from nitrogen, oxygen, and sulfur. In some such embodiments of Formula II, $R^x$ is

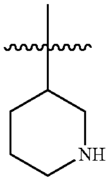 or
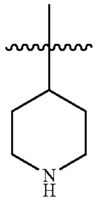.

In some embodiments of Formula II, $R^x$ is a 6-membered partially unsaturated heterocyclic ring having 1-2 heteroatoms independently selected from nitrogen, oxygen, and sulfur. In some such embodiments of Formula II, $R^x$ is

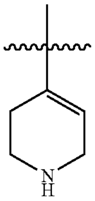.

In some embodiments of Formula II, $R^x$ is an optionally substituted 8- to 10-membered heteroaryl ring having 1-2 heteroatoms independently selected from nitrogen, oxygen, and sulfur. In some embodiments of Formula II, $R^x$ is an optionally substituted 9-membered heteroaryl ring having 1-2 heteroatoms independently selected from nitrogen, oxygen, and sulfur. In some such embodiments of Formula II, $R^x$ is

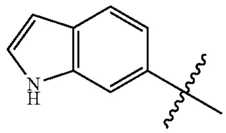.

In some embodiments, $R^3$ is selected from

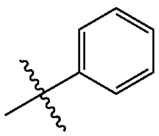
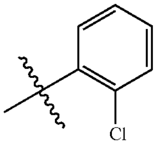
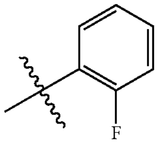
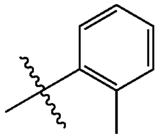
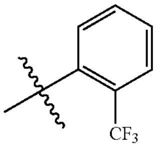
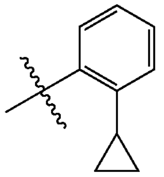
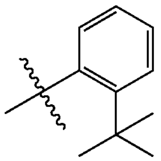
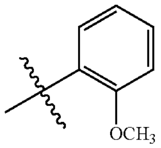
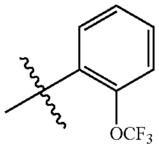
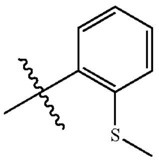
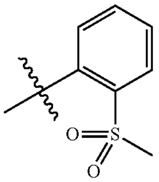
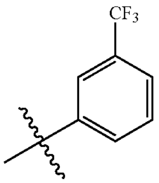
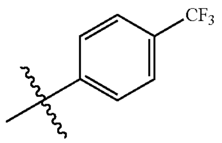
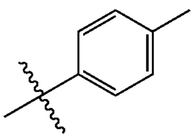
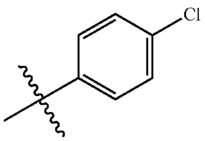
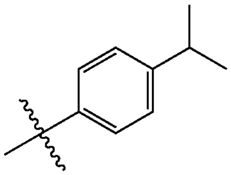
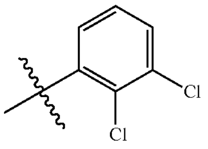
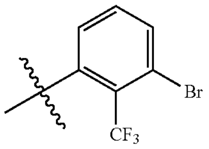

-continued
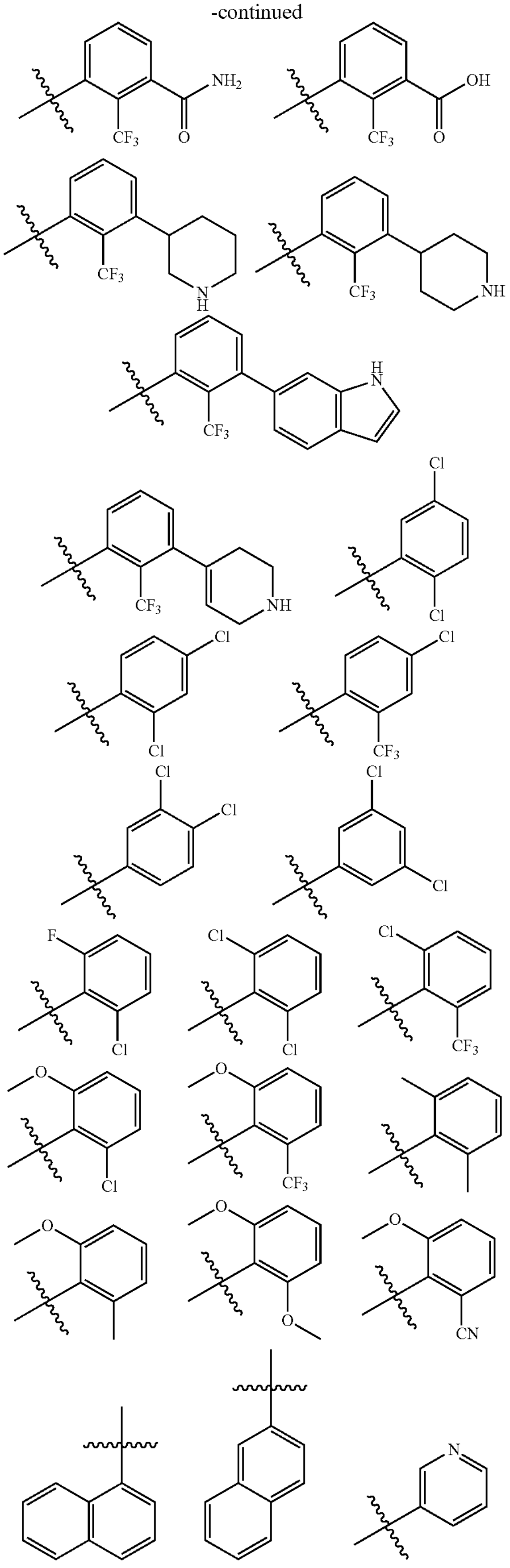
-continued
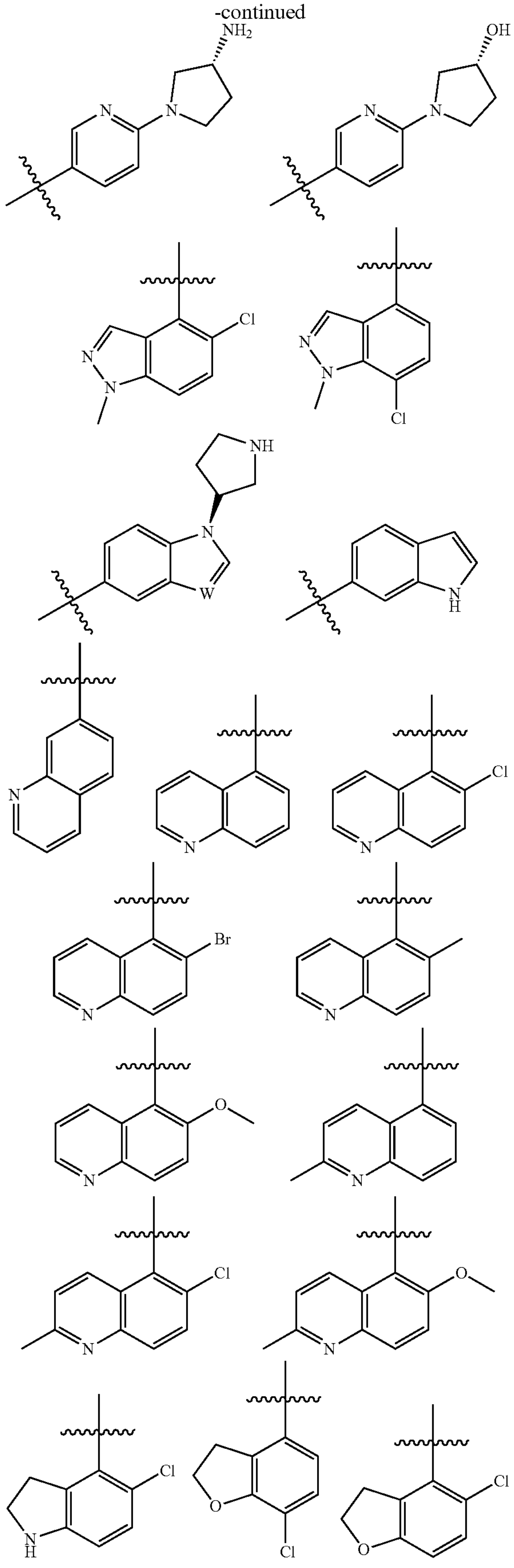

-continued

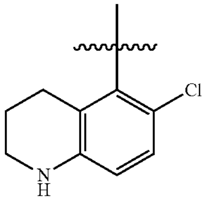

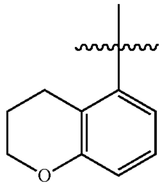

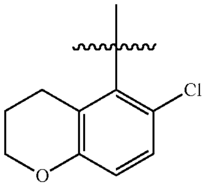

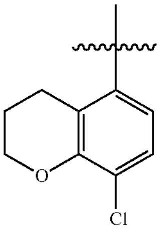

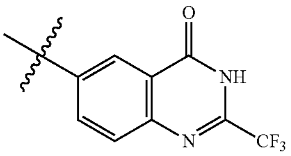

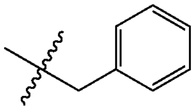

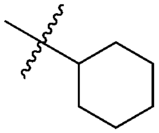

As defined generally above, $R^4$ is —R. In some embodiments, $R^4$ is —R. In some such embodiments, —R is hydrogen. Accordingly, in some embodiments, $R^4$ is hydrogen. In some embodiments, $R^4$ is —R, wherein R is optionally substituted $C_{1-6}$ aliphatic. In some embodiments, $R^4$ is —R, wherein R is $C_{1-6}$ aliphatic. In some embodiments, $R^4$ is —R, wherein R is $C_{1-6}$ alkyl. In some embodiments, $R^4$ is —R, wherein R is $C_{1-3}$ alkyl. In some embodiments, $R^4$ is —R, wherein R is $—CH_3$. Accordingly, in some embodiments, $R^4$ is $—CH_3$. In some embodiments, $R^4$ is —R, wherein R is $—CH_2CH_3$. Accordingly, in some embodiments, $R^4$ is $—CH_2CH_3$. In some embodiments, $R^4$ is —R, wherein R is $—CH_2CH_2CH_3$. Accordingly, in some embodiments, $R^4$ is $—CH_2CH_2CH_3$. In some embodiments, $R^4$ is —R, wherein R is $—CH(CH_3)_2$. Accordingly, in some embodiments, $R^4$ is $—CH(CH_3)_2$.

In some embodiments, $R^4$ is —R, wherein R is $C_{1-6}$ aliphatic substituted with a group selected from $—(CH_2)_{0-4}R^{\circ}$, $—(CH_2)_{0-4}OR^{\circ}$, $—(CH_2)_{0-4}N(R^{\circ})_2$, $—(CH_2)_{0-4}S(O)_2R^{\circ}$, $—(CH_2)_{0-4}C(O)R^{\circ}$, $—(CH_2)_{0-4}C(O)N(R^{\circ})_2$, or $—(CH_2)_{0-4}C(O)OR^{\circ}$. In some embodiments, $R^4$ is —R, wherein R is $C_{1-6}$ aliphatic substituted with $—(CH_2)_{0-4}R^{\circ}$. In some such embodiments, $R^{\circ}$ is a 5- to 6-membered saturated, partially unsaturated, or aryl ring having 0-4 heteroatoms independently selected from nitrogen, oxygen, or sulfur. In some embodiments, $R^4$ is —R, wherein R is $C_{1-6}$ aliphatic substituted with phenyl. In some embodiments, $R^4$ is —R, wherein R is $C_{1-6}$ aliphatic substituted with

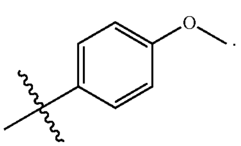 [SMILES: *c1ccc(OC)cc1]

In some embodiments, $R^4$ is —R, wherein R is $C_{1-6}$ aliphatic substituted with a 5-membered heteroaryl ring having 1-3 heteroatoms independently selected from nitrogen, oxygen, or sulfur. In some embodiments, $R^4$ is —R, wherein R is $C_{1-6}$ aliphatic substituted with

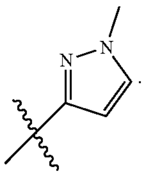 [SMILES: *c1ccn(C)n1]

In some embodiments, $R^4$ is —R, wherein R is $C_{1-6}$ aliphatic substituted with a 6-membered heteroaryl ring having 1-3 heteroatoms independently selected from nitrogen, oxygen, or sulfur. In some embodiments, $R^4$ is —R, wherein R is $C_{1-6}$ aliphatic substituted with

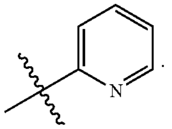

In some embodiments, $R^4$ is —R, wherein R is $C_{1-6}$ aliphatic substituted with a 8- to 10-membered bicyclic aryl ring having 0-4 heteroatoms independently selected from nitrogen, oxygen, or sulfur. In some embodiments, $R^4$ is —R, wherein R is $C_{1-6}$ aliphatic substituted with

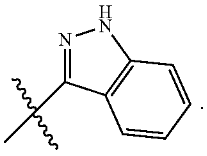 [SMILES: *c1n[nH]c2ccccc12]

In some embodiments, $R^4$ is —R, wherein R is $C_{1-6}$ aliphatic substituted with a 5-membered saturated heterocyclic ring having 1-2 heteroatoms independently selected from nitrogen, oxygen, or sulfur. In some embodiments, $R^4$ is —R, wherein R is $C_{1-6}$ aliphatic substituted with

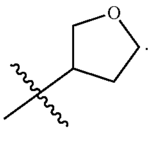 [SMILES: *C1CCOC1]

In some embodiments, $R^4$ is —R, wherein R is $C_{1-6}$ aliphatic substituted with $—(CH_2)_{0-4}OR^{\circ}$. In some embodiments, $R^4$ is —R, wherein R is $C_{1-6}$ aliphatic substituted with $—OR^{\circ}$. In some embodiments, $R^4$ is —R, wherein R is $C_{1-6}$ aliphatic substituted with —OH. In some embodiments, $R^4$ is —R, wherein R is $C_{1-6}$ aliphatic substituted with $—OCH_3$. In some embodiments, $R^4$ is —R, wherein R is $C_{1-6}$ aliphatic substituted with $—OCH_2CH_2OCH_2C{\equiv}CH$.

In some embodiments, $R^4$ is —R, wherein R is $C_{1-6}$ aliphatic substituted with $—(CH_2)_{0-4}N(R^{\circ})_2$. In some embodiments, $R^4$ is —R, wherein R is $C_{1-6}$ aliphatic substituted with —$N(R^{\circ})_2$. In some embodiments, $R^4$ is —R, wherein R is $C_{1-6}$ aliphatic substituted with —$NH_2$. In some embodiments, $R^4$ is —R, wherein R is $C_{1-6}$ aliphatic substituted with —$N(CH_3)_2$.

In some embodiments, $R^4$ is —R, wherein R is $C_{1-6}$ aliphatic substituted with —$(CH_2)_{0-4}S(O)_2R^{\circ}$. In some embodiments, $R^4$ is —R, wherein R is $C_{1-6}$ aliphatic substituted with —$S(O)_2R^{\circ}$. In some embodiments, $R^4$ is —R, wherein R is $C_{1-6}$ aliphatic substituted with —$S(O)_2CH_3$.

In some embodiments, $R^4$ is —R, wherein R is $C_{1-6}$ aliphatic substituted with —$(CH_2)_{0-4}C(O)N(R^{\circ})_2$. In some embodiments, $R^4$ is —R, wherein R is $C_{1-6}$ aliphatic substituted with —$C(O)N(R^{\circ})_2$. In some embodiments, $R^4$ is —R, wherein R is $C_{1-6}$ aliphatic substituted with —$C(O)NH_2$. In some embodiments, $R^4$ is —R, wherein R is $C_{1-6}$ aliphatic substituted with —$C(O)N(R^{\circ})_2$, wherein two independent occurrences of $R^{\circ}$, taken together with their intervening atom(s), form a 3- to 12-membered saturated, partially unsaturated, or aryl mono- or bicyclic ring having 0-4 heteroatoms independently selected from nitrogen, oxygen, or sulfur. In some embodiments, $R^4$ is —R, wherein R is $C_{1-6}$ aliphatic substituted with —$C(O)N(R^{\circ})_2$, wherein two independent occurrences of $R^{\circ}$, taken together with their intervening atom(s), form a 5- to 6-membered saturated monocyclic ring having 1-2 heteroatoms independently selected from nitrogen, oxygen, or sulfur. In some such embodiments, $R^4$ is —R, wherein R is $C_{1-6}$ aliphatic substituted with

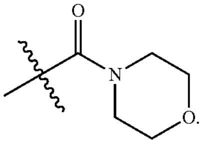 [SMILES: *C(=O)N1CCOCC1]

In some embodiments, $R^4$ is —R, wherein R is $C_{1-6}$ aliphatic substituted with

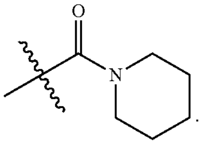

In some embodiments, $R^4$ is —R, wherein R is $C_{1-6}$ aliphatic substituted with

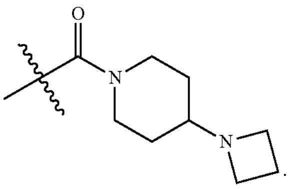 [SMILES: *C(=O)N1CCC(N2CCC2)CC1]

In some embodiments, $R^4$ is —R, wherein R is $C_{1-6}$ aliphatic substituted with —$(CH_2)_{0-4}C(O)OR^{\circ}$. In some embodiments, $R^4$ is —R, wherein R is $C_{1-6}$ aliphatic substituted with —$C(O)OR^{\circ}$. In some embodiments, $R^4$ is —R, wherein R is $C_{1-6}$ aliphatic substituted with —C(O)OH.

In some embodiments, $R^4$ is H, —$CH_3$, —$CH_2CH_3$, —$CH_2CH_2CH_3$, —$CH(CH_3)_2$, or a group selected from

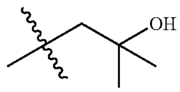 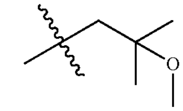

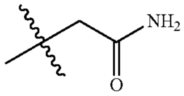 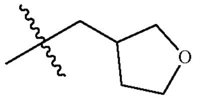

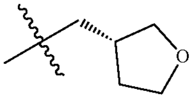 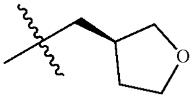

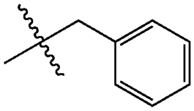 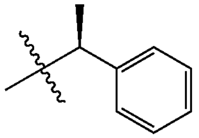

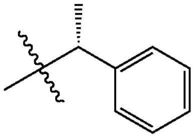 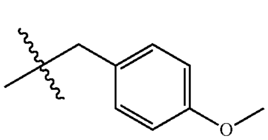

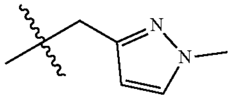 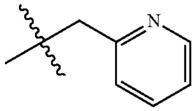

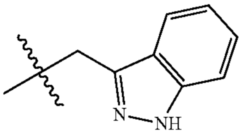 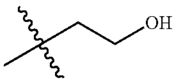

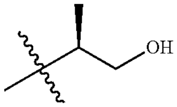 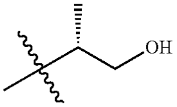

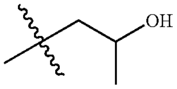 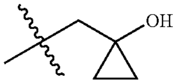

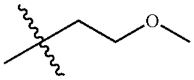 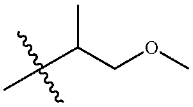

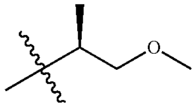 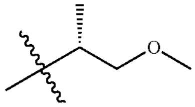

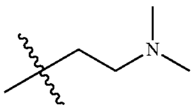 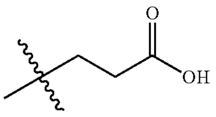

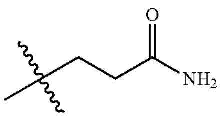 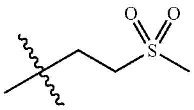

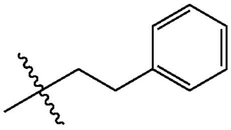

-continued

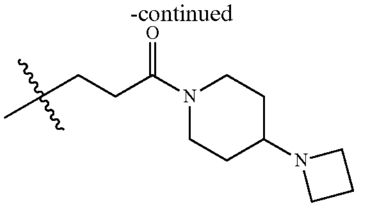

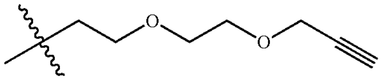

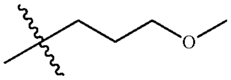

As defined generally above, each R is independently hydrogen or optionally substituted $C_{1-6}$ aliphatic; or two instances of R, together with the atom to which they are attached, form a 3- to 6-membered saturated or partially unsaturated heterocyclic ring.

In some embodiments, R is hydrogen. In some embodiments, R is optionally substituted $C_{1-6}$ aliphatic. In some such embodiments, R is $-C_{1-6}$ alkyl. In some embodiments, R is $-CH_3$. In some embodiments, R is $C_{1-6}$ aliphatic optionally substituted with halogen. In some embodiments, R is $C_{1-6}$ aliphatic optionally substituted with $-(CH_2)_{0-4}R^{\circ}$. In some embodiments, R is $C_{1-6}$ aliphatic optionally substituted with $-R^{\circ}$. In some embodiments, R is $C_{1-6}$ aliphatic optionally substituted with $-(CH_2)_{0-4}OR^{\circ}$. In some embodiments, R is $C_{1-6}$ aliphatic optionally substituted with $-OR^{\circ}$. In some embodiments, R is $C_{1-6}$ aliphatic optionally substituted with $-(CH_2)_{0-4}N(R^{\circ})_2$. In some embodiments, R is $C_{1-6}$ aliphatic optionally substituted with $-N(R^{\circ})_2$. In some embodiments, R is $C_{1-6}$ aliphatic optionally substituted with $-(CH_2)_{0-4}C(O)OR^{\circ}$. In some embodiments, R is $C_{1-6}$ aliphatic optionally substituted with $-C(O)OR^{\circ}$. In some embodiments, R is $C_{1-6}$ aliphatic optionally substituted with $-(CH_2)_{0-4}C(O)N(R^{\circ})_2$. In some embodiments, R is $C_{1-6}$ aliphatic optionally substituted with $-C(O)N(R^{\circ})_2$. In some embodiments, R is $C_{1-6}$ aliphatic optionally substituted with $-(CH_2)_{0-4}S(O)_2R^{\circ}$. In some embodiments, R is $C_{1-6}$ aliphatic optionally substituted with $-S(O)_2R^{\circ}$.

In some embodiments, two instances of R, together with the atom to which they are attached, form a 3- to 6-membered saturated or partially unsaturated heterocyclic ring. In some embodiments, two instances of R, together with the atom to which they are attached, form a 6-membered saturated or partially unsaturated heterocyclic ring. In some embodiments, two instances of R, together with the atom to which they are attached, form a pyrrolidinyl ring. In some embodiments, two instances of R, together with the atom to which they are attached, form a morpholinyl ring. In some embodiments, two instances of R, together with the atom to which they are attached, form a piperidinyl ring. In some embodiments, two instances of R, together with the atom to which they are attached, form a 2-azabicyclo[2.2.2]octanyl ring.

As defined generally above for Formula II, each R is independently hydrogen, an optionally substituted $C_{1-6}$ aliphatic, an optionally substituted phenyl, or an optionally substituted 3- to 7-membered saturated or partially unsaturated carbocyclic ring, or two instances of R, together with the atom to which they are attached, form a 3- to 6-membered saturated or partially unsaturated heterocyclic ring. In some embodiments of Formula II, R is hydrogen. In some embodiments of Formula II, R is optionally substituted $C_{1-6}$ aliphatic. In some such embodiments, R is $-C_{1-6}$ alkyl. In some embodiments of Formula II, R is $-CH_3$.

In some embodiments of Formula II, R is $C_{1-6}$ aliphatic optionally substituted with halogen. In some embodiments of Formula II, R is $C_{1-6}$ aliphatic optionally substituted with $-(CH_2)_{0-4}R^{\circ}$. In some embodiments of Formula II, R is $C_{1-6}$ aliphatic optionally substituted with $-R^{\circ}$. In some embodiments of Formula II, R is $C_{1-6}$ aliphatic optionally substituted with $-(CH_2)_{0-4}OR^{\circ}$. In some embodiments of Formula II, R is $C_{1-6}$ aliphatic optionally substituted with $-OR^{\circ}$. In some embodiments of Formula II, R is $C_{1-6}$ aliphatic optionally substituted with $-(CH_2)_{0-4}N(R^{\circ})_2$. In some embodiments of Formula II, R is $C_{1-6}$ aliphatic optionally substituted with $-N(R^{\circ})_2$. In some embodiments of Formula II, R is $C_{1-6}$ aliphatic optionally substituted with $-(CH_2)_{0-4}C(O)OR^{\circ}$. In some embodiments of Formula II, R is $C_{1-6}$ aliphatic optionally substituted with $-C(O)OR^{\circ}$. In some embodiments of Formula II, R is $C_{1-6}$ aliphatic optionally substituted with $-(CH_2)_{0-4}C(O)N(R^{\circ})_2$. In some embodiments of Formula II, R is $C_{1-6}$ aliphatic optionally substituted with $-C(O)N(R^{\circ})_2$. In some embodiments of Formula II, R is $C_{1-6}$ aliphatic optionally substituted with $-(CH_2)_{0-4}S(O)_2R^{\circ}$. In some embodiments of Formula II, R is $C_{1-6}$ aliphatic optionally substituted with $-S(O)_2R^{\circ}$.

In some embodiments of Formula II, two instances of R, together with the atom to which they are attached, form a 3- to 6-membered saturated or partially unsaturated heterocyclic ring. In some embodiments of Formula II, two instances of R, together with the atom to which they are attached, form a 6-membered saturated or partially unsaturated heterocyclic ring. In some embodiments of Formula II, two instances of R, together with the atom to which they are attached, form a pyrrolidinyl ring. In some embodiments of Formula II, two instances of R, together with the atom to which they are attached, form a morpholinyl ring. In some embodiments of Formula II, two instances of R, together with the atom to which they are attached, form a piperidinyl ring. In some embodiments of Formula II, two instances of R, together with the atom to which they are attached, form a 2-azabicyclo[2.2.2]octanyl ring.

It will be appreciated that compounds of Formula I or Formula II having the structure

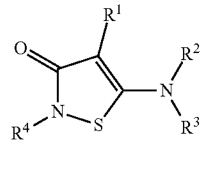

II can exist in two tautomeric forms when $R^4$ is H:

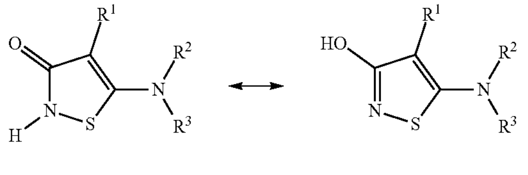

Accordingly, it will be appreciated that compounds of Formula I or Formula II wherein $R^4$ is H can be drawn in either tautomeric form.

In some embodiments of Formula I or Formula II, $R^1$ is —CN. Accordingly, in some embodiments, the present disclosure provides a compound of Formula I-a:

I-a

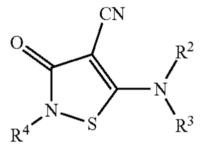

or a pharmaceutically acceptable salt thereof, wherein each of $R^2$, $R^3$ and $R^4$ is as defined above and described herein.

In some embodiments of Formula I or Formula II, $R^1$ is —CON(R)$_2$. Accordingly, in some embodiments, the present disclosure provides a compound of Formula I-b:

I-b

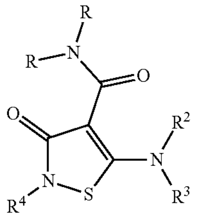

or a pharmaceutically acceptable salt thereof, wherein each of $R^2$, $R^3$, $R^4$ and R is as defined above and described herein.

In some embodiments of Formula I or Formula II, $R^1$ is —C(=NR)N(R)$_2$. Accordingly, in some embodiments, the present disclosure provides a compound of Formula I-c:

I-c

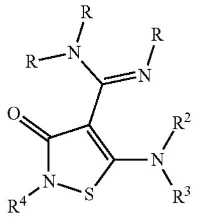

or a pharmaceutically acceptable salt thereof, wherein each of $R^2$, $R^3$, $R^4$ and R is as defined above and described herein.

In some embodiments of Formula I-a, I-b, or I-c, $R^2$ is H. Accordingly, the present disclosure provides a compound of Formula I-a-i, I-b-i, or I-c-i:

I-a-i

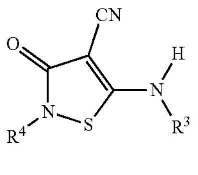

-continued

I-b-i

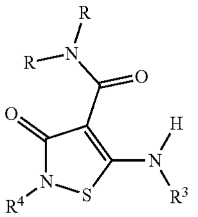

I-c-i

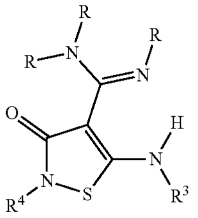

or a pharmaceutically acceptable salt thereof, wherein each of $R^3$, $R^4$ and R is as defined above and described herein.

In some embodiments of Formula I-a-i, I-b-i, or I-c-i, $R^3$ is Cy. Accordingly, the present disclosure provides a compound of Formula I-a-ii, I-b-ii, or I-c-ii:

I-a-ii

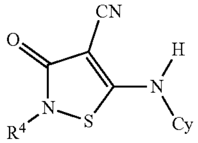

I-b-ii

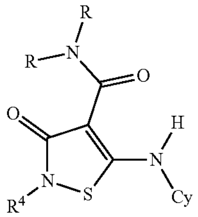

I-c-ii

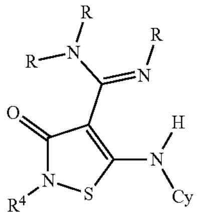

or a pharmaceutically acceptable salt thereof, wherein each of Cy, $R^4$ and R is as defined above and described herein.

In some embodiments of Formula I-a, I-b, or I-c, $R^4$ is hydrogen. Accordingly, the present disclosure provides a compound of Formula I-a-iii, I-b-iii, or I-c-iii:

I-a-iii

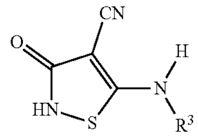

-continued

I-b-iii

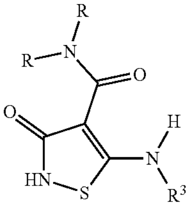

I-c-iii

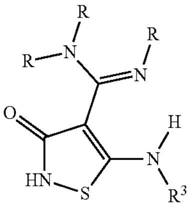

or a pharmaceutically acceptable salt thereof, wherein each of $R^2$, $R^3$, and R is as defined above and described herein.

In some embodiments of Formula I-a-iii, I-b-iii, or I-c-iii, $R^3$ is Cy. Accordingly, the present disclosure provides a compound of Formula I-a-iv, I-b-iv, or I-c-iv:

I-a-iv

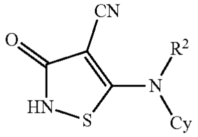

I-b-iv

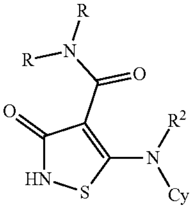

I-c-iv

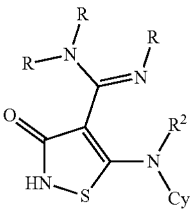

or a pharmaceutically acceptable salt thereof, wherein each of Cy, $R^2$, and R is as defined above and described herein.

In some embodiments of Formula I-a, I-b, or I-c, $R^3$ is -Cy, wherein -Cy is phenyl substituted with 0-4 $R^x$ groups. Accordingly, in some embodiments, the present disclosure provides a compound of Formula I-a-v, or I-b-v, or I-c-v:

I-a-v

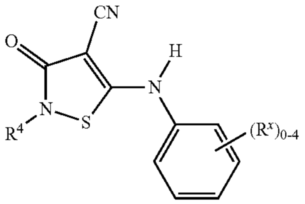

I-b-v

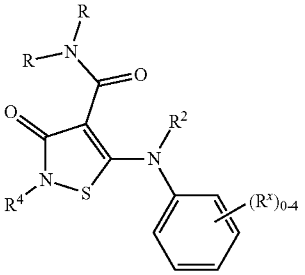

I-c-v

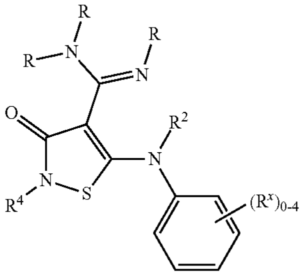

or a pharmaceutically acceptable salt thereof, wherein each of $R^2$, $R^4$, R and $R^x$ is as defined above and described herein.

In some embodiments of Formula I-a, I-b, or I-c, $R^3$ is -Cy, wherein -Cy is quinolin-5-yl substituted with 0-4 $R^x$ groups. Accordingly, in some embodiments, the present disclosure provides a compound of Formula I-a-vi, or I-b-vi, or I-c-vi:

I-a-vi

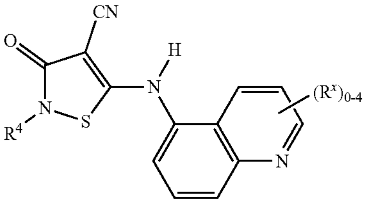

I-b-vi

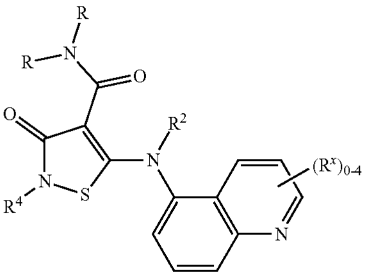

-continued
I-c-vi
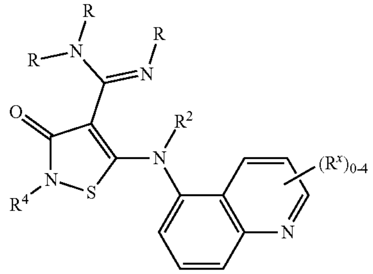
or a pharmaceutically acceptable salt thereof, wherein each of $R^2$, $R^4$, R and $R^x$ is as defined above and described herein.
In some embodiments, the present disclosure provides a compound selected from:
| Example | Structure |
| --- | --- |
| 1 | 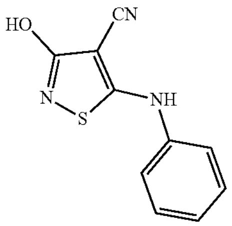 [SMILES: N#Cc1c(O)nsc1Nc1ccccc1] |
| 2 | 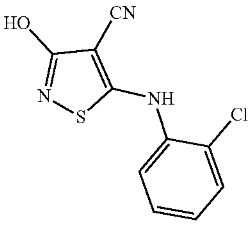 [SMILES: N#Cc1c(O)nsc1Nc1ccccc1Cl] |
| 3 | 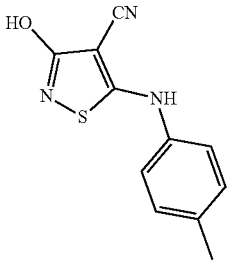 [SMILES: Cc1ccc(Nc2snc(O)c2C#N)cc1] |
| 4 | 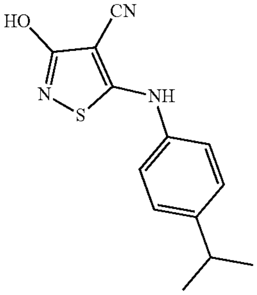 [SMILES: CC(C)c1ccc(Nc2snc(O)c2C#N)cc1] |
-continued
| Example | Structure |
| --- | --- |
| 5 | 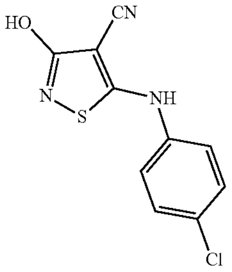 [SMILES: N#Cc1c(O)nsc1Nc1ccc(Cl)cc1] |
| 6 | 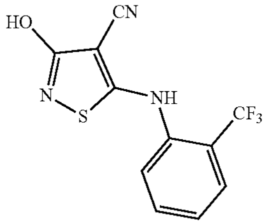 [SMILES: N#Cc1c(O)nsc1Nc1ccccc1C(F)(F)F] |
| 7 | 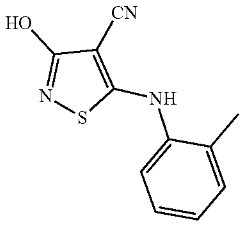 [SMILES: Cc1ccccc1Nc1snc(O)c1C#N] |
| 8 | 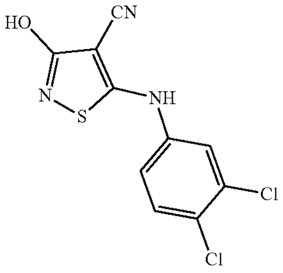 [SMILES: N#Cc1c(O)nsc1Nc1ccc(Cl)c(Cl)c1] |
| 9 | 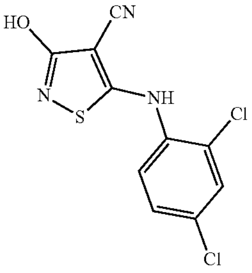 [SMILES: N#Cc1c(O)nsc1Nc1ccc(Cl)cc1Cl] |
| 10 | 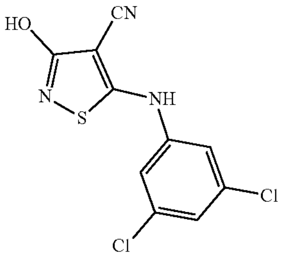 [SMILES: N#Cc1c(O)nsc1Nc1cc(Cl)cc(Cl)c1] |

-continued
| Example | Structure |
|---|---|
| 11 | 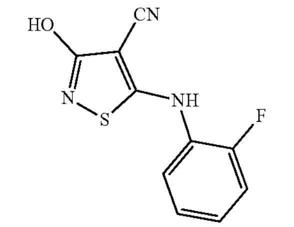 [SMILES: N#Cc1c(O)nsc1Nc1ccccc1F] |
| 12 | 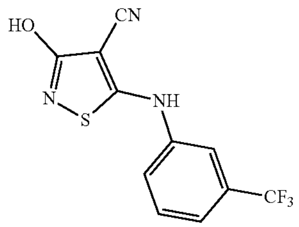 [SMILES: N#Cc1c(O)nsc1Nc1cccc(C(F)(F)F)c1] |
| 13 | 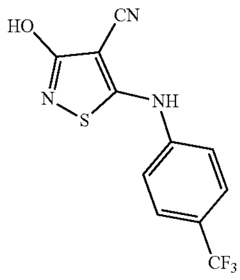 [SMILES: N#Cc1c(O)nsc1Nc1ccc(C(F)(F)F)cc1] |
| 14 | 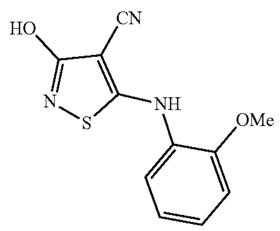 [SMILES: COc1ccccc1Nc1snc(O)c1C#N] |
| 15 | 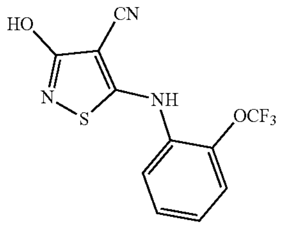 [SMILES: N#Cc1c(O)nsc1Nc1ccccc1OC(F)(F)F] |
| 16 | 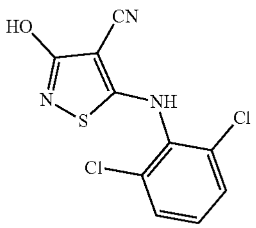 [SMILES: N#Cc1c(O)nsc1Nc1c(Cl)cccc1Cl] |
-continued
| Example | Structure |
|---|---|
| 17 | 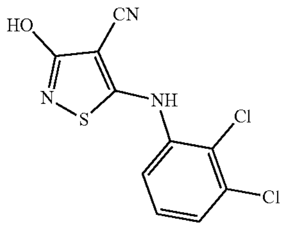 [SMILES: N#Cc1c(O)nsc1Nc1cccc(Cl)c1Cl] |
| 18 | 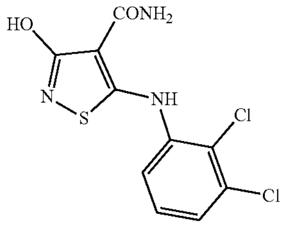 [SMILES: NC(=O)c1c(O)nsc1Nc1cccc(Cl)c1Cl] |
| 19 | 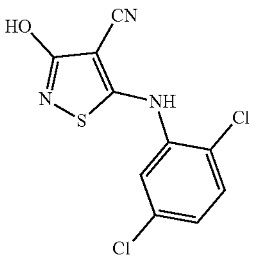 [SMILES: N#Cc1c(O)nsc1Nc1cc(Cl)ccc1Cl] |
| 20 | 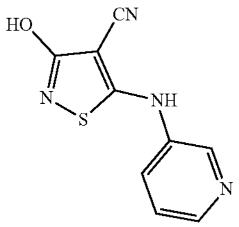 [SMILES: N#Cc1c(O)nsc1Nc1cccnc1] |
| 21 | 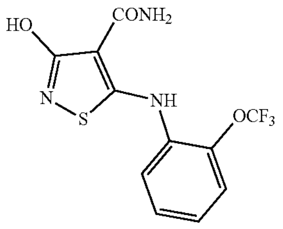 [SMILES: NC(=O)c1c(O)nsc1Nc1ccccc1OC(F)(F)F] |
| 22 | 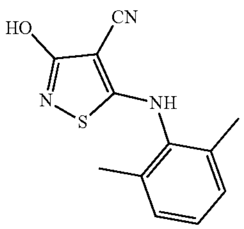 [SMILES: Cc1cccc(C)c1Nc1snc(O)c1C#N] |

-continued
| Example | Structure |
|---|---|
| 23 | 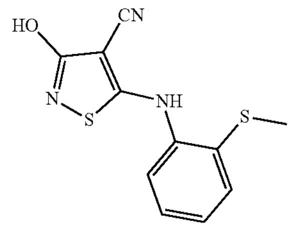 [SMILES: CSc1ccccc1Nc1snc(O)c1C#N] |
| 24 | 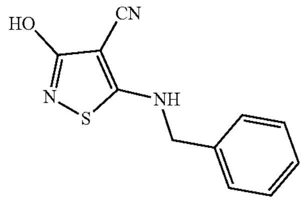 [SMILES: N#Cc1c(O)nsc1NCc1ccccc1] |
| 25 | 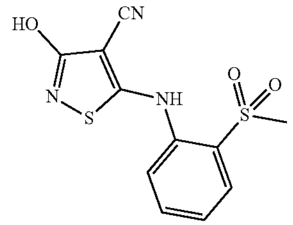 [SMILES: CS(=O)(=O)c1ccccc1Nc1snc(O)c1C#N] |
| 26 | 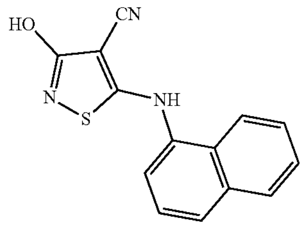 [SMILES: N#Cc1c(O)nsc1Nc1cccc2ccccc12] |
| 27 | 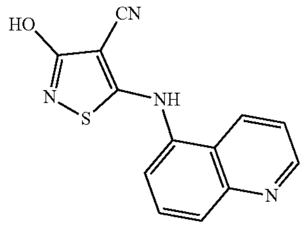 [SMILES: N#Cc1c(O)nsc1Nc1cccc2ncccc12] |
| 28 | 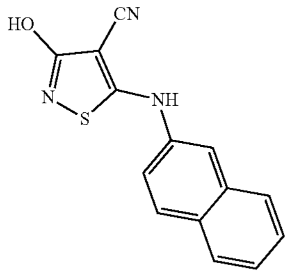 [SMILES: N#Cc1c(O)nsc1Nc1ccc2ccccc2c1] |
-continued
| Example | Structure |
|---|---|
| 29 | 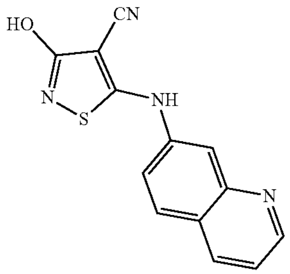 [SMILES: N#Cc1c(O)nsc1Nc1ccc2cccnc2c1] |
| 30 | 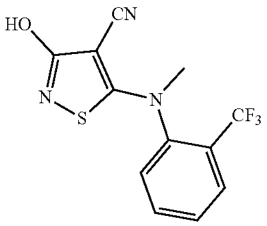 [SMILES: CN(c1ccccc1C(F)(F)F)c1snc(O)c1C#N] |
| 31 | 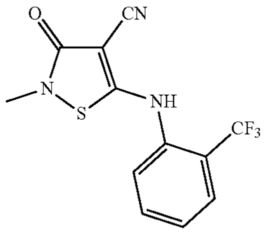 [SMILES: Cn1sc(Nc2ccccc2C(F)(F)F)c(C#N)c1=O] |
| 32 | 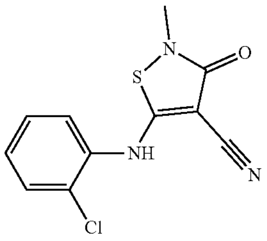 [SMILES: Cn1sc(Nc2ccccc2Cl)c(C#N)c1=O] |
| 33 | 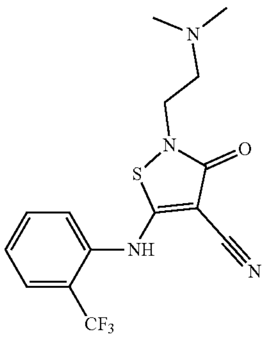 [SMILES: CN(C)CCn1sc(Nc2ccccc2C(F)(F)F)c(C#N)c1=O] |

-continued
| Example | Structure |
| --- | --- |
| 34 | 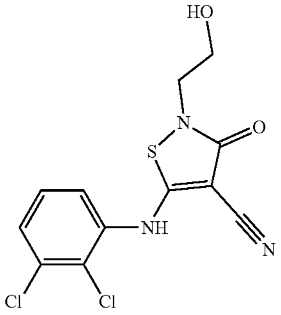 [SMILES: N#Cc1c(Nc2cccc(Cl)c2Cl)sn(CCO)c1=O] |
| 35 | 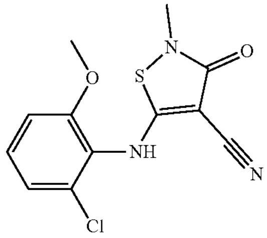 [SMILES: COc1cccc(Cl)c1Nc1sn(C)c(=O)c1C#N] |
| 36 | 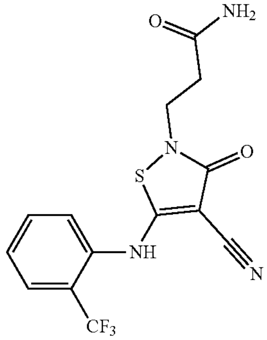 [SMILES: N#Cc1c(Nc2ccccc2C(F)(F)F)sn(CCC(N)=O)c1=O] |
| 37 | 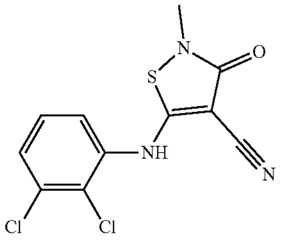 [SMILES: Cn1sc(Nc2cccc(Cl)c2Cl)c(C#N)c1=O] |
| 38 | 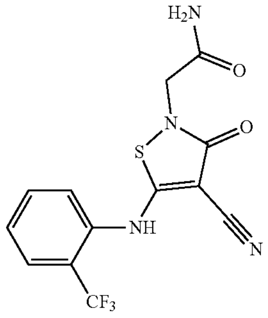 [SMILES: N#Cc1c(Nc2ccccc2C(F)(F)F)sn(CC(N)=O)c1=O] |
-continued
| Example | Structure |
| --- | --- |
| 39 | 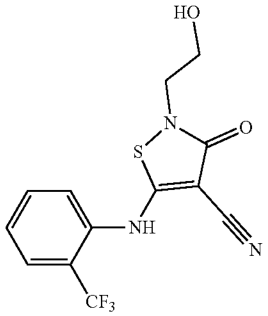 [SMILES: N#Cc1c(Nc2ccccc2C(F)(F)F)sn(CCO)c1=O] |
| 40 | 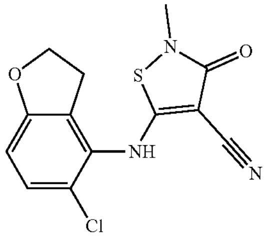 [SMILES: Cn1sc(Nc2c(Cl)ccc3c2CCO3)c(C#N)c1=O] |
| 41 | 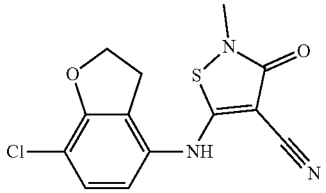 [SMILES: Cn1sc(Nc2ccc(Cl)c3c2CCO3)c(C#N)c1=O] |
| 42 | 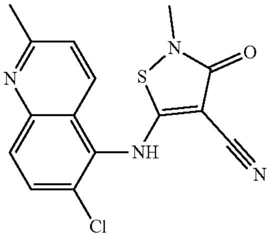 [SMILES: Cc1ccc2c(Nc3sn(C)c(=O)c3C#N)c(Cl)ccc2n1] |
| 43 | 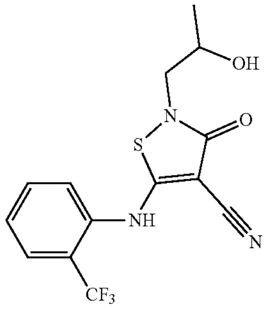 [SMILES: CC(O)Cn1sc(Nc2ccccc2C(F)(F)F)c(C#N)c1=O] |

-continued
| Example | Structure |
|---|---|
| 44 | 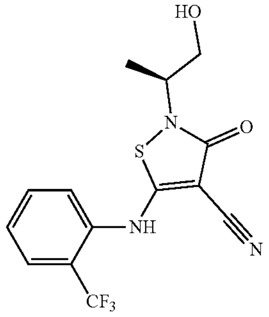 [SMILES: C[C@@H](CO)n1sc(Nc2ccccc2C(F)(F)F)c(C#N)c1=O] |
| 45 | 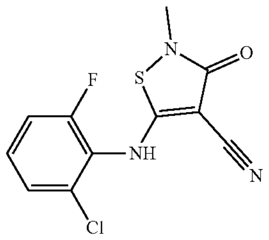 [SMILES: Cn1sc(Nc2c(F)cccc2Cl)c(C#N)c1=O] |
| 46 | 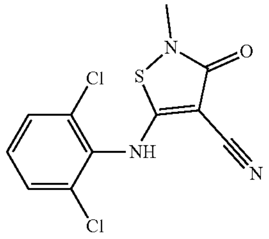 [SMILES: Cn1sc(Nc2c(Cl)cccc2Cl)c(C#N)c1=O] |
| 47 | 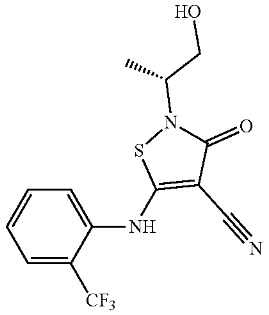 [SMILES: C[C@H](CO)n1sc(Nc2ccccc2C(F)(F)F)c(C#N)c1=O] |
| 48 | 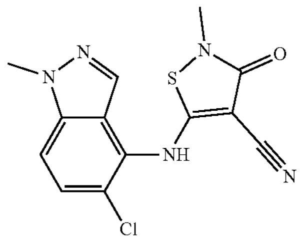 [SMILES: Cn1sc(Nc2c(Cl)ccc3c2cnn3C)c(C#N)c1=O] |
| 49 | 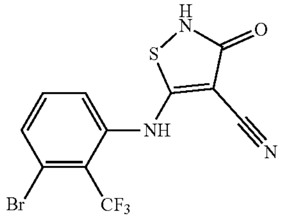 [SMILES: N#Cc1c(Nc2cccc(Br)c2C(F)(F)F)s[nH]c1=O] |
-continued
| Example | Structure |
|---|---|
| 50 | 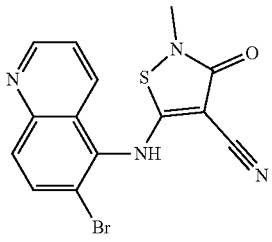 [SMILES: Cn1sc(Nc2c(Br)ccc3ncccc23)c(C#N)c1=O] |
| 51 | 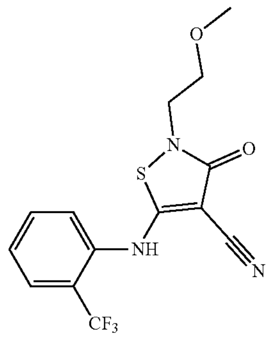 [SMILES: COCCn1sc(Nc2ccccc2C(F)(F)F)c(C#N)c1=O] |
| 52 | 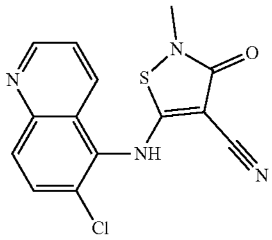 [SMILES: Cn1sc(Nc2c(Cl)ccc3ncccc23)c(C#N)c1=O] |
| 53 | 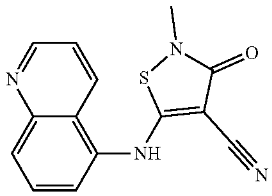 [SMILES: Cn1sc(Nc2cccc3ncccc23)c(C#N)c1=O] |
| 54 | 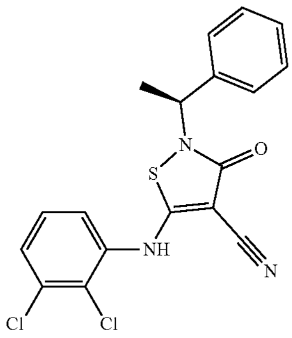 [SMILES: C[C@@H](c1ccccc1)n1sc(Nc2cccc(Cl)c2Cl)c(C#N)c1=O] |

-continued
| Example | Structure |
|---|---|
| 55 | 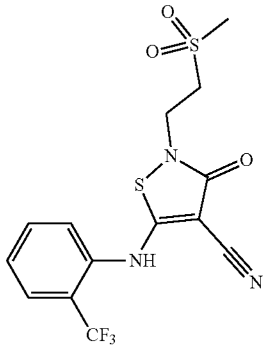 [SMILES: CS(=O)(=O)CCn1sc(Nc2ccccc2C(F)(F)F)c(C#N)c1=O] |
| 56 | 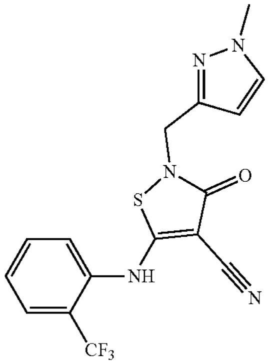 [SMILES: Cn1ccc(Cn2sc(Nc3ccccc3C(F)(F)F)c(C#N)c2=O)n1] |
| 57 | 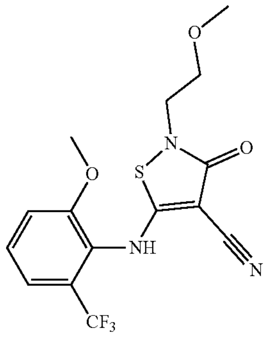 [SMILES: COCCn1sc(Nc2c(OC)cccc2C(F)(F)F)c(C#N)c1=O] |
| 58 | 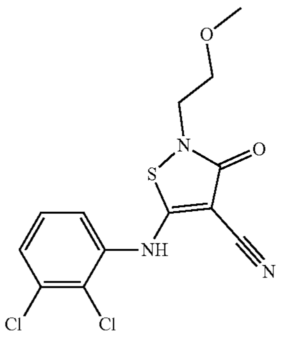 [SMILES: COCCn1sc(Nc2cccc(Cl)c2Cl)c(C#N)c1=O] |
-continued
| Example | Structure |
|---|---|
| 59 | 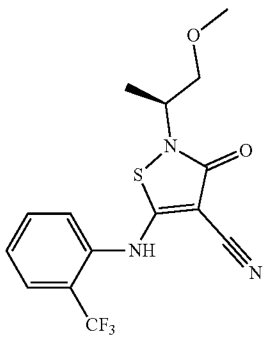 [SMILES: COC[C@H](C)n1sc(Nc2ccccc2C(F)(F)F)c(C#N)c1=O] |
| 60 | 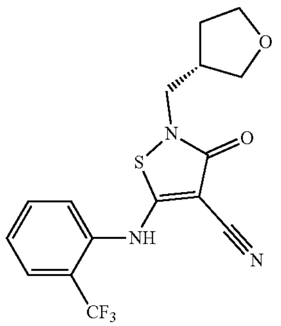 [SMILES: N#Cc1c(Nc2ccccc2C(F)(F)F)sn(C[C@@H]2CCOC2)c1=O] |
| 61 | 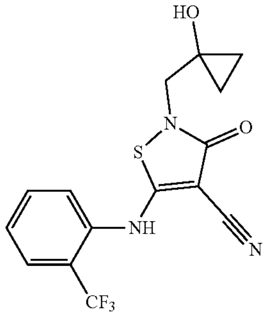 [SMILES: N#Cc1c(Nc2ccccc2C(F)(F)F)sn(CC2(O)CC2)c1=O] |
| 62 | 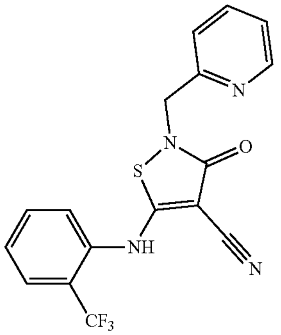 [SMILES: N#Cc1c(Nc2ccccc2C(F)(F)F)sn(Cc2ccccn2)c1=O] |

-continued
| Example | Structure |
| --- | --- |
| 63 | 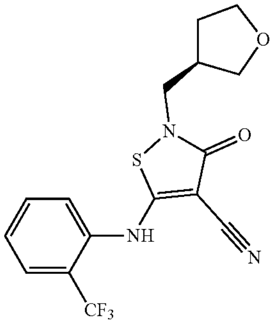 [SMILES: N#Cc1c(Nc2ccccc2C(F)(F)F)sn(C[C@H]2CCOC2)c1=O] |
| 64 | 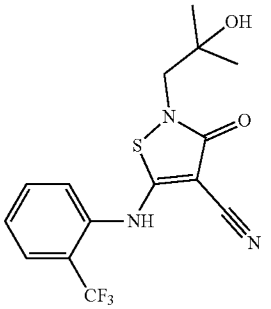 [SMILES: CC(C)(O)Cn1sc(Nc2ccccc2C(F)(F)F)c(C#N)c1=O] |
| 65 | 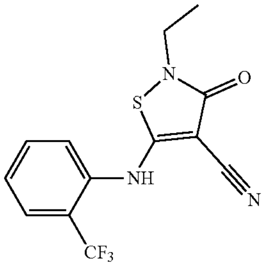 [SMILES: CCn1sc(Nc2ccccc2C(F)(F)F)c(C#N)c1=O] |
| 66 | 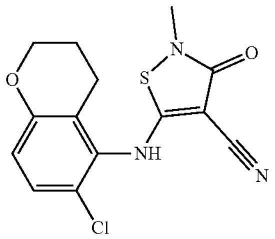 [SMILES: Cn1sc(Nc2c(Cl)ccc3c2CCCO3)c(C#N)c1=O] |
| 67 | 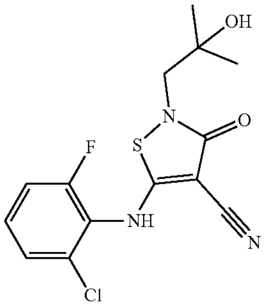 [SMILES: CC(C)(O)Cn1sc(Nc2c(F)cccc2Cl)c(C#N)c1=O] |
-continued
| Example | Structure |
| --- | --- |
| 68 | 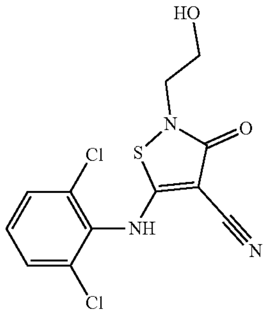 [SMILES: N#Cc1c(Nc2c(Cl)cccc2Cl)sn(CCO)c1=O] |
| 69 | 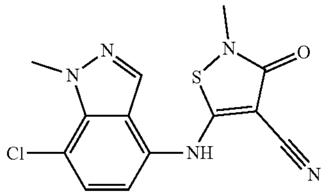 [SMILES: Cn1sc(Nc2ccc(Cl)c3c2cnn3C)c(C#N)c1=O] |
| 70 | 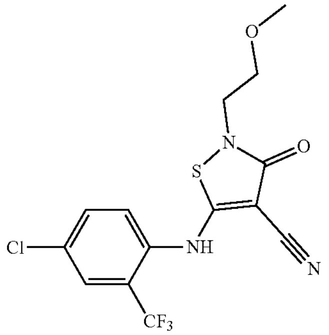 [SMILES: COCCn1sc(Nc2ccc(Cl)cc2C(F)(F)F)c(C#N)c1=O] |
| 71 | 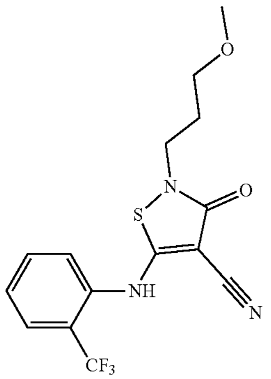 [SMILES: COCCCn1sc(Nc2ccccc2C(F)(F)F)c(C#N)c1=O] |
| 72 | 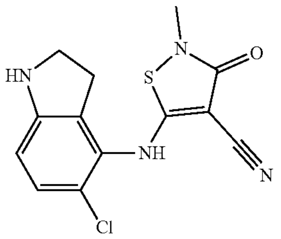 [SMILES: Cn1sc(Nc2c(Cl)ccc3c2CCN3)c(C#N)c1=O] |

-continued
| Example | Structure |
| --- | --- |
| 73 | 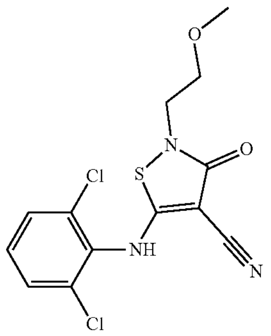 [SMILES: COCCn1sc(Nc2c(Cl)cccc2Cl)c(C#N)c1=O] |
| 74 | 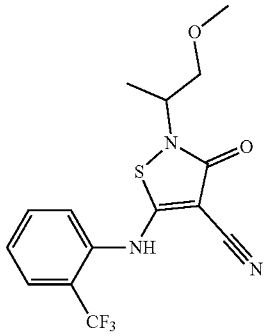 [SMILES: COCC(C)n1sc(Nc2ccccc2C(F)(F)F)c(C#N)c1=O] |
| 75 | 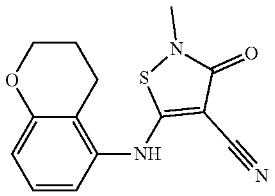 [SMILES: Cn1sc(Nc2cccc3c2CCCO3)c(C#N)c1=O] |
| 76 | 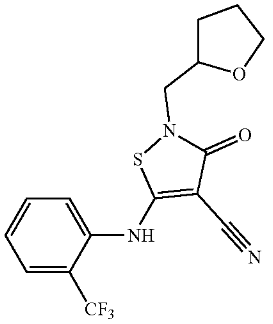 [SMILES: N#Cc1c(Nc2ccccc2C(F)(F)F)sn(CC2CCCO2)c1=O] |
| 77 | 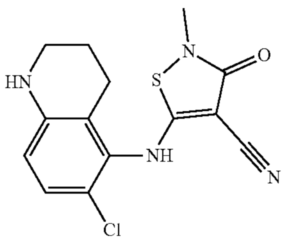 [SMILES: Cn1sc(Nc2c(Cl)ccc3c2CCCN3)c(C#N)c1=O] |
-continued
| Example | Structure |
| --- | --- |
| 78 | 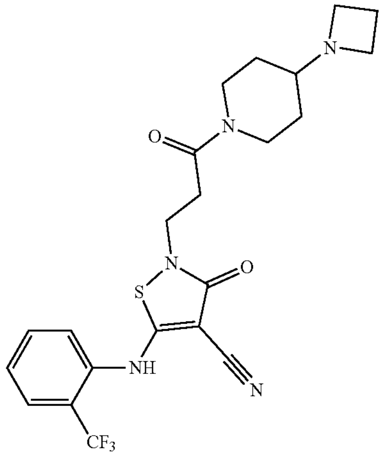 [SMILES: N#Cc1c(Nc2ccccc2C(F)(F)F)sn(CCC(=O)N2CCC(N3CCC3)CC2)c1=O] |
| 79 | 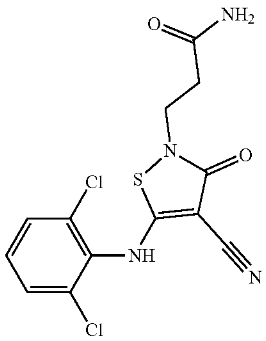 [SMILES: N#Cc1c(Nc2c(Cl)cccc2Cl)sn(CCC(N)=O)c1=O] |
| 80 | 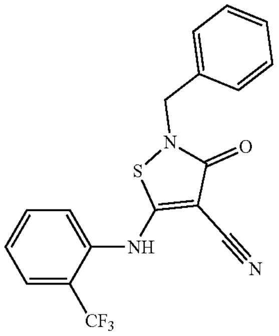 [SMILES: N#Cc1c(Nc2ccccc2C(F)(F)F)sn(Cc2ccccc2)c1=O] |
| 81 | 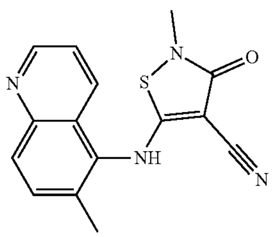 [SMILES: Cc1ccc2ncccc2c1Nc1sn(C)c(=O)c1C#N] |

-continued
| Example | Structure |
|---|---|
| 82 | 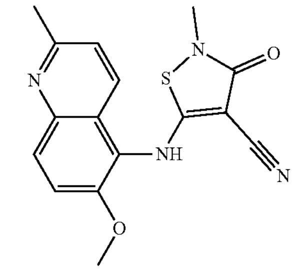 [SMILES: COc1ccc2nc(C)ccc2c1Nc1sn(C)c(=O)c1C#N] |
| 83 | 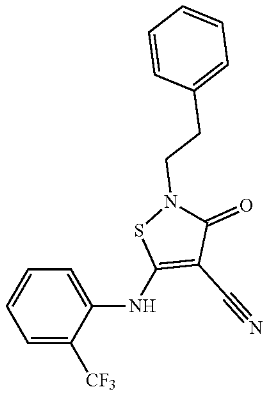 [SMILES: N#Cc1c(Nc2ccccc2C(F)(F)F)sn(CCc2ccccc2)c1=O] |
| 84 | 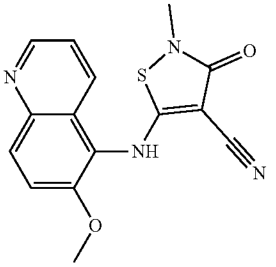 [SMILES: COc1ccc2ncccc2c1Nc1sn(C)c(=O)c1C#N] |
| 85 | 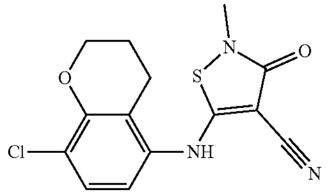 [SMILES: Cn1sc(Nc2ccc(Cl)c3c2CCCO3)c(C#N)c1=O] |
| 86 | 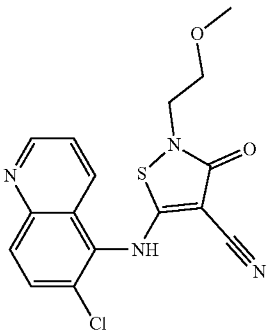 [SMILES: COCCn1sc(Nc2c(Cl)ccc3ncccc23)c(C#N)c1=O] |
| 87 | 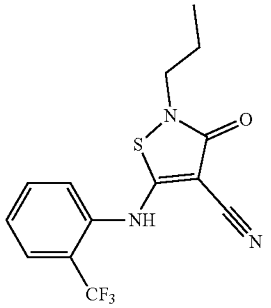 |
| 88 | 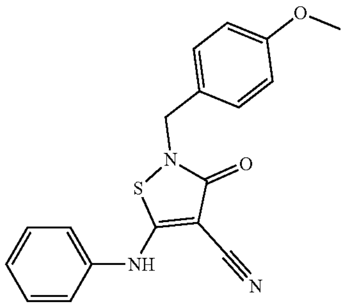 [SMILES: COc1ccc(Cn2sc(Nc3ccccc3)c(C#N)c2=O)cc1] |
| 89 | 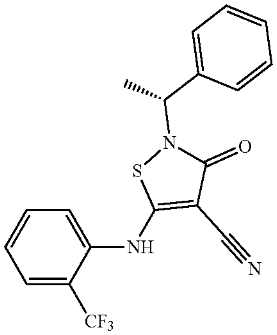 [SMILES: C[C@H](c1ccccc1)n1sc(Nc2ccccc2C(F)(F)F)c(C#N)c1=O] |
| 90 | 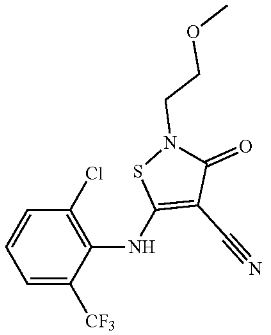 [SMILES: COCCn1sc(Nc2c(Cl)cccc2C(F)(F)F)c(C#N)c1=O] |
| 91 | 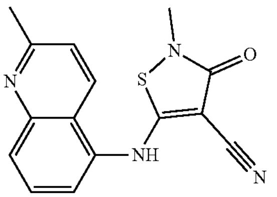 [SMILES: Cc1ccc2c(Nc3sn(C)c(=O)c3C#N)cccc2n1] |

-continued
| Example | Structure |
|---|---|
| 92 | 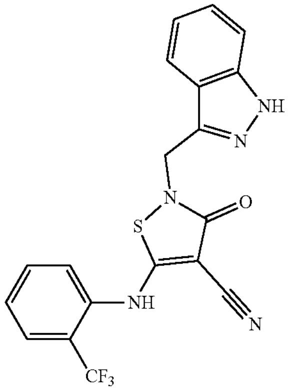 [SMILES: N#Cc1c(Nc2ccccc2C(F)(F)F)sn(Cc2n[nH]c3ccccc23)c1=O] |
| 93 | 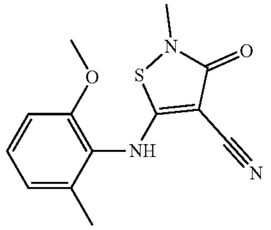 [SMILES: COc1cccc(C)c1Nc1sn(C)c(=O)c1C#N] |
| 94 | 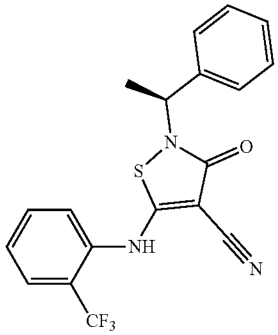 [SMILES: C[C@@H](c1ccccc1)n1sc(Nc2ccccc2C(F)(F)F)c(C#N)c1=O] |
| 95 | 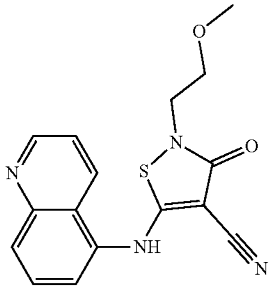 [SMILES: COCCn1sc(Nc2cccc3ncccc23)c(C#N)c1=O] |
| 96 | 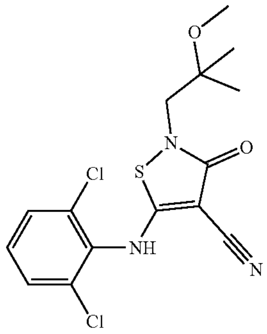 [SMILES: COC(C)(C)Cn1sc(Nc2c(Cl)cccc2Cl)c(C#N)c1=O] |
-continued
| Example | Structure |
|---|---|
| 97 | 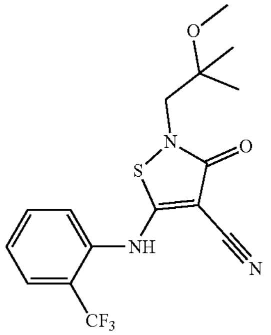 [SMILES: COC(C)(C)Cn1sc(Nc2ccccc2C(F)(F)F)c(C#N)c1=O] |
| 98 | 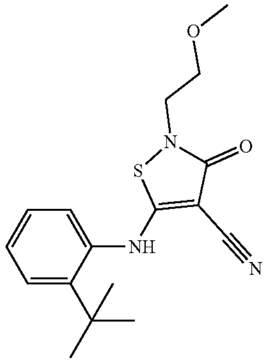 [SMILES: COCCn1sc(Nc2ccccc2C(C)(C)C)c(C#N)c1=O] |
| 99 | 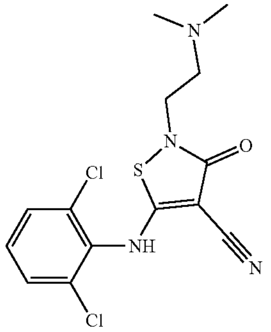 [SMILES: CN(C)CCn1sc(Nc2c(Cl)cccc2Cl)c(C#N)c1=O] |
| 100 | 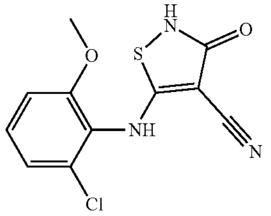 [SMILES: COc1cccc(Cl)c1Nc1s[nH]c(=O)c1C#N] |
| 101 | 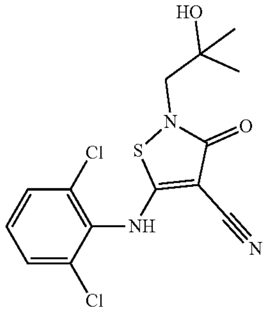 [SMILES: CC(C)(O)Cn1sc(Nc2c(Cl)cccc2Cl)c(C#N)c1=O] |

-continued
| Example | Structure |
|---|---|
| 102 | 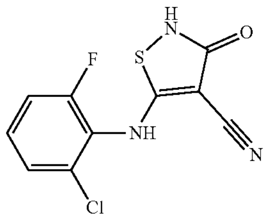 [SMILES: N#Cc1c(Nc2c(F)cccc2Cl)s[nH]c1=O] |
| 103 | 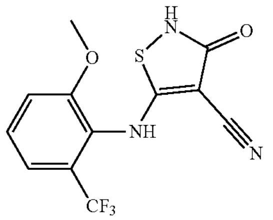 [SMILES: COc1cccc(C(F)(F)F)c1Nc1s[nH]c(=O)c1C#N] |
| 104 | 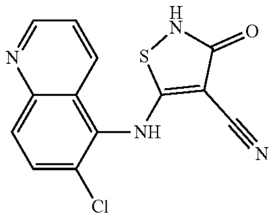 [SMILES: N#Cc1c(Nc2c(Cl)ccc3ncccc23)s[nH]c1=O] |
| 105 | 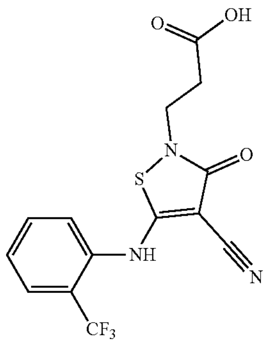 |
| 106 | 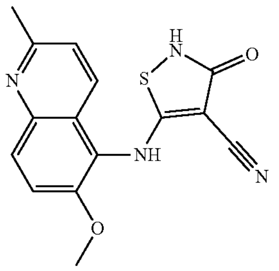 [SMILES: COc1ccc2nc(C)ccc2c1Nc1s[nH]c(=O)c1C#N] |
| 107 | 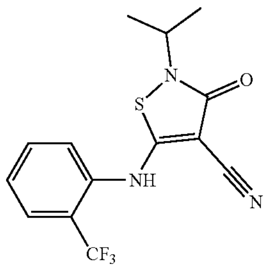 |
-continued
| Example | Structure |
|---|---|
| 108 | 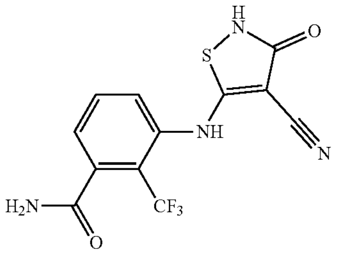 [SMILES: N#Cc1c(Nc2cccc(C(N)=O)c2C(F)(F)F)s[nH]c1=O] |
| 109 | 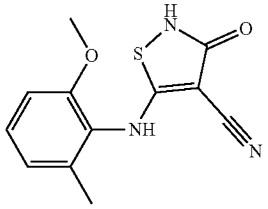 [SMILES: COc1cccc(C)c1Nc1s[nH]c(=O)c1C#N] |
| 110 | 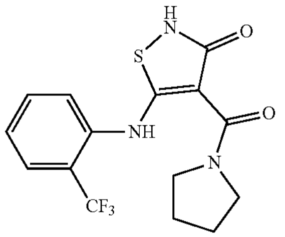 [SMILES: O=C(c1c(Nc2ccccc2C(F)(F)F)s[nH]c1=O)N1CCCC1] |
| 111 | 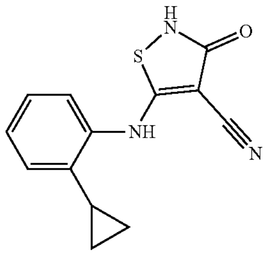 [SMILES: N#Cc1c(Nc2ccccc2C2CC2)s[nH]c1=O] |
| 112 | 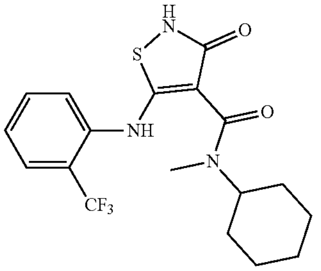 [SMILES: CN(C(=O)c1c(Nc2ccccc2C(F)(F)F)s[nH]c1=O)C1CCCCC1] |
| 113 | 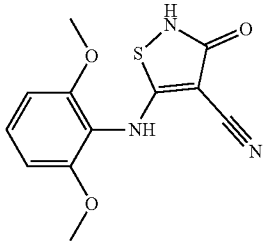 [SMILES: COc1cccc(OC)c1Nc1s[nH]c(=O)c1C#N] |

-continued
| Example | Structure |
|---|---|
| 114 | 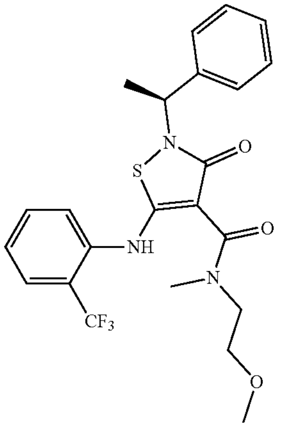 [SMILES: COCCN(C)C(=O)c1c(Nc2ccccc2C(F)(F)F)sn([C@@H](C)c2ccccc2)c1=O] |
| 115 | 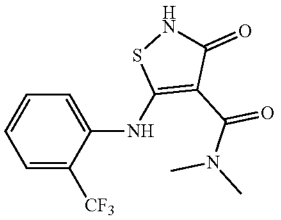 [SMILES: CN(C)C(=O)c1c(Nc2ccccc2C(F)(F)F)s[nH]c1=O] |
| 116 | 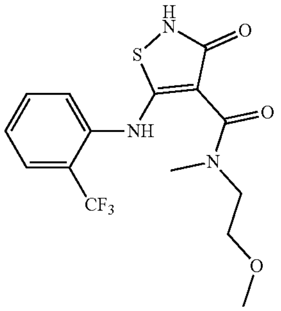 [SMILES: COCCN(C)C(=O)c1c(Nc2ccccc2C(F)(F)F)s[nH]c1=O] |
| 117 | 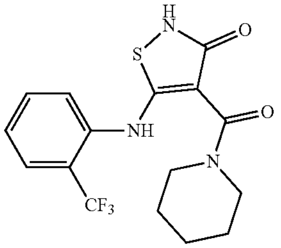 [SMILES: O=C(c1c(Nc2ccccc2C(F)(F)F)s[nH]c1=O)N1CCCCC1] |
| 118 | 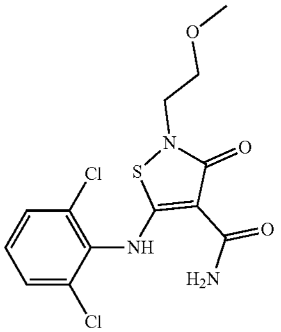 [SMILES: COCCn1sc(Nc2c(Cl)cccc2Cl)c(C(N)=O)c1=O] |
-continued
| Example | Structure |
|---|---|
| 119 | 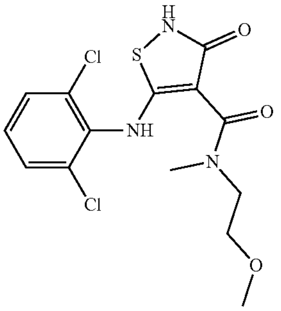 [SMILES: COCCN(C)C(=O)c1c(Nc2c(Cl)cccc2Cl)s[nH]c1=O] |
| 120 | 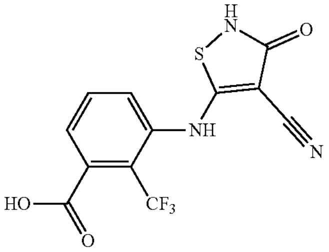 [SMILES: N#Cc1c(Nc2cccc(C(=O)O)c2C(F)(F)F)s[nH]c1=O] |
| 121 | 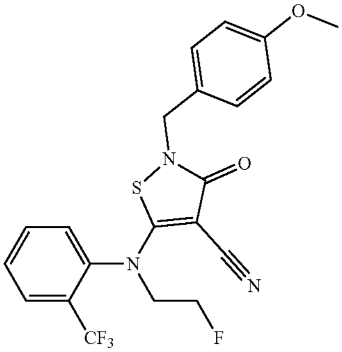 [SMILES: COc1ccc(Cn2sc(N(CCF)c3ccccc3C(F)(F)F)c(C#N)c2=O)cc1] |
| 122 | 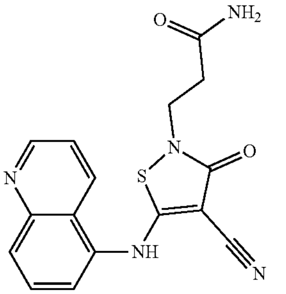 [SMILES: N#Cc1c(Nc2cccc3ncccc23)sn(CCC(N)=O)c1=O] |
| 123 | 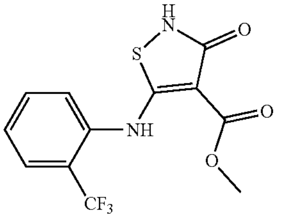 [SMILES: COC(=O)c1c(Nc2ccccc2C(F)(F)F)s[nH]c1=O] |

-continued
| Example | Structure |
| --- | --- |
| 124 | 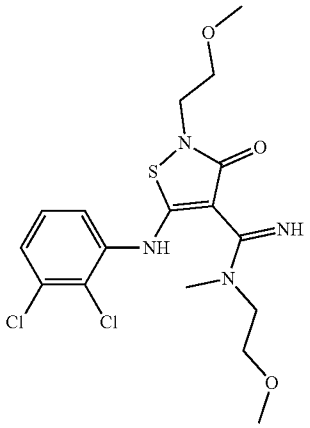 [SMILES: COCCN(C)C(=N)c1c(Nc2cccc(Cl)c2Cl)sn(CCOC)c1=O] |
| 125 | 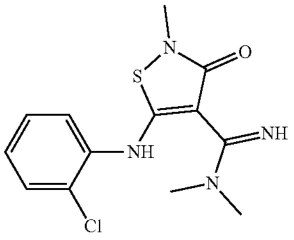 [SMILES: CN(C)C(=N)c1c(Nc2ccccc2Cl)sn(C)c1=O] |
| 126 | 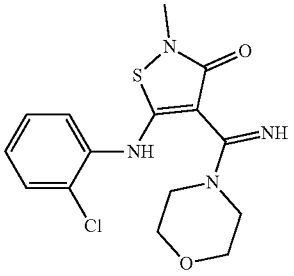 [SMILES: Cn1sc(Nc2ccccc2Cl)c(C(=N)N2CCOCC2)c1=O] |
| 127 | 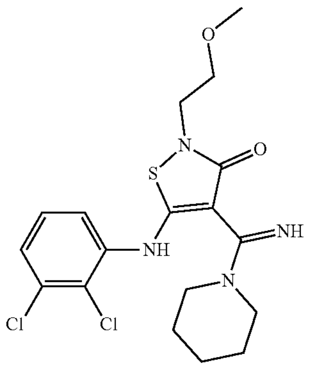 [SMILES: COCCn1sc(Nc2cccc(Cl)c2Cl)c(C(=N)N2CCCCC2)c1=O] |
-continued
| Example | Structure |
| --- | --- |
| 128 | 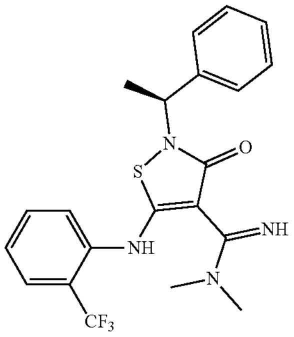 [SMILES: C[C@@H](c1ccccc1)n1sc(Nc2ccccc2C(F)(F)F)c(C(=N)N(C)C)c1=O] |
| 129 | 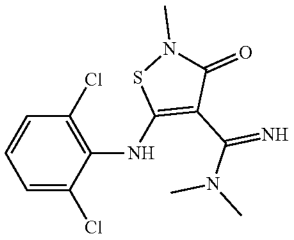 [SMILES: CN(C)C(=N)c1c(Nc2c(Cl)cccc2Cl)sn(C)c1=O] |
| 130 | 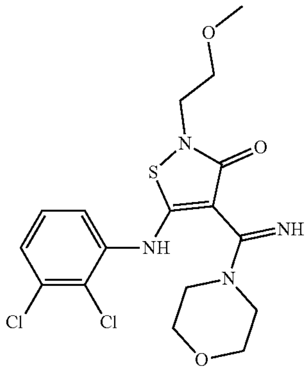 [SMILES: COCCn1sc(Nc2cccc(Cl)c2Cl)c(C(=N)N2CCOCC2)c1=O] |
| 131 | 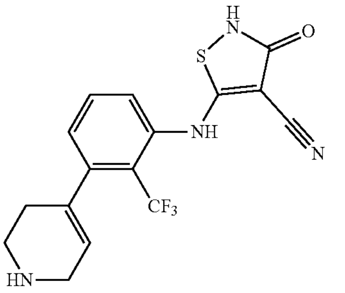 [SMILES: N#Cc1c(Nc2cccc(C3=CCNCC3)c2C(F)(F)F)s[nH]c1=O] |
| 132 | 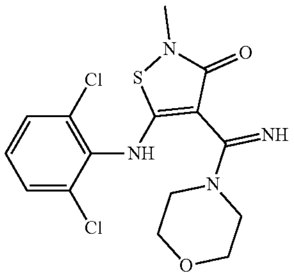 [SMILES: Cn1sc(Nc2c(Cl)cccc2Cl)c(C(=N)N2CCOCC2)c1=O] |

-continued
| Example | Structure |
| --- | --- |
| 133 | 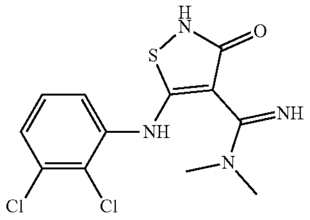 [SMILES: CN(C)C(=N)c1c(Nc2cccc(Cl)c2Cl)s[nH]c1=O] |
| 134 | 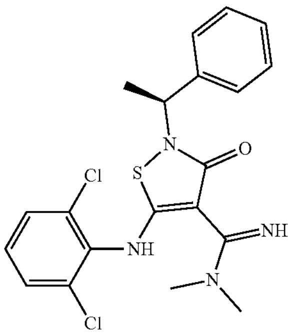 [SMILES: C[C@@H](c1ccccc1)n1sc(Nc2c(Cl)cccc2Cl)c(C(=N)N(C)C)c1=O] |
| 135 | 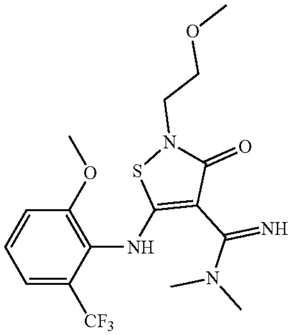 [SMILES: COCCn1sc(Nc2c(OC)cccc2C(F)(F)F)c(C(=N)N(C)C)c1=O] |
| 136 | 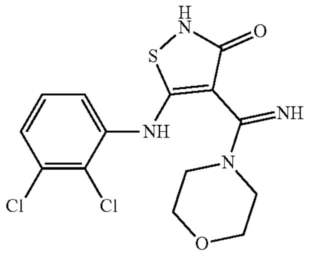 [SMILES: N=C(c1c(Nc2cccc(Cl)c2Cl)s[nH]c1=O)N1CCOCC1] |
| 137 | 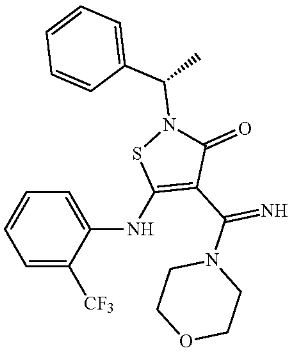 [SMILES: C[C@@H](c1ccccc1)n1sc(Nc2ccccc2C(F)(F)F)c(C(=N)N2CCOCC2)c1=O] |
-continued
| Example | Structure |
| --- | --- |
| 138 | 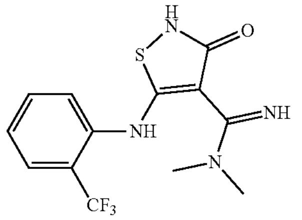 [SMILES: CN(C)C(=N)c1c(Nc2ccccc2C(F)(F)F)s[nH]c1=O] |
| 139 | 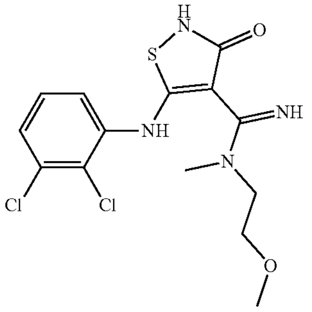 [SMILES: COCCN(C)C(=N)c1c(Nc2cccc(Cl)c2Cl)s[nH]c1=O] |
| 140 | 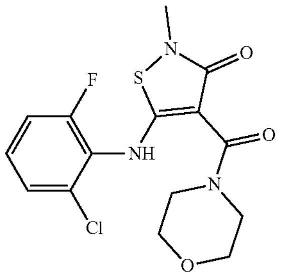 [SMILES: Cn1sc(Nc2c(F)cccc2Cl)c(C(=O)N2CCOCC2)c1=O] |
| 141 | 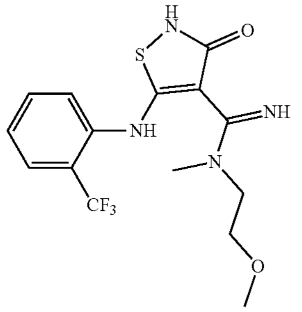 [SMILES: COCCN(C)C(=N)c1c(Nc2ccccc2C(F)(F)F)s[nH]c1=O] |
| 142 | 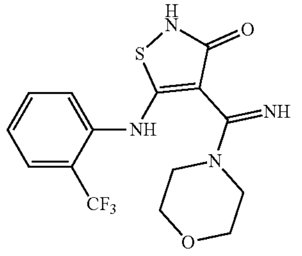 [SMILES: N=C(c1c(Nc2ccccc2C(F)(F)F)s[nH]c1=O)N1CCOCC1] |

-continued
| Example | Structure |
| --- | --- |
| 143 | 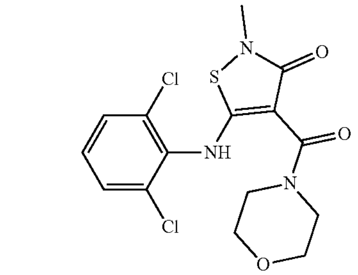 [SMILES: Cn1sc(Nc2c(Cl)cccc2Cl)c(C(=O)N2CCOCC2)c1=O] |
| 144 | 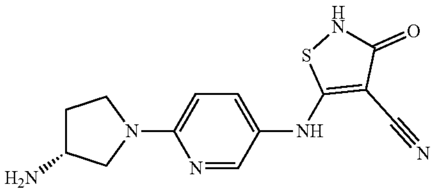 [SMILES: N#Cc1c(Nc2ccc(N3CC[C@@H](N)C3)nc2)s[nH]c1=O] |
| 145 | 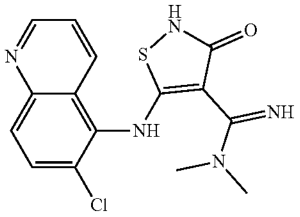 [SMILES: CN(C)C(=N)c1c(Nc2c(Cl)ccc3ncccc23)s[nH]c1=O] |
| 146 | 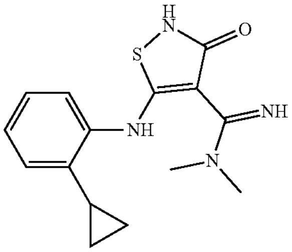 [SMILES: CN(C)C(=N)c1c(Nc2ccccc2C2CC2)s[nH]c1=O] |
| 147 | 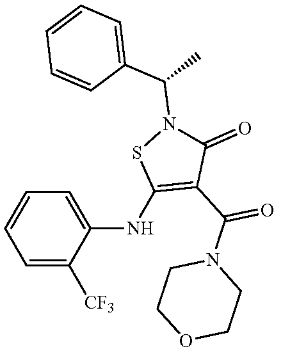 [SMILES: C[C@@H](c1ccccc1)n1sc(Nc2ccccc2C(F)(F)F)c(C(=O)N2CCOCC2)c1=O] |
| 148 | 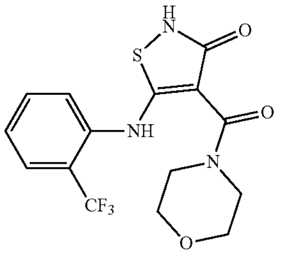 [SMILES: O=C(c1c(Nc2ccccc2C(F)(F)F)s[nH]c1=O)N1CCOCC1] |
-continued
| Example | Structure |
| --- | --- |
| 149 | 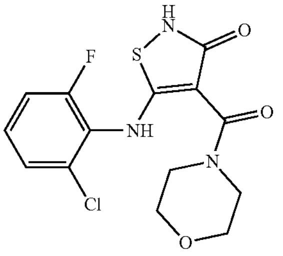 [SMILES: O=C(c1c(Nc2c(F)cccc2Cl)s[nH]c1=O)N1CCOCC1] |
| 150 | 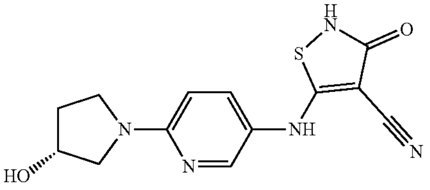 [SMILES: N#Cc1c(Nc2ccc(N3CC[C@@H](O)C3)nc2)s[nH]c1=O] |
| 151 | 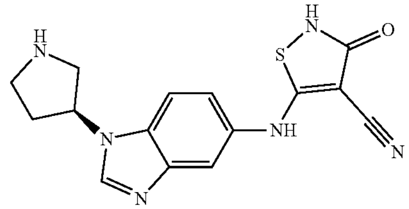 [SMILES: N#Cc1c(Nc2ccc3c(c2)ncn3[C@H]2CCNC2)s[nH]c1=O] |
| 152 | 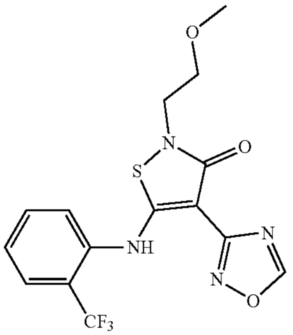 [SMILES: COCCn1sc(Nc2ccccc2C(F)(F)F)c(-c2ncon2)c1=O] |
| 153 | 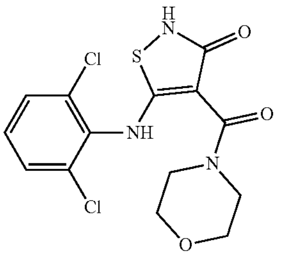 |

-continued
| Example | Structure |
|---|---|
| 154 | 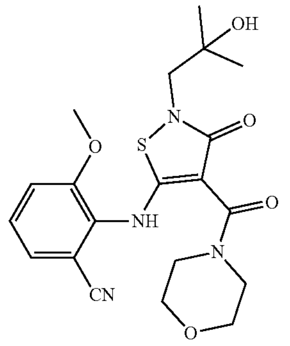 [SMILES: COc1cccc(C#N)c1Nc1sn(CC(C)(C)O)c(=O)c1C(=O)N1CCOCC1] |
| 155 | 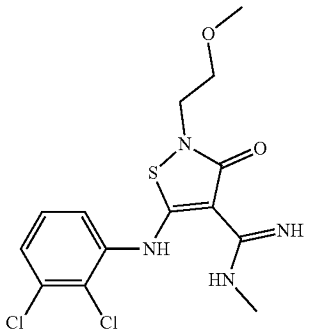 [SMILES: CNC(=N)c1c(Nc2cccc(Cl)c2Cl)sn(CCOC)c1=O] |
| 156 | 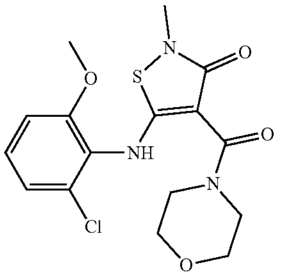 |
| 157 | 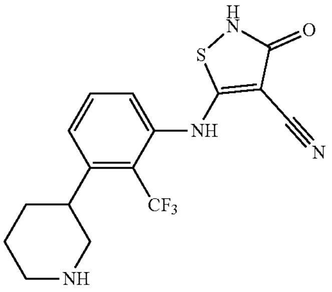 [SMILES: N#Cc1c(Nc2cccc(C3CCCNC3)c2C(F)(F)F)s[nH]c1=O] |
| 158 | 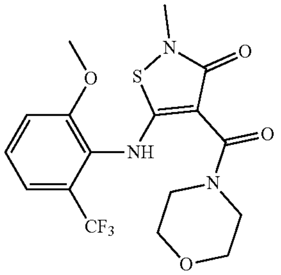 [SMILES: COc1cccc(C(F)(F)F)c1Nc1sn(C)c(=O)c1C(=O)N1CCOCC1] |
-continued
| Example | Structure |
|---|---|
| 159 | 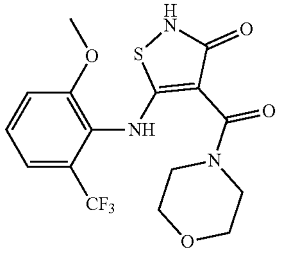 [SMILES: COc1cccc(C(F)(F)F)c1Nc1s[nH]c(=O)c1C(=O)N1CCOCC1] |
| 160 | 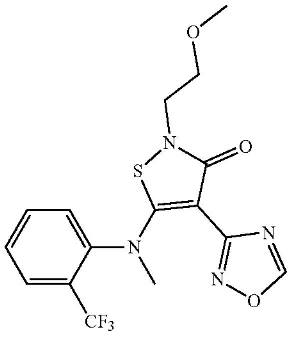 [SMILES: COCCn1sc(N(C)c2ccccc2C(F)(F)F)c(-c2ncon2)c1=O] |
| 161 | 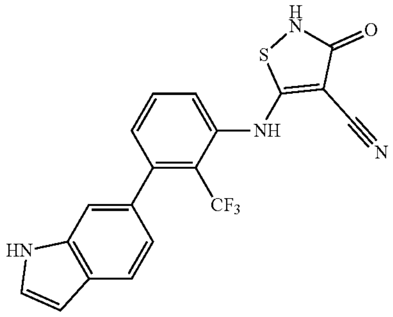 [SMILES: N#Cc1c(Nc2cccc(-c3ccc4cc[nH]c4c3)c2C(F)(F)F)s[nH]c1=O] |
| 162 | 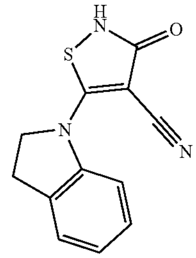 [SMILES: N#Cc1c(N2CCc3ccccc32)s[nH]c1=O] |
| 163 | 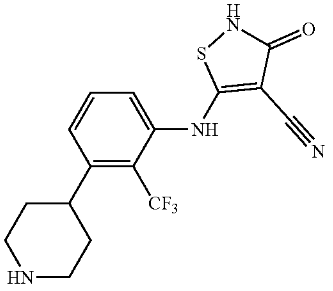 [SMILES: N#Cc1c(Nc2cccc(C3CCNCC3)c2C(F)(F)F)s[nH]c1=O] |

-continued
| Example | Structure |
| --- | --- |
| 164 | 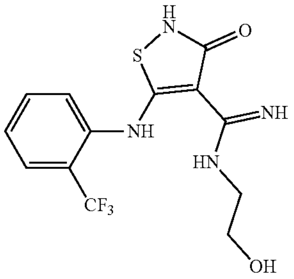 [SMILES: N=C(NCCO)c1c(Nc2ccccc2C(F)(F)F)s[nH]c1=O] |
| 165 | 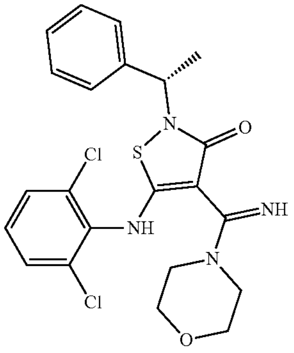 [SMILES: C[C@@H](c1ccccc1)n1sc(Nc2c(Cl)cccc2Cl)c(C(=N)N2CCOCC2)c1=O] |
| 166 | 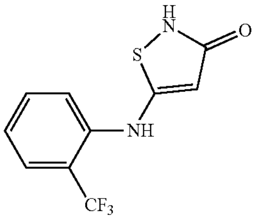 [SMILES: O=c1cc(Nc2ccccc2C(F)(F)F)s[nH]1] |
| 167 | 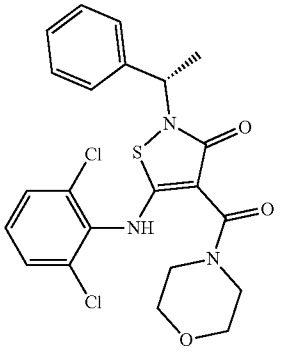 [SMILES: C[C@@H](c1ccccc1)n1sc(Nc2c(Cl)cccc2Cl)c(C(=O)N2CCOCC2)c1=O] |
| 168 | 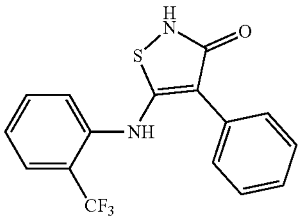 [SMILES: O=c1[nH]sc(Nc2ccccc2C(F)(F)F)c1-c1ccccc1] |
-continued
| Example | Structure |
| --- | --- |
| 169 | 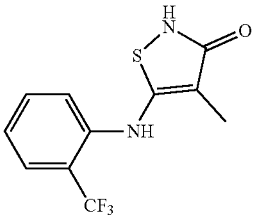 |
| 170 | 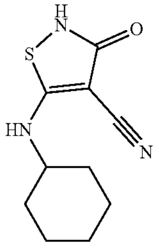 [SMILES: N#Cc1c(NC2CCCCC2)s[nH]c1=O] |
| 171 | 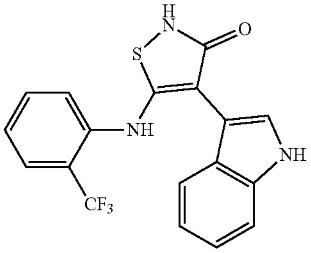 [SMILES: O=c1[nH]sc(Nc2ccccc2C(F)(F)F)c1-c1c[nH]c2ccccc12] |
| 172 | 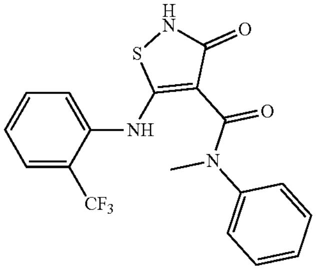 [SMILES: CN(C(=O)c1c(Nc2ccccc2C(F)(F)F)s[nH]c1=O)c1ccccc1] |
| 173 | 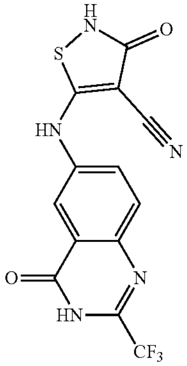 [SMILES: N#Cc1c(Nc2ccc3nc(C(F)(F)F)[nH]c(=O)c3c2)s[nH]c1=O] |

-continued

| Example | Structure |
|---|---|
| 174 | 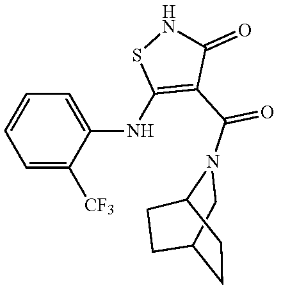 [SMILES: O=C(c1c(Nc2ccccc2C(F)(F)F)s[nH]c1=O)N1CC2CCC1CC2] |

Tool Compounds

In some embodiments, one or more compounds of Formula I or Formula II are tethered to a detectable moiety to form a tool compound. In some embodiments, a tool compound comprises a compound of Formula I or Formula II, a detectable moiety and a tethering moiety that attaches the detectable moiety to the compound of Formula I or Formula II. In some embodiments, a tool compound comprises a compound of Formula I or Formula II and a moiety that comprises a functional group capable of binding to or reacting with a detectable moiety.

In some embodiments, the present disclosure provides a compound of Formula III.

III

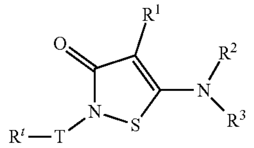

or a pharmaceutically acceptable salt thereof, wherein each of $R^1$, $R^2$, and $R^3$ is as defined above with respect to Formula II, and described in classes and subclasses herein; T is a bivalent tethering moiety; and $R^t$ is a detectable moiety.

In some embodiments, $R^t$ is a detectable moiety selected from a primary label or a secondary label. In certain embodiments, $R^t$ is a detectable moiety selected from a fluorescent label (e.g., a fluorescent dye or a fluorophore), a mass-tag, a chemiluminescent group, a chromophore, an electron dense group, and an energy transfer agent.

As used herein, the term "detectable moiety" is used interchangeably with the term "label" and "reporter" and relates to any moiety capable of being detected, e.g., primary labels and secondary labels. A presence of a detectable moiety can be measured using methods for quantifying (in absolute, approximate or relative terms) the detectable moiety in a system under study. In some embodiments, such methods are well known to one of ordinary skill in the art and include any methods that quantify a reporter moiety (e.g., a label, a dye, a photocrosslinker, a cytotoxic compound, a drug, an affinity label, a photoaffinity label, a reactive compound, an antibody or antibody fragment, a biomaterial, a nanoparticle, a spin label, a fluorophore, a metal-containing moiety, a radioactive moiety, quantum dot(s), a novel functional group, a group that covalently or noncovalently interacts with other molecules, a photocaged moiety, an actinic radiation excitable moiety, a ligand, a photoisomerizable moiety, biotin, a biotin analog (e.g., biotin sulfoxide), a moiety incorporating a heavy atom, a chemically cleavable group, a photocleavable group, a redox-active agent, an isotopically labeled moiety, a biophysical probe, a phosphorescent group, a chemiluminescent group, an electron dense group, a magnetic group, an intercalating group, a chromophore, an energy transfer agent, a biologically active agent, a detectable label, and any combination of the above).

Primary labels, such as radioisotopes (e.g., tritium, $^{32}P$, $^{33}P$, $^{35}C$, $^{123}I$, $^{124}I$, $^{125}I$, or $^{131}I$), mass-tags including, but not limited to, stable isotopes (e.g., $^{13}C$, $^{2}H$, $^{17}O$, $^{18}O$, $^{15}N$, $^{19}F$, and $^{127}I$), positron emitting isotopes (e.g., $^{11}C$, $^{18}F$, $^{13}N$, $^{124}I$, and $^{15}O$), and fluorescent labels are signal generating reporter groups which can be detected without further modifications. Detectable moities may be analyzed by methods including, but not limited to fluorescence, positron emission tomography, SPECT medical imaging, chemiluminescence, electron-spin resonance, ultraviolet/visible absorbance spectroscopy, mass spectrometry, nuclear magnetic resonance, magnetic resonance, flow cytometry, autoradiography, scintillation counting, phosphoimaging, and electrochemical methods.

The term "secondary label" as used herein refers to moieties such as biotin and various protein antigens that require the presence of a second intermediate for production of a detectable signal. For biotin, the secondary intermediate may include streptavidin-enzyme conjugates. For antigen labels, secondary intermediates may include antibody-enzyme conjugates. Some fluorescent groups act as secondary labels because they transfer energy to another group in the process of nonradiative fluorescent resonance energy transfer (FRET), and the second group produces the detected signal.

The terms "fluorescent label", "fluorescent dye", and "fluorophore" as used herein refer to moieties that absorb light energy at a defined excitation wavelength and emit light energy at a different wavelength. Examples of fluorescent labels include, but are not limited to: Alexa Fluor dyes (Alexa Fluor 350, Alexa Fluor 488, Alexa Fluor 532, Alexa Fluor 546, Alexa Fluor 568, Alexa Fluor 594, Alexa Fluor 633, Alexa Fluor 660 and Alexa Fluor 680), AMCA, AMCA-S, BODIPY dyes (BODIPY FL, BODIPY R6G, BODIPY TMR, BODIPY TR, BODIPY 493/503, BODIPY 530/550, BODIPY 558/568, BODIPY 564/570, BODIPY 576/589, BODIPY 581/591, BODIPY 630/650, BODIPY 650/665), Carboxyrhodamine 6G, carboxy-X-rhodamine (ROX), Cascade Blue, Cascade Yellow, Coumarin 343, Cyanine dyes (Cy3, Cy5, Cy3.5, Cy5.5), Dansyl, Dapoxyl, Dialkylaminocoumarin, 4',5'-Dichloro-2',7'-dimethoxy-fluorescein, DM-NERF, Eosin, Erythrosin, Fluorescein, FAM, Hydroxycoumarin, IRDyes (IRD40, IRD 700, IRD 800), JOE, Lissamine rhodamine B, Marina Blue, Methoxy-coumarin, Naphthofluorescein, Oregon Green 488, Oregon Green 500, Oregon Green 514, Pacific Blue, PyMPO, Pyrene, Rhodamine B, Rhodamine 6G, Rhodamine Green, Rhodamine Red, Rhodol Green, 2',4',5',7'-Tetra-bromo-sulfone-fluorescein, Tetramethyl-rhodamine (TMR), Carboxytetramethylrhodamine (TAMRA), Texas Red, Texas Red-X, 5(6)-Carboxyfluorescein, 2,7-Dichlorofluorescein, N,N-Bis-(2,4,6-trimethylphenyl)-3,4:9,10-perylenebis(dicarboximide, HPTS, Ethyl Eosin, DY-490XL MegaStokes, DY-485XL MegaStokes, Adirondack Green 520, ATTO 465, ATTO 488, ATTO 495, YOYO-1,5-FAM, BCECF, dichlorofluorescein, rhodamine 110, rhodamine 123, YO-PRO-1, SYTOX Green, Sodium Green, SYBR Green I, Alexa Fluor 500, FITC, Fluo-3, Fluo-4, fluoro-emerald, YoYo-1 ssDNA, YoYo-1 dsDNA, YoYo-1, SYTO RNASelect, Diversa Green-FP, Dragon Green, EvaGreen, Surf Green EX, Spectrum Green, NeuroTrace 500525, NBD-X, MitoTracker Green FM, LysoTracker Green DND-26, CBQCA, PA-GFP (post-activation), WEGFP (post-activation), FlASH-CCXXCC, Azami Green monomeric, Azami Green, green fluorescent protein (GFP), EGFP (Campbell Tsien 2003), EGFP (Patterson 2001), Kaede Green, 7-Benzylamino-4-Nitrobenz-2-Oxa-1,3-Diazole, Bexl, Doxorubicin, Lumio Green, and SuperGlo GFP.

The term "mass-tag" as used herein refers to any moiety that is capable of being uniquely detected by virtue of its mass using mass spectrometry (MS) detection techniques. Examples of mass-tags include electrophore release tags such as N-[3-[4'-[(p-Methoxytetrafluorobenzyl)oxy]phenyl]-3-methylglyceronyl]isonipecotic Acid, 4'-[2,3,5,6-Tetrafluoro-4-(pentafluorophenoxyl)]methyl acetophenone, and their derivatives. The synthesis and utility of these mass-tags is described in U.S. Pat. Nos. 4,650,750, 4,709,016, 5,360,8191, 5,516,931, 5,602,273, 5,604,104, 5,610,020, and 5,650,270. Other examples of mass-tags include, but are not limited to, nucleotides, dideoxynucleotides, oligonucleotides of varying length and base composition, oligopeptides, oligosaccharides, and other synthetic polymers of varying length and monomer composition. A large variety of organic molecules, both neutral and charged (biomolecules or synthetic compounds) of an appropriate mass range (100-2000 Daltons) may also be used as mass-tags. Stable isotopes (e.g., $^{13}C$, $^{2}H$, $^{17}O$, $^{18}O$, and $^{15}N$) may also be used as mass-tags.

The term "chemiluminescent group," as used herein, refers to a group which emits light as a result of a chemical reaction without the addition of heat. By way of example, luminol (5-amino-2,3-dihydro-1,4-phthalazinedione) reacts with oxidants like hydrogen peroxide ($H_2O_2$) in the presence of a base and a metal catalyst to produce an excited state product (3-aminophthalate, 3-APA).

The term "chromophore," as used herein, refers to a molecule which absorbs light of visible wavelengths, UV wavelengths or IR wavelengths.

The term "dye," as used herein, refers to a soluble, coloring substance which contains a chromophore.

The term "electron dense group," as used herein, refers to a group which scatters electrons when irradiated with an electron beam. Such groups include, but are not limited to, ammonium molybdate, bismuth subnitrate, cadmium iodide, carbohydrazide, ferric chloride hexahydrate, hexamethylene tetramine, indium trichloride anhydrous, lanthanum nitrate, lead acetate trihydrate, lead citrate trihydrate, lead nitrate, periodic acid, phosphomolybdic acid, phosphotungstic acid, potassium ferricyanide, potassium ferrocyanide, ruthenium red, silver nitrate, silver proteinate (Ag Assay: 8.0-8.5%) "Strong", silver tetraphenylporphin (S-TPPS), sodium chloroaurate, sodium tungstate, thallium nitrate, thiosemicarbazide (TSC), uranyl acetate, uranyl nitrate, and vanadyl sulfate.

The term "energy transfer agent," as used herein, refers to a molecule which either donates or accepts energy from another molecule. By way of example only, fluorescence resonance energy transfer (FRET) is a dipole-dipole coupling process by which the excited-state energy of a fluorescence donor molecule is non-radiatively transferred to an unexcited acceptor molecule which then fluorescently emits the donated energy at a longer wavelength.

The term "moiety incorporating a heavy atom," as used herein, refers to a group which incorporates an ion of atom which is usually heavier than carbon. In some embodiments, such ions or atoms include, but are not limited to, silicon, tungsten, gold, lead, and uranium.

The term "photoaffinity label," as used herein, refers to a label with a group, which, upon exposure to light, forms a linkage with a molecule for which the label has an affinity.

The term "photocaged moiety," as used herein, refers to a group which, upon illumination at certain wavelengths, covalently or non-covalently binds other ions or molecules.

The term "photoisomerizable moiety," as used herein, refers to a group wherein upon illumination with light changes from one isomeric form to another.

The term "radioactive moiety," as used herein, refers to a group whose nuclei spontaneously give off nuclear radiation, such as alpha, beta, or gamma particles; wherein, alpha particles are helium nuclei, beta particles are electrons, and gamma particles are high energy photons.

The term "spin label," as used herein, refers to molecules which contain an atom or a group of atoms exhibiting an unpaired electron spin (i.e. a stable paramagnetic group) that in some embodiments are detected by electron spin resonance spectroscopy and in other embodiments are attached to another molecule. Such spin-label molecules include, but are not limited to, nitryl radicals and nitroxides, and in some embodiments are single spin-labels or double spin-labels.

The term "quantum dots," as used herein, refers to colloidal semiconductor nanocrystals that in some embodiments are detected in the near-infrared and have extremely high quantum yields (i.e., very bright upon modest illumination).

One of ordinary skill in the art will recognize that a detectable moiety may be attached to a provided compound via a suitable substituent. As used herein, the term "suitable substituent" refers to a moiety that is capable of covalent attachment to a detectable moiety. Such moieties are well known to one of ordinary skill in the art and include groups containing, e.g., a carboxylate moiety, an amino moiety, a thiol moiety, or a hydroxyl moiety, to name but a few. It will be appreciated that such moieties may be directly attached to a provided compound or via a tethering moiety, such as a bivalent saturated or unsaturated hydrocarbon chain.

In some embodiments, -T- is selected from $-(CH_2CH_2O)_n-$, $-(C_{1-6}$ alkyl)N(R)C(O)($C_{1-6}$ alkyl)-, and $-(CH_2CH_2O)_n(C_{1-6}$ alkyl)N(R)C(O)($C_{1-6}$ alkyl)-, wherein n is 1-4. In some embodiments, -T- is selected from $-(CH_2CH_2O)_n-$, $-(C_{3-5}$ alkyl)N(R)C(O)($C_{2-4}$ alkyl)-, and $-(CH_2CH_2O)_n(C_{3-5}$ alkyl)N(R)C(O)($C_{2-4}$ alkyl)-, wherein n is 2-3. In some embodiments, -T- is selected from the group consisting of

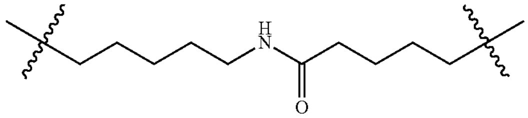

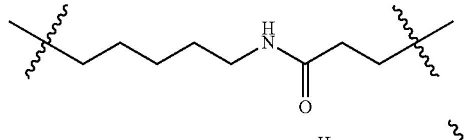

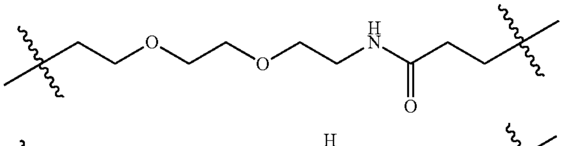

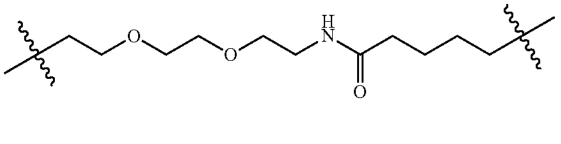

-continued

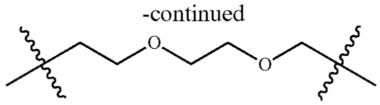

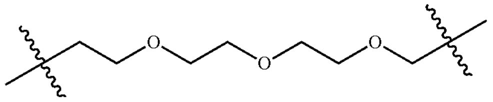

In some embodiments, a detectable moiety R′ is attached to a compound of Formula I or Formula II via click chemistry. In some embodiments, a compound of Formula I or Formula II is attached to -T-R′ via a 1,3-cycloaddition of an azide with an alkyne, optionally in the presence of a copper catalyst. Methods of using click chemistry are known in the art and include those described by Rostovtsev et al., Angew. Chem. Int. Ed. 2002, 41, 2596-99 and Sun et al., Bioconjugate Chem., 2006, 17, 52-57. In some embodiments, a compound of Formula IV is a click ready inhibitor. In some such embodiments, a click ready inhibitor of Formula IV is reacted with a click ready -T-R′ moiety. As used herein, "click ready" refers to a moiety containing an azide or alkyne for use in a click chemistry reaction. In some embodiments, the click ready inhibitor moiety comprises an azide. In certain embodiments, the click ready -T-R′ moiety comprises a strained cyclooctyne for use in a copper-free click chemistry reaction (for example, using methods described in Baskin et al., Proc. Natl. Acad. Sci. USA 2007, 104, 16793-16797).

In some embodiments, a compound of Formula III is selected from

| Example | Structure |
|---|---|
| 175 | 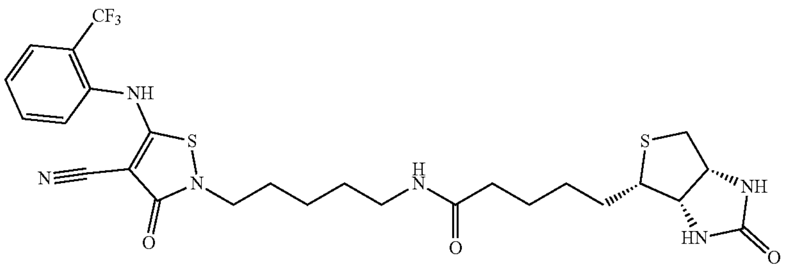 [SMILES: N#Cc1c(Nc2ccccc2C(F)(F)F)sn(CCCCCNC(=O)CCCC[C@@H]2SC[C@@H]3NC(=O)N[C@@H]32)c1=O] |
| 176 | 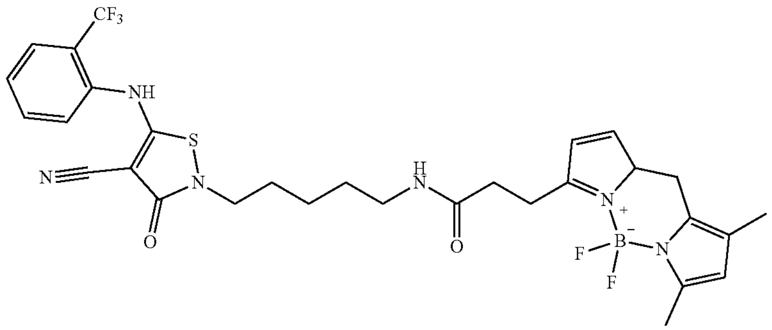 [SMILES: Cc1cc(C)n2c1CC1C=CC(CCC(=O)NCCCCCn3sc(Nc4ccccc4C(F)(F)F)c(C#N)c3=O)=[N+]1[B-]2(F)F] |
| 177 | 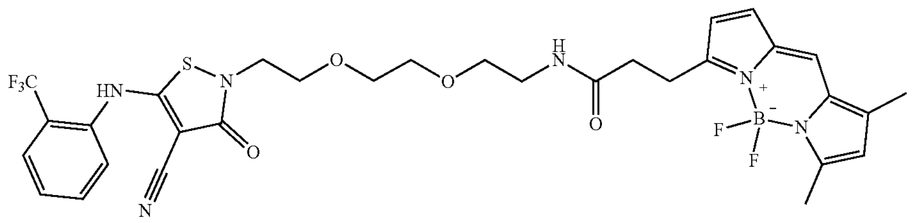 |
| 178 | 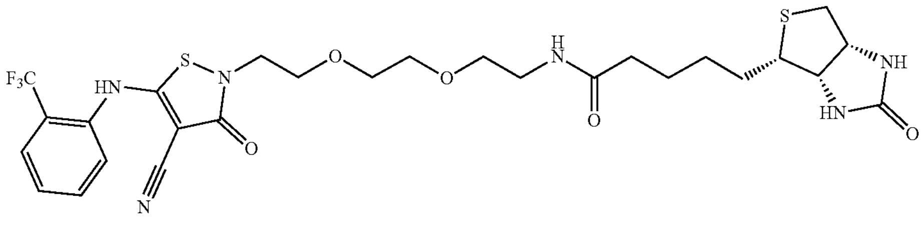 [SMILES: N#Cc1c(Nc2ccccc2C(F)(F)F)sn(CCOCCOCCNC(=O)CCCC[C@@H]2SC[C@@H]3NC(=O)N[C@@H]32)c1=O] |

-continued

| Example | Structure |
|---|---|
| 179 | 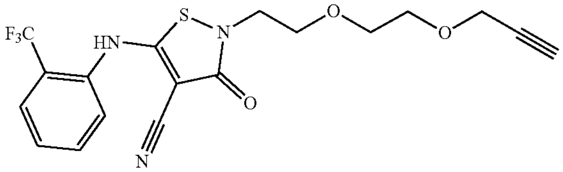 [SMILES: C#CCOCCOCCn1sc(Nc2ccccc2C(F)(F)F)c(C#N)c1=O] |
| 180 | 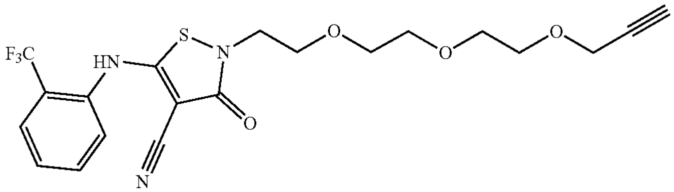 [SMILES: C#CCOCCOCCOCCn1sc(Nc2ccccc2C(F)(F)F)c(C#N)c1=O] |

In some embodiments, one or more compounds of Formula I or Formula II covalently inhibit SARM1. In some embodiments, one or more compounds of Formula I or Formula II covalently modify a cysteine residue of SARM1. In some embodiments, one or more compounds of Formula I or Formula II covalently modify Cys635 of SARM1. In some embodiments, one or more compounds of Formula I or Formula II covalently modify Cys629 of SARM1. In some embodiments, one or more compounds of Formula I or Formula II covalently modify Cys649 of SARM1. Without wishing to be bound by any particular theory, in some embodiments, one or more compounds of Formula I or Formula II denature the SARM1 protein via covalent modification of a cysteine residue. In some embodiments, one or more compounds of Formula I or Formula II denature the SARM1 protein via covalent modification of Cys635. In some embodiments, one or more compounds of Formula I or Formula II denature the SARM1 protein via covalent modification of Cys629. In some embodiments, one or more compounds of Formula I or Formula II denature the SARM1 protein via covalent modification of Cys649.

In some aspects, the present disclosure provides a compound according to the following embodiments:

Embodiment 1. A compound of Formula II:

II

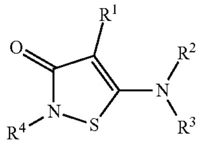

or a pharmaceutically acceptable salt thereof, wherein $R^1$ is selected from —CN, —$NO_2$, —C(O)R, —$S(O)_2R$, —$CON(R)_2$, —$S(O)_2N(R)_2$, —$CO_2R$, —C(=NR)N$(R)_2$, and a 5-membered heteroaryl ring having 2-3 heteroatoms independently selected from nitrogen, oxygen, and sulfur;

$R^2$ is —R;

$R^3$ is —$(CH_2)_{0-2}$Cy, or:

$R^2$ and $R^3$, together with the nitrogen atom to which they are attached, form a 4- to 7-membered saturated or partially unsaturated ring fused to Cy or a 4- to 7-membered saturated or partially unsaturated ring substituted with -Cy;

Cy is selected from phenyl, a 3- to 7-membered saturated or partially unsaturated carbocyclic ring, a 5- to 6-membered heteroaryl ring having 1-3 heteroatoms independently selected from nitrogen, oxygen, and sulfur, an 8- to 10-membered bicyclic heteroaryl ring having 1-3 heteroatoms independently selected from nitrogen, oxygen, and sulfur, and an 8- to 10-membered bicyclic aryl ring, wherein each phenyl, carbocyclic, heteroaryl and aryl ring is substituted with 0-4 $R^x$;

each $R^x$ is independently selected from halogen, —CN, —$NO_2$, —OR, —SR, —$N(R)_2$, —$SO_2R$, —$SO_2N(R)_2$, —$CO_2R$, —$CON(R)_2$, —$N(R)SO_2R$, —N(R)C(O)R, an optionally substituted $C_{1-6}$ aliphatic group, an optionally substituted 5- to 6-membered saturated or partially unsaturated heterocyclic ring having 1-2 heteroatoms independently selected from nitrogen, oxygen, and sulfur, and an optionally substituted 8- to 10-membered heteroaryl ring having 1-2 heteroatoms independently selected from nitrogen, oxygen, and sulfur;

$R^4$ is —R; and each R is independently hydrogen, an optionally substituted $C_{1-6}$ aliphatic, an optionally substituted phenyl, and an optionally substituted 3- to 7-membered saturated or partially unsaturated carbocyclic ring, or:

two instances of R, together with the atom to which they are attached, form a 3- to 6-membered saturated or partially unsaturated heterocyclic ring.

Embodiment 2. A compound of Formula I:

I

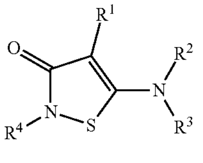

or a pharmaceutically acceptable salt thereof, wherein $R^1$ is selected from —CN, —$NO_2$, —C(O)R, —$S(O)_2R$, —$CON(R)_2$, —$S(O)_2N(R)_2$, and —$CO_2R$;

$R^2$ is —R;

$R^3$ is selected from —$(CH_2)_{0-2}$Cy, or:

$R^2$ and $R^3$, together with the nitrogen atom to which they are attached, form a 4- to 7-membered saturated or partially unsaturated ring fused to Cy or a 4- to 7-membered saturated or partially unsaturated ring substituted with -Cy;

Cy is selected from phenyl, a 5- to 6-membered heteroaryl ring having 1-3 heteroatoms independently selected from nitrogen, oxygen, and sulfur, an 8- to 10-membered bicyclic heteroaryl ring having 1-3 heteroatoms independently selected from nitrogen, oxygen, and sulfur, and an 8- to 10-membered bicyclic aryl ring, wherein each phenyl, heteroaryl and aryl ring is substituted with 0-4 $R^x$;

each $R^x$ is independently selected from halogen, —CN, —$NO_2$, —OR, —SR, —$N(R)_2$, —$SO_2R$, —$SO_2N(R)_2$, —$CO_2R$, —$CON(R)_2$, —$N(R)SO_2R$, —N(R)C(O)R, and optionally substituted $C_{1-6}$ aliphatic;

$R^4$ is —R;

each R is independently hydrogen or optionally substituted $C_{1-6}$ aliphatic; or:

two instances of R, together with the atom to which they are attached, form a 3- to 6-membered saturated or partially unsaturated heterocyclic ring.

Embodiment 3. The compound according to embodiment 1 or embodiment 2, wherein $R^2$ is —H.

Embodiment 4. The compound according to embodiment 1 or embodiment 2, wherein $R^2$ is —R.

Embodiment 5. The compound according to embodiment 4, wherein —R is $C_{1-6}$ aliphatic.

Embodiment 6. The compound according to embodiment 5, wherein R is —$C_{1-6}$ alkyl.

Embodiment 7. The compound according to embodiment 6, wherein R is —$CH_3$.

Embodiment 8. The compound according to any one of embodiments 1-7, wherein $R^1$ is —CN.

Embodiment 9. The compound according to any one of embodiments 1-7, wherein $R^1$ is —$C(O)N(R)_2$.

Embodiment 10. The compound according to any one of embodiments 1-7, wherein $R^1$ is selected from

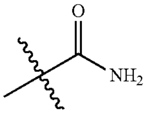 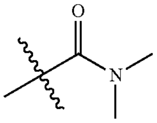

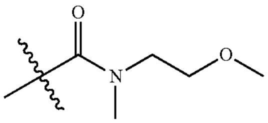 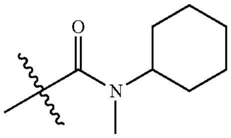

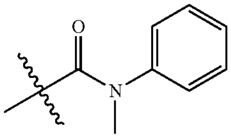 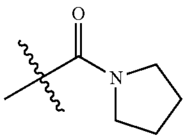

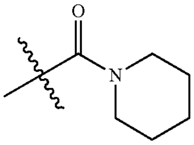 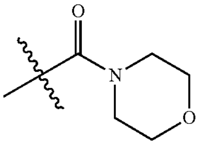 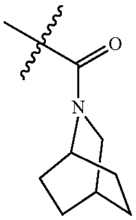

Embodiment 11. The compound according to any one of embodiments 1-7, wherein $R^1$ is —$CO_2R$.

Embodiment 12. The compound according to any one of embodiments 1-7, wherein $R^1$ is —$NO_2$.

Embodiment 13. The compound according to any one of embodiments 1-7, wherein $R^1$ is —C(O)R.

Embodiment 14. The compound according to any one of embodiments 1-7, wherein $R^1$ is —$S(O)_2R$.

Embodiment 15. The compound according to any one of embodiments 1-7, wherein $R^1$ is —$S(O)_2N(R)_2$.

Embodiment 16. The compound according to any one of embodiments 1-7, wherein $R^1$ is —$C(=NR)C(R)_2$.

Embodiment 17. The compound according to embodiment 16, wherein $R^1$ is selected from

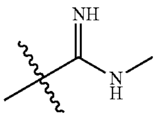 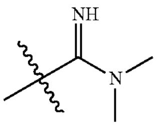 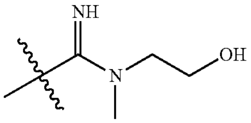

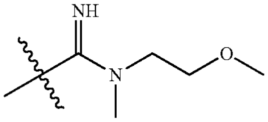 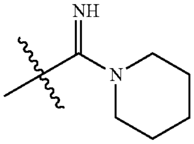

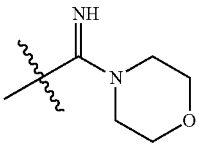

Embodiment 18. The compound according to any one of embodiments 1-7, wherein $R^1$ is a 5-membered heteroaryl ring having 2-3 heteroatoms independently selected from nitrogen, oxygen, and sulfur.

Embodiment 19. The compound according to embodiment 18, wherein $R^1$ is

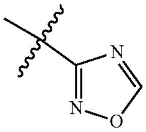.

Embodiment 20. The compound according to any one of embodiments 1-19, wherein $R^4$ is —H.

Embodiment 21. The compound according to any one of embodiments 1-19, wherein $R^4$ is —R, wherein —R is optionally substituted $C_{1-6}$ aliphatic.

Embodiment 22. The compound according to embodiment 21, wherein R is —$C_{1-6}$ alkyl.

Embodiment 23. The compound according to embodiment 22, wherein R is —$CH_3$.

Embodiment 24. The compound according to embodiment 22, wherein R is —$CH_2CH_3$.

Embodiment 25. The compound according to embodiment 22, wherein R is —$CH_2CH_2CH_3$.

Embodiment 26. The compound according to embodiment 22, wherein R is —$CH(CH_3)_2$.

Embodiment 27. The compound according to embodiment 21, wherein R is selected from —$CH_2C(O)NH_2$, —$CH_2CH_2N(CH_3)_2$, —$CH_2CH_2OH$, —$CH_2CH(CH_3)OH$, —$CH(CH_3)CH_2OH$, —$CH_2C(CH_3)_{20}H$, —$CH_2CH_2OCH_3$, —$CH_2C(CH_3)_2OCH_3$, —$CH(CH_3)CH_2OCH_3$, —$CH_2CH_2C(O)NH_2$, —$CH_2CH_2C(O)OH$, —$CH_2CH_2S(O)_2CH_3$, —$CH_2CH_2CH_2OCH_3$,

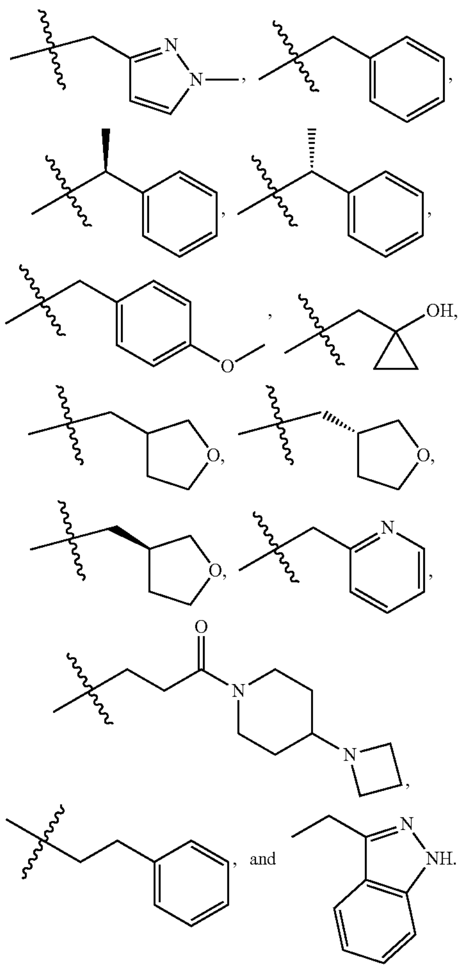

Embodiment 28. The compound according to any one of embodiments 1-27, wherein $R^3$ is -Cy.

Embodiment 29. The compound according to any one of embodiments 1-27, wherein $R^3$ is $—CH_2Cy$.

Embodiment 30. The compound according to embodiment 28 or embodiment 29, wherein -Cy is phenyl.

Embodiment 31. The compound according to embodiment 28 embodiment or embodiment 29, wherein -Cy is a 5- to 6-membered heteroaryl ring having 1-3 heteroatoms independently selected from nitrogen, oxygen, and sulfur.

Embodiment 32. The compound according to embodiment 31, wherein -Cy is a 6-membered heteroaryl ring having 1-3 nitrogen atoms.

Embodiment 33. The compound according to embodiment 32, wherein -Cy is pyridinyl.

Embodiment 34. The compound according to embodiment 28 or embodiment 29, wherein -Cy is an 8- to 10-membered bicyclic heteroaryl ring having 1-3 heteroatoms independently selected from nitrogen, oxygen, and sulfur.

Embodiment 35. The compound according to embodiment 34, wherein -Cy is a 10-membered bicyclic heteroaryl ring having 1-3 heteroatoms independently selected from nitrogen, oxygen, and sulfur.

Embodiment 36. The compound according to embodiment 35, wherein -Cy is a 10-membered bicyclic heteroaryl ring having 1 nitrogen atom.

Embodiment 37. The compound according to embodiment 36, wherein -Cy is quinolinyl.

Embodiment 38. The compound according to embodiment 28 or embodiment 29, wherein -Cy is an 8- to 10-membered bicyclic aryl ring.

Embodiment 39. The compound according to embodiment 38, wherein -Cy is a 10-membered bicyclic aryl ring.

Embodiment 40. The compound according to embodiment 39, wherein -Cy is 1-naphthyl.

Embodiment 41. The compound according to embodiment 39, wherein -Cy is 2-naphthyl.

Embodiment 42. The compound according to embodiment 28, wherein -Cy is selected from the group consisting of

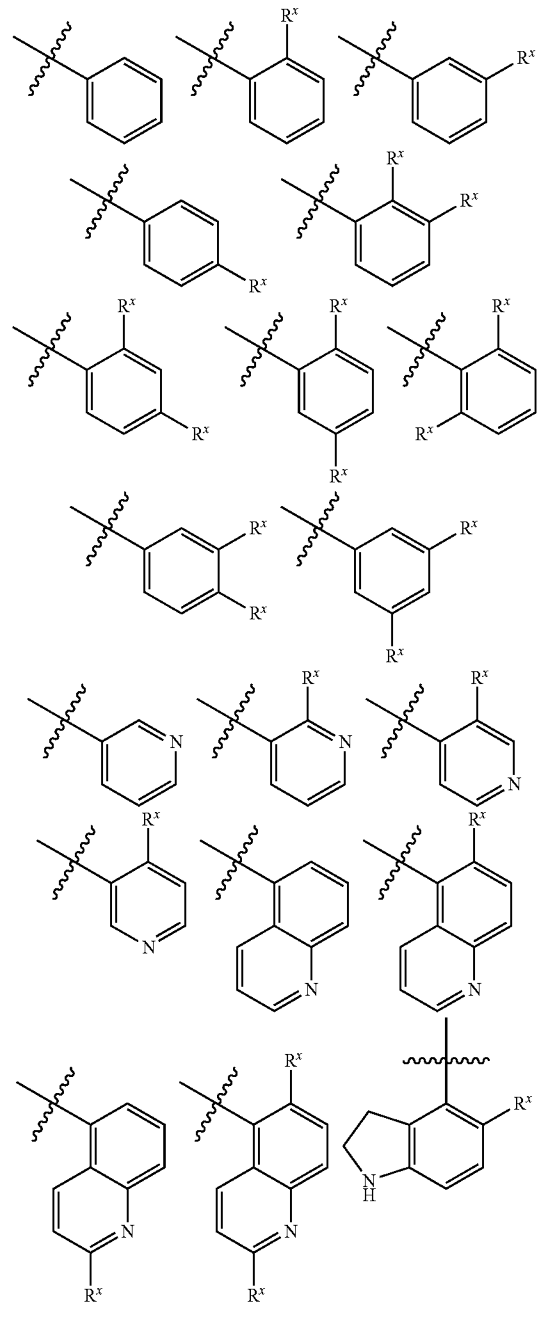

-continued

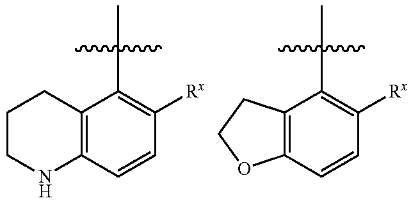

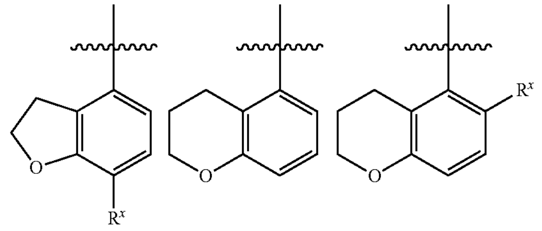

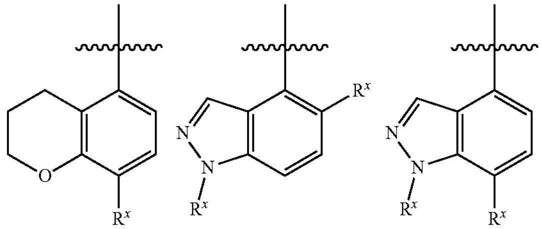

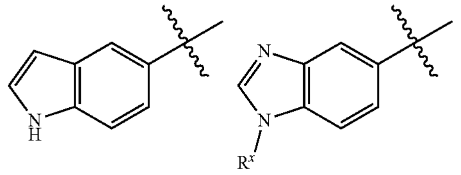

Embodiment 43. The compound according to embodiment 28, wherein -Cy is selected from the group consisting of

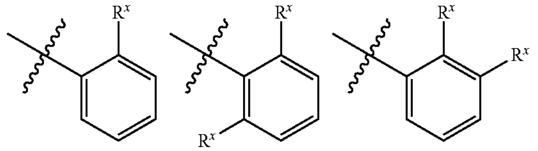

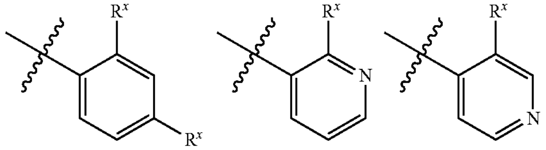

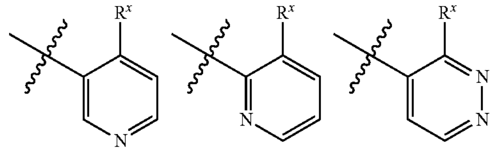

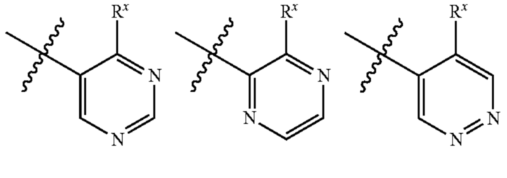

-continued

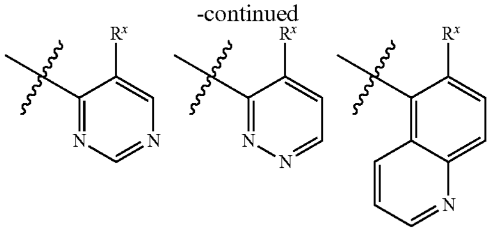

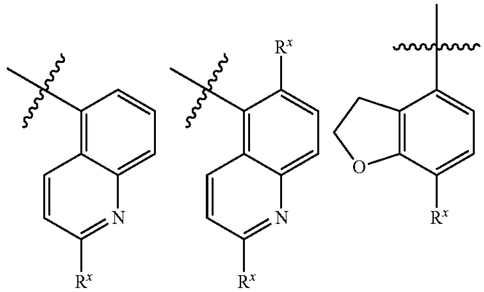

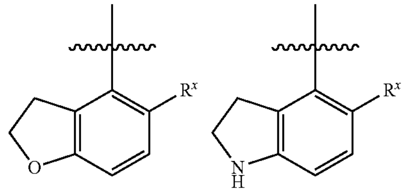

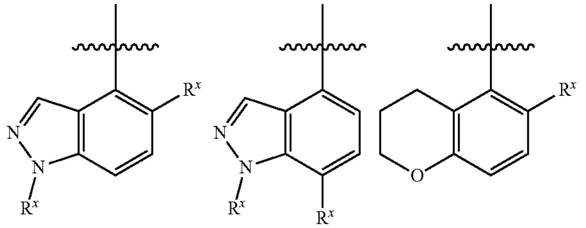

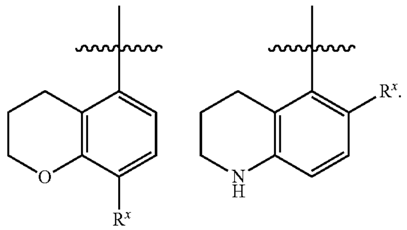

Embodiment 44. The compound according to any one of embodiments 28-43, wherein $R^x$ is halogen.

Embodiment 45. The compound according to embodiment 44, wherein $R^x$ is chloro.

Embodiment 46. The compound according to embodiment 44, wherein $R^x$ is fluoro.

Embodiment 47. The compound according to any one of embodiments 28-43, wherein $R^x$ is optionally substituted $-C_{1-6}$ aliphatic.

Embodiment 48. The compound according to embodiment 47, wherein $R^x$ is $-C_{1-6}$ alkyl.

Embodiment 49. The compound according to embodiment 48, wherein $R^x$ is $-CH_3$.

Embodiment 50. The compound according to embodiment 48, wherein $R^x$ is $-CH(CH_3)_2$.

Embodiment 51. The compound according to embodiment 47, wherein $R^x$ is $-C_{1-6}$ aliphatic optionally substituted with halogen.

Embodiment 52. The compound according to embodiment 51, wherein $R^x$ is $-CF_3$.

Embodiment 53. The compound according to any one of embodiments 28-43, wherein $R^x$ is $-OR$.

Embodiment 54. The compound according to embodiment 53, wherein R is optionally substituted —$C_{1-6}$ aliphatic.

Embodiment 55. The compound according to embodiment 54, wherein R is —$C_{1-6}$ alkyl.

Embodiment 56. The compound according to embodiment 55, wherein R is —$CH_3$.

Embodiment 57. The compound according to embodiment 54, wherein R is —$C_{1-6}$ aliphatic optionally substituted with halogen.

Embodiment 58. The compound according to embodiment 57, wherein R is —$CF_3$.

Embodiment 59. The compound according to any one of embodiments 28-43, wherein $R^x$ is —SR.

Embodiment 60. The compound according to embodiment 59, wherein —R is optionally substituted —$C_{1-6}$ aliphatic.

Embodiment 61. The compound according to embodiment 60, wherein —R is —$C_{1-6}$ alkyl.

Embodiment 62. The compound according to embodiment 61, wherein —R is —$CH_3$.

Embodiment 63. The compound according to any one of embodiments 28-43, wherein —$R^x$ is —$SO_2R$.

Embodiment 64. The compound according to embodiment 63, wherein R is —$C_{1-6}$ alkyl.

Embodiment 65. The compound according to embodiment 64, wherein R is —$CH_3$.

Embodiment 66. The compound according to embodiment 1 or embodiment 2, wherein:

$R^1$ is selected from —CN and —$CONH_2$; and $R^2$ is selected from —H and —$CH_3$.

Embodiment 67. The compound according to embodiment 1 or embodiment 2, wherein:

$R^1$ is selected from —CN and —$CONH_2$;

$R^2$ is selected from —H and —$CH_3$;

$R^3$ is -Cy; and

—Cy is selected from

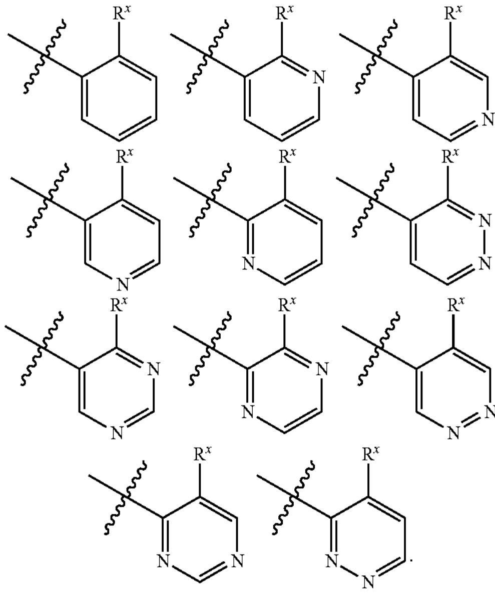

Embodiment 68. The compound according to embodiment 67, wherein:

$R^1$ is —CN; and $R^2$ is —H.

Embodiment 69. The compound according to embodiment 67, wherein:

$R^1$ is —$CONH_2$; and $R^2$ is —H.

Preparation of Compounds of Formula I or Formula II

Compounds of Formula I or Formula II may be prepared as shown in Scheme Ia and Ib below.

Scheme Ia:

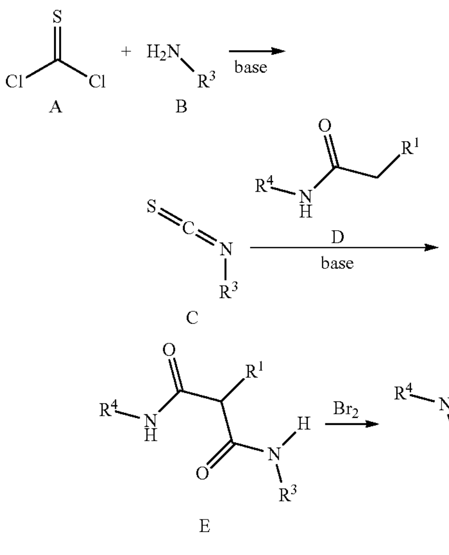

In Scheme Ia, thiophosgene A and amine B are coupled together in the presence of a suitable base to give the isothiocyanate C. Treatment of isocyanate C with amide D in the presence of a suitable base affords the thioamide E that is subjected to treatment with bromine to give the compound of general Formula I or Formula II where $R^2$ is H and $R^1$ is —CN or —$CONH_2$, the latter resulting from hydrolysis of the CN during this step.

Scheme Ib:

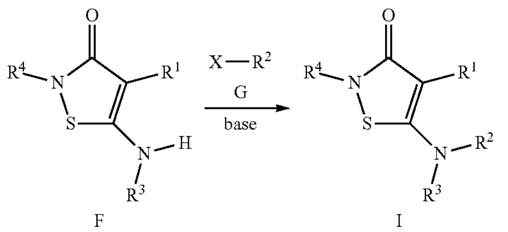

In Scheme Ib, compound F is treated with a suitable base and compound G where X is a suitable leaving group to afford compounds of general Formula I or Formula II where $R^2$ is —$C_{1-6}$ alkyl.

Compositions

In some embodiments, a compound of Formula I or Formula II may be provided in a composition, e.g., in combination (e.g., admixture) with one or more other components.

In some embodiments, the present disclosure provides compositions that comprise and/or deliver a compound of Formula I or Formula II, or an active metabolite thereof, e.g., when contacted with or otherwise administered to a system or environment e.g., which system or environment may include SARM1 NADase activity; in some embodiments, administration of such a composition to the system or environment achieves inhibition of SARM1 activity as described herein.

In some embodiments, a provided composition as described herein may be a pharmaceutical composition in that it comprises an active agent and one or more pharmaceutically acceptable excipients; in some such embodiments, a provided pharmaceutical composition comprises and/or delivers a compound of Formula I or Formula II, or an active metabolite thereof to a relevant system or environment (e.g., to a subject in need thereof) as described herein.

In some embodiments, one or more compounds of Formula I or Formula II is provided and/or utilized in a pharmaceutically acceptable salt form.

Among other things, the present disclosure provides compositions comprising a compound of Formula I or Formula II, or a pharmaceutically acceptable salt or derivative thereof, and a pharmaceutically acceptable carrier, adjuvant, or vehicle. The amount of compound in provided compositions is such that is effective to measurably inhibit axonal degeneration in a biological sample or in a patient. In certain embodiments, a provided compound or composition is formulated for administration to a patient in need of such composition. The compounds and compositions, according to the methods of the present disclosure, may be administered using any amount and any route of administration effective for treating or lessening the severity of any disease or disorder described herein. Provided compounds are preferably formulated in dosage unit form for ease of administration and uniformity of dosage. The expression "dosage unit form" as used herein refers to a physically discrete unit of agent appropriate for the patient to be treated. It will be understood, however, that the total daily usage of the provided compounds and compositions will be decided by the attending physician within the scope of sound medical judgment. The specific effective dose level for any particular patient or organism will vary from subject to subject, depending on a variety of factors, including the disorder being treated and the severity of the disorder; the activity of the specific compound employed; the specific composition employed and its route of administration; the species, age, body weight, sex and diet of the patient; the general condition of the subject; the time of administration; the rate of excretion of the specific compound employed; the duration of the treatment; drugs used in combination or coincidental with the specific compound employed, and the like.

Provided compositions may be administered orally, parenterally, by inhalation or nasal spray, topically (e.g., as by powders, ointments, or drops), rectally, buccally, intravaginally, intraperitoneally, intracisternally or via an implanted reservoir, depending on the severity of the condition being treated. Preferably, the compositions are administered orally, intraperitoneally or intravenously. In certain embodiments, provided compounds are administered orally or parenterally at dosage levels of about 0.01 mg/kg to about 50 mg/kg, of subject body weight per day, one or more times a day, to obtain the desired therapeutic effect.

The term "parenteral" as used herein includes subcutaneous, intravenous, intramuscular, intra-articular, intra-synovial, intrasternal, intrathecal, intrahepatic, intralesional and intracranial injection or infusion techniques. Sterile injectable forms of provided compositions may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a provided compound, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Pharmaceutically acceptable compositions described herein may be orally administered in any orally acceptable dosage form including, but not limited to, capsules, tablets, aqueous suspensions or solutions. In such solid dosage forms the active compound may be admixed with at least one inert diluent such as sucrose, lactose or starch. Such dosage forms may also comprise, as is normal practice, additional substances other than inert diluents, e.g., lubricants and other tableting aids such a magnesium stearate and microcrystalline cellulose. When aqueous suspensions are required for oral use, the active ingredient is combined with emulsifying and suspending agents. If desired, certain sweetening, flavoring or coloring agents may also be added.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and/or i) lubricants such as talc, calcium stearate, magnesium stearate, solid polyethylene glycols, sodium lauryl sulfate, and mixtures thereof. In the case of capsules, tablets and pills, the dosage form may also comprise buffering agents. The active compounds can also be in micro-encapsulated form with one or more excipients as noted above.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings (i.e. buffering agents) and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Alternatively, pharmaceutically acceptable compositions described herein may be administered in the form of suppositories for rectal or vaginal administration. These can be prepared by mixing the compounds of the present disclosure with suitable non-irritating excipients or carriers that are solid at room temperature but liquid at body (e.g. rectal or vaginal) temperature and therefore will melt in the rectum or vaginal cavity to release the active compound. Such materials include cocoa butter, a suppository wax (e.g., beeswax) and polyethylene glycols.

Pharmaceutically acceptable compositions described herein may also be administered topically, especially when the target of treatment includes areas or organs readily accessible by topical application, including diseases of the eye, the skin, or the lower intestinal tract. Topical application for the lower intestinal tract can be effected in a rectal suppository formulation (see above) or in a suitable enema formulation.

Dosage forms for topical or transdermal administration of a provided compound include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulations, ear drops, and eye drops are also contemplated as being within the scope of this disclosure. Additionally, the present disclosure contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

For topical applications, provided pharmaceutically acceptable compositions may be formulated in a suitable ointment containing the active component suspended or dissolved in one or more carriers. Carriers for topical administration of compounds of this disclosure include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this disclosure may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this disclosure are formulated for oral administration.

Identification and/or Characterization of Compounds and/or Compositions

Among other things, the present disclosure provides various technologies for identification and/or characterization of compounds and/or compositions as described herein. For example, the present disclosure provides various assays for assessing SARM1 inhibitory activity, and specifically for assessing SARM1 inhibitory activity.

In some embodiments, performance of one or more compounds or compositions of interest in an assay as described herein is compared with that of an appropriate reference. For example, in some embodiments, a reference may be absence of the relevant compound or composition. Alternatively or additionally, in some embodiments, a reference may be presence of an alternative compound or composition, e.g., which alternative compound or composition has known performance (e.g., as a positive control or a negative control, as is understood in the art) in the relevant assay. In some embodiments, a reference may be an alternative but comparable set of conditions (e.g., temperature, pH, salt concentration, etc.). In some embodiments, a reference may be performance of the compound or composition with respect to a SARM1 variant.

Still further alternatively or additionally, in some embodiments, performance of one or more compounds or compositions of interest in an assay as described herein may be assessed in the presence of an appropriate reference compound or composition, for example, so that ability of the compound or composition to compete with the reference is determined.

In some embodiments, a plurality of compounds or compositions of interest may be subjected to analysis in a particular assay and/or compared with the same reference. In some embodiments, such a plurality of compounds or compositions may be or include a set of compounds or compositions that is considered to be a "library" because multiple members share one or more features (e.g., structural elements, source identity, synthetic similarities, etc.).

Certain exemplary assays that may be useful in the practice of the present disclosure are exemplified in the Examples below. Those skilled in the art, reading the present disclosure, will be aware that useful or relevant systems for identifying and/or characterizing compounds and/or compositions in accordance with the present disclosure are not limited to those included in the Examples, or otherwise discussed below.

In some embodiments, compounds and/or compositions may be identified based on and/or characterized by one or more activities or characteristics such as, for example: promoting axonal integrity, cytoskeletal stability, and/or neuronal survival. In some embodiments, provided SARM1 inhibitors inhibit catabolism of NAD+ to by SARM1. In some embodiments, provided SARM1 inhibitors slow the rate of NAD+ catabolism.

In some embodiments, provided SARM1 inhibitors reduce or inhibit binding of NAD+ by SARM1. In some embodiments, provided SARM1 inhibitors bind to SARM1 within a pocket comprising one or more catalytic residues (e.g., a catalytic cleft of SARM1). Examples of such catalytic residues include the glutamic acid at position 642 (E642).

In some embodiments, provided SARM1 inhibitors disrupt and/or prevent multimerization of the TIR1 domain of SARM1. In some embodiments, provided SARM1 inhibitors disrupt the multimerization of the SAM domains. In some embodiments, provided SARM1 inhibitors disrupt the axonal signaling cascade that leads to depletion of NAD+.

In some embodiments, the present disclosure provides assays useful for identifying and/or characterizing one or more activities and/or characteristics of compound and/or compositions of interest. For example, in some embodiments, the present disclosure provides in vitro, cellular, and/or in vivo systems for assessing one or more such activities and/or characteristics.

SARM1 Activity Assays

In some embodiments, a method of identifying a SARM1 inhibitor comprises: a) providing a mixture comprising i) a mutant or fragment of SARM1, ii) NAD+ and iii) a candidate inhibitor, wherein the mutant or fragment has constitutive activity; b) incubating the mixture; c) quantifying NAD+ in the mixture after the incubating; and d) identifying the candidate inhibitor compound as an inhibitor if the amount of NAD+ is greater than that of a control mixture that does not contain the candidate inhibitor.

In some embodiments, provided are methods of identifying a SARM1 inhibitor, comprising: a) providing a mixture comprising i) a full-length SARM1, ii) NAD+ and iii) a candidate inhibitor, wherein the full-length SARM1 has constitutive activity; b) incubating the mixture; c) quantifying NAD+ and ADPR (or cADPR) in the mixture after the incubating; d) determining the molar ratio of NAD+: ADPR (or cADPR); and e) identifying the candidate inhibitor compound as an inhibitor if the molar ratio is greater than that of a control mixture that does not contain the candidate inhibitor.

In some embodiments, provided are methods of identifying a SARM1 inhibitor, comprising: a) providing a mixture comprising a solid support to which is bound i) a full-length SARM1 and at least one tag, ii) NAD+, and iii) a candidate inhibitor; b) incubating the mixture; c) quantifying the NAD+ after the incubating; and d) identifying the candidate inhibitor compound as a SARM1 inhibitor if the concentration of NAD+ is greater than that of a control.

SARM1 Binding Assays

In some embodiments, the efficacy of provided SARM1 inhibitors can be determined according to, e.g., the assays described in WO 2018/057989, published on Mar. 29, 2018, which is hereby incorporated by reference in its entirety. In some embodiments, the provided SARM1 inhibitors can be applied to a solution containing SARM1 or a fragment thereof. In some embodiments, the provided SARM1 inhibitors can be applied to an in vitro system. In some embodiments, the provided SARM1 inhibitors can be applied to an in vivo. In some embodiments, the provided SARM1 inhibitors can be applied to a patient. In some embodiments, a SARM1 inhibitor can be mixed with SARM1 or fragment thereof that has been labeled with an epitope tag. In some embodiments, the amount of bound SARM1 inhibitor can be compared to the amount of unbound SARM1 inhibitor, yielding the affinity for the SARM1 inhibitor.

In some embodiments, the mutant or fragment of SARM1 is a SAM-TIR fragment having constitutive activity. Fragments of SARM1 having constitutive activity include, for example and without limitation, a SARM1 with the autoinhibitory domain deleted; at least one point mutation of SARM1 that renders the autoinhibitory domain inactive; a fragment of SARM1 containing a TIR domain; or a fragment of SARM1 consisting of SAM and TIR domains. In some embodiments a SARM1 polypeptide can include one or more additional amino acid sequences that can act as tags, such as a His tag, a streptavidin tag, or a combination thereof. In some embodiments a SARM1 polypeptide can include a tag at the amino terminus, at the carboxy terminus, or a combination thereof. In some embodiments, SARM1 or fragment thereof labeled with an epitope tag can be used to measure the binding efficacy of provided SARM1 inhibitors.

Purification of SARM1-TIR Domains

In some embodiments, a SARM1-TIR domain can be engineered with various protein, or epitope, tags, that can be useful, for example, in purification. In some embodiments, the present disclosure also provides for a NRK1-HEK293T cell line comprising HEK293T cells transformed with a Nicotinamide Riboside Kinase 1 (NRK1). In some embodiments, HEK293T cells transformed or transfected with a DNA sequence encoding Nicotinamide Riboside Kinase 1 (NRK1). In some embodiments, the DNA encoding NRK1 can be genomic or cDNA. In some embodiments, HEK293T cells are stably or transiently transfected with DNA encoding NRK1 from a source exogenous to the host cell. In some embodiments, HEK293T cells are stably or transiently transfected with DNA encoding NRK1 such that the cells express NRK1 at an elevated level compared to control cells. In some embodiments, DNA encoding NRK1 is under the control of one or more exogenous regulatory DNA sequences such as a promoter, an enhancer or a combination thereof. In some embodiments, a combination of a DNA sequences encoding NRK1 and regulatory sequences is a non-naturally occurring combination. In some embodiments, DNA encoding NRK1, either genomic or cDNA, comprises an expression vector such as an FCIV expression vector. In some embodiments, DNA encoding NRK1 is derived from genomic DNA or cDNA from a vertebrate or invertebrate species such as, but not limited to, human, mouse, zebrafish or a *Drosophila*. In some configurations, the NRK1 DNA is a human NRK1 DNA.

Applications and Uses

The present disclosure provides a variety of uses and applications for compounds and/or compositions as described herein, for example in light of their activities and/or characteristics as described herein. In some embodiments, such uses may include therapeutic and/or diagnostic uses. Alternatively, in some embodiments such uses may include research, production, and/or other technological uses.

In one aspect, the present disclosure provides methods comprising administering one or more compounds of Formula I or Formula II to a subject, e.g., to treat, prevent, or reduce the risk of developing one or more conditions characterized by axonal degeneration. In some such embodiments, the compound of Formula I or Formula II is a SARM1 inhibitor.

Another embodiment of the present disclosure relates to a method of inhibiting SARM1 activity in a patient comprising steps of administering to said patient a provided compound, or a composition comprising said compound.

Inhibition of enzymes in a biological sample is useful for a variety of purposes that are known to one of skill in the art. Examples of such purposes include, but are not limited to biological assays, gene expression studies, and biological target identification.

In certain embodiments, the present disclosure relates to a method of treating axonal degeneration in a biological sample comprising the step of contacting said biological sample with a compound or composition of Formula I or Formula II. In some embodiments, one or more compounds and/or compositions as described herein are useful, for example as a method of for inhibiting the degradation of neurons derived from a subject. In some embodiments, one or more compounds and/or compositions as described herein, are useful for inhibiting the degeneration of a neuron, or portion thereof, cultured in vitro. In some embodiments, one or more compounds and/or compositions as described herein, are useful as stabilizing agents to promote in vitro neuronal survival.

In some embodiments, provided compounds and/or compositions inhibit NADase activity of SARM1. Alternatively or additionally, in some embodiments, provided compounds alleviate one or more attributes of neurodegeneration. In some embodiments, the present disclosure provides methods of treating a neurodegenerative disease or disorder associated with axonal degeneration.

In some embodiments, one or more compounds and/or compositions as described herein are useful, for example, in the practice of medicine. In some embodiments, one or more compounds and/or compositions as described herein are useful, for example, to treat, prevent, or ameliorate axonal degeneration (e.g., one or more features or characteristics thereof). In some embodiments, one or more compounds and/or compositions as described herein are useful, for example to inhibit axonal degeneration, including axonal degeneration that results from reduction or depletion of NAD+. In some embodiments, one or more compounds and/or compositions as described herein are useful, for example to prevent the axon distal to an axonal injury from degenerating.

In some embodiments, one or more compounds and/or compositions as described herein are useful, for example as a method for inhibiting the degradation of a peripheral nervous system neuron or a portion thereof. In some embodiments, one or more compounds and/or compositions as described herein are useful, for example as a method for inhibiting or preventing degeneration of a central nervous system (neuron) or a portion thereof. In some embodiments, one or more compounds or compositions as described herein is characterized that, when administered to a population of subjects, reduces one or more symptoms or features of neurodegeneration. For example, in some embodiments, a relevant symptom or feature may be selected from the group consisting of extent, rate, and/or timing of neuronal disruption.

In certain embodiments, the present disclosure provides compounds that are useful, for example, as analytical tools, as probes in biological assays, or as therapeutic agents in accordance with the present disclosure. Compounds provided by this disclosure are also useful for the study of SARM1 activity in biological and pathological phenomena and the comparative evaluation of new SARM1 activity inhibitors in vitro or in vivo. In certain embodiments, the present disclosure provides assays for identifying and/or characterizing compounds and/or compositions provided herein. In some embodiments, provided assays utilize particular reagents and/or systems (e.g., certain vector constructs and/or polypeptides) useful in assaying SARM1 activity. For example, in some embodiments, provided assays may utilize, for example, a SAM-TIR in which the SARM1 N-terminal auto-inhibitory domain is deleted, and/or one or more tagged versions of a TIR domain.

In some embodiments, one or more compounds and/or compositions as described herein are useful, for example as a method of for inhibiting the degradation of neurons derived from a subject. In some embodiments, one or more compounds and/or compositions as described herein, are useful for inhibiting the degeneration of a neuron, or portion thereof, cultured in vitro. In some embodiments, one or more compounds and/or compositions as described herein, are useful as stabilizing agents to promote in vitro neuronal survival.

In some embodiments, one or more compounds and/or compositions as described herein are useful, for example in affecting biomarkers associated with neurodegeneration. In some embodiments, changes in biomarkers can be detected systemically or with a sample of cerebral spinal fluid (CSF), plasma, serum, and/or tissue from a subject. In some embodiments, one or more compounds and/or compositions can be used to affect a change in the concentration of neurofilament protein light (NF-L) and/or neurofilament protein heavy (NF-H) contained the cerebral spinal fluid of a subject. In some embodiments, one or more compounds and/or compositions as described herein can affect constitutive NAD and/or cADPR levels in neurons and/or axons.

In some embodiments, one or more compounds and/or compositions as described herein can affect a detectable change in the levels of one or more neurodegeneration-associated proteins in a subject. Such proteins include, but are not limited to, albumin, amyloid-β (Aβ)38, Aβ40, Aβ42, glial fibrillary acid protein (GFAP), heart-type fatty acid binding protein (hFABP), monocyte chemoattractin protein (MCP)-1, neurogranin, neuron specific enolayse (NSE), soluble amyloid precursor protein (sAPP)α, sAPPβ, soluble triggering receptor expressed on myeloid cells (sTREM) 2, phospho-tau, and/or total-tau. In some embodiments, one or more compounds and/or compositions as described herein can affect a change in cytokines and/or chemokines, including, but not limited to, Ccl2, Ccl7, Ccl12, Csf1, and/or Il6.

Diseases, Disorders, and Conditions

In some embodiments, compounds and/or compositions as described herein may be administered to subjects suffering from one or more diseases, disorders, or conditions.

In some embodiments, the condition is an acute condition. In some embodiments, the condition is a chronic condition.

In some embodiments, the condition is characterized by axonal degeneration in the central nervous system, the peripheral nervous system, the optic nerve, the cranial nerves, or a combination thereof.

In some embodiments, the condition is or comprises acute injury to the central nervous system, e.g., injury to the spinal cord and/or traumatic brain injury. In some embodiments, the condition is or comprises a chronic injury to the central nervous system, e.g., injury to the spinal cord, traumatic brain injury, and/or traumatic axonal injury. In some embodiments, the condition is or comprises chronic traumatic encephalopathy (CTE).

In some embodiments, the condition is a chronic condition affecting the central nervous system, e.g., Parkinson's disease, amyotrophic lateral sclerosis, multiple sclerosis, or Huntington disease, Alzheimer's disease.

In some embodiments, the condition is an acute peripheral neuropathy. Chemotherapy-induced peripheral neuropathy (CIPN) is an example of an acute peripheral neuropathy. CIPN can be associated with various drugs, such as, but not limited to, thalidomide, epothilones (e.g., ixabepilone), taxanes (e.g., paclitaxel and docetaxel), vinca alkaloids (e.g., vinblastine, vinorelbine, vincristine, and vindesine), proteasome inhibitors (e.g., bortezomib), platinum-based drugs (e.g., cisplatin, oxaliplatin, and carboplatin).

In some embodiments, the condition is a chronic condition affecting the peripheral nervous system, e.g., diabetic neuropathy, HIV neuropathy, Charcot Marie Tooth disease, or amyotrophic lateral sclerosis.

In some embodiments, the condition is an acute condition affecting the optic nerve, e.g., acute optic neuropathy (AON) or acute angle closure glaucoma.

In some embodiments, the condition is a chronic condition affecting the optic nerve, e.g., Leber's congenital amaurosis, Leber's hereditary optic neuropathy, primary open angle glaucoma, and autosomal dominant optic atrophy.

In some embodiments, one or more compounds and/or compositions as described herein are useful, for example, to treat one or more neurodegenerative diseases, disorders or conditions selected from the group consisting of neuropathies or axonopathies. In some embodiments, one or more compounds and/or compositions as described herein are useful, for example to treat a neuropathy or axonopathy associated with axonal degeneration. In some embodiments, a neuropathy associated with axonal degeneration is a hereditary or congenital neuropathy or axonopathy. In some embodiments, a neuropathy associated with axonal degeneration results from a de novo or somatic mutation. In some embodiments, a neuropathy associated with axonal degeneration is selected from a list contained herein. In some embodiments, a neuropathy or axonopathy is associated with axonal degeneration, including, but not limited to Parkinson's disease, non-Parkinson's disease, Alzheimer's disease, Herpes infection, diabetes, amyotrophic lateral sclerosis, a demyelinating disease, ischemia or stroke, chemical injury, thermal injury, and AIDS.

In some embodiments, one or more compounds or compositions as described herein is characterized that, when administered to a population of subjects, reduces one or more symptoms or features of neurodegeneration. For example, in some embodiments, a relevant symptom or feature may be selected from the group consisting of extent, rate, and/or timing of neuronal disruption. In some embodiments, neuronal disruption may be or comprise axonal degradation, loss of synapses, loss of dendrites, loss of synaptic density, loss of dendritic arborization, loss of axonal branching, loss of neuronal density, loss of myelination, loss of neuronal cell bodies, loss of synaptic potentiation, loss of action-potential potentiation, loss of cytoskeletal stability, loss of axonal transport, loss of ion channel synthesis and turnover, loss of neurotransmitter synthesis, loss of neurotransmitter release and reuptake capabilities, loss of axon-potential propagation, neuronal hyperexitability, and/or neuronal hypoexcitability. In some embodiments, neuronal disruption is characterized by an inability to maintain an appropriate resting neuronal membrane potential. In some embodiments, neuronal disruption is characterized by the appearance of inclusion bodies, plaques, and/or neurofibrillary tangles. In some embodiments, neuronal disruption is characterized by the appearance of stress granules. In some embodiments, neuronal disruption is characterized by the intracellular activation of one or more members of the cysteine-aspartic protease (Caspase) family. In some embodiments, neuronal disruption is characterized by a neuron undergoing programed cell death (e.g. apoptosis, pyroptosis, ferroapoptosis, and/or necrosis) and/or inflammation.

In some embodiments, the neurodegenerative or neurological disease or disorder is associated with axonal degeneration, axonal damage, axonopathy, a demyelinating disease, a central pontine myelinolysis, a nerve injury disease or disorder, a metabolic disease, a mitochondrial disease, metabolic axonal degeneration, axonal damage resulting from a leukoencephalopathy or a leukodystrophy. In some embodiments, the neurodegenerative or neurological disease or disorder is selected from the group consisting of spinal cord injury, stroke, multiple sclerosis, progressive multifocal leukoencephalopathy, congenital hypomyelination, encephalomyelitis, acute disseminated encephalomyelitis, central pontine myelolysis, osmotic hyponatremia, hypoxic demyelination, ischemic demyelination, adrenoleukodystrophy, Alexander's disease, Niemann-Pick disease, Pelizaeus Merzbacher disease, periventricular leukomalacia, globoid cell leukodystrophy (Krabbe's disease), Wallerian degeneration, optic neuritis, transverse myelitis, amyotrophic lateral sclerosis (ALS, Lou Gehrig's disease), Huntington's disease, Alzheimer's disease, Parkinson's disease, Tay-Sacks disease, Gaucher's disease, Hurler Syndrome, traumatic brain injury, post radiation injury, neurologic complications of chemotherapy (chemotherapy induced neuropathy; CIPN), neuropathy, acute ischemic optic neuropathy, vitamin B12 deficiency, isolated vitamin E deficiency syndrome, Bassen-Kornzweig syndrome, Glaucoma, Leber's hereditary optic atrophy (neuropathy), Leber congenital amaurosis, neuromyelitis optica, metachromatic leukodystrophy, acute hemorrhagic leukoencephalitis, trigeminal neuralgia, Bell's palsy, cerebral ischemia, multiple system atrophy, traumatic glaucoma, tropical spastic paraparesis human T-lymphotropic virus 1 (HTLV-1) associated myelopathy, west Nile virus encephalopathy, La Crosse virus encephalitis, Bunyavirus encephalitis, pediatric viral encephalitis, essential tremor, Charcot-Marie-Tooth disease, motor neuron disease, spinal muscular atrophy (SMA), hereditary sensory and autonomic neuropathy (HSAN), adrenomyeloneuropathy, progressive supra nuclear palsy (PSP), Friedrich's ataxia, hereditary ataxias, noise induced hearing loss, congenital hearing loss, Lewy Body Dementia, frontotemporal dementia, amyloidosis, diabetic neuropathy, HIV neuropathy, enteric neuropathies and axonopathies, Guillain-Barre syndrome, severe acute motor axonal neuropathy (AMAN), Creutzfeldt-Jakob disease, transmissible spongiform encephalopathy, spinocerebellar ataxias, pre-eclampsia, hereditary spastic paraplegias, spastic paraparesis, familial spastic paraplegia, French settlement disease, Strumpell-Lorrain disease, and non-alcoholic steatohepatitis (NASH).

In some embodiments, the present disclosure provides inhibitors of SARM1 activity for treatment of neurodegenerative or neurological diseases or disorders that involve axon degeneration or axonopathy. The present disclosure also provides methods of using inhibitors of SARM1 activity to treat, prevent or ameliorate axonal degeneration, axonopathies and neurodegenerative or neurological diseases or disorders that involve axonal degeneration.

In some embodiments, the present disclosure provides methods of treating neurodegenerative or neurological diseases or disorders related to axonal degeneration, axonal damage, axonopathies, demyelinating diseases, central pontine myelinolysis, nerve injury diseases or disorders, metabolic diseases, mitochondrial diseases, metabolic axonal degeneration, axonal damage resulting from a leukoencephalopathy or a leukodystrophy.

In some embodiments, neuropathies and axonopathies include any disease or condition involving neurons and/or supporting cells, such as for example, glia, muscle cells or fibroblasts, and, in particular, those diseases or conditions involving axonal damage. Axonal damage can be caused by traumatic injury or by non-mechanical injury due to diseases, conditions, or exposure to toxic molecules or drugs. The result of such damage can be degeneration or dysfunction of the axon and loss of functional neuronal activity. Disease and conditions producing or associated with such axonal damage are among a large number of neuropathic diseases and conditions. Such neuropathies can include peripheral neuropathies, central neuropathies, and combinations thereof. Furthermore, peripheral neuropathic manifestations can be produced by diseases focused primarily in the central nervous systems and central nervous system manifestations can be produced by essentially peripheral or systemic diseases.

In some embodiments, a peripheral neuropathy can involve damage to the peripheral nerves, and/or can be caused by diseases of the nerves or as the result of systemic illnesses. Some such diseases can include diabetes, uremia, infectious diseases such as AIDs or leprosy, nutritional deficiencies, vascular or collagen disorders such as atherosclerosis, and autoimmune diseases such as systemic lupus erythematosus, scleroderma, sarcoidosis, rheumatoid arthritis, and polyarteritis nodosa. In some embodiments, peripheral nerve degeneration results from traumatic (mechanical) damage to nerves as well as chemical or thermal damage to nerves. Such conditions that injure peripheral nerves include compression or entrapment injuries such as glaucoma, carpal tunnel syndrome, direct trauma, penetrating injuries, contusions, fracture or dislocated bones; pressure involving superficial nerves (ulna, radial, or peroneal) which can result from prolonged use of crutches or staying in one position for too long, or from a tumor; intraneural hemorrhage; ischemia; exposure to cold or radiation or certain medicines or toxic substances such as herbicides or pesticides. In particular, the nerve damage can result from chemical injury due to a cytotoxic anticancer agent such as, for example, taxol, cisplatinin, a proteasome inhibitor, or a vinca alkaloid such as vincristine. Typical symptoms of such peripheral neuropathies include weakness, numbness, paresthesia (abnormal sensations such as burning, tickling, pricking or tingling) and pain in the arms, hands, legs and/or feet. In some embodiments, a neuropathy is associated with mitochondrial dysfunction. Such neuropathies can exhibit decreased energy levels, i.e., decreased levels of NAD and ATP.

In some embodiments, peripheral neuropathy is a metabolic and endocrine neuropathy which includes a wide spectrum of peripheral nerve disorders associated with systemic diseases of metabolic origin. These diseases include, for example, diabetes mellitus, hypoglycemia, uremia, hypothyroidism, hepatic failure, polycythemia, amyloidosis, acromegaly, porphyria, disorders of lipid/glycolipid metabolism, nutritional/vitamin deficiencies, and mitochondrial disorders, among others. The common hallmark of these diseases is involvement of peripheral nerves by alteration of the structure or function of myelin and axons due to metabolic pathway dysregulation.

In some embodiments, neuropathies include optic neuropathies such as glaucoma; retinal ganglion degeneration such as those associated with retinitis pigmentosa and outer retinal neuropathies; optic nerve neuritis and/or degeneration including that associated with multiple sclerosis; traumatic injury to the optic nerve which can include, for example, injury during tumor removal; hereditary optic neuropathies such as Kjer's disease and Leber's hereditary optic neuropathy; ischemic optic neuropathies, such as those secondary to giant cell arteritis; metabolic optic neuropathies such as neurodegenerative diseases including Leber's neuropathy mentioned earlier, nutritional deficiencies such as deficiencies in vitamins B12 or folic acid, and toxicities such as due to ethambutol or cyanide; neuropathies caused by adverse drug reactions and neuropathies caused by vitamin deficiency. Ischemic optic neuropathies also include non-arteritic anterior ischemic optic neuropathy.

In some embodiments neurodegenerative diseases that are associated with neuropathy or axonopathy in the central nervous system include a variety of diseases. Such diseases include those involving progressive dementia such as, for example, Alzheimer's disease, senile dementia, Pick's disease, and Huntington's disease; central nervous system diseases affecting muscle function such as, for example, Parkinson's disease, motor neuron diseases and progressive ataxias such as amyotrophic lateral sclerosis; demyelinating diseases such as, for example multiple sclerosis; viral encephalitides such as, for example, those caused by enteroviruses, arboviruses, and herpes simplex virus; and prion diseases. Mechanical injuries such as glaucoma or traumatic injuries to the head and spine can also cause nerve injury and degeneration in the brain and spinal cord. In addition, ischemia and stroke as well as conditions such as nutritional deficiency and chemical toxicity such as with chemotherapeutic agents can cause central nervous system neuropathies.

In some embodiments, the present disclosure provides a method of treating a neuropathy or axonopathy associated with axonal degeneration. In some such embodiments, a neuropathy or axonopathy associated with axonal degeneration can be any of a number of neuropathies or axonopathies such as, for example, those that are hereditary or congenital or associated with Parkinson's disease, Alzheimer's disease, Herpes infection, diabetes, amyotrophic lateral sclerosis, a demyelinating disease, ischemia or stroke, chemical injury, thermal injury, and AIDS. In addition, neurodegenerative diseases not mentioned above as well as a subset of the above mentioned diseases can also be treated with the methods of the present disclosure. Such subsets of diseases can include Parkinson's disease or non-Parkinson's diseases, or Alzheimer's disease.

Subjects

In some embodiments, compounds and/or compositions as described herein are administered to subjects suffering from or susceptible to a disease, disorder or condition as described herein; in some embodiments, such a disease, disorder or condition is characterized by axonal degeneration, such as one of the conditions mentioned herein.

In some embodiments, a subject to whom a compound or composition is administered as described herein exhibits one or more signs or symptoms associated with axonal degeneration; in some embodiments, the subject does not exhibit any signs or symptoms of neurodegeneration.

In some embodiments, provided methods comprise administering a compound of Formula I or Formula II to a patient in need thereof. In some such embodiments, the patient is at risk of developing a condition characterized by axonal degeneration. In some embodiments, the patient has a condition characterized by axonal degeneration. In some embodiments, the patient has been diagnosed with a condition characterized by axonal degeneration.

In some embodiments, provided methods comprise administering a composition as described herein to a patient population of in need thereof. In some embodiments, the population is drawn from individuals who engage in activities where the potential for traumatic neuronal injury is high. In some embodiments, the population is drawn from athletes who engage in contact sports or other high-risk activities.

In some embodiments, the subject is at risk of developing a condition characterized by axonal degeneration. In some embodiments, the subject is identified as being at risk of axonal degeneration, e.g., based on the subject's genotype, a diagnosis of a condition associated with axonal degeneration, and/or exposure to an agent and/or a condition that induces axonal degeneration.

In some embodiments, the patient is at risk of developing a neurodegenerative disorder. In some embodiments the patient is elderly. In some embodiments, the patient is known to has a genetic risk factor for neurodegeneration. In some embodiments the patient has In some embodiments, the patient has a family history of neurodegenerative disease. In some embodiments, the patient expresses one or more copies of a known genetic risk factor for neurodegeneration. In some embodiments, the patient is drawn from a population with a high incidence of neurodegeneration. In some embodiments, the patient has a hexanucleotide repeat expansion in chromosome 9 open reading frame 72. In some embodiments, the patient has one or more copies of the ApoE4 allele.

In some embodiments, subjects to which a compound or composition as described herein is administered may be or comprise subjects suffering from or susceptible to a neurodegenerative disease, disorder or condition. In some embodiments, a neurodegenerative disease, disorder or condition may be or comprise a traumatic neuronal injury. In some embodiments, a traumatic neuronal injury is blunt force trauma, a closed-head injury, an open head injury, exposure to a concussive and/or explosive force, a penetrating injury in to the brain cavity or innervated region of the body. In some embodiments, a traumatic neuronal injury is a force which causes the axons to deform, stretch, crush or sheer.

In some embodiments, the subject engages in an activity identified as a risk factor for neuronal degradation, e.g., a subject that engages in contact sports or occupations with a high chance for traumatic neuronal injury.

For example, the subject may be a patient who is receiving, or is prescribed, a chemotherapy associated with peripheral neuropathy. Examples of chemotherapeutic agents include, but not limited to, thalidomide, epothilones (e.g., ixabepilone), taxanes (e.g., paclitaxel and docetaxel), vinca alkaloids (e.g., vinblastine, vinorelbine, vincristine, and vindesine), proteasome inhibitors (e.g., bortezomib), platinum-based drugs (e.g., cisplatin, oxaliplatin, and carboplatin).

In some embodiments, provided methods comprise administering a composition as described herein to a patient or patient population based on the presence or absence of one or more biomarkers. In some embodiments, provided methods further comprise monitoring the level of a biomarker in a patient or patient population and adjusting the dosing regimen accordingly.

Dosing

Those of skill in the art will appreciate that, in some embodiments, the exact amount of a particular compound included in and/or delivered by administration of a pharmaceutical composition or regimen as described herein may be selected by a medical practitioner and may be different for different subjects, for example, upon consideration of one or more of species, age, and general condition of the subject, and/or identity of the particular compound or composition, its mode of administration, and the like. Alternatively, in some embodiments, the amount of a particular compound included in and/or delivered by administration of a pharmaceutical composition or regimen as described herein may be standardized across a relevant patient population (e.g., all patients, all patients of a particular age or stage of disease or expressing a particular biomarker, etc.).

A provided compound or composition of the present disclosure is preferably formulated in dosage unit form for ease of administration and uniformity of dosage. The expression "dosage unit form" as used herein refers to a physically discrete unit of agent appropriate for the patient to be treated. It will be understood, however, that the total daily usage of a provided compound or composition of the present disclosure will be decided by the attending physician within the scope of sound medical judgment. The specific effective dose level for any particular patient or organism will depend upon a variety of factors including the disorder being treated and the severity of the disorder; the clinical condition of the individual patient; the cause of the disorder; the activity of the specific compound employed; the specific composition employed; the age, body weight, general health, sex and diet of the patient; the time of administration, delivery site of the agent, route of administration, and rate of excretion of the specific compound employed; the duration of the treatment; drugs used in combination or coincidental with the specific compound employed, and like factors well known in the medical arts. The effective amount of the compound to be administered will be governed by such considerations, and is the minimum amount necessary to inhibit SARM1 activity as required to prevent or treat the undesired disease or disorder, such as for example, neurodegeneration or traumatic neural injury.

A pharmaceutically acceptable composition of this disclosure can be administered to humans and other animals orally, rectally, intravenously, parenterally, intracisternally, intravaginally, intraperitoneally, topically (as by powders, ointments, or drops), bucally, as an oral or nasal spray, or the like, depending on the severity of the disease, disorder or infection being treated. The daily dose is, in certain embodiments, given as a single daily dose or in divided doses two to six times a day, or in sustained release form. This dosage regimen may be adjusted to provide the optimal therapeutic response. The compounds may be administered on a regimen of 1 to 4 times per day, preferably once or twice per day.

In some embodiments, compositions of the present disclosure may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intradermal, intraocular, intralesional and intracranial injection or infusion techniques. Preferably, the compositions are administered orally, intraperitoneally or intravenously.

In some embodiments, pharmaceutically acceptable compositions of this disclosure may also be administered topically, especially when the target of treatment includes areas or organs readily accessible by topical application, including diseases of the eye, the skin, or the lower intestinal tract. Suitable topical formulations are readily prepared for each of these areas or organs.

Most preferably, pharmaceutically acceptable compositions of this disclosure are formulated for oral administration. Such formulations may be administered with or without food. In some embodiments, pharmaceutically acceptable compositions of this disclosure are administered without food. In other embodiments, pharmaceutically acceptable compositions of this disclosure are administered with food.

Those additional agents may be administered separately from a provided compound or composition thereof, as part of a multiple dosage regimen. Alternatively, those agents may be part of a single dosage form, mixed together with a provided compound in a single composition. If administered as part of a multiple dosage regime, the two active agents may be submitted simultaneously, sequentially or within a period of time from one another, normally within five hours from one another.

It should also be understood that a specific dosage and treatment regimen for any particular patient may depend upon a variety of factors, including the activity of the specific compound employed, the age, body weight, general health, sex, diet, time of administration, rate of excretion, drug combination, and the judgment of the treating physician and the severity of the particular disease being treated. In some embodiments, the amount of a compound of the present disclosure in the composition will also depend upon the particular compound in the composition.

In some embodiments, SARM1 inhibition as described herein may be utilized in combination with one or more other therapies to treat a relevant disease, disorder, or condition. In some embodiments, dosing of a SARM1 inhibitor is altered when utilized in combination therapy as compared with when administered as monotherapy; alternatively or additionally, in some embodiments, a therapy that is administered in combination with SARM1 inhibition as described herein is administered according to a regimen or protocol that differs from its regimen or protocol when administered alone or in combination with one or more therapies other than SARM1 inhibition. In some embodiments, compositions which comprise an additional therapeutic agent, that additional therapeutic agent and a provided compound may act synergistically. In some embodiments, one or both therapies utilized in a combination regimen is administered at a lower level or less frequently than when it is utilized as monotherapy.

In some embodiments, compounds and/or compositions described herein are administered with a chemotherapeutic agent including, but not limited to, alkylating agents, anthracyclines, taxanes, epothilones, histone deacetylase inhibitors, topoisomerase inhibitors, kinase inhibitors, nucleotide analogs, peptide antibiotics, platinum-based agents, retinoids, vinca alkaloids and derivatives. In some embodiments, compounds and/or compositions described herein are administered in combination with PARP inhibitors.

EXEMPLIFICATION

The present teachings including descriptions provided in the Examples that are not intended to limit the scope of any claim. Unless specifically presented in the past tense, inclusion in the Examples is not intended to imply that the experiments were actually performed. The following non-limiting examples are provided to further illustrate the present teachings. Those of skill in the art, in light of the present disclosure, will appreciate that many changes can be made in the specific embodiments that are disclosed and still obtain a like or similar result without departing from the spirit and scope of the present teachings.

Methods.

Some methods and compositions described herein utilize laboratory techniques well known to skilled artisans, and can be found in laboratory manuals such as Sambrook, J., et al., Molecular Cloning: A Laboratory Manual, 3rd ed. Cold Spring Harbor Laboratory Press, Cold Spring Harbor, N.Y., 2001; Methods In Molecular Biology, ed. Richard, Humana Press, NJ, 1995; Spector, D. L. et al., Cells: A Laboratory Manual, Cold Spring Harbor Laboratory Press, Cold Spring Harbor, N.Y., 1998; and Harlow, E., Using Antibodies: A Laboratory Manual, Cold Spring Harbor Laboratory Press, Cold Spring Harbor, N.Y., 1999. Methods of administration of pharmaceuticals and dosage regimes, can be determined according to standard principles of pharmacology, using methods provided by standard reference texts such as Remington: the Science and Practice of Pharmacy (Alfonso R. Gennaro ed. 19th ed. 1995); Hardman, J. G., et al., Goodman & Gilman's The Pharmacological Basis of Therapeutics, Ninth Edition, McGraw-Hill, 1996; and Rowe, R. C., et al., Handbook of Pharmaceutical Excipients, Fourth Edition, Pharmaceutical Press, 2003.

Example 1: Characterization of Compounds

LCMS Methods:

Analytical LC/MS Analysis Method A:

ESI+/−ion mode 100-1000 Da

Column: XBridge C18, 50×4.6 mm, 3.5 um

Temperature: 40° C.

Gradient:

| Time (min) | Water (10 mM NH $NH_4HCO_3$) | acetonitrile | Flow (mL/min) |
|---|---|---|---|
| 0 | 95% | 5% | 2.0 |
| 1.2 | 5% | 95% | 2.0 |
| 3.0 | 5% | 95% | 2.0 |

Analytical LC/MS Analysis Method B:

ESI+/−ion mode 150-850 Da

Column: Phenomenex Kinetix-XB C18, Part No. 00D-4498-AN, 2.1×100 mm, 1.7 um

Temperature: 40° C.

Gradient:
| Time (min) | Water + 0.1% formic acid | Acetonitrile + 0.1% formic acid | Flow (mL/min) |
|---|---|---|---|
| 0.00 | 95% | 5% | 0.6 |
| 5.30 | 0% | 100% | 0.6 |
| 5.80 | 0% | 100% | 0.6 |
| 5.82 | 95% | 5% | 0.6 |
| 7.00 | 95% | 5% | 0.6 |
Analytical LC/MS Analysis Method C:
ESI+/−ion mode 100-1000 Da
Column: XBridge C18, 50×4.6 mm, 3.5 um
Temperature: 40° C.
Gradient:
| Time (min) | Water + 0.1% TFA | Acetonitrile + 0.1% TFA | Flow (mL/min) |
|---|---|---|---|
| 0 | 95% | 5% | 1.8 |
| 1.8 | 5% | 95% | 1.8 |
| 3.0 | 5% | 95% | 1.8 |
Results are presented in Table 1:
TABLE 1
| Example | Structure | LCMS method | RT (min) | Mol ion (m/z) |
|---|---|---|---|---|
| 1 | 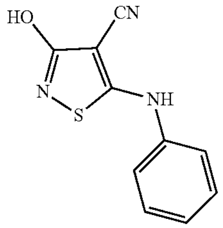 [SMILES: N#Cc1c(O)nsc1Nc1ccccc1] | B | 1.83 | 218.0 |
| 2 | 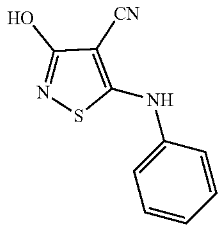 [SMILES: N#Cc1c(O)nsc1Nc1ccccc1] | A | 1.21 | 252.0 |
| 3 | 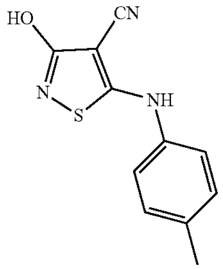 [SMILES: Cc1ccc(Nc2snc(O)c2C#N)cc1] | B | 2.16 | 232.0 |
| 4 | 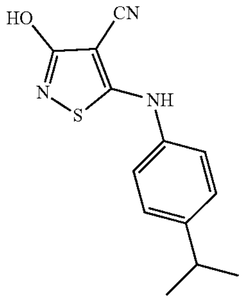 [SMILES: CC(C)c1ccc(Nc2snc(O)c2C#N)cc1] | B | 2.77 | 260.0 |

TABLE 1-continued
| Example | Structure | LCMS method | RT (min) | Mol ion (m/z) |
|---|---|---|---|---|
| 5 | 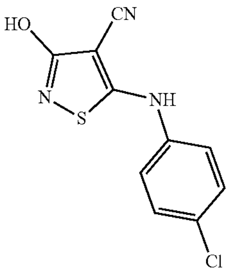 [SMILES: N#Cc1c(O)nsc1Nc1ccc(Cl)cc1] | B | 2.30 | 252.0 |
| 6 | 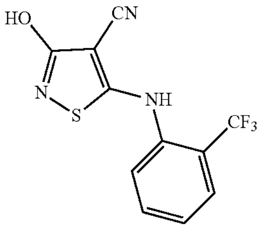 [SMILES: N#Cc1c(O)nsc1Nc1ccccc1C(F)(F)F] | A | 1.25 | 286.0 |
| 7 | 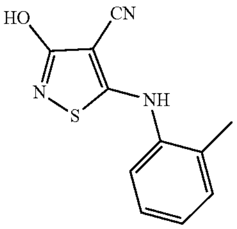 [SMILES: Cc1ccccc1Nc1snc(O)c1C#N] | A | 1.20 | 232.0 |
| 8 | 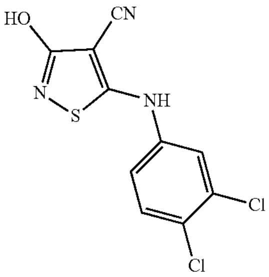 [SMILES: N#Cc1c(O)nsc1Nc1ccc(Cl)c(Cl)c1] | B | 2.72 | 286.0 |
| 9 | 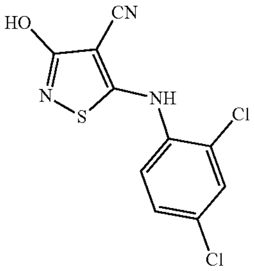 [SMILES: N#Cc1c(O)nsc1Nc1ccc(Cl)cc1Cl] | B | 2.45 | 286.0 |
| 10 | 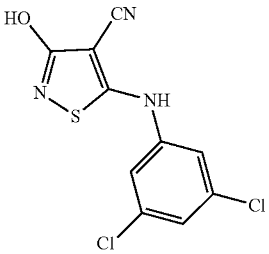 [SMILES: N#Cc1c(O)nsc1Nc1cc(Cl)cc(Cl)c1] | B | 2.84 | 286.0 |

TABLE 1-continued
| Example | Structure | LCMS method | RT (min) | Mol ion (m/z) |
|---|---|---|---|---|
| 11 | 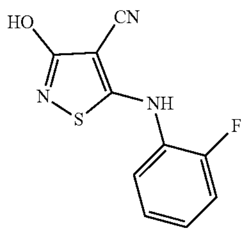 [SMILES: N#Cc1c(O)nsc1Nc1ccccc1F] | B | 1.78 | 236.0 |
| 12 | 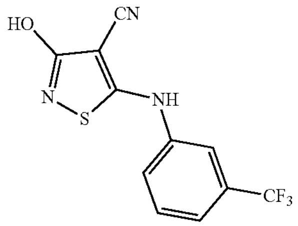 [SMILES: N#Cc1c(O)nsc1Nc1cccc(C(F)(F)F)c1] | B | 2.53 | 285.24 |
| 13 | 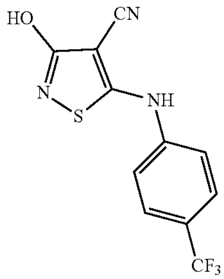 [SMILES: N#Cc1c(O)nsc1Nc1ccc(C(F)(F)F)cc1] | B | 2.62 | 286.0 |
| 14 | 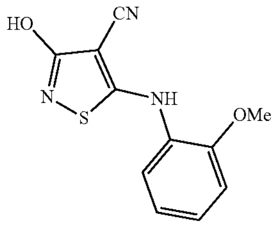 [SMILES: COc1ccccc1Nc1snc(O)c1C#N] | B | 1.90 | 248.0 |
| 15 | 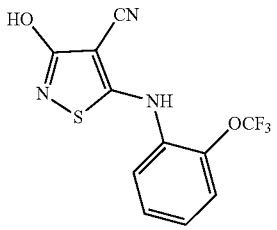 [SMILES: N#Cc1c(O)nsc1Nc1ccccc1OC(F)(F)F] | B | 2.34 | 302.0 |
| 16 | 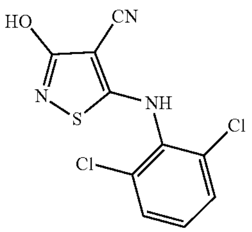 [SMILES: N#Cc1c(O)nsc1Nc1c(Cl)cccc1Cl] | B | 2.03 | 286.0 |

TABLE 1-continued
| Example | Structure | LCMS method | RT (min) | Mol ion (m/z) |
|---|---|---|---|---|
| 17 | 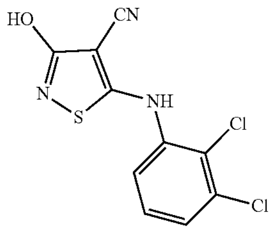 [SMILES: N#Cc1c(O)nsc1Nc1cccc(Cl)c1Cl] | B | 2.39 | 286.0 |
| 18 | 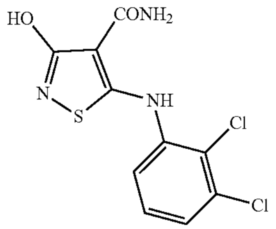 [SMILES: NC(=O)c1c(O)nsc1Nc1cccc(Cl)c1Cl] | B | 2.78 | 304.0 |
| 19 | 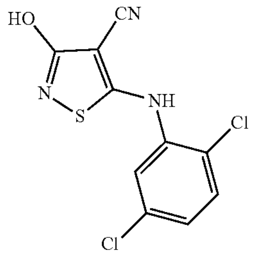 [SMILES: N#Cc1c(O)nsc1Nc1cc(Cl)ccc1Cl] | B | 2.38 | 286.0 |
| 20 | 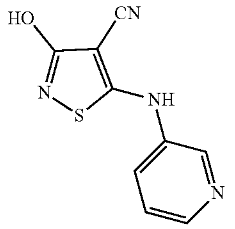 [SMILES: N#Cc1c(O)nsc1Nc1cccnc1] | B | 0.90 | 219.0 |
| 21 | 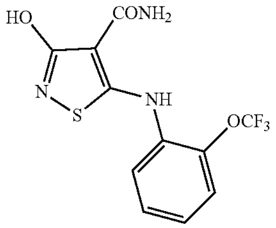 [SMILES: NC(=O)c1c(O)nsc1Nc1ccccc1OC(F)(F)F] | B | 2.24 | 320.0 |
| 22 | 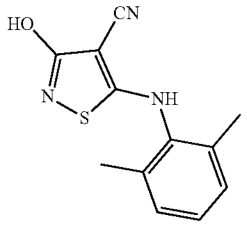 [SMILES: Cc1cccc(C)c1Nc1snc(O)c1C#N] | B | 2.12 | 246.0 |

TABLE 1-continued
| Ex-ample | Structure | LCMS method | RT (min) | Mol ion (m/z) |
|---|---|---|---|---|
| 23 | 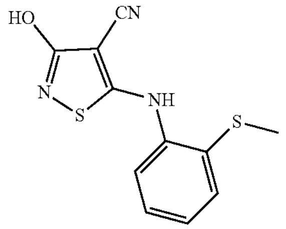 [SMILES: CSc1ccccc1Nc1snc(O)c1C#N] | B | 2.05 | 264.0 |
| 24 | 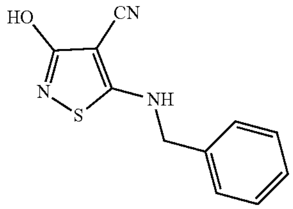 [SMILES: N#Cc1c(O)nsc1NCc1ccccc1] | B | 1.88 | 232.0 |
| 25 | 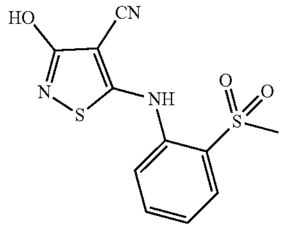 [SMILES: CS(=O)(=O)c1ccccc1Nc1snc(O)c1C#N] | B | 1.66 | 296.0 |
| 26 | 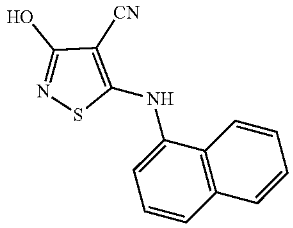 [SMILES: N#Cc1c(O)nsc1Nc1cccc2ccccc12] | A | 1.28 | 268.0 |
| 27 | 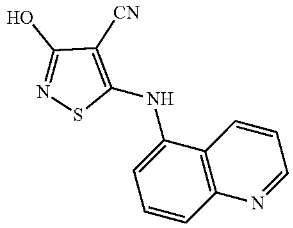 [SMILES: N#Cc1c(O)nsc1Nc1cccc2ncccc12] | A | 1.07 | 269.0 |
| 28 | 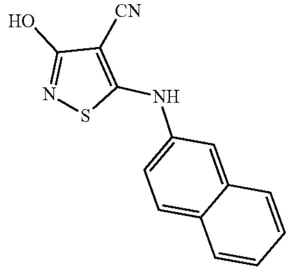 [SMILES: N#Cc1c(O)nsc1Nc1ccc2ccccc2c1] | A | 1.29 | 268.0 |

TABLE 1-continued
| Example | Structure | LCMS method | RT (min) | Mol ion (m/z) |
|---|---|---|---|---|
| 29 | 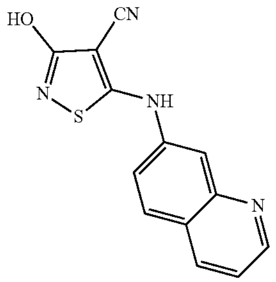 [SMILES: N#Cc1c(O)nsc1Nc1ccc2cccnc2c1] | A | 1.08 | 269.0 |
| 30 | 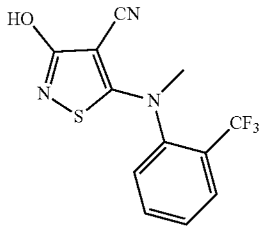 [SMILES: CN(c1ccccc1C(F)(F)F)c1snc(O)c1C#N] | A | 1.26 | 300.0 |
| 31 | 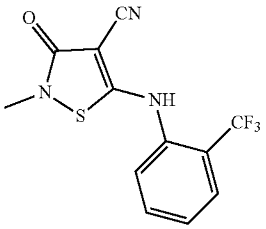 [SMILES: Cn1sc(Nc2ccccc2C(F)(F)F)c(C#N)c1=O] | A | 1.25 | 300.0 |
| 32 | 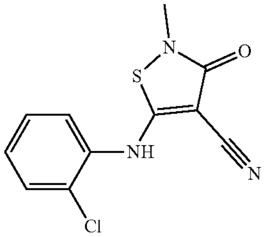 [SMILES: Cn1sc(Nc2ccccc2Cl)c(C#N)c1=O] | B | 2.14 | 266.1 |
| 33 | 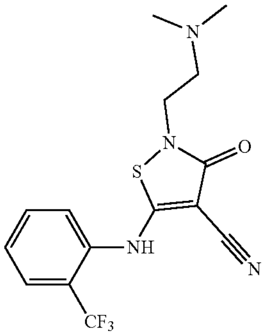 [SMILES: CN(C)CCn1sc(Nc2ccccc2C(F)(F)F)c(C#N)c1=O] | A | 1.4 | 357 |

TABLE 1-continued
| Example | Structure | LCMS method | RT (min) | Mol ion (m/z) |
|---|---|---|---|---|
| 34 | 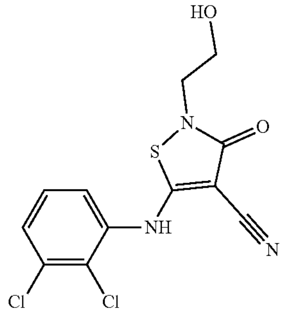 [SMILES: N#Cc1c(Nc2cccc(Cl)c2Cl)sn(CCO)c1=O] | A | 1.23 | 330, 332 |
| 35 | 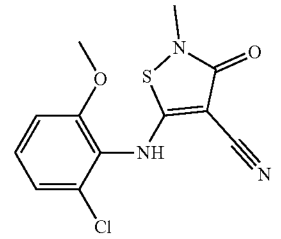 [SMILES: COc1cccc(Cl)c1Nc1sn(C)c(=O)c1C#N] | A | 1.32 | 296, 298 |
| 36 | 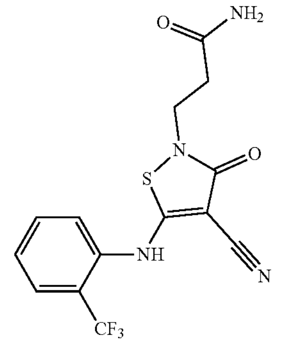 [SMILES: N#Cc1c(Nc2ccccc2C(F)(F)F)sn(CCC(N)=O)c1=O] | A | 1.28 | 357 |
| 37 | 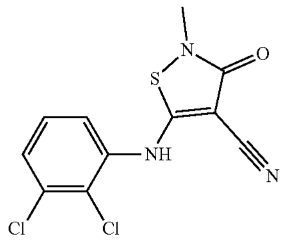 [SMILES: Cn1sc(Nc2cccc(Cl)c2Cl)c(C#N)c1=O] | A | 1.25 | 300, 302 |
| 38 | 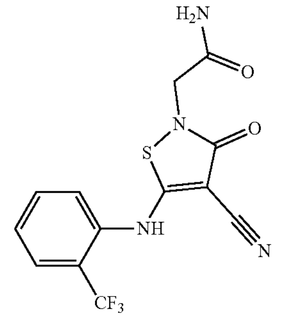 [SMILES: N#Cc1c(Nc2ccccc2C(F)(F)F)sn(CC(N)=O)c1=O] | A | 1.266 | 343 |

TABLE 1-continued
| Example | Structure | LCMS method | RT (min) | Mol ion (m/z) |
|---|---|---|---|---|
| 39 | 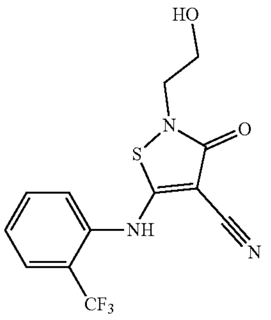 [SMILES: N#Cc1c(Nc2ccccc2C(F)(F)F)sn(CCO)c1=O] | A | 1.33 | 330 |
| 40 | 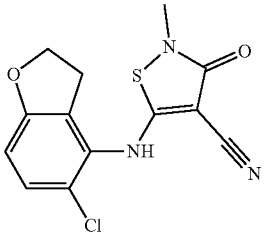 [SMILES: Cn1sc(Nc2c(Cl)ccc3c2CCO3)c(C#N)c1=O] | A | 1.338 | 308, 310 |
| 41 | 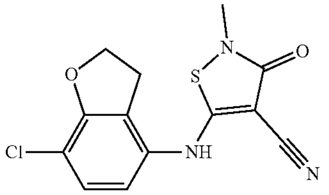 [SMILES: Cn1sc(Nc2ccc(Cl)c3c2CCO3)c(C#N)c1=O] | A | 1.429 | 308, 309.9 |
| 42 | 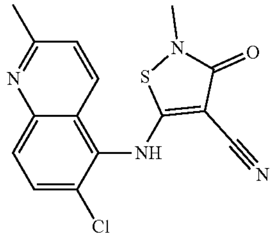 [SMILES: Cc1ccc2c(Nc3sn(C)c(=O)c3C#N)c(Cl)ccc2n1] | A | 1.382 | 331.1, 333.1 |
| 43 | 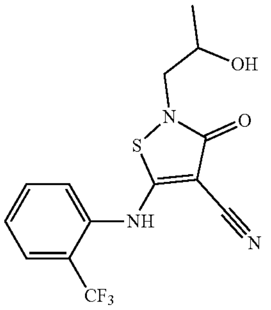 [SMILES: CC(O)Cn1sc(Nc2ccccc2C(F)(F)F)c(C#N)c1=O] | A | 1.26 | 344 |

TABLE 1-continued
| Example | Structure | LCMS method | RT (min) | Mol ion (m/z) |
|---|---|---|---|---|
| 44 | 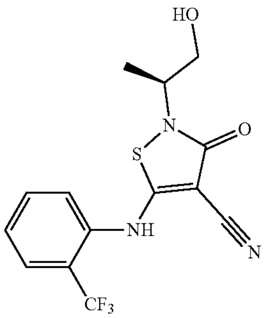 [SMILES: C[C@@H](CO)n1sc(Nc2ccccc2C(F)(F)F)c(C#N)c1=O] | A | 1.45 | 344 |
| 45 | 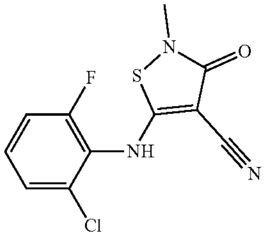 [SMILES: Cn1sc(Nc2c(F)cccc2Cl)c(C#N)c1=O] | B | 2.06 | 284.1 |
| 46 | 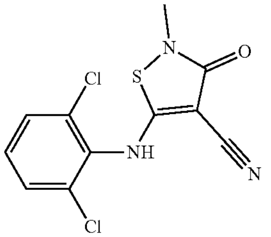 [SMILES: Cn1sc(Nc2c(Cl)cccc2Cl)c(C#N)c1=O] | A | 1.35 | 299.9, 302.00 |
| 47 | 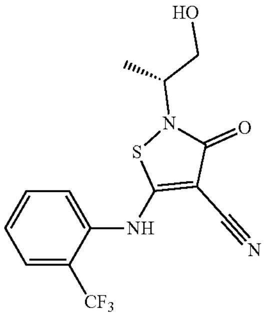 [SMILES: C[C@H](CO)n1sc(Nc2ccccc2C(F)(F)F)c(C#N)c1=O] | A | 1.45 | 344 |
| 48 | 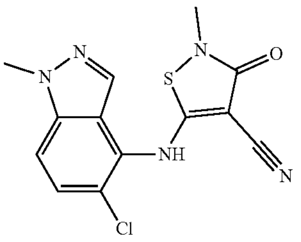 [SMILES: Cn1sc(Nc2c(Cl)ccc3c2cnn3C)c(C#N)c1=O] | A | 1.316 | 320.1, 322.1 |

TABLE 1-continued
| Example | Structure | LCMS method | RT (min) | Mol ion (m/z) |
|---|---|---|---|---|
| 49 | 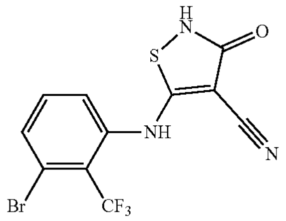 [SMILES: N#Cc1c(Nc2cccc(Br)c2C(F)(F)F)s[nH]c1=O] | A | 1.35 | 363.9, 366 |
| 50 | 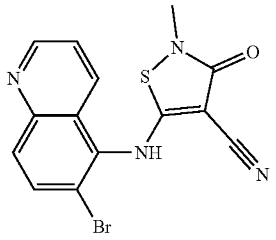 | A | 1.302 | 360.9, 362.9 |
| 51 | 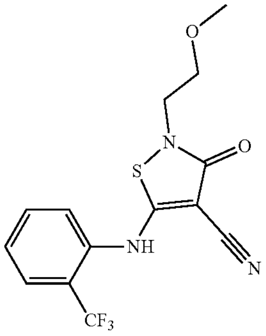 [SMILES: COCCn1sc(Nc2ccccc2C(F)(F)F)c(C#N)c1=O] | A | 1.41 | 344 |
| 52 | 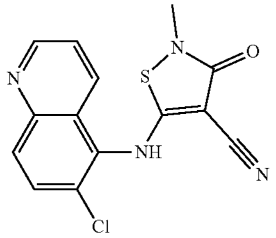 [SMILES: Cn1sc(Nc2c(Cl)ccc3ncccc23)c(C#N)c1=O] | A | 1.246 | 317, 318.9 |
| 53 | 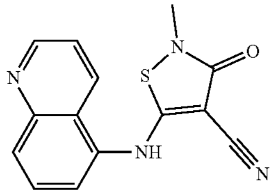 [SMILES: Cn1sc(Nc2cccc3ncccc23)c(C#N)c1=O] | A | 1.164 | 283 |

TABLE 1-continued
| Example | Structure | LCMS method | RT (min) | Mol ion (m/z) |
|---|---|---|---|---|
| 54 | 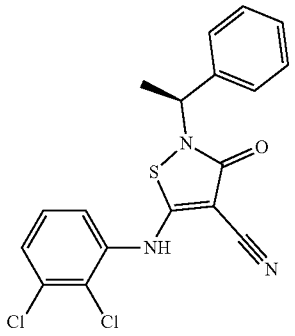 [SMILES: C[C@@H](c1ccccc1)n1sc(Nc2cccc(Cl)c2Cl)c(C#N)c1=O] | B | 3.51 | 390.1/ 392.1 |
| 55 | 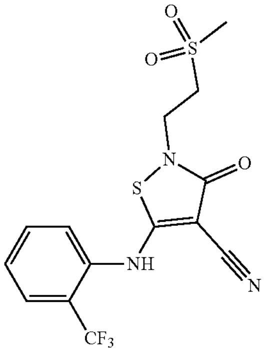 [SMILES: CS(=O)(=O)CCn1sc(Nc2ccccc2C(F)(F)F)c(C#N)c1=O] | A | 1.36 | 392 |
| 56 | 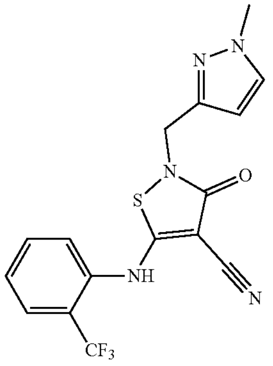 | A | 1.39 | 380 |
| 57 | 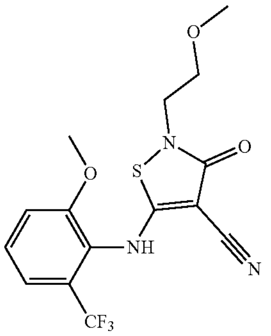 [SMILES: COCCn1sc(Nc2c(OC)cccc2C(F)(F)F)c(C#N)c1=O] | A | 1.435 | 374 |

TABLE 1-continued
| Example | Structure | LCMS method | RT (min) | Mol ion (m/z) |
|---|---|---|---|---|
| 58 | 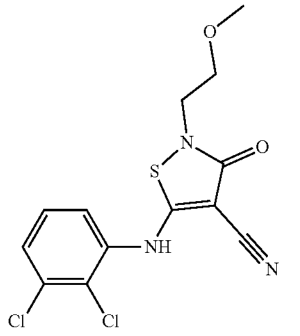 [SMILES: COCCn1sc(Nc2cccc(Cl)c2Cl)c(C#N)c1=O] | A | 1.44 | 345 |
| 59 | 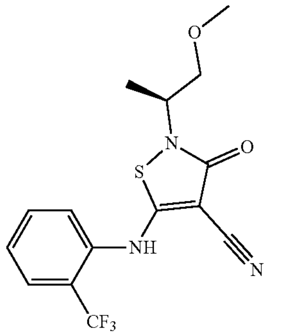 [SMILES: COC[C@H](C)n1sc(Nc2ccccc2C(F)(F)F)c(C#N)c1=O] | A | 1.35 | 358 |
| 60 | 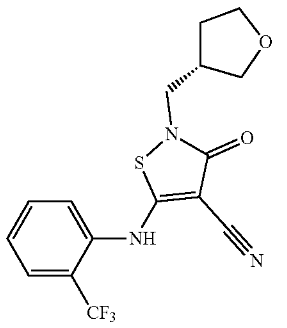 [SMILES: N#Cc1c(Nc2ccccc2C(F)(F)F)sn(C[C@@H]2CCOC2)c1=O] | A | 1.42 | 370 |
| 61 | 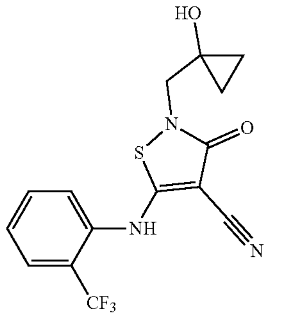 [SMILES: N#Cc1c(Nc2ccccc2C(F)(F)F)sn(CC2(O)CC2)c1=O] | A | 1.38 | 356 |

TABLE 1-continued
| Example | Structure | LCMS method | RT (min) | Mol ion (m/z) |
|---|---|---|---|---|
| 62 | 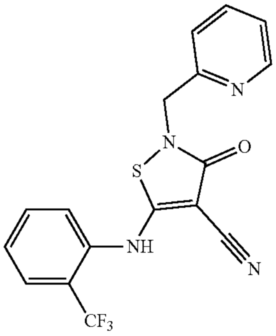 [SMILES: N#Cc1c(Nc2ccccc2C(F)(F)F)sn(Cc2ccccn2)c1=O] | A | 1.42 | 377 |
| 63 | 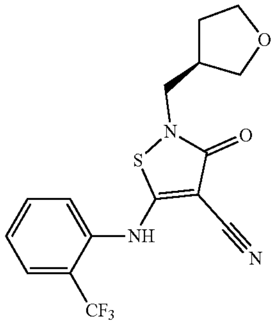 [SMILES: N#Cc1c(Nc2ccccc2C(F)(F)F)sn(C[C@H]2CCOC2)c1=O] | A | 1.42 | 370 |
| 64 | 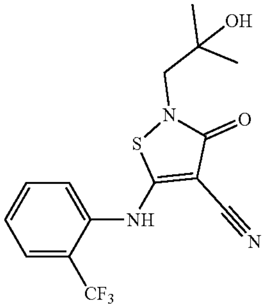 [SMILES: CC(C)(O)Cn1sc(Nc2ccccc2C(F)(F)F)c(C#N)c1=O] | A | 1.29 | 358 |
| 65 | 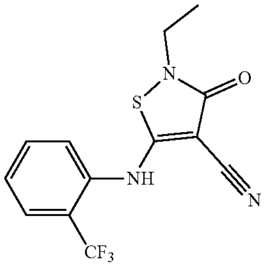 [SMILES: CCn1sc(Nc2ccccc2C(F)(F)F)c(C#N)c1=O] | A | 1.47 | 314 |
| 66 | 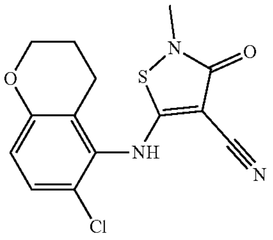 [SMILES: Cn1sc(Nc2c(Cl)ccc3c2CCCO3)c(C#N)c1=O] | A | 1.674 | 322, 324 |

TABLE 1-continued
| Example | Structure | LCMS method | RT (min) | Mol ion (m/z) |
|---|---|---|---|---|
| 67 | 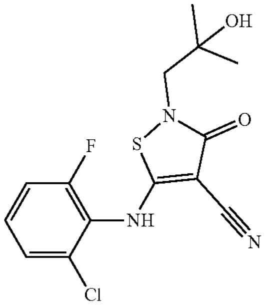 [SMILES: CC(C)(O)Cn1sc(Nc2c(F)cccc2Cl)c(C#N)c1=O] | B | 2.06 | 342.1 |
| 68 | 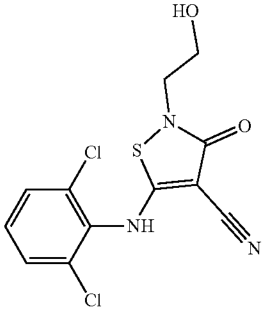 [SMILES: N#Cc1c(Nc2c(Cl)cccc2Cl)sn(CCO)c1=O] | A | 1.39 | 330.0, 331.9 |
| 69 | 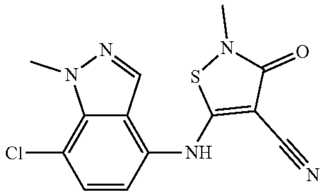 [SMILES: Cn1sc(Nc2ccc(Cl)c3c2cnn3C)c(C#N)c1=O] | C | 1.917 | 320.2, 322.1 |
| 70 | 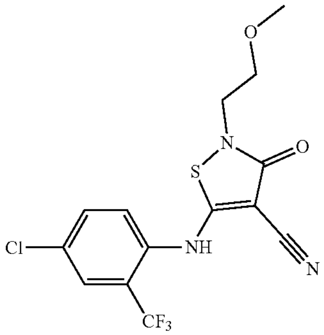 [SMILES: COCCn1sc(Nc2ccc(Cl)cc2C(F)(F)F)c(C#N)c1=O] | A | 1.51 | 378 |
| 71 | 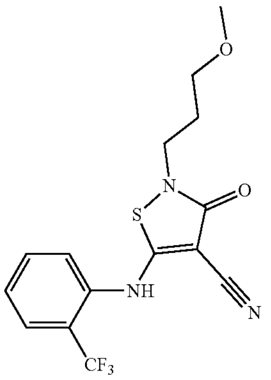 [SMILES: COCCCn1sc(Nc2ccccc2C(F)(F)F)c(C#N)c1=O] | A | 1.45 | 358 |

TABLE 1-continued
| Example | Structure | LCMS method | RT (min) | Mol ion (m/z) |
|---|---|---|---|---|
| 72 | 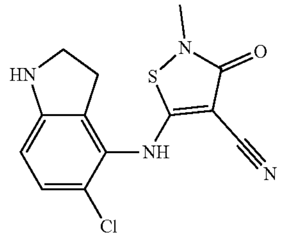 [SMILES: Cn1sc(Nc2c(Cl)ccc3c2CCN3)c(C#N)c1=O] | A | 1.255 | 307, 309 |
| 73 | 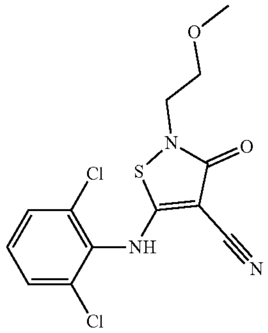 [SMILES: COCCn1sc(Nc2c(Cl)cccc2Cl)c(C#N)c1=O] | A | 1.53 | 344.0, 346.0 |
| 74 | 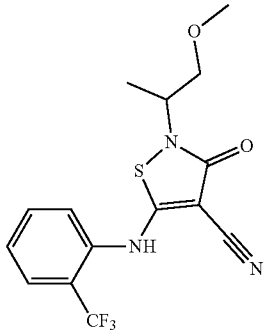 [SMILES: COCC(C)n1sc(Nc2ccccc2C(F)(F)F)c(C#N)c1=O] | C | 1.55 | 358 |
| 75 | 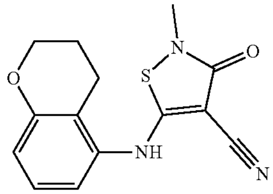 [SMILES: Cn1sc(Nc2cccc3c2CCCO3)c(C#N)c1=O] | A | 1.421 | 288 |
| 76 | 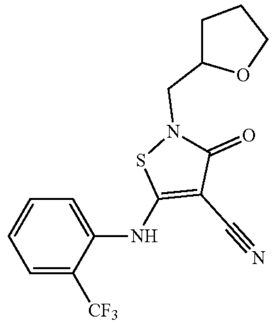 [SMILES: N#Cc1c(Nc2ccccc2C(F)(F)F)sn(CC2CCCO2)c1=O] | A | 1.48 | 370 |

TABLE 1-continued
| Example | Structure | LCMS method | RT (min) | Mol ion (m/z) |
|---|---|---|---|---|
| 77 | 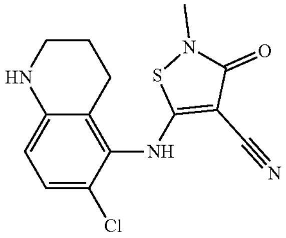 [SMILES: Cn1sc(Nc2c(Cl)ccc3c2CCCN3)c(C#N)c1=O] | A | 1.296 | 321.0, 323.0 |
| 78 | 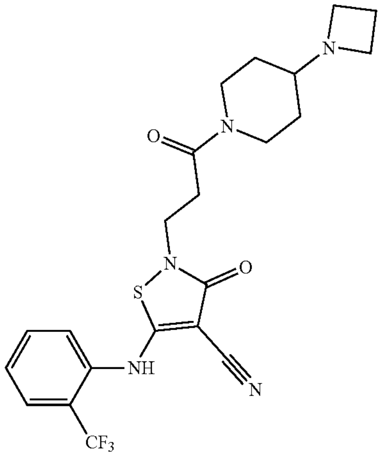 [SMILES: N#Cc1c(Nc2ccccc2C(F)(F)F)sn(CCC(=O)N2CCC(N3CCC3)CC2)c1=O] | A | 1.347 | 180 |
| 79 | 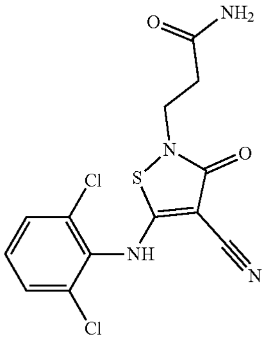 [SMILES: N#Cc1c(Nc2c(Cl)cccc2Cl)sn(CCC(N)=O)c1=O] | A | 1.077 | 357, 359 |
| 80 | 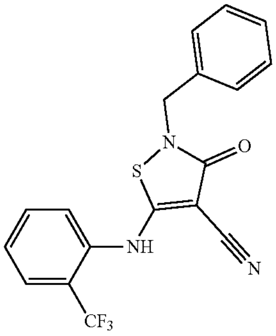 [SMILES: N#Cc1c(Nc2ccccc2C(F)(F)F)sn(Cc2ccccc2)c1=O] | A | 1.58 | 376 |

TABLE 1-continued
| Example | Structure | LCMS method | RT (min) | Mol ion (m/z) |
|---|---|---|---|---|
| 81 | 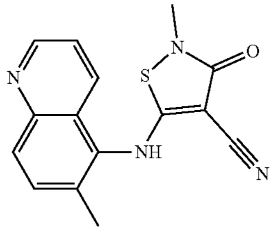 [SMILES: Cc1ccc2ncccc2c1Nc1sn(C)c(=O)c1C#N] | A | 1.295 | 297 |
| 82 | 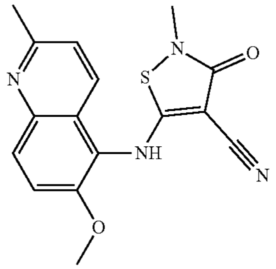 [SMILES: COc1ccc2nc(C)ccc2c1Nc1sn(C)c(=O)c1C#N] | A | 1.22 | 327 |
| 83 | 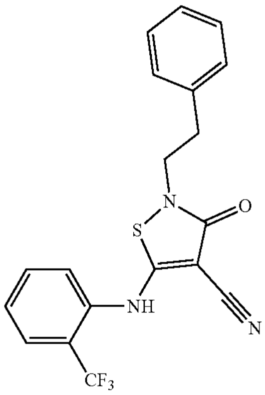 [SMILES: N#Cc1c(Nc2ccccc2C(F)(F)F)sn(CCc2ccccc2)c1=O] | A | 1.47 | 390 |
| 84 | 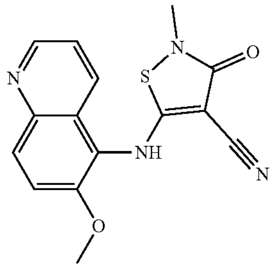 [SMILES: COc1ccc2ncccc2c1Nc1sn(C)c(=O)c1C#N] | A | 1.18 | 313 |
| 85 | 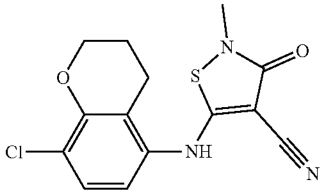 [SMILES: Cn1sc(Nc2ccc(Cl)c3c2CCCO3)c(C#N)c1=O] | A | 1.483 | 321.9, 324 |

TABLE 1-continued
| Example | Structure | LCMS method | RT (min) | Mol ion (m/z) |
|---|---|---|---|---|
| 86 | 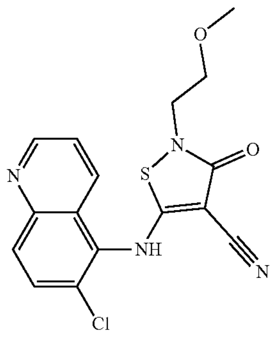 [SMILES: COCCn1sc(Nc2c(Cl)ccc3ncccc23)c(C#N)c1=O] | A | 1.327 | 360.9, 362.9 |
| 87 | 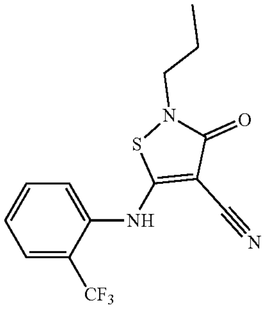 [SMILES: CCCn1sc(Nc2ccccc2C(F)(F)F)c(C#N)c1=O] | A | 1.5 | 328 |
| 88 | 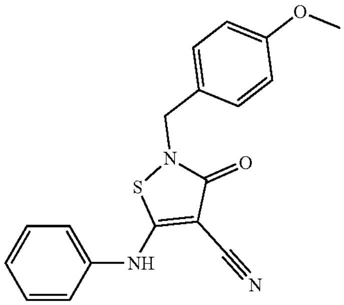 [SMILES: COc1ccc(Cn2sc(Nc3ccccc3)c(C#N)c2=O)cc1] | B | 3 | 338.2 |
| 89 | 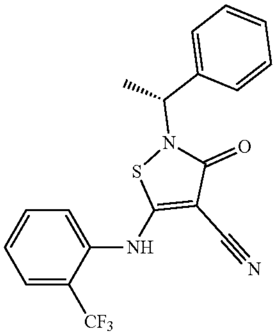 [SMILES: C[C@H](c1ccccc1)n1sc(Nc2ccccc2C(F)(F)F)c(C#N)c1=O] | A | 1.607 | 390 |

TABLE 1-continued
| Example | Structure | LCMS method | RT (min) | Mol ion (m/z) |
|---|---|---|---|---|
| 90 | 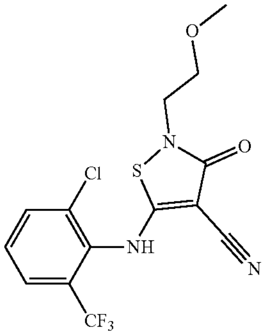 [SMILES: COCCn1sc(Nc2c(Cl)cccc2C(F)(F)F)c(C#N)c1=O] | A | 1.42 | 378 |
| 91 | 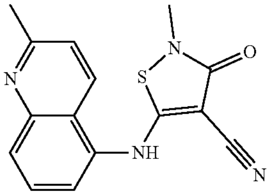 [SMILES: Cc1ccc2c(Nc3sn(C)c(=O)c3C#N)cccc2n1] | C | 0.862 | 297 |
| 92 | 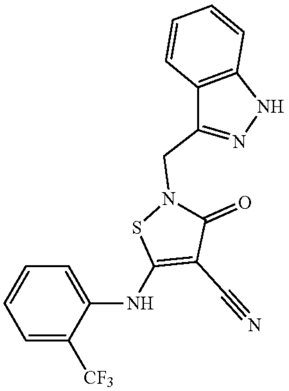 [SMILES: N#Cc1c(Nc2ccccc2C(F)(F)F)sn(Cc2n[nH]c3ccccc23)c1=O] | A | 1.44 | 416 |
| 93 | 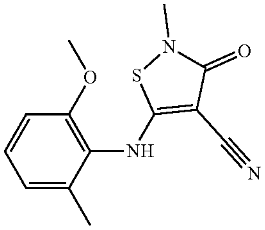 [SMILES: COc1cccc(C)c1Nc1sn(C)c(=O)c1C#N] | B | 2.27 | 276.1 |
| 94 | 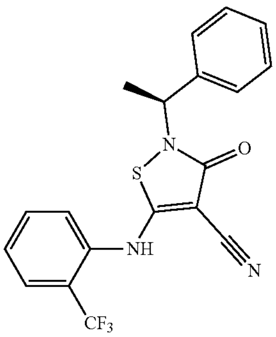 [SMILES: C[C@@H](c1ccccc1)n1sc(Nc2ccccc2C(F)(F)F)c(C#N)c1=O] | A | 1.78 | 390 |

TABLE 1-continued
| Example | Structure | LCMS method | RT (min) | Mol ion (m/z) |
|---|---|---|---|---|
| 95 | 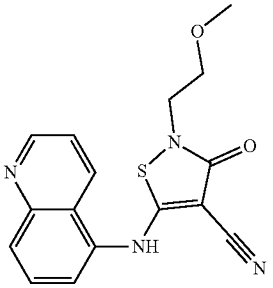 [SMILES: COCCn1sc(Nc2cccc3ncccc23)c(C#N)c1=O] | A | 1.206 | 327 |
| 96 | 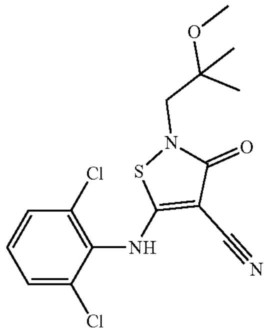 [SMILES: COC(C)(C)Cn1sc(Nc2c(Cl)cccc2Cl)c(C#N)c1=O] | A | 1.34 | 372, 374 |
| 97 | 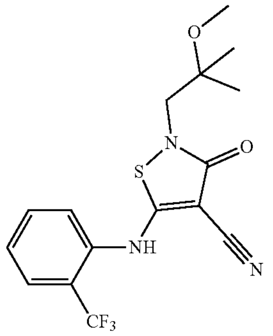 [SMILES: COC(C)(C)Cn1sc(Nc2ccccc2C(F)(F)F)c(C#N)c1=O] | A | 1.5 | 372 |
| 98 | 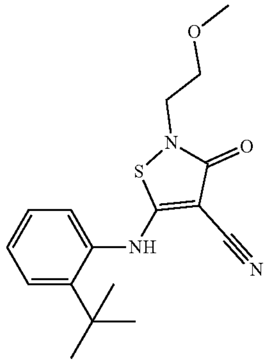 [SMILES: COCCn1sc(Nc2ccccc2C(C)(C)C)c(C#N)c1=O] | A | 1.61 | 332 |

TABLE 1-continued
| Example | Structure | LCMS method | RT (min) | Mol ion (m/z) |
|---|---|---|---|---|
| 99 | 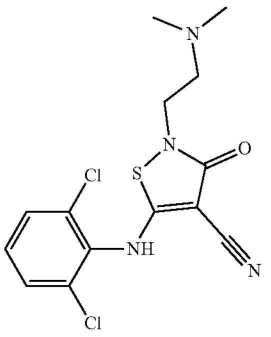 [SMILES: CN(C)CCn1sc(Nc2c(Cl)cccc2Cl)c(C#N)c1=O] | A | 1.36 | 356.9, 359 |
| 100 | 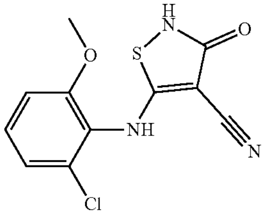 [SMILES: COc1cccc(Cl)c1Nc1s[nH]c(=O)c1C#N] | B | 1.95 | 279.2/281.2 |
| 101 | 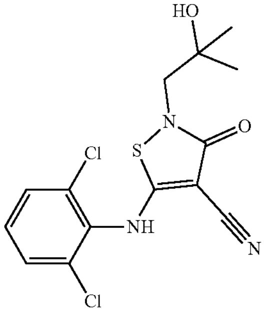 [SMILES: CC(C)(O)Cn1sc(Nc2c(Cl)cccc2Cl)c(C#N)c1=O] | C | 1.49 | 358, 360 |
| 102 | 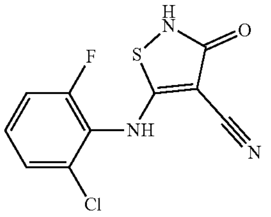 [SMILES: N#Cc1c(Nc2c(F)cccc2Cl)s[nH]c1=O] | B | 1.88 | 270/272 |
| 103 | 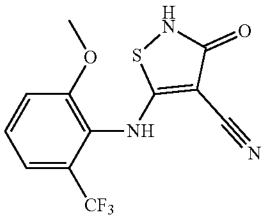 [SMILES: COc1cccc(C(F)(F)F)c1Nc1s[nH]c(=O)c1C#N] | B | 2.1 | 316.1 |
| 104 | 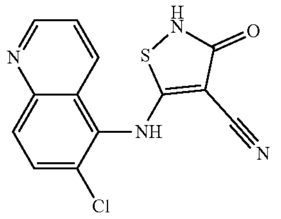 [SMILES: N#Cc1c(Nc2c(Cl)ccc3ncccc23)s[nH]c1=O] | A | 1.118 | 303, 305 |

TABLE 1-continued
| Example | Structure | LCMS method | RT (min) | Mol ion (m/z) |
|---|---|---|---|---|
| 105 | 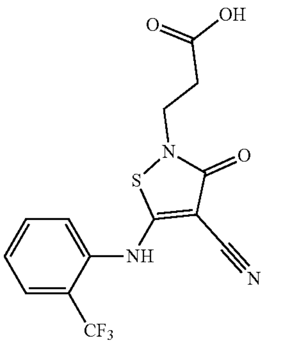 [SMILES: N#Cc1c(Nc2ccccc2C(F)(F)F)sn(CCC(=O)O)c1=O] | A | 1.13 | 358 |
| 106 | 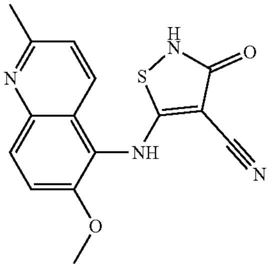 [SMILES: COc1ccc2nc(C)ccc2c1Nc1s[nH]c(=O)c1C#N] | B | 0.87 | 313.1 |
| 107 | 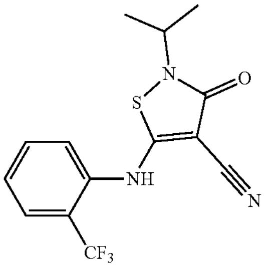 [SMILES: CC(C)n1sc(Nc2ccccc2C(F)(F)F)c(C#N)c1=O] | A | 1.5 | 328 |
| 108 | 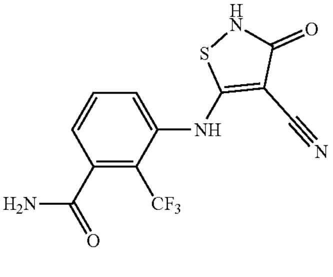 [SMILES: N#Cc1c(Nc2cccc(C(N)=O)c2C(F)(F)F)s[nH]c1=O] | A | 0.39 | 329 |
| 109 | 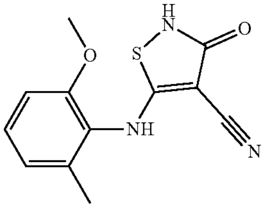 [SMILES: COc1cccc(C)c1Nc1s[nH]c(=O)c1C#N] | B | 1.96 | 262.1 |

TABLE 1-continued
| Example | Structure | LCMS method | RT (min) | Mol ion (m/z) |
|---|---|---|---|---|
| 110 | 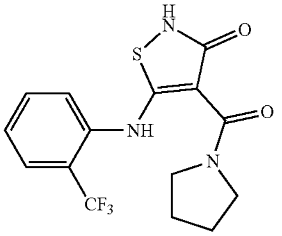 [SMILES: O=C(c1c(Nc2ccccc2C(F)(F)F)s[nH]c1=O)N1CCCC1] | B | 2.56 | 358.1 |
| 111 | 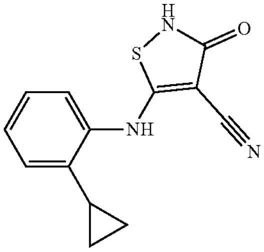 [SMILES: N#Cc1c(Nc2ccccc2C2CC2)s[nH]c1=O] | A | 1.27 | 258 |
| 112 | 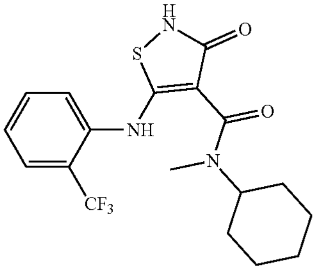 [SMILES: CN(C(=O)c1c(Nc2ccccc2C(F)(F)F)s[nH]c1=O)C1CCCCC1] | B | 3.37 | 400.2 |
| 113 | 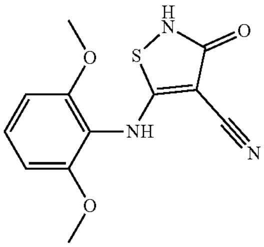 [SMILES: COc1cccc(OC)c1Nc1s[nH]c(=O)c1C#N] | B | 1.75 | 278.1 |
| 114 | 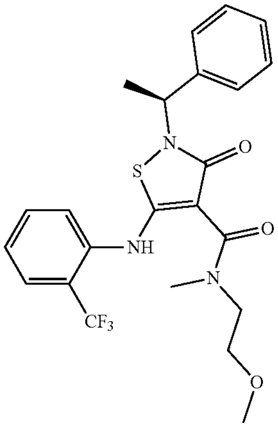 [SMILES: COCCN(C)C(=O)c1c(Nc2ccccc2C(F)(F)F)sn([C@@H](C)c2ccccc2)c1=O] | B | 3.28 | 480.0 |

TABLE 1-continued
| Ex-ample | Structure | LCMS method | RT (min) | Mol ion (m/z) |
|---|---|---|---|---|
| 115 | 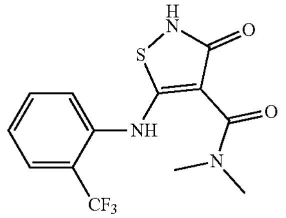 | B | 2.25 | 332.1 |
| 116 | 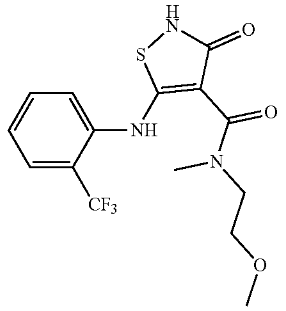 [SMILES: COCCN(C)C(=O)c1c(Nc2ccccc2C(F)(F)F)s[nH]c1=O] | B | 2.4 | 376.2 |
| 117 | 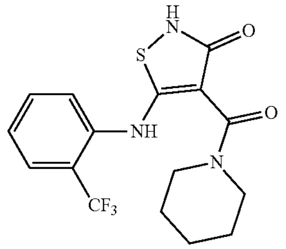 [SMILES: O=C(c1c(Nc2ccccc2C(F)(F)F)s[nH]c1=O)N1CCCCC1] | B | 2.86 | 372.2 |
| 118 | 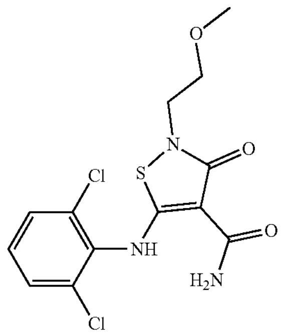 [SMILES: COCCn1sc(Nc2c(Cl)cccc2Cl)c(C(N)=O)c1=O] | A | 1.52 | 363 |
| 119 | 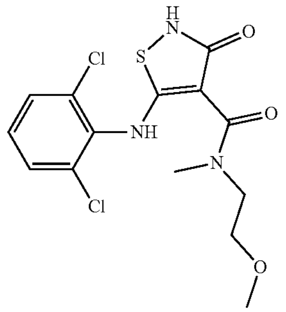 [SMILES: COCCN(C)C(=O)c1c(Nc2c(Cl)cccc2Cl)s[nH]c1=O] | B | 2.18 | 376.1/ 378.0 |

TABLE 1-continued
| Ex-ample | Structure | LCMS method | RT (min) | Mol ion (m/z) |
|---|---|---|---|---|
| 120 | 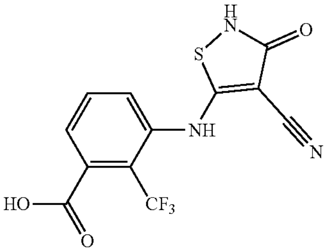 [SMILES: N#Cc1c(Nc2cccc(C(=O)O)c2C(F)(F)F)s[nH]c1=O] | A | 0.38 | 330 |
| 121 | 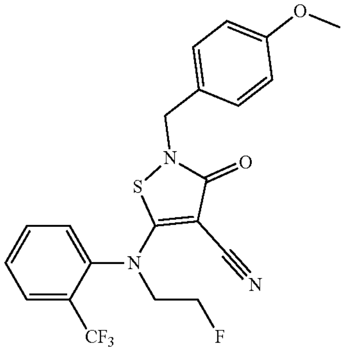 [SMILES: COc1ccc(Cn2sc(N(CCF)c3ccccc3C(F)(F)F)c(C#N)c2=O)cc1] | B | 3.29 | 452.2 |
| 122 | 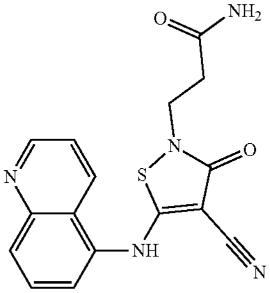 [SMILES: N#Cc1c(Nc2cccc3ncccc23)sn(CCC(N)=O)c1=O] | A | 1.091 | 340 |
| 123 | 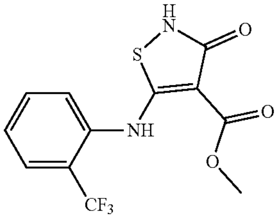 [SMILES: COC(=O)c1c(Nc2ccccc2C(F)(F)F)s[nH]c1=O] | B | 2.78 | 319.1 |
| 124 | 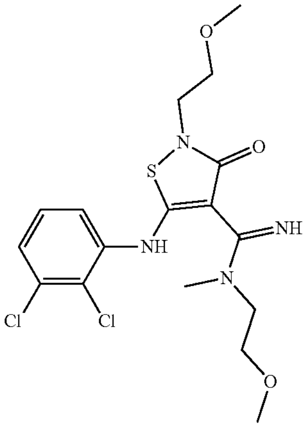 [SMILES: COCCN(C)C(=N)c1c(Nc2cccc(Cl)c2Cl)sn(CCOC)c1=O] | B | 1.75 | 433.0/ 435.0 |

TABLE 1-continued
| Example | Structure | LCMS method | RT (min) | Mol ion (m/z) |
|---|---|---|---|---|
| 125 | 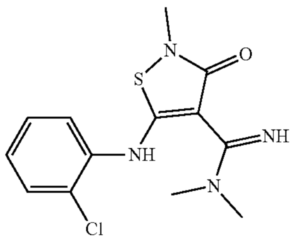 [SMILES: CN(C)C(=N)c1c(Nc2ccccc2Cl)sn(C)c1=O] | B | 1.22 | 311.1 |
| 126 | 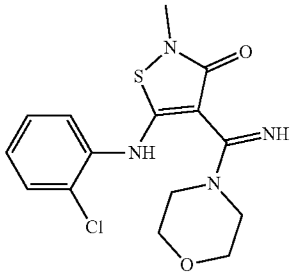 [SMILES: Cn1sc(Nc2ccccc2Cl)c(C(=N)N2CCOCC2)c1=O] | B | 1.27 | 353.2 |
| 127 | 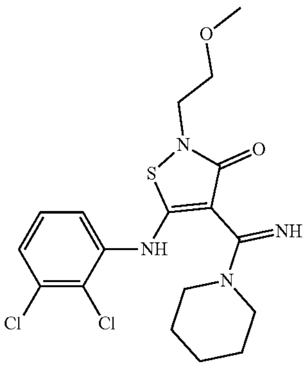 [SMILES: COCCn1sc(Nc2cccc(Cl)c2Cl)c(C(=N)N2CCCCC2)c1=O] | B | 1.87 | 429.1/ 431.2 |
| 128 | 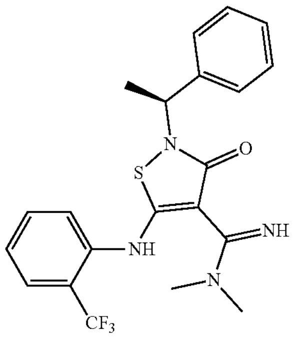 [SMILES: C[C@@H](c1ccccc1)n1sc(Nc2ccccc2C(F)(F)F)c(C(=N)N(C)C)c1=O] | A | 1.919 | 435 |
| 129 | 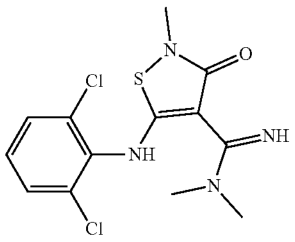 [SMILES: CN(C)C(=N)c1c(Nc2c(Cl)cccc2Cl)sn(C)c1=O] | B | 1.3 | 387.2/ 389.1 |

TABLE 1-continued
| Example | Structure | LCMS method | RT (min) | Mol ion (m/z) |
|---|---|---|---|---|
| 130 | 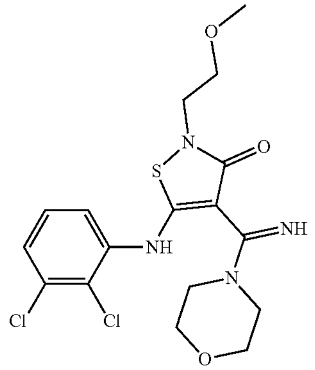 [SMILES: COCCn1sc(Nc2cccc(Cl)c2Cl)c(C(=N)N2CCOCC2)c1=O] | B | 1.67 | 431.0/ 433.0 |
| 131 | 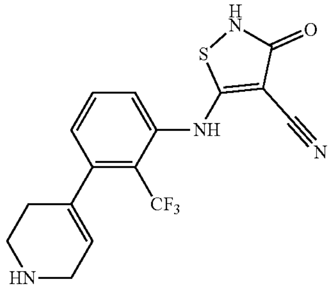 [SMILES: N#Cc1c(Nc2cccc(C3=CCNCC3)c2C(F)(F)F)s[nH]c1=O] | A | 1.078 | 367 |
| 132 | 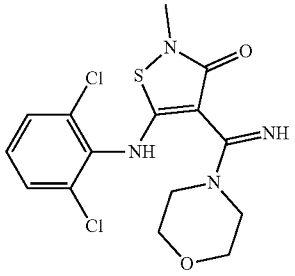 | B | 1.33 | 387.2/ 389.1 |
| 133 | 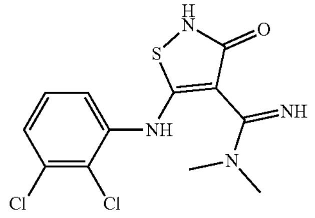 [SMILES: CN(C)C(=N)c1c(Nc2cccc(Cl)c2Cl)s[nH]c1=O] | A | 1.307 | 331, 333 |
| 134 | 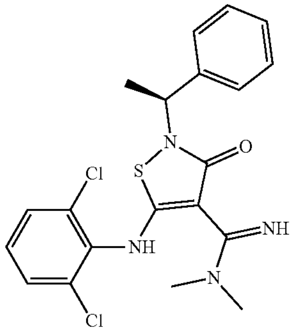 [SMILES: C[C@@H](c1ccccc1)n1sc(Nc2c(Cl)cccc2Cl)c(C(=N)N(C)C)c1=O] | A | 1.676 | 435.1, 437 |

TABLE 1-continued
| Example | Structure | LCMS method | RT (min) | Mol ion (m/z) |
|---|---|---|---|---|
| 135 | 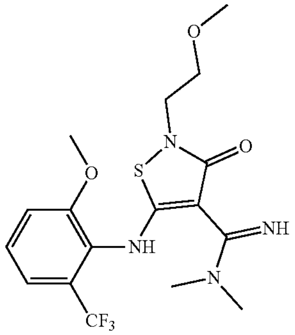 [SMILES: COCCn1sc(Nc2c(OC)cccc2C(F)(F)F)c(C(=N)N(C)C)c1=O] | A | 1.556 | 419 |
| 136 | 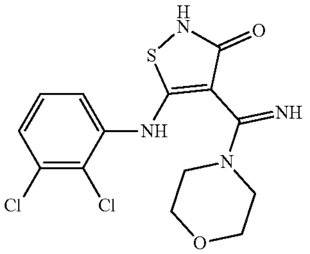 [SMILES: N=C(c1c(Nc2cccc(Cl)c2Cl)s[nH]c1=O)N1CCOCC1] | B | 1.39 | 375.2/ 377.2 |
| 137 | 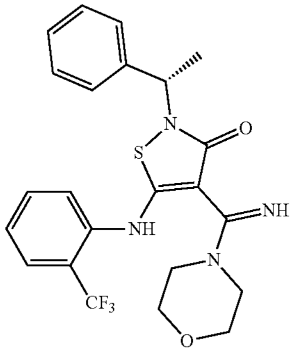 [SMILES: C[C@@H](c1ccccc1)n1sc(Nc2ccccc2C(F)(F)F)c(C(=N)N2CCOCC2)c1=O] | B | 2.18 | 477.3 |
| 138 | 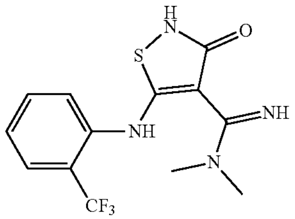 [SMILES: CN(C)C(=N)c1c(Nc2ccccc2C(F)(F)F)s[nH]c1=O] | A | 1.16 | 330.9 |
| 139 | 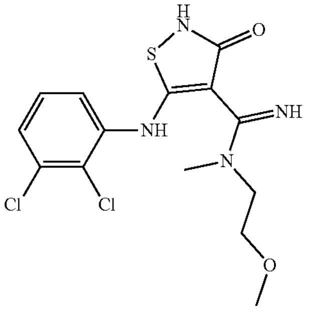 [SMILES: COCCN(C)C(=N)c1c(Nc2cccc(Cl)c2Cl)s[nH]c1=O] | A | 1.384 | 375, 377 |

TABLE 1-continued
| Ex-ample | Structure | LCMS method | RT (min) | Mol ion (m/z) |
|---|---|---|---|---|
| 140 | 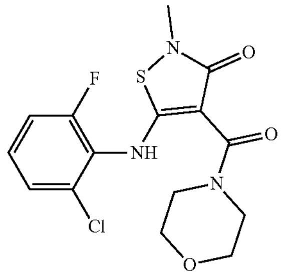 [SMILES: Cn1sc(Nc2c(F)cccc2Cl)c(C(=O)N2CCOCC2)c1=O] | B | 2.05 | 370.1 |
| 141 | 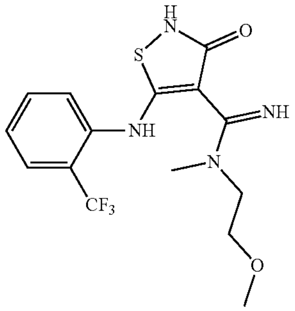 [SMILES: COCCN(C)C(=N)c1c(Nc2ccccc2C(F)(F)F)s[nH]c1=O] | A | 1.408 | 375 |
| 142 | 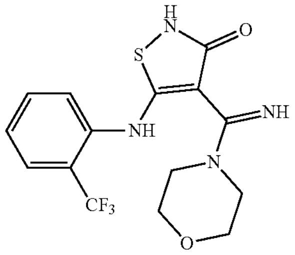 [SMILES: N=C(c1c(Nc2ccccc2C(F)(F)F)s[nH]c1=O)N1CCOCC1] | B | 1.21 | 331.2 |
| 143 | 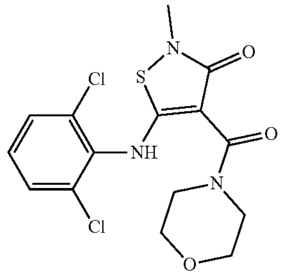 | B | 2.25 | 388 |
| 144 | 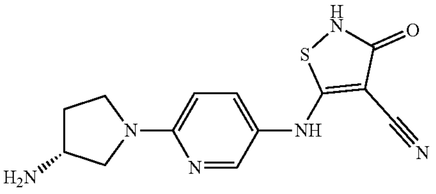 [SMILES: N#Cc1c(Nc2ccc(N3CC[C@@H](N)C3)nc2)s[nH]c1=O] | A | 0.797 | 303 |
| 145 | 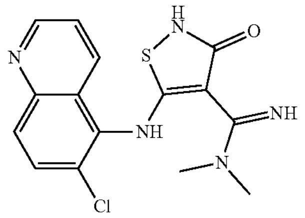 [SMILES: CN(C)C(=N)c1c(Nc2c(Cl)ccc3ncccc23)s[nH]c1=O] | A | 1.154 | 348, 350 |

TABLE 1-continued
| Example | Structure | LCMS method | RT (min) | Mol ion (m/z) |
| --- | --- | --- | --- | --- |
| 146 | 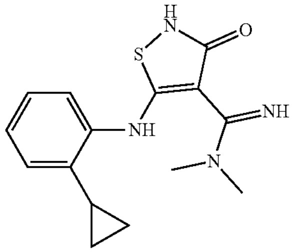 [SMILES: CN(C)C(=N)c1c(Nc2ccccc2C2CC2)s[nH]c1=O] | A | 1.343 | 303 |
| 147 | 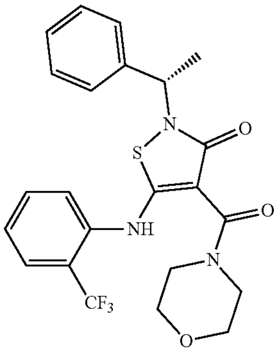 [SMILES: C[C@@H](c1ccccc1)n1sc(Nc2ccccc2C(F)(F)F)c(C(=O)N2CCOCC2)c1=O] | B | 3.51 | 478.2 |
| 148 | 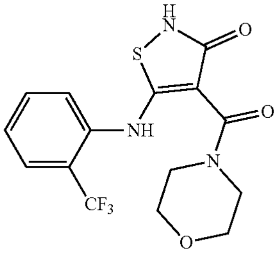 [SMILES: O=C(c1c(Nc2ccccc2C(F)(F)F)s[nH]c1=O)N1CCOCC1] | B | 2.28 | 374.1 |
| 149 | 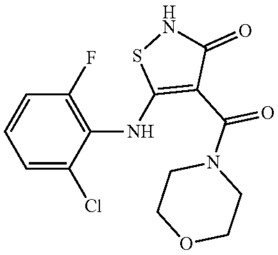 [SMILES: O=C(c1c(Nc2c(F)cccc2Cl)s[nH]c1=O)N1CCOCC1] | B | 1.84 | 358.1/ 360.1 |
| 150 | 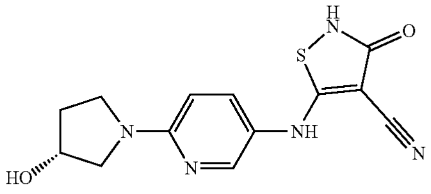 [SMILES: N#Cc1c(Nc2ccc(N3CC[C@@H](O)C3)nc2)s[nH]c1=O] | A | 1.01 | 304 |

TABLE 1-continued
| Example | Structure | LCMS method | RT (min) | Mol ion (m/z) |
|---|---|---|---|---|
| 151 | 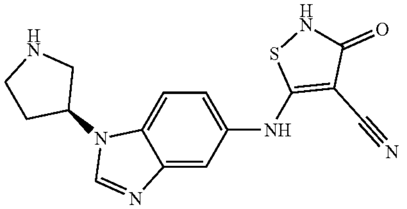 [SMILES: N#Cc1c(Nc2ccc3c(c2)ncn3[C@H]2CCNC2)s[nH]c1=O] | A | 0.96 | 327 |
| 152 | 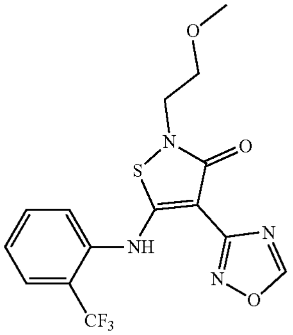 [SMILES: COCCn1sc(Nc2ccccc2C(F)(F)F)c(-c2ncon2)c1=O] | B | 2.86 | 387.1 |
| 153 | 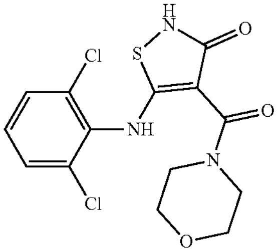 | B | 2.03 | 374.0/ 376.0 |
| 154 | 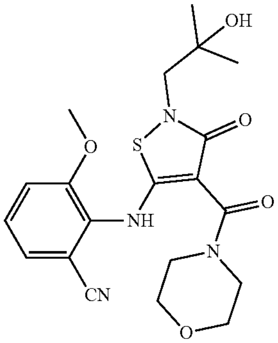 [SMILES: COc1cccc(C#N)c1Nc1sn(CC(C)(C)O)c(=O)c1C(=O)N1CCOCC1] | B | 1.79 | 433.3 |
| 155 | 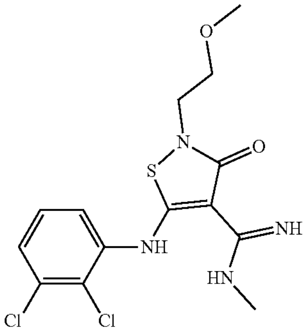 [SMILES: CNC(=N)c1c(Nc2cccc(Cl)c2Cl)sn(CCOC)c1=O] | A | 1.642 | 389.0, 390.9 |

TABLE 1-continued
| Example | Structure | LCMS method | RT (min) | Mol ion (m/z) |
|---|---|---|---|---|
| 156 | 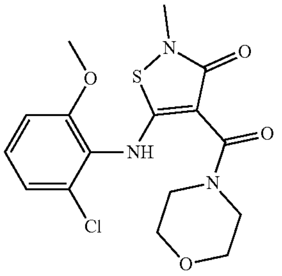 | B | 2.21 | 286.1 |
| 157 | 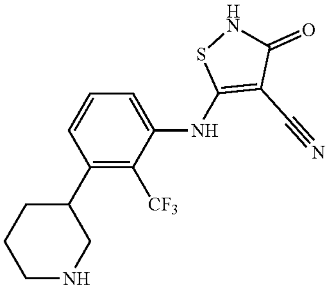 [SMILES: N#Cc1c(Nc2cccc(C3CCCNC3)c2C(F)(F)F)s[nH]c1=O] | A | 1.114 | 369 |
| 158 | 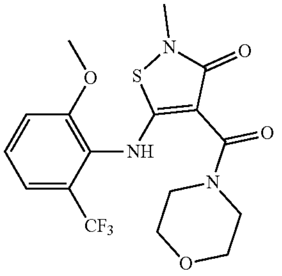 [SMILES: COc1cccc(C(F)(F)F)c1Nc1sn(C)c(=O)c1C(=O)N1CCOCC1] | B | 2.46 | 418.1 |
| 159 | 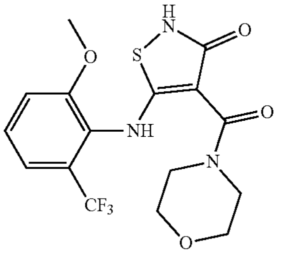 [SMILES: COc1cccc(C(F)(F)F)c1Nc1s[nH]c(=O)c1C(=O)N1CCOCC1] | B | 2.24 | 404.1 |
| 160 | 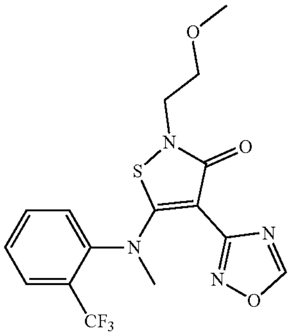 [SMILES: COCCn1sc(N(C)c2ccccc2C(F)(F)F)c(-c2ncon2)c1=O] | B | 2.63 | 401.1 |

TABLE 1-continued
| Example | Structure | LCMS method | RT (min) | Mol ion (m/z) |
|---|---|---|---|---|
| 161 | 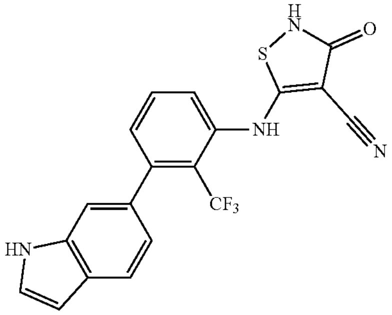 [SMILES: N#Cc1c(Nc2cccc(-c3ccc4cc[nH]c4c3)c2C(F)(F)F)s[nH]c1=O] | A | 1.539 | 401 |
| 162 | 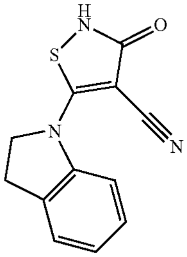 [SMILES: N#Cc1c(N2CCc3ccccc32)s[nH]c1=O] | C | 1.601 | 244.1 |
| 163 | 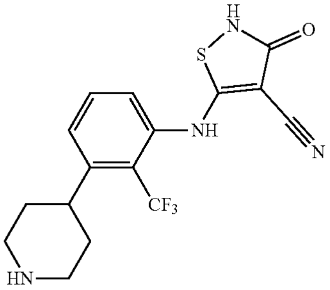 [SMILES: N#Cc1c(Nc2cccc(C3CCNCC3)c2C(F)(F)F)s[nH]c1=O] | A | 1.022 | 369 |
| 164 | 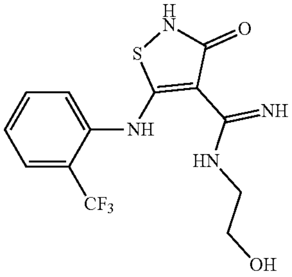 [SMILES: N=C(NCCO)c1c(Nc2ccccc2C(F)(F)F)s[nH]c1=O] | A | 1.408 | 375 |
| 165 | 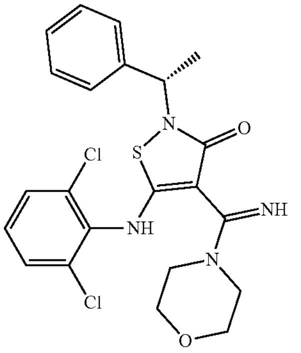 [SMILES: C[C@@H](c1ccccc1)n1sc(Nc2c(Cl)cccc2Cl)c(C(=N)N2CCOCC2)c1=O] | B | 2.16 | 477.2/ 479.2 |

TABLE 1-continued
| Ex-ample | Structure | LCMS method | RT (min) | Mol ion (m/z) |
|---|---|---|---|---|
| 166 | 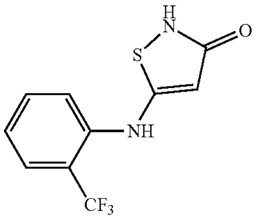 [SMILES: O=c1cc(Nc2ccccc2C(F)(F)F)s[nH]1] | A | 1.378 | 261 |
| 167 | 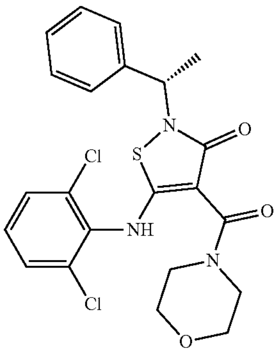 [SMILES: C[C@@H](c1ccccc1)n1sc(Nc2c(Cl)cccc2Cl)c(C(=O)N2CCOCC2)c1=O] | B | 3.28 | 478.1 |
| 168 | 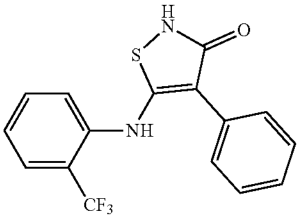 [SMILES: O=c1[nH]sc(Nc2ccccc2C(F)(F)F)c1-c1ccccc1] | B | 3.24 | 337.1 |
| 169 | 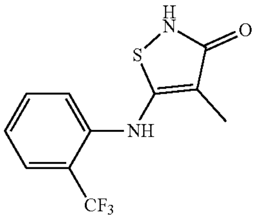 [SMILES: Cc1c(Nc2ccccc2C(F)(F)F)s[nH]c1=O] | C | 1.627 | 275.1 |
| 170 | 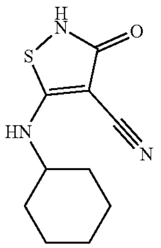 [SMILES: N#Cc1c(NC2CCCCC2)s[nH]c1=O] | B | 2.07 | 224.2 |
| 171 | 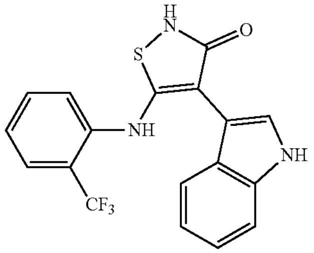 [SMILES: O=c1[nH]sc(Nc2ccccc2C(F)(F)F)c1-c1c[nH]c2ccccc12] | A | 1.222 | 242.1 |

TABLE 1-continued
| Example | Structure | LCMS method | RT (min) | Mol ion (m/z) |
|---|---|---|---|---|
| 172 | 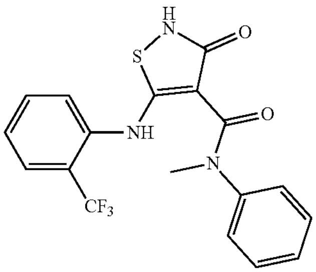 [SMILES: CN(C(=O)c1c(Nc2ccccc2C(F)(F)F)s[nH]c1=O)c1ccccc1] | B | 2.95 | 394.2 |
| 173 | 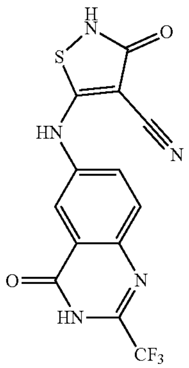 [SMILES: N#Cc1c(Nc2ccc3nc(C(F)(F)F)[nH]c(=O)c3c2)s[nH]c1=O] | A | 1.031 | 354 |
| 174 | 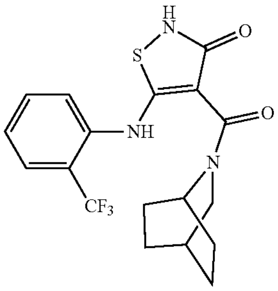 [SMILES: O=C(c1c(Nc2ccccc2C(F)(F)F)s[nH]c1=O)N1CC2CCC1CC2] | B | 3.08 | 398.3 |
| 175 | 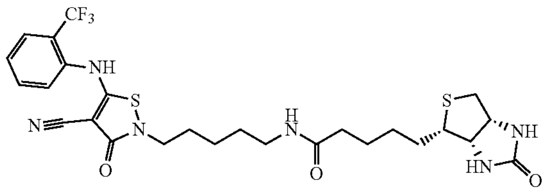 [SMILES: N#Cc1c(Nc2ccccc2C(F)(F)F)sn(CCCCCNC(=O)CCCC[C@@H]2SC[C@@H]3NC(=O)N[C@@H]32)c1=O] | A | 1.42 | 597 |
| 176 | 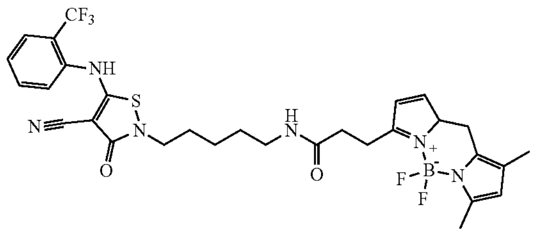 [SMILES: Cc1cc(C)n2c1CC1C=CC(CCC(=O)NCCCCCn3sc(Nc4ccccc4C(F)(F)F)c(C#N)c3=O)=[N+]1[B-]2(F)F] | A | 1.9 | 645 |
| 177 | 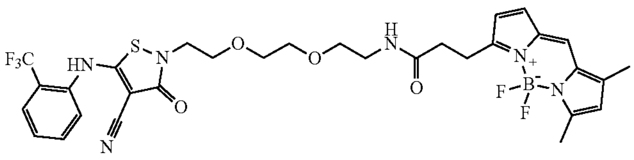 | A | 1.59 | 691 |

TABLE 1-continued

| Example | Structure | LCMS method | RT (min) | Mol ion (m/z) |
|---|---|---|---|---|
| 178 | 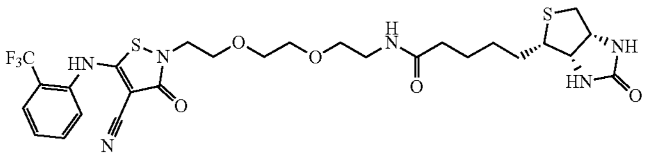 [SMILES: N#Cc1c(Nc2ccccc2C(F)(F)F)sn(CCOCCOCCNC(=O)CCCC[C@@H]2SC[C@@H]3NC(=O)N[C@@H]32)c1=O] | A | 1.34 | 643 |
| 179 | 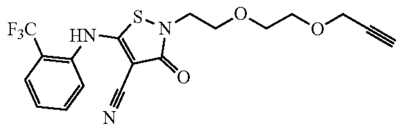 [SMILES: C#CCOCCOCCn1sc(Nc2ccccc2C(F)(F)F)c(C#N)c1=O] | A | 1.45 | 411.9 |
| 180 | 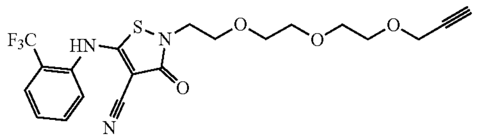 [SMILES: C#CCOCCOCCOCCn1sc(Nc2ccccc2C(F)(F)F)c(C#N)c1=O] | A | 1.308 | 455.9 |

Example 2: SAM-TIR SARM1 IC50 Assay

This Example describes an assay of SAM-TIR NADase activity and use of this assay to measure the efficacy of compounds of Formula I or Formula II to block SARM1 mediated NAD+ cleavage. This assay is optimized in such a way as to characterize the efficacy of the compounds in Formula I or Formula II to inhibit SARM1 activity and to calculate an IC50 value for each compound. This assay makes use of a fragment of the SARM1 molecule encompassing the SAM and TIR domains. As demonstrated herein, expression of this fragment without the autoinhibitory N-terminal domain generates a constitutively active enzyme that cleaves NAD+.

Preparation of SARM1 SAM-TIR Lysate (STL)

Figure 2:
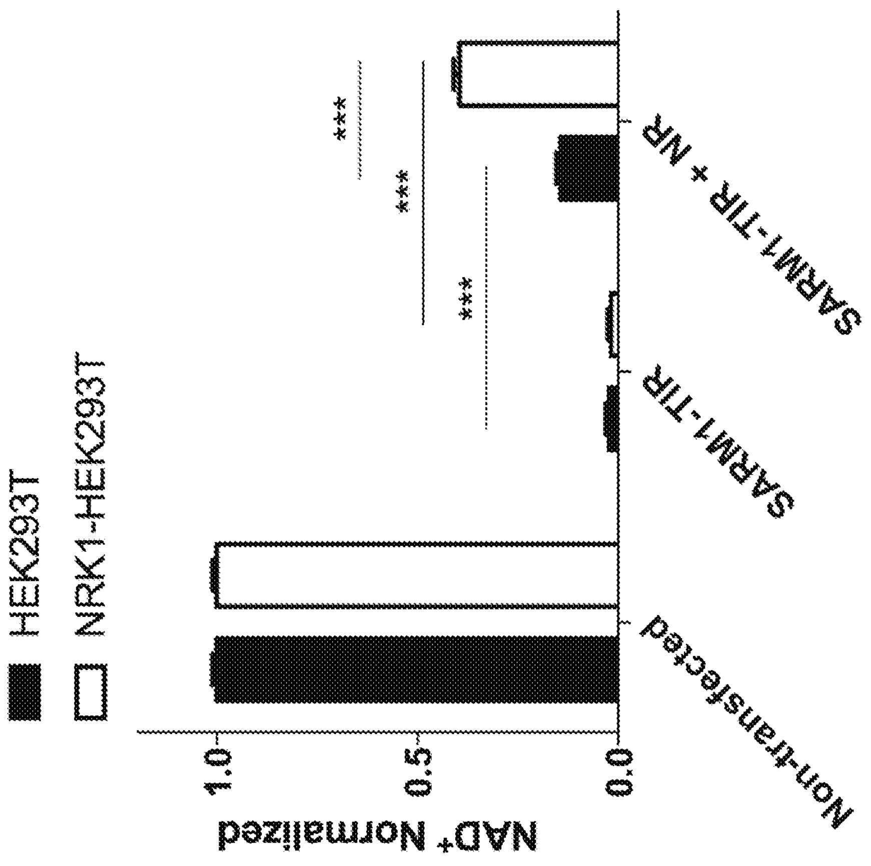
FIG. 2 illustrates that a NRK1-HEK293T stable line with NR supplementation maintains higher NAD+ levels upon SARM1-TIR expression.

NRK1-HEK293T cells refers to a cell line that has been stably e transfected with an FCIV expression vector that expresses human Nicotinamide Riboside Kinase 1 (NRK1), an enzyme that converts the NAD+ biosynthetic precursor nicotinamide riboside (NR) to NMN, the immediate precursor of NAD+. When provided with NR this cell line augments intracellular NAD+ levels and maintains cell viability, when expressing SARM1 SAM-TIR. FIG. 2 illustrates that a NRK1-HEK293T stable line with NR supplementation maintains higher NAD+ levels upon SARM1-TIR expression. Data was generated from three independent NAD+ measurements from three independent transfection experiments, and normalized to data from a non-transfected experiment run concurrently. Data are presented as mean±SEM; Error bars: SEM; *** P<0.001 two tailed student's t-test.

NRK1-HEK293T cells represent a cell line that has been stably transfected with an FCIV expression vector that expresses human Nicotinamide Riboside Kinase 1 (NRK1), an enzyme that converts the NAD+ biosynthetic precursor nicotinamide riboside (NR) to NMN, the immediate precursor of NAD+.

NRK1-HEK293T cells were seeded onto 150 $cm^2$ plates at 20×106 cells per plate. The next day, the cells were transfected with 15 μg FCIV-SST (SAM-TIR expression plasmid, SEQ ID NO: 1) using X-TREMEGENE™ 9 DNA Transfection Reagent (Roche product #06365787001).

```
                                                                     (SEQ ID NO: 1)
gtcgacggatcgggagatctcccgatcccctatggtgcactctcagtacaatctgctctgatgccgcatagttaagccagtatctgctccctgc

ttgtgtgttggaggtcgctgagtagtgcgcgagcaaaatttaagctacaacaaggcaaggcttgaccgacaattgcatgaagaatctgcttag

ggttaggcgttttgcgctgcttcgcgatgtacgggccagatatacgcgttgacattgattattgactagttattaatagtaatcaattacggggtc

attagttcatagcccatatatggagttccgcgttacataacttacggtaaatggcccgcctggctgaccgcccaacgacccccgcccattgac

gtcaataatgacgtatgttcccatagtaacgccaatagggactttccattgacgtcaatgggtggagtatttacggtaaactgcccacttggca

gtacatcaagtgtatcatatgccaagtacgccccctattgacgtcaatgacggtaaatggcccgcctggcattatgcccagtacatgaccttat

gggactttcctacttggcagtacatctacgtattagtcatcgctattaccatggtgatgcggttttggcagtacatcaatgggcgtggatagcgg

tttgactcacggggatttccaagtctccaccccattgacgtcaatgggagtttgttttggcaccaaaatcaacgggactttccaaaatgtagtaa

caactccgccccattgacgcaaatgggcggtaggcgtgtacggtgggaggtctatataagcagcgcgtttgcctgtactgggtctctctggt

tagaccagatctgagcctgggagctctctggctaactagggaacccactgcttaagcctcaataaagcttgccttgagtgcttcaagtagtgt

gtgcccgtctgttgtgtgactctggtaactagagatccctcagacccttttagtcagtgtggaaaatctctagcagtggcgcccgaacaggga
```

-continued cttgaaagcgaaagggaaaccagaggagctctctcgacgcaggactcggcttgctgaagcgcgcacggcaagaggcgaggggcggc gactggtgagtacgccaaaaattttgactagcggaggctagaaggagagagatgggtgcgagagcgtcagtattaagcgggggagaatt agatcgcgatgggaaaaaattcggttaaggccagggggaaagaaaaaatataaattaaaacatatagtatgggcaagcagggagctagaa cgattcgcagttaatcctggcctgttagaaacatcagaaggctgtagacaaatactgggacagctacaaccatcccttcagacaggatcaga agaacttagatcattatataatacagtagcaaccctctattgtgtgcatcaaaggatagagataaaagacaccaaggaagctttagacaagat agaggaagagcaaaacaaaagtaagaccaccgcacagcaagcggccgctgatcttcagacctggaggaggagatatgagggacaattg gagaagtgaattatataaatataaagtagtaaaaattgaaccattaggagtagcacccaccaaggcaaagagaagagtggtgcagagaga aaaaagagcagtgggaataggagctttgttccttgggttcttgggagcagcaggaagcactatgggcgcagcgtcaatgacgctgacggt acaggccagacaattattgtctggtatagtgcagcagcagaacaatttgctgagggctattgaggcgcaacagcatctgttgcaactcacagt ctggggcatcaagcagctccaggcaagaatcctggctgtggaaagatacctaaaggatcaacagctcctggggatttggggttgctctgga aaactcatttgcaccactgctgtgccttggaatgctagttggagtaataaatctctggaacagatttggaatcacacgacctggatggagtggg acagagaaattaacaattacacaagcttaatacactccttaattgaagaatcgcaaaaccagcaagaaaagaatgaacaagaattattggaat tagataaatgggcaagtttgtggaattggtttaacataacaaattggctgtggtatataaaattattcataatgatagtaggaggcttggtaggttt aagaatagtttttgctgtactttctatagtgaatagagttaggcagggatattcaccattatcgtttcagacccacctcccaaccccgaggggac ccgacaggcccgaaggaatagaagaagaaggtggagagagagacagagacagatccattcgattagtgaacggatcggcactgcgtgc gccaattctgcagacaaatggcagtattcatccacaattttaaaagaaaaggggggattggggggtacagtgcaggggaaagaatagtaga cataatagcaacagacatacaaactaaagaattacaaaaacaaattacaaaaattcaaaattttcgggtttattacagggacagcagagatcc agtttggttaattaagggtgcagcggcctccgcgccgggttttggcgcctcccgcgggcgcccccctcctcacggcgagcgctgccacgt cagacgaagggcgcaggagcgttcctgatccttccgcccggacgctcaggacagcggcccgctgctcataagactcggccttagaaccc cagtatcagcagaaggacattttaggacgggacttgggtgactctagggcactggttttctttccagagagcggaacaggcgaggaaaagt agtcccttctcggcgattctgcggagggatctccgtggggcggtgaacgccgatgattatataaggacgcgccgggtgtggcacagctagt tccgtcgcagccgggatttgggtcgcggttcttgtttgtggatcgctgtgatcgtcacttggtgagttgcgggctgctgggctggccggggct ttcgtggccgccgggccgctcggtgggacggaagcgtgtggagagaccgccaagggctgtagtctgggtccgcgagcaaggttgccct gaactgggggttggggggagcgcacaaaatggcggctgttcccgagtcttgaatggaagacgcttgtaaggcgggctgtgaggtcgttga aacaaggtgggggggcatggtgggcggcaagaacccaaggtcttgaggccttcgctaatgcgggaaagctcttattcgggtgagatgggct ggggcaccatctggggaccctgacgtgaagtttgtcactgactggagaactcgggtttgtcgtctggttgcgggggcggcagttatgcggt gccgttgggcagtgcacccgtacctttgggagcgcgcgcctcgtcgtgtcgtgacgtcacccgttctgttggcttataatgcagggtggggc cacctgccggtaggtgtgcggtaggcttttctccgtcgcaggacgcagggttcgggcctagggtaggctctcctgaatcgacaggcgccg gacctctggtgaggggagggataagtgaggcgtcagtttctttggtcggttttatgtacctatcttcttaagtagctgaagctccggttttgaact atgcgctcggggttggcgagtgtgttttgtgaagttttttaggcaccttttgaaatgtaatcatttgggtcaatatgtaattttcagtgttagactagt aaagcttctgcaggtcgactctagaaaattgtccgctaaattctggccgtttttggctttttttgttagacgaagcttgggctgcaggtcgactcta gaggatccGGATCCGCCACCATGTCAgctTGGAGCCACCCACAATTCGAAAAAGGCGGTG

GCTCAGGCGGTGGCTCAGGTGGCTCAGCTTGGAGCCACCCACAATTCGAAAAAGGC

GGTGGCTCATCTGGCGGAGGTGGCGGTGGCTCATCTGGCGGAGGTGCTAGCgtgcccagc tggaaggaggccgaggttcagacgtggctgcagcagatcggtttctccaagtactgcgagagcttccgggagcagcaggtggatggcga cctgcttctgcggctcacggaggaggaactccagaccgacctgggcatgaaatcgggcatcacccgcaagaggttctttagggagctcac ggagctcaagaccttcgccaactattctacgtgcgaccgcagcaacctggcggactggctgggcagcctggacccgcgcttccgccagta cacctacggcctggtcagctgcggcctggaccgctccctgctgcaccgcgtgtctgagcagcagctgctggaagactgcggcatccacct gggcgtgcaccgcgcccgcatcctcacggcggccagagaaatgctacactccccgctgccctgtactggtggcaaacccagtggggac actccagatgtcttcatcagctaccgccggaactcaggttcccagctggccagtctcctgaaggtgcacctgcagctgcatggcttcagtgtc -continued ttcattgatgtggagaagctggaagcaggcaagttcgaggacaaactcatccagagtgtcatgggtgcccgcaactttgtgttggtgctatca cctggagcactggacaagtgcatgcaagaccatgactgcaaggattgggtgcataaggagattgtgactgctttaagctgcggcaagaaca ttgtgcccatcattgatggcttcgagtggcctgagccccaggtcctgcctgaggacatgcaggctgtgcttactttcaacggtatcaagtggtc ccacgaataccaggaggccaccattgagaagatcatccgcttcctgcagggccgctcctcccgggactcatctgcaggctctgacaccagt ttggagggtgctgcacccatgggtccaacctaaactctagaattcgatatcaagcttatcgataatcaacctctggattacaaaatttgtgaaag attgactggtattcttaactatgttgctccttttacgctatgtggatacgctgctttaatgcctttgtatcatgctattgcttcccgtatggctttcatttt ctcctccttgtataaatcctggttgctgtctctttatgaggagttgtggcccgttgtcaggcaacgtggcgtggtgtgcactgtgtttgctgacgc aacccccactggttggggcattgccaccacctgtcagctcctttccgggactttcgctttccccctccctattgccacggcggaactcatcgcc gcctgccttgcccgctgctggacaggggctcggctgttgggcactgacaattccgtggtgttgtcggggaaatcatcgtcctttccttggctg ctcgcctgtgttgccacctggattctgcgcgggacgtccttctgctacgtcccttcggccctcaatccagcggaccttccttcccgcggcctg ctgccggctctgcggcctcttccgcgtcttcgccttcgccctcagacgagtcggatctccctttgggccgcctccccgcatcgataccgtcga cctcgagacctagaaaaacatggagcaatcacaagtagcaatacagcagctaccaatgctgattgtgcctggctagaagcacaagaggag gaggaggtgggttttccagtcacacctcaggtacctttaagaccaatgacttacaaggcagctgtagatcttagccactttttaaaagaaaagg ggggactggaagggctaattcactcccaacgaagacaagatatccttgatctgtggatctaccacacacaaggctacttccctgattggcag aactacacaccagggccagggatcagatatccactgacctttggatggtgctacaagctagtaccagttgagcaagagaaggtagaagaa gccaatgaaggagagaacacccgcttgttacaccctgtgagcctgcatgggatggatgacccggagagagaagtattagagtggaggttt gacagccgcctagcatttcatcacatggcccgagagctgcatccggactgtactgggtctctctggttagaccagatctgagcctgggagct ctctggctaactagggaacccactgcttaagcctcaataaagcttgccttgagtgcttcaagtagtgtgtgcccgtctgttgtgtgactctggta actagagatccctcagacccttttagtcagtgtggaaaatctctagcagggcccgtttaaacccgctgatcagcctcgactgtgccttctagtt gccagccatctgttgtttgcccctcccccgtgccttccttgaccctggaaggtgccactcccactgtcctttcctaataaaatgaggaaattgca tcgcattgtctgagtaggtgtcattctattctggggggtggggtggggcaggacagcaagggggaggattgggaagacaatagcaggcat gctggggatgcggtgggctctatggcttctgaggcggaaagaaccagctggggctctagggggtatccccacgcgccctgtagcggcgc attaagcgcggcgggtgtggtggttacgcgcagcgtgaccgctacacttgccagcgccctagcgcccgctcctttcgctttcttcccttcctt ctcgccacgttcgccggctttccccgtcaagctctaaatcgggggctccctttagggttccgatttagtgctttacggcacctagaccccaaaa aacttgattagggtgatggttcacgtagtgggccatcgccctgatagacggtttttcgccctttgacgttggagtccacgttctttaatagtggac tcttgttccaaactggaacaacactcaaccctatctcggtctattcttttgatttataagggattttgccgatttcggcctattggttaaaaaatgag ctgatttaacaaaaatttaacgcgaattaattctgtggaatgtgtgtcagttagggtgtggaaagtccccaggctccccagcaggcagaagtat gcaaagcatgcatctcaattagtcagcaaccaggtgtggaaagtccccaggctccccagcaggcagaagtatgcaaagcatgcatctcaat tagtcagcaaccatagtcccgcccctaactccgcccatcccgcccctaactccgcccagttccgcccattctccgccccatggctgactaatt ttttttatttatgcagaggccgaggccgcctctgcctctgagctattccagaagtagtgaggaggcttttttggaggcctaggcttttgcaaaaa gctcccgggagcttgtatatccattttcggatctgatcagcacgtgttgacaattaatcatcggcatagtatatcggcatagtataatacgacaa ggtgaggaactaaaccatggccaagttgaccagtgccgttccggtgctcaccgcgcgcgacgtcgccggagcggtcgagttctggaccg accggctcgggttctcccgggacttcgtggaggacgacttcgccggtgtggtccgggacgacgtgaccctgttcatcagcgcggtccagg accaggtggtgccggacaacaccctggcctgggtgtgggtgcgcggcctggacgagctgtacgccgagtggtcggaggtcgtgtccac gaacttccgggacgcctccgggccggccatgaccgagatcggcgagcagccgtgggggcgggagttcgccctgcgcgacccggccg gcaactgcgtgcacttcgtggccgaggagcaggactgacacgtgctacgagatttcgattccaccgccgccttctatgaaaggttgggcttc ggaatcgttttccgggacgccggctggatgatcctccagcgcggggatctcatgctggagttcttcgcccaccccaacttgtttattgcagctt ataatggttacaaataaagcaatagcatcacaaatttcacaaataaagcatttttttcactgcattctagttgtggtttgtccaaactcatcaatgtat cttatcatgtctgtataccgtcgacctctagctagagcttggcgtaatcatggtcatagctgtttcctgtgtgaaattgttatccgctcacaattcca cacaacatacgagccggaagcataaagtgtaaagcctggggtgcctaatgagtgagctaactcacattaattgcgttgcgctcactgcccgc tttccagtcgggaaacctgtcgtgccagctgcattaatgaatcggccaacgcgcggggagaggcggtttgcgtattgggcgctcttccgctt -continued

```
cctcgctcactgactcgctgcgctcggtcgttcggctgcggcgagcggtatcagctcactcaaaggcggtaatacggttatccacagaatca

ggggataacgcaggaaagaacatgtgagcaaaaggccagcaaaaggccaggaaccgtaaaaaggccgcgttgctggcgtttttccatag

gctccgcccccctgacgagcatcacaaaaatcgacgctcaagtcagaggtggcgaaacccgacaggactataaagataccaggcgtttcc

ccctggaagctccctcgtgcgctctcctgttccgaccctgccgcttaccggatacctgtccgcctttctcccttcgggaagcgtggcgctttct

catagctcacgctgtaggtatctcagttcggtgtaggtcgttcgctccaagctgggctgtgtgcacgaaccccccgttcagcccgaccgctg

cgccttatccggtaactatcgtcttgagtccaacccggtaagacacgacttatcgccactggcagcagccactggtaacaggattagcagag

cgaggtatgtaggcggtgctacagagttcttgaagtggtggcctaactacggctacactagaagaacagtatttggtatctgcgctctgctga

agccagttaccttcggaaaaagagttggtagctcttgatccggcaaacaaaccaccgctggtagcggtggtttttttgtttgcaagcagcagat

tacgcgcagaaaaaaaggatctcaagaagatcctttgatcttttctacggggtctgacgctcagtggaacgaaaactcacgttaagggatttt

ggtcatgagattatcaaaaaggatcttcacctagatccttttaaattaaaaatgaagttttaaatcaatctaaagtatatatgagtaaacttggtctg

acagttaccaatgcttaatcagtgaggcacctatctcagcgatctgtctatttcgttcatccatagttgcctgactccccgtcgtgtagataacta

cgatacgggagggcttaccatctggccccagtgctgcaatgataccgcgagacccacgctcaccggctccagatttatcagcaataaacca

gccagccggaagggccgagcgcagaagtggtcctgcaactttatccgcctccatccagtctattaattgttgccgggaagctagagtaagta

gttcgccagttaatagtttgcgcaacgttgttgccattgctacaggcatcgtggtgtcacgctcgtcgtttggtatggcttcattcagctccggtt

cccaacgatcaaggcgagttacatgatcccccatgttgtgcaaaaaagcggttagctccttcggtcctccgatcgttgtcagaagtaagttgg

ccgcagtgttatcactcatggttatggcagcactgcataattctcttactgtcatgccatccgtaagatgcttttctgtgactggtgagtactcaac

caagtcattctgagaatagtgtatgcggcgaccgagttgctcttgcccggcgtcaatacgggataataccgcgccacatagcagaactttaa

aagtgctcatcattggaaaacgttcttcggggcgaaaactctcaaggatcttaccgctgttgagatccagttcgatgtaacccactcgtgcacc

caactgatcttcagcatcttttactttcaccagcgtttctgggtgagcaaaaacaggaaggcaaaatgccgcaaaaaagggaataagggcga

cacggaaatgttgaatactcatactcttcctttttcaatattattgaagcatttatcagggttattgtctcatgagcggatacatatttgaatgtattta

gaaaaataaacaaataggggttccgcgcacatttccccgaaaagtgccacctgac
```

The cultures were supplemented with 1 mM NR at time of transfection to minimize toxicity from SAM-TIR over-expression. Forty-eight hours after transfection, cells were harvested, pelleted by centrifugation at 1,000 rpm (Sorvall ST 16R centrifuge, Thermo Fisher), and washed once with cold PBS (0.01 M phosphate buffered saline NaCl 0.138 M; KCl 0.0027 M; pH 7.4). The cells were resuspended in PBS with protease inhibitors (cOmplete™ protease inhibitor cocktail, Roche product #11873580001) and cell lysates were prepared by sonication (Branson Sonifer 450, output=3, 20 episodes of stroke). The lysates were centrifuged (12,000×g for 10 min at 4° C.) to remove cell debris and the supernatants (containing SARM1 SAM-TIR protein) were stored at −80° C. for later use in the in vitro SARM1 SAM-TIR NADase assay (see below). Protein concentration was determined by the Bicinchoninic (BCA) method and used to normalize lysate concentrations.

SAM-TIR IC50 Assay of Formula I or Formula II Compounds.

The enzymatic assay was performed in a 384-well polypropylene plate in Dulbecco's PBS buffer in a final assay volume of 20 μL. SAM-TIR lysate with a final concentration of 5 μg/mL was pre-incubated with the respective compound at 1% DMSO final assay concentration over 2 h at room temperature. The reaction was initiated by addition of 5 μM final assay concentration of NAD+as substrate. After a 2 hr room temperature incubation, the reaction was terminated with 40 μL of stop solution of 7.5% trichloroactetic acid in acetonitrile. The NAD+ and ADPR concentrations were analyzed by a RapidFire High Throughput Mass Spectrometry System (Agilent Technologies, Santa Clara, CA) using an API4000 triple quadrupole mass spectrometer (AB Sciex Framingham, MA).

Results are presented below in Table 2. Compounds having an activity designated as "A" provided an $IC_{50}$<1 μM; compounds having an activity designated as "B" provided an $IC_{50}$ 1-5 μM; compounds having an activity designated as "C" provided an $IC_{50}$>5 μM.

TABLE 2

| Example | SARM1 $IC_{50}$ (μM) |
|---|---|
| 1 | B |
| 2 | A |
| 3 | B |
| 4 | C |
| 5 | B |
| 6 | A |
| 7 | B |
| 8 | B |
| 9 | A |
| 10 | B |
| 11 | B |
| 12 | B |
| 13 | B |
| 14 | B |
| 15 | A |
| 16 | A |
| 17 | A |
| 18 | B |
| 19 | A |
| 20 | C |
| 21 | B |

TABLE 2-continued

| Example | SARM1 $IC_{50}$ (μM) |
| --- | --- |
| 22 | B |
| 23 | A |
| 24 | C |
| 25 | A |
| 26 | A |
| 27 | B |
| 28 | B |
| 29 | B |
| 30 | C |
| 31 | A |
| 32 | A |
| 33 | A |
| 34 | A |
| 35 | A |
| 36 | A |
| 37 | A |
| 38 | A |
| 39 | A |
| 40 | A |
| 41 | A |
| 42 | A |
| 43 | A |
| 44 | A |
| 45 | A |
| 46 | A |
| 47 | A |
| 48 | A |
| 49 | A |
| 50 | A |
| 51 | A |
| 52 | A |
| 53 | A |
| 54 | A |
| 55 | A |
| 56 | A |
| 57 | A |
| 58 | A |
| 59 | A |
| 60 | A |
| 61 | A |
| 62 | A |
| 63 | A |
| 64 | A |
| 65 | A |
| 66 | A |
| 67 | A |
| 68 | A |
| 69 | A |
| 70 | A |
| 71 | A |
| 72 | A |
| 73 | A |
| 74 | A |
| 75 | A |
| 76 | A |
| 77 | A |
| 78 | A |
| 79 | A |
| 80 | A |
| 81 | A |
| 82 | A |
| 83 | A |
| 84 | A |
| 85 | A |
| 86 | A |
| 87 | A |
| 88 | A |
| 89 | A |
| 90 | A |
| 91 | A |
| 92 | A |
| 93 | A |
| 94 | A |
| 95 | A |
| 96 | A |
| 97 | A |
| 98 | A |

TABLE 2-continued

| Example | SARM1 $IC_{50}$ (μM) |
| --- | --- |
| 99 | A |
| 100 | A |
| 101 | A |
| 102 | A |
| 103 | A |
| 104 | B |
| 105 | A |
| 106 | B |
| 107 | A |
| 108 | B |
| 109 | B |
| 110 | B |
| 111 | B |
| 112 | B |
| 113 | B |
| 114 | C |
| 115 | B |
| 116 | C |
| 117 | B |
| 118 | C |
| 119 | C |
| 120 | C |
| 121 | C |
| 122 | A |
| 123 | C |
| 124 | A |
| 125 | A |
| 126 | A |
| 127 | A |
| 128 | A |
| 129 | A |
| 130 | A |
| 131 | A |
| 132 | A |
| 133 | A |
| 134 | B |
| 135 | B |
| 136 | B |
| 137 | B |
| 138 | B |
| 139 | B |
| 140 | B |
| 141 | B |
| 142 | B |
| 143 | B |
| 144 | B |
| 145 | B |
| 146 | B |
| 147 | B |
| 148 | B |
| 149 | B |
| 150 | B |
| 151 | B |
| 152 | C |
| 153 | B |
| 154 | C |
| 155 | C |
| 156 | C |
| 157 | C |
| 158 | C |
| 159 | C |
| 160 | C |
| 161 | C |
| 162 | C |
| 163 | C |
| 164 | C |
| 165 | C |
| 166 | B |
| 167 | B |
| 168 | C |
| 169 | C |
| 170 | C |
| 171 | C |
| 172 | B |
| 173 | C |
| 174 | C |
| 175 | A |

TABLE 2-continued

| Example | SARM1 $IC_{50}$ (μM) |
|---|---|
| 176 | B |
| 177 | A |
| 178 | A |
| 179 | A |
| 180 | A |

Example 3: Axonal Degeneration Index

This Example illustrates an in vitro axon degeneration assay used to characterize compounds of Formula I or Formula II. This assay is used to test the efficacy of the compounds of Formula I or Formula II to prevent axonal degeneration in a mouse dorsal root ganglion (DRG) drop culture.

Mouse DRG Drop culture: Mouse dorsal root ganglion neurons (DRGs) were dissected out of E12.5 CD1 mice (50 ganglion per embryo) and incubated with 0.5% Trypsin solution containing 0.02% EDTA (Gibco) at 37° C. for 15 min. The cells were then triturated by gentle pipetting and washed 3 times with DRG growth medium (Neurobasal medium (Gibco) containing 2% B27 (Invitrogen), 100 ng/ml 2.5S NGF (Harland Bioproducts), 1 mM 5-fluoro-2'deoxyuridine (Sigma), penicillin, and streptomycin). Cells were suspended in the DRG growth medium. DRG drop cultures were created by spotting 5000 cells/well into the center of each well of a 96-well tissue culture plate coated with poly-D-Lysine (0.1 mg/ml; Sigma) and laminin (3 mg/ml; Invitrogen). Cells were allowed to adhere to the plates in a humidified tissue culture incubator (5% $CO_2$) for 15 min and then DRG growth medium was gently added (100 ml well).

Axon degeneration assay: Axonal degeneration was stimulated either by manual axonal transection using a scalpel blade, or chemotoxic stimuli. After an appropriate experimental time period, the DRG cultures were fixed in 1% PFA plus sucrose and kept in the fridge prior to imaging. Bright-field images of DRG axons and cell bodies were collected using the 20× water immersion lens of a Phenix automated confocal microscope (PerkinElmer) and quantitation of axonal performed using in-house developed scripts (Acapella, PerkinElmer).

Results are presented below in Table 3. Compounds described herein demonstrate protection of axon fragmentation in a cellular assay and are binned by $IC_{50}$ 10-30 μM (B), <10 μM (A).

TABLE 3

| Example | Axon Degeneration $IC_{50}$ |
|---|---|
| 6 | B |
| 7 | B |
| 27 | A |
| 12 | A |
| 31 | B |

The invention claimed is:
1. A compound, which is selected from the group consisting of:
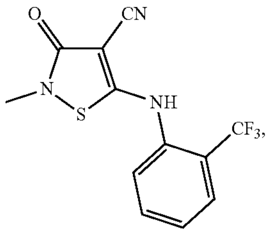
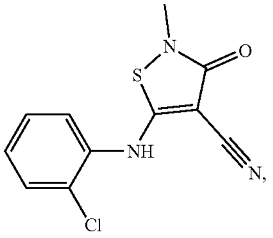
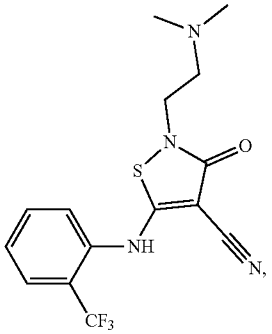
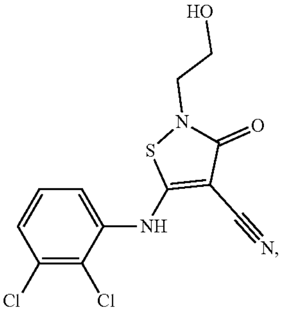
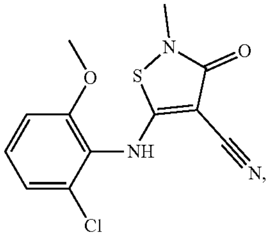
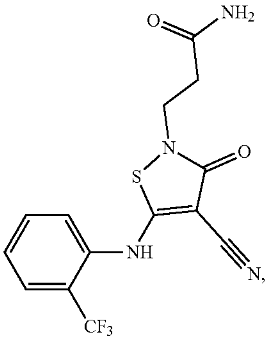
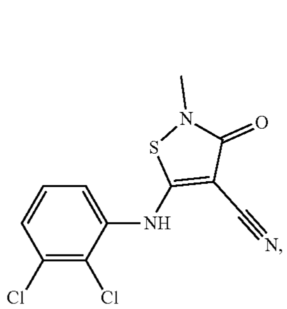
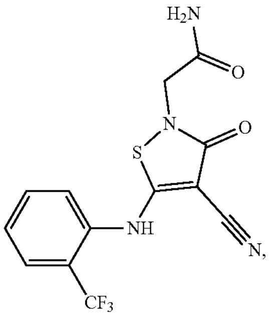
-continued
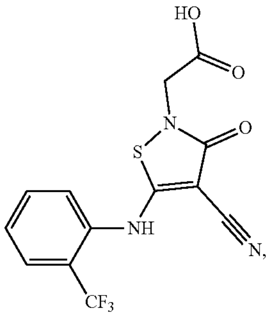
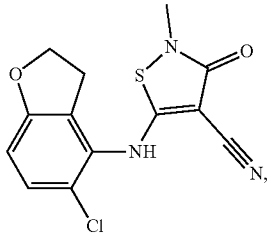
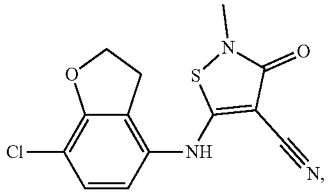
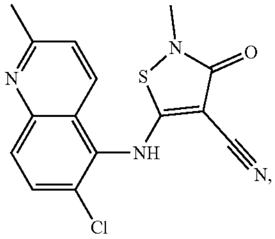
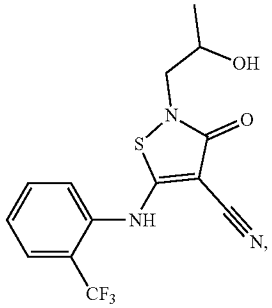
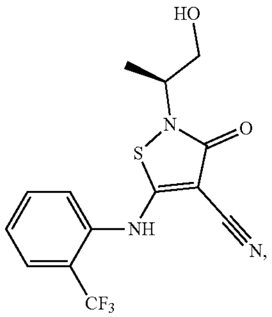
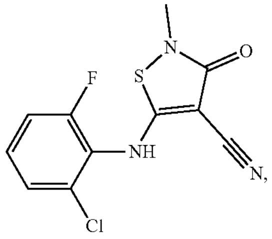
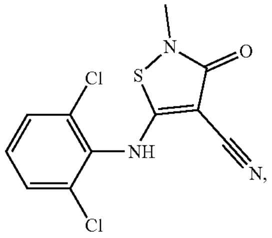
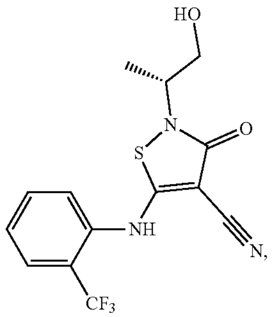

-continued
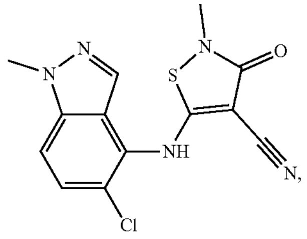
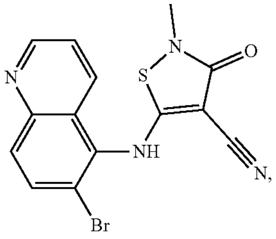
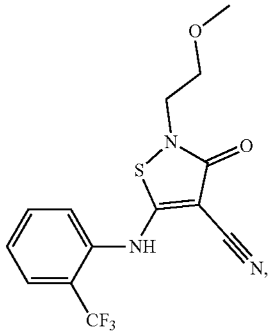
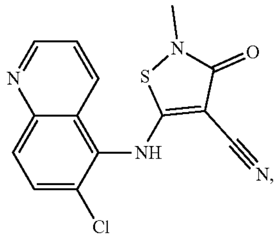
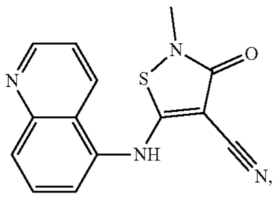
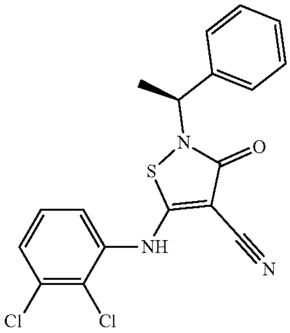
,
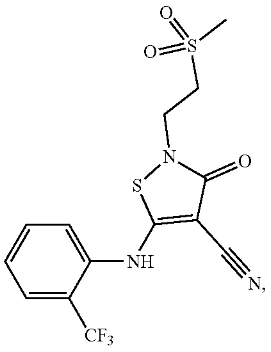
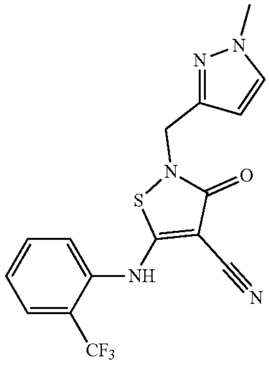
,
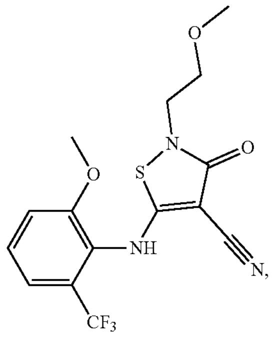
-continued
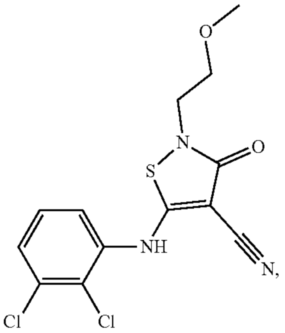
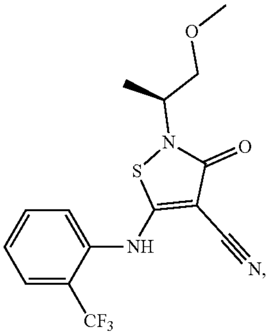
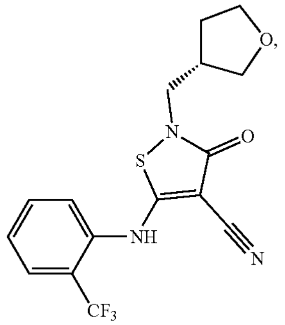
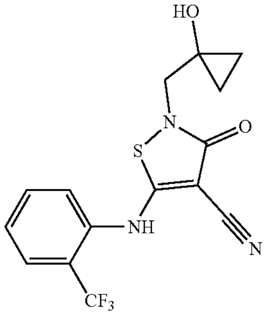
,
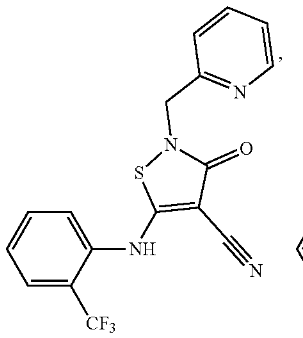
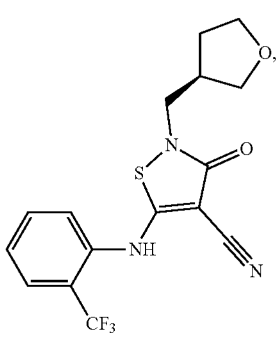
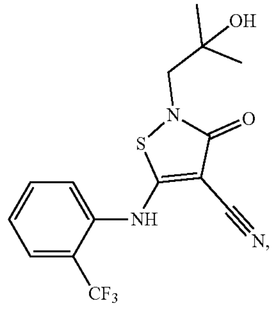
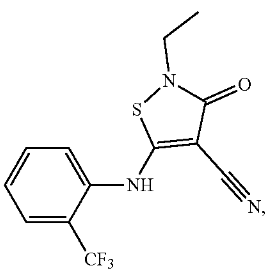
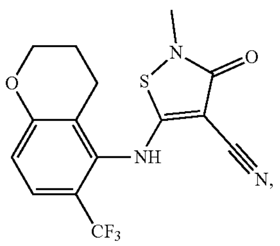
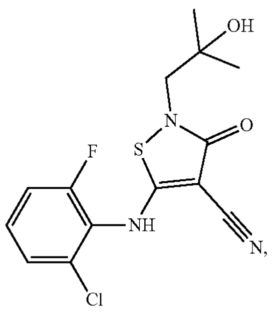

-continued
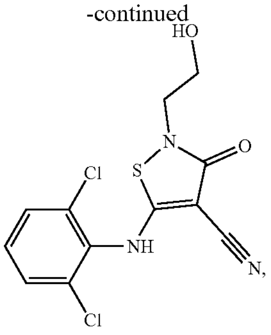
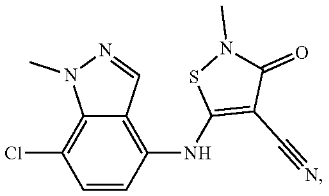
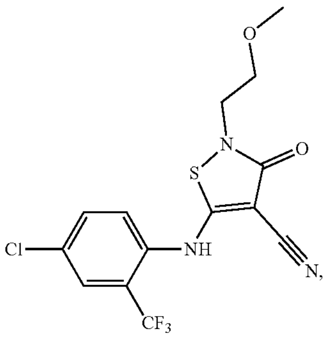
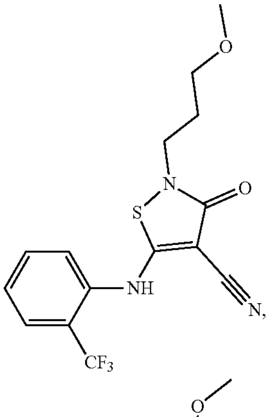
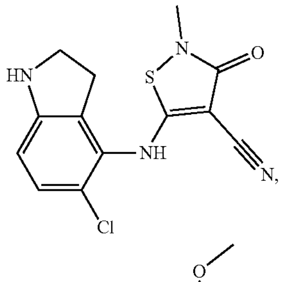
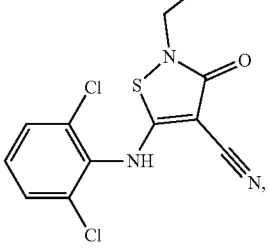
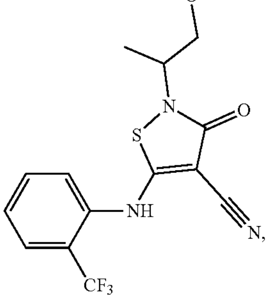
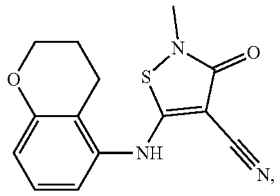
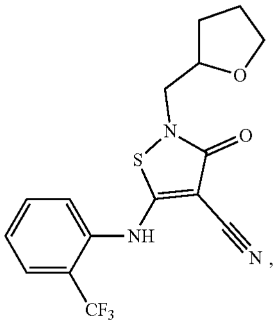
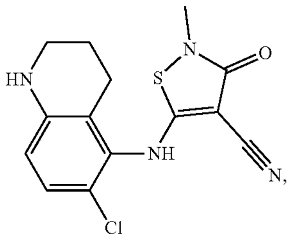
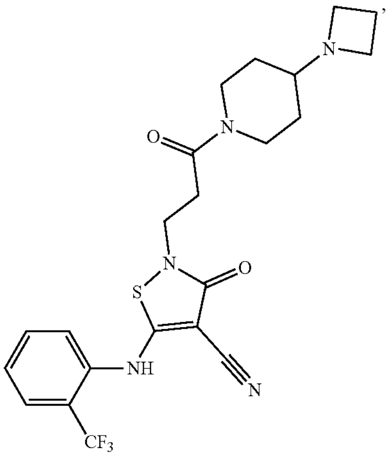
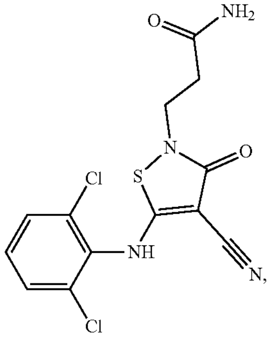
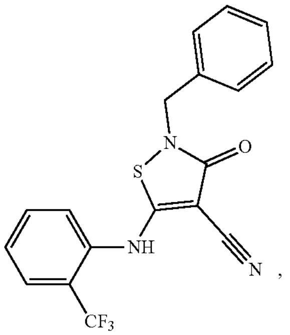
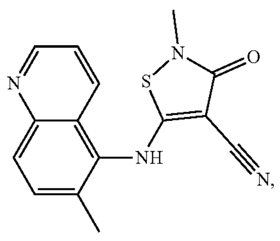
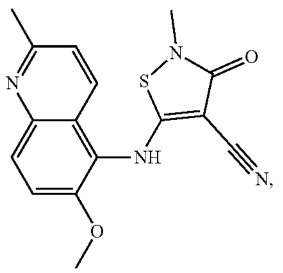

-continued
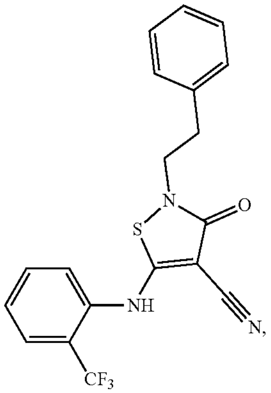
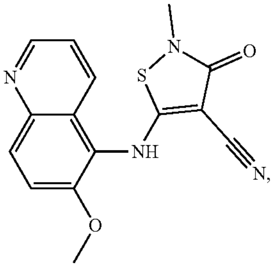
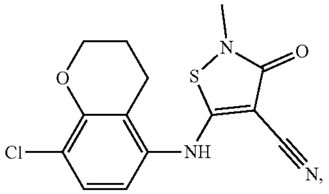
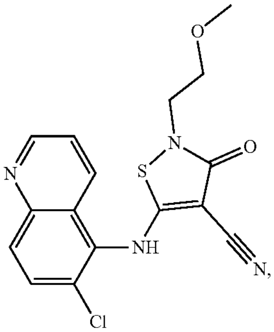
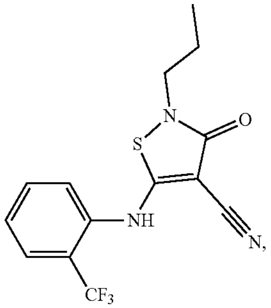
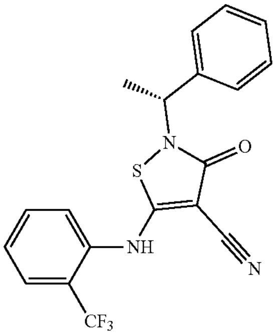
,
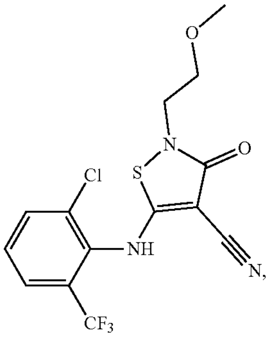
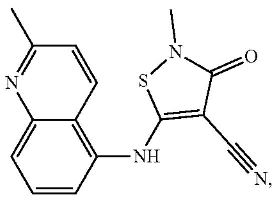
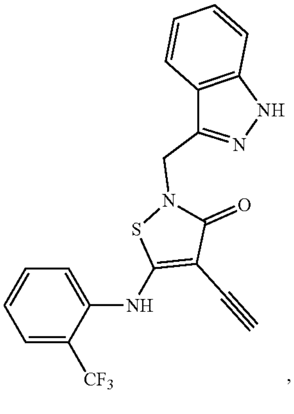
,
-continued
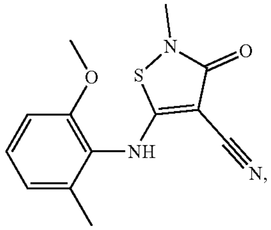
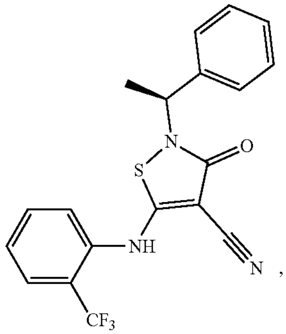
,
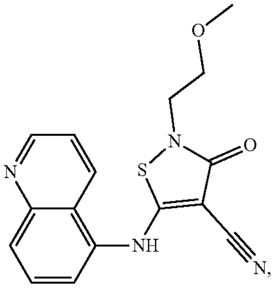
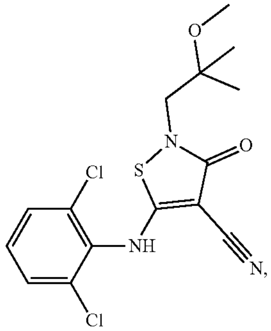
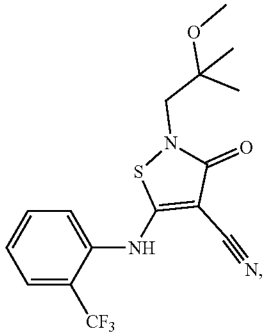
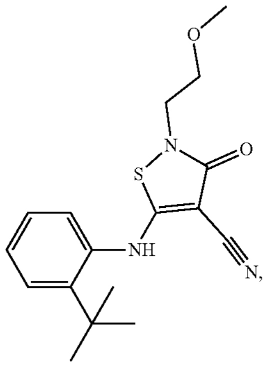

-continued
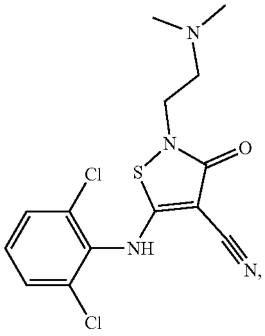
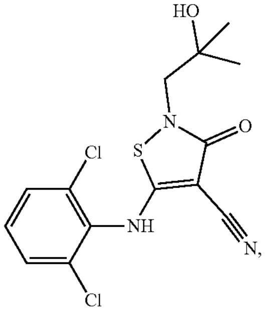
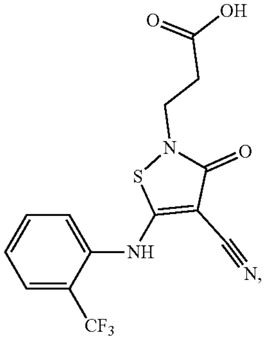
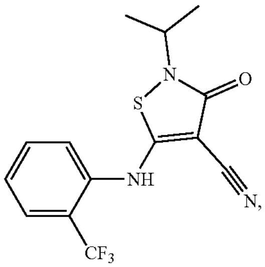
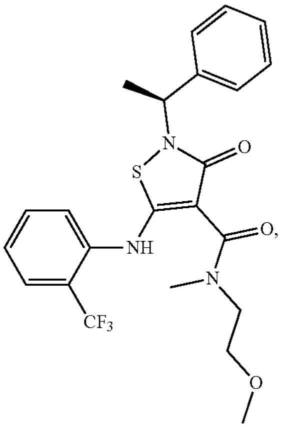
-continued
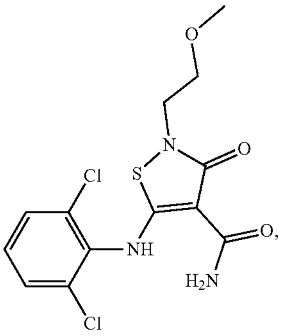
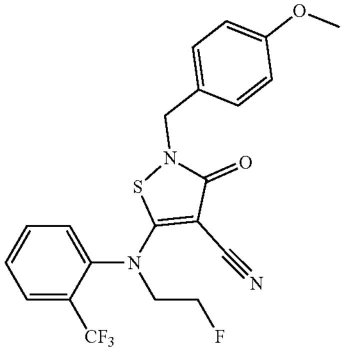
,
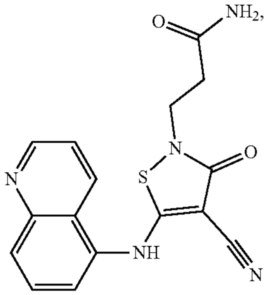
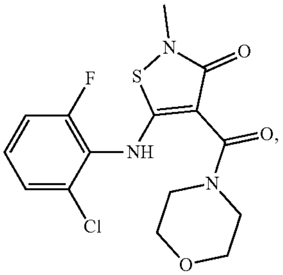
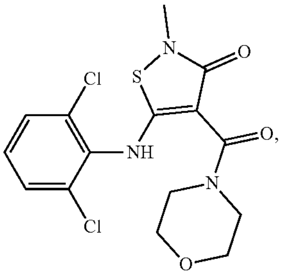

-continued
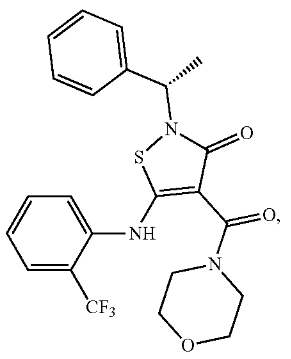
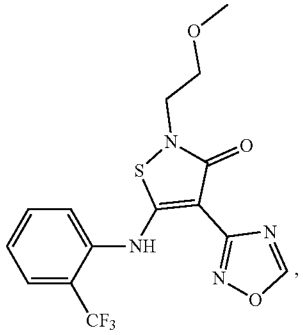
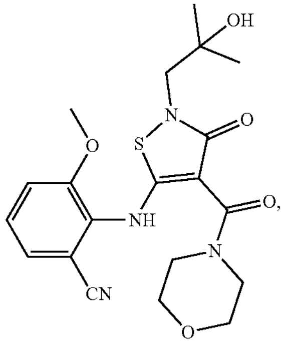
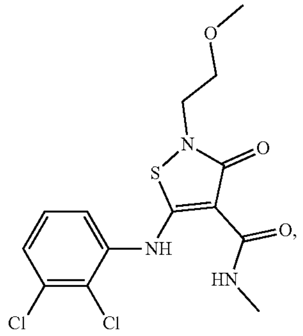
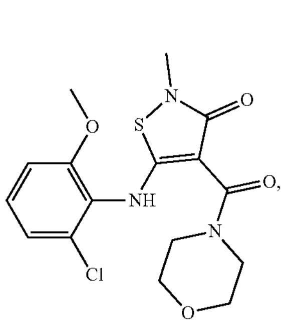
-continued
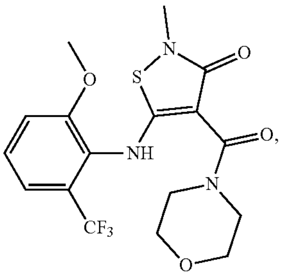
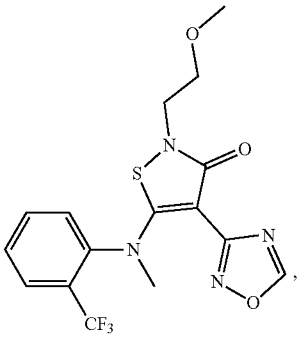
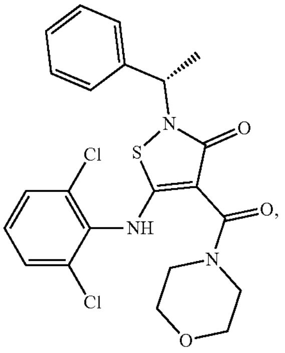
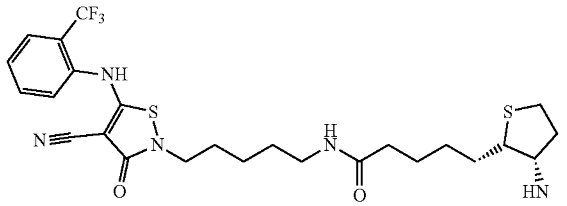
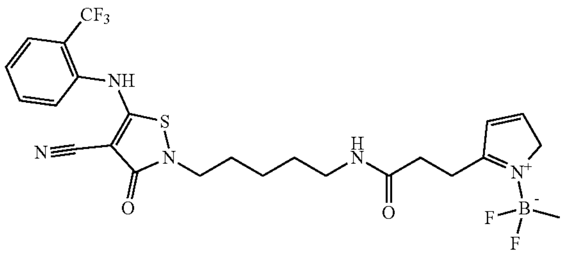
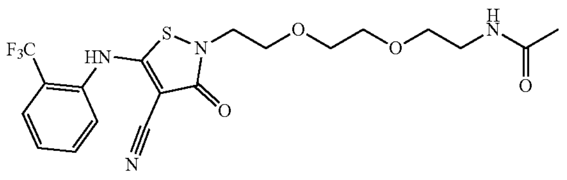

-continued
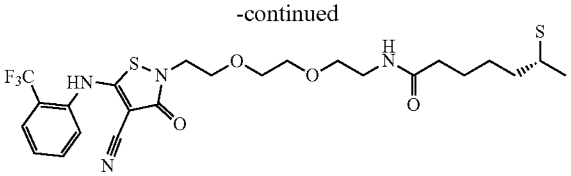
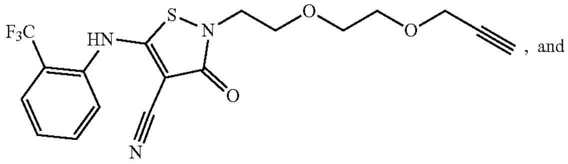
, and
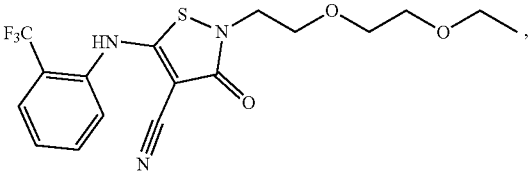
,
or a pharmaceutically acceptable salt thereof.
* * * * *